US012570728B2

(12) United States Patent
Li et al.

(10) Patent No.: US 12,570,728 B2
(45) Date of Patent: Mar. 10, 2026

(54) **COMBINATIONS OF ANTIBODIES AND BISPECIFIC ANTIBODIES COMPRISING ANTIGEN-BINDING SPECIFICALLY RECOGNIZING *PSEUDOMONAS* PCRV AND PSL**

(71) Applicant: Beijing Solobio Genetechnology Co., Ltd., Beijing (CN)

(72) Inventors: Zhong Li, Beijing (CN); Maorong Yu, Beijing (CN)

(73) Assignee: Beijing Solobio Genetechnology Co., Ltd., Beijing (CN)

( * ) Notice: Subject to any disclaimer, the term of this patent is extended or adjusted under 35 U.S.C. 154(b) by 526 days.

(21) Appl. No.: 18/036,949

(22) PCT Filed: Nov. 18, 2021

(86) PCT No.: PCT/CN2021/131391
§ 371 (c)(1),
(2) Date: May 15, 2023

(87) PCT Pub. No.: WO2022/105818
PCT Pub. Date: May 27, 2022

(65) Prior Publication Data
US 2024/0002482 A1 Jan. 4, 2024

(30) Foreign Application Priority Data

Nov. 18, 2020 (WO) ................ PCT/CN2020/129675

(51) Int. Cl.
*C07K 16/12* (2006.01)
*A61K 39/00* (2006.01)
*A61P 31/04* (2006.01)
*C07K 16/1214* (2026.01)

(52) U.S. Cl.
CPC .......... *C07K 16/1214* (2013.01); *A61P 31/04* (2018.01); *A61K 2039/505* (2013.01); *C07K 2317/31* (2013.01); *C07K 2317/33* (2013.01); *C07K 2317/55* (2013.01); *C07K 2317/622* (2013.01); *C07K 2317/76* (2013.01); *C07K 2317/92* (2013.01)

(58) Field of Classification Search
CPC ...... C07K 16/1214; A61P 31/04; A61K 39/40
See application file for complete search history.

(56) References Cited

U.S. PATENT DOCUMENTS

2015/0284450 A1 10/2015 Digiandomenico et al.
2017/0183397 A1 6/2017 Digiandomenico et al.

FOREIGN PATENT DOCUMENTS

| JP | 2014533249 A | 12/2014 |
| JP | 2015535005 A | 12/2015 |
| JP | 2019520085 A | 7/2019 |
| WO | WO2013070615 A1 | 5/2013 |
| WO | WO2021004446 A1 | 1/2021 |

OTHER PUBLICATIONS

Digiandomenico et al., A multifunctional bispecific antibody protects against Pseudomonas aeruginosa, Antimicrobial Therapeutics, Nov. 2014, vol. 6, No. 262, p. 1-12.
Haq et al., A multifunctional bispecific antibody against Pseudomonas aeruginosa as a potential therapeutic strategy, Annals of Translational Medicine, 2016, vol. 4, No. 1, Art. 12, p. 1-4.
Thanabalasuriar et al., Bispecific antibody targets multiple Pseudomonas aeruginosa evasion mechanisms in the ung vasculature, The Journal of Clinical Investigation, Jun. 2017, vol. 127, No. 6, p. 2249-2261.
Tabor et al., Pseudomonas aeruginosa PcrV and Psl, the Molecular Targets of Bispecific Antibody MEDI3902, Are Conserved Among Diverse Global Clinical Isolates, The Journal of Infectious Diseases, Dec. 2018, vol. 218, p. 1983-1994.

*Primary Examiner* — Prema M Mertz
(74) *Attorney, Agent, or Firm* — Bret E. Field; Bozicevic, Field & Francis LLP

(57) ABSTRACT

Provided are bispecific antibodies that specifically recognize PcrV and/or Psl from *Pseudomonas aeruginosa*, pharmaceutical compositions comprising antibodies specifically recognizing non-overlapping epitopes of *Pseudomonas* PcrV and/or Psl. Also provided are methods of making and using these antibodies.

13 Claims, 20 Drawing Sheets

Specification includes a Sequence Listing.

SEQUENCE LISTING

<160> NUMBER OF SEQ ID NOS: 214

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

```
Asp Asn Tyr Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Asp Asn His Met Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct

<400> SEQUENCE: 3

Asp Tyr Pro Met Ser
1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic Construct

<400> SEQUENCE: 4

Val Ile Ser Glu Ser Gly Gly Ser Thr Asn Tyr Ala Asp Ser Val Lys
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: Synthetic Construct

<400> SEQUENCE: 5

Gly Ile Ser Glu Ser Gly Gly Ser Thr Asn Tyr Ala Asp Ser Val Lys
1               5                   10                  15

Gly

<210> SEQ ID NO 6
<211> LENGTH: 19
<212> TYPE: PRT
<213> ORGANISM: Artificial Sequence
<220> FEATURE:
<223> OTHER INFORMATION: Synthetic Construct

<400> SEQUENCE: 6

Gly Arg Phe Ser Thr Leu Ser Ser His Phe Phe Arg Ala Val Tyr Gly
1               5                   10                  15

Met Asp Val

<210> SEQ ID NO 7
<211> LENGTH: 19
<212> TYPE: PRT
<213> ORGANISM: Artificial Sequence
```

-continued

```
<220> FEATURE:
<223> OTHER INFORMATION: Synthetic Construct

<400> SEQUENCE: 7

Gly Arg Phe Ser Thr Ser Ser Ser His Phe Tyr Arg Ala Val Tyr Gly
1               5                   10                  15

Met Asp Val

<210> SEQ ID NO 8
<211> LENGTH: 19
<212> TYPE: PRT
<213> ORGANISM: Artificial Sequence
<220> FEATURE:
<223> OTHER INFORMATION: Synthetic Construct

<400> SEQUENCE: 8

Gly Arg Phe Ser Thr Asn Ser Ala His Phe Phe Arg Ala Val Tyr Gly
1               5                   10                  15

Met Asp Val

<210> SEQ ID NO 9
<211> LENGTH: 19
<212> TYPE: PRT
<213> ORGANISM: Artificial Sequence
<220> FEATURE:
<223> OTHER INFORMATION: Synthetic Construct

<400> SEQUENCE: 9

Gly Arg Phe Ser Thr Asp Ser Ser His Phe Tyr Arg Ala Val Tyr Gly
1               5                   10                  15

Met Asp Val

<210> SEQ ID NO 10
<211> LENGTH: 11
<212> TYPE: PRT
<213> ORGANISM: Artificial Sequence
<220> FEATURE:
<223> OTHER INFORMATION: Synthetic Construct

<400> SEQUENCE: 10

Arg Ala Ser Gln Gly Ile Ser Ser Tyr Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Ala Ala Ser Thr Leu Gln Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Gln Gln Leu Ser Ser Tyr Pro Leu Thr
1               5
```

```
<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Gln Gln Leu Ser Ser Tyr Pro Leu Ser
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Tyr or His

<400> SEQUENCE: 14

Asp Asn Xaa Met Ser
1               5

<210> SEQ ID NO 15
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Val or Gly

<400> SEQUENCE: 15

Xaa Ile Ser Glu Ser Gly Gly Ser Thr Asn Tyr Ala Asp Ser Val Lys
1               5                   10                  15

Gly

<210> SEQ ID NO 16
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Leu or Ser
<220> FEATURE:
<221> NAME/KEY: VARIANT
<222> LOCATION: 11
<223> OTHER INFORMATION: Xaa = Phe or Tyr

<400> SEQUENCE: 16

Gly Arg Phe Ser Thr Xaa Ser Ser His Phe Xaa Arg Ala Val Tyr Gly
1               5                   10                  15

Met Asp Val

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct
```

-continued

```
<220> FEATURE:
<221> NAME/KEY: VARIANT
<222> LOCATION: 1
<223> OTHER INFORMATION: Xaa = Asp or Ser
<220> FEATURE:
<221> NAME/KEY: VARIANT
<222> LOCATION: 2
<223> OTHER INFORMATION: Xaa = Tyr or Asn
<220> FEATURE:
<221> NAME/KEY: VARIANT
<222> LOCATION: 3
<223> OTHER INFORMATION: Xaa = Pro, His, Tyr, or Ser

<400> SEQUENCE: 17

Xaa Xaa Xaa Met Ser
1               5

<210> SEQ ID NO 18
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Gly or Val
<220> FEATURE:
<221> NAME/KEY: VARIANT
<222> LOCATION: 10
<223> OTHER INFORMATION: Xaa = Asn or Tyr
<220> FEATURE:
<221> NAME/KEY: VARIANT
<222> LOCATION: 11
<223> OTHER INFORMATION: Xaa = Asp or Tyr

<400> SEQUENCE: 18

Xaa Ile Ser Glu Ser Gly Gly Ser Thr Xaa Xaa Ala Asp Ser Val Lys
1               5                   10                  15

Gly

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9
<223> OTHER INFORMATION: Xaa = Ser or Thr

<400> SEQUENCE: 19

Gln Gln Leu Ser Ser Tyr Pro Leu Xaa
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Asn or Tyr
<220> FEATURE:
<221> NAME/KEY: VARIANT
<222> LOCATION: 3
<223> OTHER INFORMATION: Xaa = Tyr, His, or Pro

<400> SEQUENCE: 20
```

-continued

```
Asp Xaa Xaa Met Ser
1               5

<210> SEQ ID NO 21
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Leu, Ser, Asn, or Asp
<220> FEATURE:
<221> NAME/KEY: VARIANT
<222> LOCATION: 8
<223> OTHER INFORMATION: Xaa = Ser or Ala
<220> FEATURE:
<221> NAME/KEY: VARIANT
<222> LOCATION: 11
<223> OTHER INFORMATION: Xaa = Phe or Tyr

<400> SEQUENCE: 21

Gly Arg Phe Ser Thr Xaa Ser Xaa His Phe Xaa Arg Ala Val Tyr Gly
1               5                   10                  15

Met Asp Val

<210> SEQ ID NO 22
<211> LENGTH: 5
<212> TYPE: PRT
<213> ORGANISM: Artificial Sequence
<220> FEATURE:
<223> OTHER INFORMATION: Synthetic Construct

<400> SEQUENCE: 22

Ser Tyr Trp Met His
1               5

<210> SEQ ID NO 23
<211> LENGTH: 17
<212> TYPE: PRT
<213> ORGANISM: Artificial Sequence
<220> FEATURE:
<223> OTHER INFORMATION: Synthetic Construct

<400> SEQUENCE: 23

Arg Ile Asn Glu Asp Glu Thr Ser Ile Ser Tyr Ala Asp Ser Val Lys
1               5                   10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: Synthetic Construct

<400> SEQUENCE: 24

Arg Ile Asn Glu Asn Glu Gly Ser Ile Ser Tyr Ala Asp Ser Val Lys
1               5                   10                  15

Gly

<210> SEQ ID NO 25
<211> LENGTH: 17
<212> TYPE: PRT
<213> ORGANISM: Artificial Sequence
```

-continued

```
<220> FEATURE:
<223> OTHER INFORMATION: Synthetic Construct

<400> SEQUENCE: 25

Arg Ile Asn Glu Asp Glu Arg Ser Ile Ser Tyr Ala Asp Ser Val Lys
1               5                   10                  15

Gly

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Asp Gly Pro Tyr Asp Ser Leu Asp Ile
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27

Asp Gly Pro Tyr Asp Ala Leu Asp Ile
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Asp Gly Pro Tyr Asp Thr Leu Asp Ile
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct

<400> SEQUENCE: 29

Asp Gly Pro Tyr Asp Ser Phe Asp Ile
1               5

<210> SEQ ID NO 30
<211> LENGTH: 11
<212> TYPE: PRT
<213> ORGANISM: Artificial Sequence
<220> FEATURE:
<223> OTHER INFORMATION: Synthetic Construct

<400> SEQUENCE: 30

Arg Ala Ser Gln Ser Val Ser Ser Asn Leu Ala
1               5                   10

<210> SEQ ID NO 31
<211> LENGTH: 11
<212> TYPE: PRT
```

```
<213> ORGANISM: Artificial Sequence
<220> FEATURE:
<223> OTHER INFORMATION: Synthetic Construct

<400> SEQUENCE: 31

Arg Ala Ser Gln Gly Val Arg Asn Asn Leu Ala
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Arg Ala Ser Gln Asn Val Lys Asn Asn Leu Ala
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Synthetic Construct

<400> SEQUENCE: 33

Asp Ala Ser Ser Arg Ala Thr
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic Construct

<400> SEQUENCE: 34

His Ala Ser Ser Arg Ala Thr
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct

<400> SEQUENCE: 35

Gln Gln Tyr Gly Ser Ser Pro Leu Thr
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Construct

<400> SEQUENCE: 36

Gln Gln Tyr Gly Leu Gln Pro Ile Thr
1               5

<210> SEQ ID NO 37
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 37

Gln Gln Tyr Gly Asn Glu Pro Ile Thr
1               5

<210> SEQ ID NO 38
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ser or Cys
<220> FEATURE:
<221> NAME/KEY: VARIANT
<222> LOCATION: 5
<223> OTHER INFORMATION: Xaa = Thr, Gly, Asp, Tyr, Gln, or Ala
<220> FEATURE:
<221> NAME/KEY: VARIANT
<222> LOCATION: 6
<223> OTHER INFORMATION: Xaa = Ser, Asp, Asn, Glu, Leu, Ala, or Tyr
<220> FEATURE:
<221> NAME/KEY: VARIANT
<222> LOCATION: 7
<223> OTHER INFORMATION: Xaa = Ser, Thr, Tyr, or Ala
<220> FEATURE:
<221> NAME/KEY: VARIANT
<222> LOCATION: 8
<223> OTHER INFORMATION: Xaa = Ser, His, Gln, Ala, Arg, Lys, Gly, Glu,
      Tyr, or Asp
<220> FEATURE:
<221> NAME/KEY: VARIANT
<222> LOCATION: 9
<223> OTHER INFORMATION: Xaa = His or Cys
<220> FEATURE:
<221> NAME/KEY: VARIANT
<222> LOCATION: 11
<223> OTHER INFORMATION: Xaa = Phe or Tyr

<400> SEQUENCE: 38

Gly Arg Phe Xaa Xaa Xaa Xaa Xaa Xaa Phe Xaa Arg Ala Val Tyr Gly
1               5                   10                  15

Met Asp Val

<210> SEQ ID NO 39
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Asp or Asn
<220> FEATURE:
<221> NAME/KEY: VARIANT
<222> LOCATION: 7
<223> OTHER INFORMATION: Xaa = Thr or Gly

<400> SEQUENCE: 39

Arg Ile Asn Glu Xaa Glu Xaa Ser Ile Ser Tyr Ala Asp Ser Val Lys
1               5                   10                  15

Gly

<210> SEQ ID NO 40
<211> LENGTH: 9
<212> TYPE: PRT
```

-continued

```
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Ser or Ala

<400> SEQUENCE: 40

Asp Gly Pro Tyr Asp Xaa Leu Asp Ile
1               5

<210> SEQ ID NO 41
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser or Gly
<220> FEATURE:
<221> NAME/KEY: VARIANT
<222> LOCATION: 7
<223> OTHER INFORMATION: Xaa = Ser or Arg
<220> FEATURE:
<221> NAME/KEY: VARIANT
<222> LOCATION: 8
<223> OTHER INFORMATION: Xaa = Ser or Asn

<400> SEQUENCE: 41

Arg Ala Ser Gln Xaa Val Xaa Xaa Asn Leu Ala
1               5                   10

<210> SEQ ID NO 42
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp or His

<400> SEQUENCE: 42

Xaa Ala Ser Ser Arg Ala Thr
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser or Leu
<220> FEATURE:
<221> NAME/KEY: VARIANT
<222> LOCATION: 6
<223> OTHER INFORMATION: Xaa = Ser or Gln
<220> FEATURE:
<221> NAME/KEY: VARIANT
<222> LOCATION: 8
<223> OTHER INFORMATION: Xaa = Leu or Ile

<400> SEQUENCE: 43

Gln Gln Tyr Gly Xaa Xaa Pro Xaa Thr
1               5
```

```
<210> SEQ ID NO 44
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Asp or Asn
<220> FEATURE:
<221> NAME/KEY: VARIANT
<222> LOCATION: 7
<223> OTHER INFORMATION: Xaa = Thr, Gly, or Arg

<400> SEQUENCE: 44

Arg Ile Asn Glu Xaa Glu Xaa Ser Ile Ser Tyr Ala Asp Ser Val Lys
1               5                   10                  15

Gly

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Ser, Ala, or Thr
<220> FEATURE:
<221> NAME/KEY: VARIANT
<222> LOCATION: 7
<223> OTHER INFORMATION: Xaa = Phe or Leu

<400> SEQUENCE: 45

Asp Gly Pro Tyr Asp Xaa Xaa Asp Ile
1               5

<210> SEQ ID NO 46
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser, Gly, or Asn
<220> FEATURE:
<221> NAME/KEY: VARIANT
<222> LOCATION: 7
<223> OTHER INFORMATION: Xaa = Ser, Arg, or Lys
<220> FEATURE:
<221> NAME/KEY: VARIANT
<222> LOCATION: 8
<223> OTHER INFORMATION: Xaa = Ser or Asn

<400> SEQUENCE: 46

Arg Ala Ser Gln Xaa Val Xaa Xaa Asn Leu Ala
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
```

```
<222> LOCATION: 5
<223> OTHER INFORMATION: Xaa = Ser, Leu, or Asn
<220> FEATURE:
<221> NAME/KEY: VARIANT
<222> LOCATION: 6
<223> OTHER INFORMATION: Xaa = Ser, Gln, or Glu
<220> FEATURE:
<221> NAME/KEY: VARIANT
<222> LOCATION: 8
<223> OTHER INFORMATION: Xaa = Leu or Ile

<400> SEQUENCE: 47

Gln Gln Tyr Gly Xaa Xaa Pro Xaa Thr
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic Construct

<400> SEQUENCE: 48

Ser Ser Gly Asp Tyr Trp Gly
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic Construct

<400> SEQUENCE: 49

Asp Tyr Tyr Trp Ser
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic Construct

<400> SEQUENCE: 50

Ile His Ser Val His
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic Construct

<400> SEQUENCE: 51

Ser Asp Ser Tyr Trp Gly
1               5

<210> SEQ ID NO 52
<211> LENGTH: 16
<212> TYPE: PRT
<213> ORGANISM: Artificial Sequence
<220> FEATURE:
<223> OTHER INFORMATION: Synthetic Construct

<400> SEQUENCE: 52

Ser Ile His Asn Gln Gly Ser Thr Tyr Tyr Asn Pro Ser Leu Lys Gly
```

```
1              5               10              15
```

<210> SEQ ID NO 53
<211> LENGTH: 16
<212> TYPE: PRT
<213> ORGANISM: Artificial Sequence
<220> FEATURE:
<223> OTHER INFORMATION: Synthetic Construct

<400> SEQUENCE: 53

```
Ser Ile His Asn Ser Gly Ser Thr Tyr Tyr Asn Pro Ser Leu Lys Gly
1              5               10              15
```

<210> SEQ ID NO 54
<211> LENGTH: 16
<212> TYPE: PRT
<213> ORGANISM: Artificial Sequence
<220> FEATURE:
<223> OTHER INFORMATION: Synthetic Construct

<400> SEQUENCE: 54

```
Tyr Ile His Ser Ser Gly Ser Thr Asp Tyr Asn Pro Ser Leu Lys Ser
1              5               10              15
```

<210> SEQ ID NO 55
<211> LENGTH: 17
<212> TYPE: PRT
<213> ORGANISM: Artificial Sequence
<220> FEATURE:
<223> OTHER INFORMATION: Synthetic Construct

<400> SEQUENCE: 55

```
Thr Ile Ile Ser Ser Gly Thr Thr Thr Thr Tyr Ala Gln Ser Phe Gln
1              5               10              15

Asp
```

<210> SEQ ID NO 56
<211> LENGTH: 16
<212> TYPE: PRT
<213> ORGANISM: Artificial Sequence
<220> FEATURE:
<223> OTHER INFORMATION: Synthetic Construct

<400> SEQUENCE: 56

```
Thr Ile Tyr Tyr Asp Gly Thr Thr Phe Tyr Asn Pro Ser Leu Arg Ser
1              5               10              15
```

<210> SEQ ID NO 57
<211> LENGTH: 13
<212> TYPE: PRT
<213> ORGANISM: Artificial Sequence
<220> FEATURE:
<223> OTHER INFORMATION: Synthetic Construct

<400> SEQUENCE: 57

```
Gln Phe Gly Ser Glu Thr Tyr Tyr Thr Gly Ile Asp Pro
1              5               10
```

<210> SEQ ID NO 58
<211> LENGTH: 13
<212> TYPE: PRT
<213> ORGANISM: Artificial Sequence
<220> FEATURE:
<223> OTHER INFORMATION: Synthetic Construct

<400> SEQUENCE: 58

```
Gln Phe Gly Ser Glu Thr Tyr Tyr Asn Gly Ile Gln Pro
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic Construct

<400> SEQUENCE: 59

Gln Phe Gly Ser Glu Thr Tyr Tyr Pro Gly Ile Asp Pro
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Synthetic Construct

<400> SEQUENCE: 60

Gln Phe Gly Ser Glu Thr Tyr Tyr Asn Gly Ile Asp Pro
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Synthetic Construct

<400> SEQUENCE: 61

Ala Gln Gly Gly Ser Arg Arg Thr Leu Asp Tyr
1               5                   10

<210> SEQ ID NO 62
<211> LENGTH: 4
<212> TYPE: PRT
<213> ORGANISM: Artificial Sequence
<220> FEATURE:
<223> OTHER INFORMATION: Synthetic Construct

<400> SEQUENCE: 62

Asp Gly Asp Ser
1

<210> SEQ ID NO 63
<211> LENGTH: 4
<212> TYPE: PRT
<213> ORGANISM: Artificial Sequence
<220> FEATURE:
<223> OTHER INFORMATION: Synthetic Construct

<400> SEQUENCE: 63

Asp Gly Thr Ser
1

<210> SEQ ID NO 64
<211> LENGTH: 14
<212> TYPE: PRT
<213> ORGANISM: Artificial Sequence
<220> FEATURE:
<223> OTHER INFORMATION: Synthetic Construct

<400> SEQUENCE: 64

His Glu Ser Gly Gln Gln Leu Val Asn Asn Trp Phe Asp Pro
```

-continued

```
1               5               10
```

<210> SEQ ID NO 65
<211> LENGTH: 16
<212> TYPE: PRT
<213> ORGANISM: Artificial Sequence
<220> FEATURE:
<223> OTHER INFORMATION: Synthetic Construct

<400> SEQUENCE: 65

```
Arg Ser Ser Gln Ser Leu Leu His Ser Asn Gly Tyr Asn Tyr Leu Asp
1               5               10              15
```

<210> SEQ ID NO 66
<211> LENGTH: 16
<212> TYPE: PRT
<213> ORGANISM: Artificial Sequence
<220> FEATURE:
<223> OTHER INFORMATION: Synthetic Construct

<400> SEQUENCE: 66

```
Arg Ser Ser Gln Ser Leu Leu His Ser Arg Gly Tyr Asn Tyr Leu Asp
1               5               10              15
```

<210> SEQ ID NO 67
<211> LENGTH: 11
<212> TYPE: PRT
<213> ORGANISM: Artificial Sequence
<220> FEATURE:
<223> OTHER INFORMATION: Synthetic Construct

<400> SEQUENCE: 67

```
Arg Ala Ser Gln Thr Ile Ser Ser Tyr Leu Asn
1               5               10
```

<210> SEQ ID NO 68
<211> LENGTH: 11
<212> TYPE: PRT
<213> ORGANISM: Artificial Sequence
<220> FEATURE:
<223> OTHER INFORMATION: Synthetic Construct

<400> SEQUENCE: 68

```
Arg Ala Ser Gln Gly Ile Ser Ser Trp Leu Ala
1               5               10
```

<210> SEQ ID NO 69
<211> LENGTH: 11
<212> TYPE: PRT
<213> ORGANISM: Artificial Sequence
<220> FEATURE:
<223> OTHER INFORMATION: Synthetic Construct

<400> SEQUENCE: 69

```
Arg Ala Ser Gln Ser Val Ser Ser Asn Leu Ala
1               5               10
```

<210> SEQ ID NO 70
<211> LENGTH: 7
<212> TYPE: PRT
<213> ORGANISM: Artificial Sequence
<220> FEATURE:
<223> OTHER INFORMATION: Synthetic Construct

<400> SEQUENCE: 70

```
Leu Gly Ser Asn Arg Ala Ser
1               5
```

```
<210> SEQ ID NO 71
<211> LENGTH: 7
<212> TYPE: PRT
<213> ORGANISM: Artificial Sequence
<220> FEATURE:
<223> OTHER INFORMATION: Synthetic Construct

<400> SEQUENCE: 71

Ala Ala Ser Ser Leu Gln Ser
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic Construct

<400> SEQUENCE: 72

His Ala Ser Thr Leu Glu Ser
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic Construct

<400> SEQUENCE: 73

Gly Ala Ser Thr Arg Ala Thr
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic Construct

<400> SEQUENCE: 74

Met Gln Ala Leu Gln Thr Pro Tyr Thr
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic Construct

<400> SEQUENCE: 75

Gln Gln Ser Tyr Ser Thr Pro Tyr Thr
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic Construct

<400> SEQUENCE: 76

Leu Gln Ala Asn Ser Leu Pro His Thr
1               5
```

-continued

```
<210> SEQ ID NO 77
<211> LENGTH: 9
<212> TYPE: PRT
<213> ORGANISM: Artificial Sequence
<220> FEATURE:
<223> OTHER INFORMATION: Synthetic Construct

<400> SEQUENCE: 77

Leu Gln Ala Phe Ser Leu Pro His Thr
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Construct

<400> SEQUENCE: 78

Leu Gln Ala Ser Ser Leu Pro His Thr
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic Construct

<400> SEQUENCE: 79

Leu Gln Ala Lys Ser Leu Pro His Thr
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic Construct

<400> SEQUENCE: 80

Gln Gln Ser Gly Asp Ser Leu Val Thr
1               5

<210> SEQ ID NO 81
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser or Gln

<400> SEQUENCE: 81

Ser Ile His Asn Xaa Gly Ser Thr Tyr Tyr Asn Pro Ser Leu Lys Gly
1               5                   10                  15

<210> SEQ ID NO 82
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9
```

```
<223> OTHER INFORMATION: Xaa = Thr, Asn, or Pro
<220> FEATURE:
<221> NAME/KEY: VARIANT
<222> LOCATION: 12
<223> OTHER INFORMATION: Xaa = Asp or Gln

<400> SEQUENCE: 82

Gln Phe Gly Ser Glu Thr Tyr Tyr Xaa Gly Ile Xaa Pro
1               5                   10

<210> SEQ ID NO 83
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 10
<223> OTHER INFORMATION: Xaa = Asn or Arg

<400> SEQUENCE: 83

Arg Ser Ser Gln Ser Leu Leu His Ser Xaa Gly Tyr Asn Tyr Leu Asp
1               5                   10                  15

<210> SEQ ID NO 84
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Asp or Thr

<400> SEQUENCE: 84

Asp Gly Xaa Ser
1

<210> SEQ ID NO 85
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Asn, Phe, Ser, or Lys

<400> SEQUENCE: 85

Leu Gln Ala Xaa Ser Leu Pro His Thr
1               5

<210> SEQ ID NO 86
<211> LENGTH: 294
<212> TYPE: PRT
<213> ORGANISM: Pseudomonas aeruginosa

<400> SEQUENCE: 86

Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45
```

-continued

```
Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
                100                 105                 110

Val Ile Gly Val Tyr Lys Asp Val Leu Gln Thr Gln Asp Gly Lys Arg
            115                 120                 125

Lys Ala Leu Leu Asp Glu Leu Lys Ala Leu Thr Ala Glu Leu Lys Val
    130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
                180                 185                 190

Ala Leu Leu Ser Asn Leu Asp Thr Phe Ser Gly Lys Leu Ser Ile Lys
            195                 200                 205

Asp Phe Leu Ser Gly Ser Pro Lys Gln Ser Gly Glu Leu Lys Gly Leu
    210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
                260                 265                 270

Val Glu Ala Leu Asn Arg Phe Ile Gln Lys Tyr Asp Ser Val Leu Arg
            275                 280                 285

Asp Ile Leu Ser Ala Ile
    290

<210> SEQ ID NO 87
<211> LENGTH: 19
<212> TYPE: PRT
<213> ORGANISM: Artificial Sequence
<220> FEATURE:
<223> OTHER INFORMATION: Synthetic Construct

<400> SEQUENCE: 87

Gly Gly Gly Gly Ser Gly Gly Gly Gly Ser Gly Gly Gly Gly Ser Gly
1               5                   10                  15

Gly Gly Gly

<210> SEQ ID NO 88
<211> LENGTH: 107
<212> TYPE: PRT
<213> ORGANISM: Homo sapiens

<400> SEQUENCE: 88

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45
```

```
Ser Gly Asn Ser Gln Glu Ser Val Thr Glu Gln Asp Ser Lys Asp Ser
    50              55              60

Thr Tyr Ser Leu Ser Ser Thr Leu Thr Leu Ser Lys Ala Asp Tyr Glu
65              70              75              80

Lys His Lys Val Tyr Ala Cys Glu Val Thr His Gln Gly Leu Ser Ser
            85              90              95

Pro Val Thr Lys Ser Phe Asn Arg Gly Glu Cys
            100             105

<210> SEQ ID NO 89
<211> LENGTH: 330
<212> TYPE: PRT
<213> ORGANISM: Homo sapiens

<400> SEQUENCE: 89

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
            85              90              95

Lys Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
            115             120             125

Lys Pro Lys Asp Thr Leu Met Ile Ser Arg Thr Pro Glu Val Thr Cys
            130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
            165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
            210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
```

-continued

```
305               310               315               320

Gln Lys Ser Leu Ser Leu Ser Pro Gly Lys
                325               330

<210> SEQ ID NO 90
<211> LENGTH: 327
<212> TYPE: PRT
<213> ORGANISM: Homo sapiens

<400> SEQUENCE: 90

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 91
<211> LENGTH: 128
```

```
<212> TYPE: PRT
<213> ORGANISM: Artificial Sequence
<220> FEATURE:
<223> OTHER INFORMATION: Synthetic Construct

<400> SEQUENCE: 91

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30

Tyr Met Ser Trp Val Arg Gln Ala Pro Gly Lys Gly Leu Asp Trp Val
        35                  40                  45

Ser Val Ile Ser Glu Ser Gly Gly Ser Thr Asn Tyr Ala Asp Ser Val
        50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
            115                 120                 125

<210> SEQ ID NO 92
<211> LENGTH: 128
<212> TYPE: PRT
<213> ORGANISM: Artificial Sequence
<220> FEATURE:
<223> OTHER INFORMATION: Synthetic Construct

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30

His Met Ser Trp Val Arg Gln Ala Pro Gly Lys Gly Leu Asp Trp Val
        35                  40                  45

Ser Gly Ile Ser Glu Ser Gly Gly Ser Thr Asn Tyr Ala Asp Ser Val
        50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Ser Ser Ser His Phe Tyr Arg Ala Val
            100                 105                 110

Tyr Gly Met Asp Val Trp Gly Gln Gly Thr Ala Val Thr Val Ser Ser
            115                 120                 125

<210> SEQ ID NO 93
<211> LENGTH: 128
<212> TYPE: PRT
<213> ORGANISM: Artificial Sequence
<220> FEATURE:
<223> OTHER INFORMATION: Synthetic Construct

<400> SEQUENCE: 93

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
```

-continued

```
                20                25                30

His Met Ser Trp Val Arg Gln Ala Pro Gly Lys Gly Leu Asp Trp Val
            35                40                45

Ser Gly Ile Ser Glu Ser Gly Gly Ser Thr Asn Tyr Ala Asp Ser Val
        50                55                60

Lys Gly Arg Phe Ser Thr Ser Arg Asp Asn Ser Lys Ser Thr Leu Tyr
65                  70                75                80

Leu Asp Met Asn Ser Leu Arg Ala Glu Asp Thr Ala Ile Tyr Tyr Cys
                85                90                95

Ala Lys Gly Arg Phe Ser Thr Asn Ser Ala His Phe Phe Arg Ala Val
                100               105               110

Tyr Gly Met Asp Val Trp Gly Gln Gly Thr Ala Val Thr Val Ser Ser
            115               120               125

<210> SEQ ID NO 94
<211> LENGTH: 128
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Leu Glu Ser Gly Gly Gly Leu Val Gln Pro Gly Gly
1               5                10                15

Ser Leu Arg Leu Ser Cys Thr Ala Ser Gly Phe Thr Phe Ser Asp Tyr
            20                25                30

Pro Met Ser Trp Val Arg Gln Ala Pro Gly Lys Gly Leu Asp Trp Val
            35                40                45

Ser Gly Ile Ser Glu Ser Gly Gly Ser Thr Asn Tyr Ala Asp Ser Val
        50                55                60

Lys Gly Arg Phe Ser Thr Ser Arg Asp Asn Ser Lys Ser Thr Leu Tyr
65                  70                75                80

Leu Asp Met Asn Ser Leu Arg Ala Glu Asp Thr Ala Ile Tyr Tyr Cys
                85                90                95

Ala Lys Gly Arg Phe Ser Thr Asp Ser Ser His Phe Tyr Arg Ala Val
                100               105               110

Tyr Gly Met Asp Val Trp Gly Gln Gly Thr Ala Val Thr Val Ser Ser
            115               120               125

<210> SEQ ID NO 95
<211> LENGTH: 118
<212> TYPE: PRT
<213> ORGANISM: Artificial Sequence
<220> FEATURE:
<223> OTHER INFORMATION: Synthetic Construct

<400> SEQUENCE: 95

Gln Val Gln Leu Val Glu Ser Gly Gly Gly Leu Val Gln Pro Gly Gly
1               5                10                15

Ser Leu Arg Leu Ser Cys Ala Ala Ser Gly Phe Ser Phe Ser Ser Tyr
            20                25                30

Trp Met His Trp Val Arg Gln Ala Pro Gly Lys Gly Leu Val Trp Val
            35                40                45

Ser Arg Ile Asn Glu Asp Glu Thr Ser Ile Ser Tyr Ala Asp Ser Val
        50                55                60

Lys Gly Arg Phe Thr Ile Ser Arg Asp Asn Ala Lys Asn Thr Leu Tyr
65                  70                75                80
```

-continued

```
Leu Gln Met Asn Gly Leu Arg Ala Glu Asp Thr Ala Val Tyr Tyr Cys
                85                  90                  95

Val Arg Asp Gly Pro Tyr Asp Ser Leu Asp Ile Trp Gly Gln Gly Thr
            100                 105                 110

Met Val Thr Val Ser Ser
        115

<210> SEQ ID NO 96
<211> LENGTH: 118
<212> TYPE: PRT
<213> ORGANISM: Artificial Sequence
<220> FEATURE:
<223> OTHER INFORMATION: Synthetic Construct

<400> SEQUENCE: 96

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Trp Met His Trp Val Arg Gln Ala Pro Gly Lys Gly Leu Val Trp Val
        35                  40                  45

Ser Arg Ile Asn Glu Asn Glu Gly Ser Ile Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Ala Glu Asp Thr Ala Val Tyr Tyr Cys
                85                  90                  95

Val Arg Asp Gly Pro Tyr Asp Ala Leu Asp Ile Trp Gly Gln Gly Thr
            100                 105                 110

Met Val Thr Val Ser Ser
        115

<210> SEQ ID NO 97
<211> LENGTH: 118
<212> TYPE: PRT
<213> ORGANISM: Artificial Sequence
<220> FEATURE:
<223> OTHER INFORMATION: Synthetic Construct

<400> SEQUENCE: 97

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Trp Met His Trp Val Arg Gln Ala Pro Gly Lys Gly Leu Val Trp Val
        35                  40                  45

Ser Arg Ile Asn Glu Asp Glu Arg Ser Ile Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Ala Glu Asp Thr Ala Val Tyr Tyr Cys
                85                  90                  95

Val Arg Asp Gly Pro Tyr Asp Ala Leu Asp Ile Trp Gly Gln Gly Thr
            100                 105                 110

Met Val Thr Val Ser Ser
        115

<210> SEQ ID NO 98
```

<211> LENGTH: 118
<212> TYPE: PRT
<213> ORGANISM: Artificial Sequence
<220> FEATURE:
<223> OTHER INFORMATION: Synthetic Construct

<400> SEQUENCE: 98

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Trp Met His Trp Val Arg Gln Ala Pro Gly Lys Gly Leu Val Trp Val
        35                  40                  45

Ser Arg Ile Asn Glu Asp Glu Arg Ser Ile Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Ala Glu Asp Thr Ala Val Tyr Tyr Cys
                85                  90                  95

Val Arg Asp Gly Pro Tyr Asp Thr Leu Asp Ile Trp Gly Gln Gly Thr
            100                 105                 110

Met Val Thr Val Ser Ser
        115

<210> SEQ ID NO 99
<211> LENGTH: 118
<212> TYPE: PRT
<213> ORGANISM: Artificial Sequence
<220> FEATURE:
<223> OTHER INFORMATION: Synthetic Construct

<400> SEQUENCE: 99

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Trp Met His Trp Val Arg Gln Ala Pro Gly Lys Gly Leu Val Trp Val
        35                  40                  45

Ser Arg Ile Asn Glu Asn Glu Gly Ser Ile Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Ala Glu Asp Thr Ala Val Tyr Tyr Cys
                85                  90                  95

Val Arg Asp Gly Pro Tyr Asp Thr Leu Asp Ile Trp Gly Gln Gly Thr
            100                 105                 110

Met Val Thr Val Ser Ser
        115

<210> SEQ ID NO 100
<211> LENGTH: 118
<212> TYPE: PRT
<213> ORGANISM: Artificial Sequence
<220> FEATURE:
<223> OTHER INFORMATION: Synthetic Construct

<400> SEQUENCE: 100

Gln Val Gln Leu Val Glu Ser Gly Gly Gly Leu Val Gln Pro Gly Gly
1               5                   10                  15

-continued

Ser Leu Arg Leu Ser Cys Ala Ala Ser Gly Phe Ser Phe Ser Ser Tyr
         20                  25                  30

Trp Met His Trp Val Arg Gln Ala Pro Gly Lys Gly Leu Val Trp Val
         35                  40                  45

Ser Arg Ile Asn Glu Asp Glu Arg Ser Ile Ser Tyr Ala Asp Ser Val
     50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Ala Glu Asp Thr Ala Val Tyr Tyr Cys
                 85                  90                  95

Val Arg Asp Gly Pro Tyr Asp Ser Leu Asp Ile Trp Gly Gln Gly Thr
             100                 105                 110

Met Val Thr Val Ser Ser
         115

<210> SEQ ID NO 101
<211> LENGTH: 118
<212> TYPE: PRT
<213> ORGANISM: Artificial Sequence
<220> FEATURE:
<223> OTHER INFORMATION: Synthetic Construct

<400> SEQUENCE: 101

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
         20                  25                  30

Trp Met His Trp Val Arg Gln Ala Pro Gly Lys Gly Leu Val Trp Val
         35                  40                  45

Ser Arg Ile Asn Glu Asn Glu Gly Ser Ile Ser Tyr Ala Asp Ser Val
     50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Ala Glu Asp Thr Ala Val Tyr Tyr Cys
                 85                  90                  95

Val Arg Asp Gly Pro Tyr Asp Ser Leu Asp Ile Trp Gly Gln Gly Thr
             100                 105                 110

Met Val Thr Val Ser Ser
         115

<210> SEQ ID NO 102
<211> LENGTH: 118
<212> TYPE: PRT
<213> ORGANISM: Artificial Sequence
<220> FEATURE:
<223> OTHER INFORMATION: Synthetic Construct

<400> SEQUENCE: 102

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Arg Ser Tyr
         20                  25                  30

Trp Met His Trp Val Arg Gln Ala Pro Gly Lys Gly Leu Val Trp Val
         35                  40                  45

Ser Arg Ile Asn Glu Asp Glu Thr Ser Ile Ser Tyr Ala Asp Ser Val
     50                  55                  60

Lys Gly Arg Phe Thr Ile Ser Arg Asp Asn Ala Lys Asn Thr Leu Tyr
65                  70                  75                  80

-continued

Leu Gln Met Asn Gly Leu Arg Ala Glu Asp Thr Ala Val Tyr Tyr Cys
                85                  90                  95

Ala Arg Asp Gly Pro Tyr Asp Ser Phe Asp Ile Trp Gly Gln Gly Thr
            100                 105                 110

Met Val Thr Val Ser Ser
        115

<210> SEQ ID NO 103
<211> LENGTH: 123
<212> TYPE: PRT
<213> ORGANISM: Artificial Sequence
<220> FEATURE:
<223> OTHER INFORMATION: Synthetic Construct

<400> SEQUENCE: 103

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Gln Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Thr Gly Ile Asp Pro
            100                 105                 110

Trp Gly Gln Gly Thr Leu Val Thr Val Ser Ser
        115                 120

<210> SEQ ID NO 104
<211> LENGTH: 123
<212> TYPE: PRT
<213> ORGANISM: Artificial Sequence
<220> FEATURE:
<223> OTHER INFORMATION: Synthetic Construct

<400> SEQUENCE: 104

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Asn Gly Ile Gln Pro
            100                 105                 110

Trp Gly Gln Gly Thr Leu Val Thr Val Ser Ser
        115                 120

-continued

<210> SEQ ID NO 105
<211> LENGTH: 123
<212> TYPE: PRT
<213> ORGANISM: Artificial Sequence
<220> FEATURE:
<223> OTHER INFORMATION: Synthetic Construct

<400> SEQUENCE: 105

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Gln Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Pro Gly Ile Asp Pro
            100                 105                 110

Trp Gly Gln Gly Thr Leu Val Thr Val Ser Ser
        115                 120

<210> SEQ ID NO 106
<211> LENGTH: 123
<212> TYPE: PRT
<213> ORGANISM: Artificial Sequence
<220> FEATURE:
<223> OTHER INFORMATION: Synthetic Construct

<400> SEQUENCE: 106

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Gly Leu Glu
        35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Asn Gly Ile Asp Pro
            100                 105                 110

Trp Gly Gln Gly Thr Leu Val Thr Val Ser Ser
        115                 120

<210> SEQ ID NO 107
<211> LENGTH: 119
<212> TYPE: PRT
<213> ORGANISM: Artificial Sequence
<220> FEATURE:
<223> OTHER INFORMATION: Synthetic Construct

<400> SEQUENCE: 107

Gln Val Gln Leu Gln Gln Ser Gly Pro Gly Leu Val Lys Thr Ser Glu
1               5                   10                  15

-continued

```
Thr Leu Ser Leu Thr Cys Thr Val Ser Gly Gly Ser Val Ser Asp Tyr
        20                  25                  30

Tyr Trp Ser Trp Ile Arg Gln Pro Pro Gly Lys Gly Leu Glu Trp Ile
        35                  40                  45

Gly Tyr Ile His Ser Ser Gly Ser Thr Asp Tyr Asn Pro Ser Leu Lys
    50                  55                  60

Ser Arg Leu Thr Ile Ser Gly Asp Ala Ala Lys Lys Gln Phe Ser Leu
65                  70                  75                  80

Asn Leu Ser Ser Val Thr Ala Ala Asp Thr Ala Leu Tyr Tyr Cys Ala
                85                  90                  95

Arg Ala Gln Gly Gly Ser Arg Arg Thr Leu Asp Tyr Trp Gly Gln Gly
            100                 105                 110

Thr Leu Val Thr Val Ser Ser
        115
```

```
<210> SEQ ID NO 108
<211> LENGTH: 119
<212> TYPE: PRT
<213> ORGANISM: Artificial Sequence
<220> FEATURE:
<223> OTHER INFORMATION: Synthetic Construct

<400> SEQUENCE: 108
```

```
Gln Val Gln Leu Gln Gln Ser Gly Pro Gly Leu Val Lys Thr Ser Glu
1               5                   10                  15

Thr Leu Ser Leu Thr Cys Thr Val Ser Gly Gly Ser Val Ser Asp Tyr
        20                  25                  30

Tyr Trp Ser Trp Ile Arg Gln Pro Pro Gly Lys Gly Leu Glu Trp Ile
        35                  40                  45

Gly Tyr Ile His Ser Ser Gly Ser Thr Asp Tyr Asn Pro Ser Leu Lys
    50                  55                  60

Ser Arg Leu Thr Ile Ser Gly Asp Ala Ala Lys Lys Gln Phe Ser Leu
65                  70                  75                  80

Lys Leu Ser Ser Val Thr Ala Ala Asp Thr Ala Leu Tyr Tyr Cys Ala
                85                  90                  95

Arg Ala Gln Gly Gly Ser Arg Arg Thr Leu Asp Tyr Trp Gly Gln Gly
            100                 105                 110

Thr Leu Val Thr Val Ser Ser
        115
```

```
<210> SEQ ID NO 109
<211> LENGTH: 113
<212> TYPE: PRT
<213> ORGANISM: Artificial Sequence
<220> FEATURE:
<223> OTHER INFORMATION: Synthetic Construct

<400> SEQUENCE: 109
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Ser Thr Ile His
        20                  25                  30

Ser Val His Trp Val Arg Gln Ala Pro Gly Gln Gly Leu Glu Trp Met
        35                  40                  45

Gly Thr Ile Ile Ser Ser Gly Thr Thr Thr Tyr Ala Gln Ser Phe
    50                  55                  60

Gln Asp Arg Val Ser Met Thr Ile Asp Arg Ser Thr Ser Thr Gly Tyr
```

```
65                  70                  75                  80
Met Glu Leu Ser Ser Leu Arg Phe Glu Asp Thr Ala Val Tyr Tyr Cys
                85                  90                  95

Thr Thr Asp Gly Asp Ser Trp Gly Gln Gly Thr Leu Val Thr Val Ser
            100                 105                 110

Ser
```

```
<210> SEQ ID NO 110
<211> LENGTH: 113
<212> TYPE: PRT
<213> ORGANISM: Artificial Sequence
<220> FEATURE:
<223> OTHER INFORMATION: Synthetic Construct

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Ser Thr Ile His
            20                  25                  30

Ser Val His Trp Val Arg Gln Ala Pro Gly Gln Gly Leu Glu Trp Met
        35                  40                  45

Gly Thr Ile Ile Ser Ser Gly Thr Thr Thr Thr Tyr Ala Gln Ser Phe
    50                  55                  60

Gln Asp Arg Val Ser Met Thr Ile Asp Arg Ser Thr Ser Thr Gly Tyr
65                  70                  75                  80

Met Glu Leu Ser Ser Leu Arg Phe Glu Asp Thr Ala Val Tyr Tyr Cys
                85                  90                  95

Thr Thr Asp Gly Thr Ser Trp Gly Gln Gly Thr Leu Val Thr Val Ser
            100                 105                 110

Ser
```

```
<210> SEQ ID NO 111
<211> LENGTH: 123
<212> TYPE: PRT
<213> ORGANISM: Artificial Sequence
<220> FEATURE:
<223> OTHER INFORMATION: Synthetic Construct

<400> SEQUENCE: 111

Gln Val Gln Leu Gln Glu Ser Gly Pro Gly Leu Val Lys Ser Ser Glu
1               5                   10                  15

Thr Leu Ser Leu Thr Cys Thr Val Ser Gly Asp Ser Ile Ser Ser Asp
            20                  25                  30

Ser Tyr Trp Gly Trp Ile Arg Gln Pro Pro Gly Lys Gly Leu Glu Trp
        35                  40                  45

Leu Ala Thr Ile Tyr Tyr Asp Gly Thr Thr Phe Tyr Asn Pro Ser Leu
    50                  55                  60

Arg Ser Arg Leu Ile Ile Ser Gly Asp Ala Ser Lys Lys Gln Phe Ser
65                  70                  75                  80

Leu Arg Leu Ser Ser Val Thr Ala Ala Asp Thr Ala Ile Tyr Tyr Cys
                85                  90                  95

Ala Arg His Glu Ser Gly Gln Gln Leu Val Asn Asn Trp Phe Asp Pro
            100                 105                 110

Trp Gly Gln Gly Thr Val Val Thr Val Ser Ser
        115                 120
```

```
<210> SEQ ID NO 112
```

```
<211> LENGTH: 107
<212> TYPE: PRT
<213> ORGANISM: Artificial Sequence
<220> FEATURE:
<223> OTHER INFORMATION: Synthetic Construct

<400> SEQUENCE: 112

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Ser Ser Tyr Pro Leu
                85                  90                  95

Thr Phe Gly Gly Gly Thr Lys Val Glu Ile Lys
            100                 105

<210> SEQ ID NO 113
<211> LENGTH: 107
<212> TYPE: PRT
<213> ORGANISM: Artificial Sequence
<220> FEATURE:
<223> OTHER INFORMATION: Synthetic Construct

<400> SEQUENCE: 113

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Ser Ser Tyr Pro Leu
                85                  90                  95

Ser Phe Gly Gly Gly Thr Lys Val Glu Ile Lys
            100                 105

<210> SEQ ID NO 114
<211> LENGTH: 107
<212> TYPE: PRT
<213> ORGANISM: Artificial Sequence
<220> FEATURE:
<223> OTHER INFORMATION: Synthetic Construct

<400> SEQUENCE: 114

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln His Lys Pro Gly Gln Ala Pro Arg Leu Leu Ile
        35                  40                  45
```

-continued

```
Tyr Asp Ala Ser Ser Arg Ala Thr Gly Ile Pro Asp Arg Phe Ser Gly
    50              55                  60

Ser Gly Ser Gly Thr Asp Phe Thr Leu Thr Ile Ser Arg Leu Glu Pro
65              70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Leu Glu Ile Lys
            100                 105

<210> SEQ ID NO 115
<211> LENGTH: 107
<212> TYPE: PRT
<213> ORGANISM: Artificial Sequence
<220> FEATURE:
<223> OTHER INFORMATION: Synthetic Construct

<400> SEQUENCE: 115

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Gly Val Arg Asn Asn
            20                  25                  30

Leu Ala Trp Tyr Gln His Lys Pro Gly Gln Ala Pro Arg Leu Leu Ile
        35                  40                  45

Tyr His Ala Ser Ser Arg Ala Thr Gly Ile Pro Asp Arg Phe Ser Gly
    50              55                  60

Ser Gly Ser Gly Thr Asp Phe Thr Leu Thr Ile Ser Arg Leu Glu Pro
65              70                  75                  80

Glu Asp Phe Ala Val Tyr Tyr Cys Gln Gln Tyr Gly Leu Gln Pro Ile
                85                  90                  95

Thr Phe Gly Gly Gly Thr Lys Leu Glu Ile Lys
            100                 105

<210> SEQ ID NO 116
<211> LENGTH: 107
<212> TYPE: PRT
<213> ORGANISM: Artificial Sequence
<220> FEATURE:
<223> OTHER INFORMATION: Synthetic Construct

<400> SEQUENCE: 116

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asn Val Lys Asn Asn
            20                  25                  30

Leu Ala Trp Tyr Gln His Lys Pro Gly Gln Ala Pro Arg Leu Leu Ile
        35                  40                  45

Tyr His Ala Ser Ser Arg Ala Thr Gly Ile Pro Asp Arg Phe Ser Gly
    50              55                  60

Ser Gly Ser Gly Thr Asp Phe Thr Leu Thr Ile Ser Arg Leu Glu Pro
65              70                  75                  80

Glu Asp Phe Ala Val Tyr Tyr Cys Gln Gln Tyr Gly Asn Glu Pro Ile
                85                  90                  95

Thr Phe Gly Gly Gly Thr Lys Leu Glu Ile Lys
            100                 105

<210> SEQ ID NO 117
<211> LENGTH: 112
<212> TYPE: PRT
<213> ORGANISM: Artificial Sequence
```

-continued

<220> FEATURE:
<223> OTHER INFORMATION: Synthetic Construct

<400> SEQUENCE: 117

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

<210> SEQ ID NO 118
<211> LENGTH: 112
<212> TYPE: PRT
<213> ORGANISM: Artificial Sequence
<220> FEATURE:
<223> OTHER INFORMATION: Synthetic Construct

<400> SEQUENCE: 118

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Arg Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

<210> SEQ ID NO 119
<211> LENGTH: 107
<212> TYPE: PRT
<213> ORGANISM: Artificial Sequence
<220> FEATURE:
<223> OTHER INFORMATION: Synthetic Construct

<400> SEQUENCE: 119

```
Glu Ile Val Met Thr Gln Ser Pro Ser Thr Leu Ser Ala Ser Val Gly
1               5                   10                  15

Asp Arg Val Ala Ile Thr Cys Arg Ala Ser Gln Thr Ile Ser Ser Tyr
            20                  25                  30

Leu Asn Trp Tyr Gln Leu Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

-continued

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                    85                  90                  95

Thr Phe Gly Gln Gly Thr Lys Val Asp Ile Lys
            100                 105

<210> SEQ ID NO 120
<211> LENGTH: 107
<212> TYPE: PRT
<213> ORGANISM: Artificial Sequence
<220> FEATURE:
<223> OTHER INFORMATION: Synthetic Construct

<400> SEQUENCE: 120

Asp Ile Gln Leu Thr Gln Ser Pro Ser Ser Val Ser Ala Ser Val Gly
1                   5                   10                  15

Asp Arg Val Thr Ile Ala Cys Arg Ala Ser Gln Gly Ile Ser Ser Trp
                    20                  25                  30

Leu Ala Trp Tyr Gln Gln Lys Pro Gly Lys Ala Pro Lys Leu Leu Ile
            35                  40                  45

Tyr His Ala Ser Thr Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Asn Ser Leu Pro His
                    85                  90                  95

Thr Phe Gly Gln Gly Thr Lys Leu Glu Ile Lys
            100                 105

<210> SEQ ID NO 121
<211> LENGTH: 107
<212> TYPE: PRT
<213> ORGANISM: Artificial Sequence
<220> FEATURE:
<223> OTHER INFORMATION: Synthetic Construct

<400> SEQUENCE: 121

Asp Ile Gln Leu Thr Gln Ser Pro Ser Ser Val Ser Ala Ser Val Gly
1                   5                   10                  15

Asp Arg Val Thr Ile Ala Cys Arg Ala Ser Gln Gly Ile Ser Ser Trp
                    20                  25                  30

Leu Ala Trp Tyr Gln Gln Lys Pro Gly Lys Ala Pro Lys Leu Leu Ile
            35                  40                  45

Tyr His Ala Ser Thr Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Phe Ser Leu Pro His
                    85                  90                  95

Thr Phe Gly Gln Gly Thr Lys Leu Glu Ile Lys
            100                 105

<210> SEQ ID NO 122
<211> LENGTH: 107
<212> TYPE: PRT
<213> ORGANISM: Artificial Sequence
<220> FEATURE:
<223> OTHER INFORMATION: Synthetic Construct -continued

```
<400> SEQUENCE: 122

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Ser Ser Leu Pro His
                85                  90                  95

Thr Phe Gly Gln Gly Thr Lys Leu Glu Ile Lys
            100                 105

<210> SEQ ID NO 123
<211> LENGTH: 107
<212> TYPE: PRT
<213> ORGANISM: Artificial Sequence
<220> FEATURE:
<223> OTHER INFORMATION: Synthetic Construct

<400> SEQUENCE: 123

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Lys Ser Leu Pro His
                85                  90                  95

Thr Phe Gly Gln Gly Thr Lys Leu Glu Ile Lys
            100                 105

<210> SEQ ID NO 124
<211> LENGTH: 107
<212> TYPE: PRT
<213> ORGANISM: Artificial Sequence
<220> FEATURE:
<223> OTHER INFORMATION: Synthetic Construct

<400> SEQUENCE: 124

Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Arg Leu Glu Pro
65                  70                  75                  80
```

```
Glu Asp Phe Ala Val Tyr Tyr Cys Gln Gln Ser Gly Asp Ser Leu Val
                85                  90                  95

Thr Phe Gly Gln Gly Thr Arg Leu Glu Ile Lys
            100                 105

<210> SEQ ID NO 125
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser, Lys, or Gln

<400> SEQUENCE: 125

Ser Ile His Asn Xaa Gly Ser Thr Tyr Tyr Asn Pro Ser Leu Lys Gly
1               5                   10                  15

<210> SEQ ID NO 126
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9
<223> OTHER INFORMATION: Xaa = Asn, Ser, Val, Thr, or Pro
<220> FEATURE:
<221> NAME/KEY: VARIANT
<222> LOCATION: 12
<223> OTHER INFORMATION: Xaa = Asp, Tyr, Cys, His, Ser, Arg, Ala, Glu,
      Gly, Lys, Trp, Val, or Gln

<400> SEQUENCE: 126

Gln Phe Gly Ser Glu Thr Tyr Tyr Xaa Gly Ile Xaa Pro
1               5                   10

<210> SEQ ID NO 127
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 10
<223> OTHER INFORMATION: Xaa = Asn, Ala, Val, Phe, Arg, Gly, His, Gln,
      Trp, or Pro

<400> SEQUENCE: 127

Arg Ser Ser Gln Ser Leu Leu His Ser Xaa Gly Tyr Asn Tyr Leu Asp
1               5                   10                  15

<210> SEQ ID NO 128
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 8
<223> OTHER INFORMATION: Xaa = Arg or Tyr

<400> SEQUENCE: 128

Met Gln Ala Leu Gln Thr Pro Xaa Thr
1               5
```

```
<210> SEQ ID NO 129
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp, Tyr, or Asn
<220> FEATURE:
<221> NAME/KEY: VARIANT
<222> LOCATION: 2
<223> OTHER INFORMATION: Xaa = Gly or Ala
<220> FEATURE:
<221> NAME/KEY: VARIANT
<222> LOCATION: 3
<223> OTHER INFORMATION: Xaa = Asp or Thr
<220> FEATURE:
<221> NAME/KEY: VARIANT
<222> LOCATION: 4
<223> OTHER INFORMATION: Xaa = Ser, Ala, or Thr

<400> SEQUENCE: 129

Xaa Xaa Xaa Xaa
1

<210> SEQ ID NO 130
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Asn, Asp, Tyr, Phe, Pro, Gly, Lys, His,
      Ala, Cys, Glu, Gln, Arg, Ser, Thr, Val, Trp, or Leu

<400> SEQUENCE: 130

Leu Gln Ala Xaa Ser Leu Pro His Thr
1               5

<210> SEQ ID NO 131
<211> LENGTH: 217
<212> TYPE: PRT
<213> ORGANISM: Artificial Sequence
<220> FEATURE:
<223> OTHER INFORMATION: Synthetic Construct

<400> SEQUENCE: 131

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
            100                 105                 110
```

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215

<210> SEQ ID NO 132
<211> LENGTH: 217
<212> TYPE: PRT
<213> ORGANISM: Artificial Sequence
<220> FEATURE:
<223> OTHER INFORMATION: Synthetic Construct

<400> SEQUENCE: 132

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215

<210> SEQ ID NO 133
<211> LENGTH: 217
<212> TYPE: PRT
<213> ORGANISM: Artificial Sequence
<220> FEATURE:

-continued

<223> OTHER INFORMATION: Synthetic Construct

<400> SEQUENCE: 133

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Leu His Glu Ala Leu His Ser His Tyr Thr Gln
        195                 200                 205

Lys Ser Leu Ser Leu Ser Pro Gly Lys
    210                 215

<210> SEQ ID NO 134
<211> LENGTH: 98
<212> TYPE: PRT
<213> ORGANISM: Artificial Sequence
<220> FEATURE:
<223> OTHER INFORMATION: Synthetic Construct

<400> SEQUENCE: 134

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 135
<211> LENGTH: 214

-continued

```
<212> TYPE: PRT
<213> ORGANISM: Artificial Sequence
<220> FEATURE:
<223> OTHER INFORMATION: Synthetic Construct

<400> SEQUENCE: 135

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Ser Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 136
<211> LENGTH: 214
<212> TYPE: PRT
<213> ORGANISM: Artificial Sequence
<220> FEATURE:
<223> OTHER INFORMATION: Synthetic Construct

<400> SEQUENCE: 136

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Ser Ser Tyr Pro Leu
                85                  90                  95

Ser Phe Gly Gly Gly Thr Lys Val Glu Ile Lys Arg Thr Val Ala Ala
            100                 105                 110
```

-continued

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 137
<211> LENGTH: 724
<212> TYPE: PRT
<213> ORGANISM: Artificial Sequence
<220> FEATURE:
<223> OTHER INFORMATION: Synthetic Construct

<400> SEQUENCE: 137

Glu Val Gln Leu Leu Glu Ser Gly Gly Gly Leu Val Gln Pro Gly Gly
1                   5                   10                  15

Ser Leu Arg Leu Ser Cys Thr Ala Ser Gly Phe Thr Phe Ser Asp Asn
            20                  25                  30

Tyr Met Ser Trp Val Arg Gln Ala Pro Gly Lys Gly Leu Asp Trp Val
            35                  40                  45

Ser Val Ile Ser Glu Ser Gly Gly Ser Thr Asn Tyr Ala Asp Ser Val
    50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
            85                  90                  95

Ala Lys Gly Arg Phe Ser Thr Leu Ser Ser His Phe Phe Arg Ala Val
        100                 105                 110

Tyr Gly Met Asp Val Trp Gly Gln Gly Thr Ala Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
            165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Gly Gly Gly Gly Ser Gly Gly Gly Gly
225                 230                 235                 240

Ser Gln Val Gln Leu Gln Gln Ser Gly Pro Gly Leu Val Lys Thr Ser
            245                 250                 255
```

```
Glu Thr Leu Ser Leu Thr Cys Thr Val Ser Gly Gly Ser Val Ser Asp
            260                 265                 270

Tyr Tyr Trp Ser Trp Ile Arg Gln Pro Pro Gly Lys Cys Leu Glu Trp
            275                 280                 285

Ile Gly Tyr Ile His Ser Ser Gly Ser Thr Asp Tyr Asn Pro Ser Leu
            290                 295                 300

Lys Ser Arg Leu Thr Ile Ser Gly Asp Ala Ala Lys Lys Gln Phe Ser
305                 310                 315                 320

Leu Asn Leu Ser Ser Val Thr Ala Ala Asp Thr Ala Leu Tyr Tyr Cys
                325                 330                 335

Ala Arg Ala Gln Gly Gly Ser Arg Arg Thr Leu Asp Tyr Trp Gly Gln
            340                 345                 350

Gly Thr Leu Val Thr Val Ser Ser Gly Gly Gly Gly Ser Gly Gly Gly
            355                 360                 365

Gly Ser Gly Gly Gly Gly Ser Gly Gly Gly Ser Glu Ile Val Met
            370                 375                 380

Thr Gln Ser Pro Ser Thr Leu Ser Ala Ser Val Gly Asp Arg Val Ala
385                 390                 395                 400

Ile Thr Cys Arg Ala Ser Gln Thr Ile Ser Ser Tyr Leu Asn Trp Tyr
                405                 410                 415

Gln Leu Lys Pro Gly Lys Ala Pro Lys Leu Leu Ile Tyr Ala Ala Ser
            420                 425                 430

Ser Leu Gln Ser Gly Val Pro Ser Arg Phe Ser Gly Ser Gly Ser Gly
            435                 440                 445

Thr Asp Phe Thr Leu Thr Ile Ser Ser Leu Gln Pro Glu Asp Phe Ala
            450                 455                 460

Thr Tyr Tyr Cys Gln Gln Ser Tyr Ser Thr Pro Tyr Thr Phe Gly Cys
465                 470                 475                 480

Gly Thr Lys Val Asp Ile Lys Gly Gly Gly Ser Gly Gly Gly Gly
                485                 490                 495

Ser Asp Lys Thr His Thr Cys Pro Pro Cys Pro Ala Pro Glu Leu Leu
                500                 505                 510

Gly Gly Pro Ser Val Phe Leu Phe Pro Pro Lys Pro Lys Asp Thr Leu
            515                 520                 525

Met Ile Ser Arg Thr Pro Glu Val Thr Cys Val Val Val Asp Val Ser
            530                 535                 540

His Glu Asp Pro Glu Val Lys Phe Asn Trp Tyr Val Asp Gly Val Glu
545                 550                 555                 560

Val His Asn Ala Lys Thr Lys Pro Arg Glu Glu Gln Tyr Asn Ser Thr
                565                 570                 575

Tyr Arg Val Val Ser Val Leu Thr Val Leu His Gln Asp Trp Leu Asn
                580                 585                 590

Gly Lys Glu Tyr Lys Cys Lys Val Ser Asn Lys Ala Leu Pro Ala Pro
            595                 600                 605

Ile Glu Lys Thr Ile Ser Lys Ala Lys Gly Gln Pro Arg Glu Pro Gln
            610                 615                 620

Val Tyr Thr Leu Pro Pro Ser Arg Glu Glu Met Thr Lys Asn Gln Val
625                 630                 635                 640

Ser Leu Thr Cys Leu Val Lys Gly Phe Tyr Pro Ser Asp Ile Ala Val
                645                 650                 655

Glu Trp Glu Ser Asn Gly Gln Pro Glu Asn Asn Tyr Lys Thr Thr Pro
            660                 665                 670
```

```
Pro Val Leu Asp Ser Asp Gly Ser Phe Phe Leu Tyr Ser Lys Leu Thr
        675             680             685

Val Asp Lys Ser Arg Trp Gln Gln Gly Asn Val Phe Ser Cys Ser Val
        690             695             700

Met His Glu Ala Leu His Asn His Tyr Thr Gln Lys Ser Leu Ser Leu
705             710             715             720

Ser Pro Gly Lys

<210> SEQ ID NO 138
<211> LENGTH: 724
<212> TYPE: PRT
<213> ORGANISM: Artificial Sequence
<220> FEATURE:
<223> OTHER INFORMATION: Synthetic Construct

<400> SEQUENCE: 138

Glu Val Gln Leu Leu Glu Ser Gly Gly Gly Leu Val Gln Pro Gly Gly
1               5               10              15

Ser Leu Arg Leu Ser Cys Thr Ala Ser Gly Phe Thr Phe Ser Asp Asn
        20              25              30

Tyr Met Ser Trp Val Arg Gln Ala Pro Gly Lys Gly Leu Asp Trp Val
        35              40              45

Ser Val Ile Ser Glu Ser Gly Gly Ser Thr Asn Tyr Ala Asp Ser Val
        50              55              60

Lys Gly Arg Phe Ser Thr Ser Arg Asp Asn Ser Lys Ser Thr Leu Tyr
65              70              75              80

Leu Asp Met Asn Ser Leu Arg Ala Glu Asp Thr Ala Ile Tyr Tyr Cys
                85              90              95

Ala Lys Gly Arg Phe Ser Thr Leu Ser Ser His Phe Phe Arg Ala Val
        100             105             110

Tyr Gly Met Asp Val Trp Gly Gln Gly Thr Ala Val Thr Val Ser Ser
        115             120             125

Ala Ser Thr Lys Gly Pro Ser Val Phe Pro Leu Ala Pro Ser Ser Lys
        130             135             140

Ser Thr Ser Gly Gly Thr Ala Ala Leu Gly Cys Leu Val Lys Asp Tyr
145             150             155             160

Phe Pro Glu Pro Val Thr Val Ser Trp Asn Ser Gly Ala Leu Thr Ser
                165             170             175

Gly Val His Thr Phe Pro Ala Val Leu Gln Ser Ser Gly Leu Tyr Ser
        180             185             190

Leu Ser Ser Val Val Thr Val Pro Ser Ser Ser Leu Gly Thr Gln Thr
        195             200             205

Tyr Ile Cys Asn Val Asn His Lys Pro Ser Asn Thr Lys Val Asp Lys
        210             215             220

Lys Val Glu Pro Lys Ser Cys Gly Gly Gly Gly Ser Gly Gly Gly Gly
225             230             235             240

Ser Gln Val Gln Leu Gln Gln Ser Gly Pro Gly Leu Val Lys Thr Ser
                245             250             255

Glu Thr Leu Ser Leu Thr Cys Thr Val Ser Gly Gly Ser Val Ser Asp
        260             265             270

Tyr Tyr Trp Ser Trp Ile Arg Gln Pro Pro Gly Lys Cys Leu Glu Trp
        275             280             285

Ile Gly Tyr Ile His Ser Ser Gly Ser Thr Asp Tyr Asn Pro Ser Leu
        290             295             300

Lys Ser Arg Leu Thr Ile Ser Gly Asp Ala Ala Lys Lys Gln Phe Ser
```

```
305                     310                     315                     320

Leu Lys Leu Ser Ser Val Thr Ala Ala Asp Thr Ala Leu Tyr Tyr Cys
                325                     330                     335

Ala Arg Ala Gln Gly Gly Ser Arg Arg Thr Leu Asp Tyr Trp Gly Gln
                340                     345                     350

Gly Thr Leu Val Thr Val Ser Ser Gly Gly Gly Gly Ser Gly Gly Gly
                355                     360                     365

Gly Ser Gly Gly Gly Gly Ser Gly Gly Gly Gly Ser Glu Ile Val Met
                370                     375                     380

Thr Gln Ser Pro Ser Thr Leu Ser Ala Ser Val Gly Asp Arg Val Ala
385                     390                     395                     400

Ile Thr Cys Arg Ala Ser Gln Thr Ile Ser Ser Tyr Leu Asn Trp Tyr
                405                     410                     415

Gln Leu Lys Pro Gly Lys Ala Pro Lys Leu Leu Ile Tyr Ala Ala Ser
                420                     425                     430

Ser Leu Gln Ser Gly Val Pro Ser Arg Phe Ser Gly Ser Gly Ser Gly
                435                     440                     445

Thr Asp Phe Thr Leu Thr Ile Ser Ser Leu Gln Pro Glu Asp Phe Ala
                450                     455                     460

Thr Tyr Tyr Cys Gln Gln Ser Tyr Ser Thr Pro Tyr Thr Phe Gly Cys
465                     470                     475                     480

Gly Thr Lys Val Asp Ile Lys Gly Gly Gly Ser Gly Gly Gly Gly
                485                     490                     495

Ser Asp Lys Thr His Thr Cys Pro Pro Cys Pro Ala Pro Glu Leu Leu
                500                     505                     510

Gly Gly Pro Ser Val Phe Leu Phe Pro Pro Lys Pro Lys Asp Thr Leu
                515                     520                     525

Met Ile Ser Arg Thr Pro Glu Val Thr Cys Val Val Val Asp Val Ser
                530                     535                     540

His Glu Asp Pro Glu Val Lys Phe Asn Trp Tyr Val Asp Gly Val Glu
545                     550                     555                     560

Val His Asn Ala Lys Thr Lys Pro Arg Glu Glu Gln Tyr Asn Ser Thr
                565                     570                     575

Tyr Arg Val Val Ser Val Leu Thr Val Leu His Gln Asp Trp Leu Asn
                580                     585                     590

Gly Lys Glu Tyr Lys Cys Lys Val Ser Asn Lys Ala Leu Pro Ala Pro
                595                     600                     605

Ile Glu Lys Thr Ile Ser Lys Ala Lys Gly Gln Pro Arg Glu Pro Gln
                610                     615                     620

Val Tyr Thr Leu Pro Pro Ser Arg Glu Glu Met Thr Lys Asn Gln Val
625                     630                     635                     640

Ser Leu Thr Cys Leu Val Lys Gly Phe Tyr Pro Ser Asp Ile Ala Val
                645                     650                     655

Glu Trp Glu Ser Asn Gly Gln Pro Glu Asn Asn Tyr Lys Thr Thr Pro
                660                     665                     670

Pro Val Leu Asp Ser Asp Gly Ser Phe Phe Leu Tyr Ser Lys Leu Thr
                675                     680                     685

Val Asp Lys Ser Arg Trp Gln Gln Gly Asn Val Phe Ser Cys Ser Val
                690                     695                     700

Met His Glu Ala Leu His Asn His Tyr Thr Gln Lys Ser Leu Ser Leu
705                     710                     715                     720

Ser Pro Gly Lys
```

<210> SEQ ID NO 139
<211> LENGTH: 722
<212> TYPE: PRT
<213> ORGANISM: Artificial Sequence
<220> FEATURE:
<223> OTHER INFORMATION: Synthetic Construct

<400> SEQUENCE: 139

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30

Tyr Met Ser Trp Val Arg Gln Ala Pro Gly Lys Gly Leu Asp Trp Val
        35                  40                  45

Ser Val Ile Ser Glu Ser Gly Gly Ser Thr Asn Tyr Ala Asp Ser Val
    50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Gly Lys Thr Gly Gly Gly Ser Gly
225                 230                 235                 240

Gly Gly Gly Ser Gln Val Gln Leu Gln Gln Ser Gly Pro Gly Leu Val
            245                 250                 255

Lys Thr Ser Glu Thr Leu Ser Leu Thr Cys Thr Val Ser Gly Gly Ser
            260                 265                 270

Val Ser Asp Tyr Tyr Trp Ser Trp Ile Arg Gln Pro Pro Gly Lys Cys
        275                 280                 285

Leu Glu Trp Ile Gly Tyr Ile His Ser Ser Gly Ser Thr Asp Tyr Asn
    290                 295                 300

Pro Ser Leu Lys Ser Arg Leu Thr Ile Ser Gly Asp Ala Ala Lys Lys
305                 310                 315                 320

Gln Phe Ser Leu Asn Leu Ser Ser Val Thr Ala Ala Asp Thr Ala Leu
            325                 330                 335

Tyr Tyr Cys Ala Arg Ala Gln Gly Gly Ser Arg Arg Thr Leu Asp Tyr
        340                 345                 350

Trp Gly Gln Gly Thr Leu Val Thr Val Ser Ser Gly Gly Gly Ser
        355                 360                 365

-continued

```
Gly Gly Gly Gly Ser Gly Gly Gly Gly Ser Gly Gly Gly Ser Glu
370             375             380

Ile Val Met Thr Gln Ser Pro Ser Thr Leu Ser Ala Ser Val Gly Asp
385                 390             395             400

Arg Val Ala Ile Thr Cys Arg Ala Ser Gln Thr Ile Ser Ser Tyr Leu
                405             410             415

Asn Trp Tyr Gln Leu Lys Pro Gly Lys Ala Pro Lys Leu Leu Ile Tyr
            420             425             430

Ala Ala Ser Ser Leu Gln Ser Gly Val Pro Ser Arg Phe Ser Gly Ser
            435             440             445

Gly Ser Gly Thr Asp Phe Thr Leu Thr Ile Ser Ser Leu Gln Pro Glu
    450             455             460

Asp Phe Ala Thr Tyr Tyr Cys Gln Gln Ser Tyr Ser Thr Pro Tyr Thr
465             470             475             480

Phe Gly Cys Gly Thr Lys Val Asp Ile Lys Gly Gly Gly Gly Ser Gly
                485             490             495

Gly Gly Gly Ser Cys Pro Pro Cys Pro Ala Pro Glu Leu Leu Gly Gly
            500             505             510

Pro Ser Val Phe Leu Phe Pro Pro Lys Pro Lys Asp Thr Leu Tyr Ile
            515             520             525

Thr Arg Glu Pro Glu Val Thr Cys Val Val Val Asp Val Ser His Glu
    530             535             540

Asp Pro Glu Val Lys Phe Asn Trp Tyr Val Asp Gly Val Glu Val His
545             550             555             560

Asn Ala Lys Thr Lys Pro Arg Glu Glu Gln Tyr Asn Ser Thr Tyr Arg
                565             570             575

Val Val Ser Val Leu Thr Val Leu His Gln Asp Trp Leu Asn Gly Lys
            580             585             590

Glu Tyr Lys Cys Lys Val Ser Asn Lys Ala Leu Pro Ala Pro Ile Glu
            595             600             605

Lys Thr Ile Ser Lys Ala Lys Gly Gln Pro Arg Glu Pro Gln Val Tyr
    610             615             620

Thr Leu Pro Pro Ser Arg Glu Glu Met Thr Lys Asn Gln Val Ser Leu
625             630             635             640

Thr Cys Leu Val Lys Gly Phe Tyr Pro Ser Asp Ile Ala Val Glu Trp
                645             650             655

Glu Ser Asn Gly Gln Pro Glu Asn Asn Tyr Lys Thr Thr Pro Pro Val
            660             665             670

Leu Asp Ser Asp Gly Ser Phe Phe Leu Tyr Ser Lys Leu Thr Val Asp
            675             680             685

Lys Ser Arg Trp Gln Gln Gly Asn Val Phe Ser Cys Ser Val Met His
    690             695             700

Glu Ala Leu His Asn His Tyr Thr Gln Lys Ser Leu Ser Leu Ser Pro
705             710             715             720

Gly Lys
```

```
<210> SEQ ID NO 140
<211> LENGTH: 722
<212> TYPE: PRT
<213> ORGANISM: Artificial Sequence
<220> FEATURE:
<223> OTHER INFORMATION: Synthetic Construct

<400> SEQUENCE: 140

Glu Val Gln Leu Leu Glu Ser Gly Gly Gly Leu Val Gln Pro Gly Gly
```

```
1                    5                      10                     15
Ser Leu Arg Leu Ser Cys Thr Ala Ser Gly Phe Thr Phe Ser Asp Asn
            20                   25                     30

Tyr Met Ser Trp Val Arg Gln Ala Pro Gly Lys Gly Leu Asp Trp Val
            35                   40                     45

Ser Val Ile Ser Glu Ser Gly Gly Ser Thr Asn Tyr Ala Asp Ser Val
         50                   55                     60

Lys Gly Arg Phe Ser Thr Ser Arg Asp Asn Ser Lys Ser Thr Leu Tyr
65                   70                   75                     80

Leu Asp Met Asn Ser Leu Arg Ala Glu Asp Thr Ala Ile Tyr Tyr Cys
                85                   90                     95

Ala Lys Gly Arg Phe Ser Thr Leu Ser Ser His Phe Phe Arg Ala Val
            100                  105                    110

Tyr Gly Met Asp Val Trp Gly Gln Gly Thr Ala Val Thr Val Ser Ser
            115                  120                    125

Ala Ser Thr Lys Gly Pro Ser Val Phe Pro Leu Ala Pro Ser Ser Lys
         130                  135                    140

Ser Thr Ser Gly Gly Thr Ala Ala Leu Gly Cys Leu Val Lys Asp Tyr
145                  150                  155                    160

Phe Pro Glu Pro Val Thr Val Ser Trp Asn Ser Gly Ala Leu Thr Ser
                165                  170                    175

Gly Val His Thr Phe Pro Ala Val Leu Gln Ser Ser Gly Leu Tyr Ser
                180                  185                    190

Leu Ser Ser Val Val Thr Val Pro Ser Ser Ser Leu Gly Thr Gln Thr
            195                  200                    205

Tyr Ile Cys Asn Val Asn His Lys Pro Ser Asn Thr Lys Val Asp Lys
         210                  215                    220

Lys Val Glu Pro Lys Ser Cys Gly Lys Thr Gly Gly Gly Gly Ser Gly
225                  230                  235                    240

Gly Gly Gly Ser Gln Val Gln Leu Gln Gln Ser Gly Pro Gly Leu Val
            245                  250                    255

Lys Thr Ser Glu Thr Leu Ser Leu Thr Cys Thr Val Ser Gly Gly Ser
            260                  265                    270

Val Ser Asp Tyr Tyr Trp Ser Trp Ile Arg Gln Pro Pro Gly Lys Cys
            275                  280                    285

Leu Glu Trp Ile Gly Tyr Ile His Ser Ser Gly Ser Thr Asp Tyr Asn
         290                  295                    300

Pro Ser Leu Lys Ser Arg Leu Thr Ile Ser Gly Asp Ala Ala Lys Lys
305                  310                  315                    320

Gln Phe Ser Leu Lys Leu Ser Ser Val Thr Ala Ala Asp Thr Ala Leu
            325                  330                    335

Tyr Tyr Cys Ala Arg Ala Gln Gly Gly Ser Arg Arg Thr Leu Asp Tyr
            340                  345                    350

Trp Gly Gln Gly Thr Leu Val Thr Val Ser Ser Gly Gly Gly Gly Ser
            355                  360                    365

Gly Gly Gly Gly Ser Gly Gly Gly Gly Ser Gly Gly Gly Gly Ser Glu
         370                  375                    380

Ile Val Met Thr Gln Ser Pro Ser Thr Leu Ser Ala Ser Val Gly Asp
385                  390                  395                    400

Arg Val Ala Ile Thr Cys Arg Ala Ser Gln Thr Ile Ser Ser Tyr Leu
                405                  410                    415

Asn Trp Tyr Gln Leu Lys Pro Gly Lys Ala Pro Lys Leu Leu Ile Tyr
            420                  425                    430
```

-continued

```
Ala Ala Ser Ser Leu Gln Ser Gly Val Pro Ser Arg Phe Ser Gly Ser
        435                 440                 445

Gly Ser Gly Thr Asp Phe Thr Leu Thr Ile Ser Ser Leu Gln Pro Glu
        450                 455                 460

Asp Phe Ala Thr Tyr Tyr Cys Gln Gln Ser Tyr Ser Thr Pro Tyr Thr
465                 470                 475                 480

Phe Gly Cys Gly Thr Lys Val Asp Ile Lys Gly Gly Gly Ser Gly
                485                 490                 495

Gly Gly Gly Ser Cys Pro Pro Cys Pro Ala Pro Glu Leu Leu Gly Gly
                500                 505                 510

Pro Ser Val Phe Leu Phe Pro Pro Lys Pro Lys Asp Thr Leu Tyr Ile
            515                 520                 525

Thr Arg Glu Pro Glu Val Thr Cys Val Val Val Asp Val Ser His Glu
        530                 535                 540

Asp Pro Glu Val Lys Phe Asn Trp Tyr Val Asp Gly Val Glu Val His
545                 550                 555                 560

Asn Ala Lys Thr Lys Pro Arg Glu Glu Gln Tyr Asn Ser Thr Tyr Arg
                565                 570                 575

Val Val Ser Val Leu Thr Val Leu His Gln Asp Trp Leu Asn Gly Lys
            580                 585                 590

Glu Tyr Lys Cys Lys Val Ser Asn Lys Ala Leu Pro Ala Pro Ile Glu
        595                 600                 605

Lys Thr Ile Ser Lys Ala Lys Gly Gln Pro Arg Glu Pro Gln Val Tyr
    610                 615                 620

Thr Leu Pro Pro Ser Arg Glu Glu Met Thr Lys Asn Gln Val Ser Leu
625                 630                 635                 640

Thr Cys Leu Val Lys Gly Phe Tyr Pro Ser Asp Ile Ala Val Glu Trp
                645                 650                 655

Glu Ser Asn Gly Gln Pro Glu Asn Asn Tyr Lys Thr Thr Pro Pro Val
                660                 665                 670

Leu Asp Ser Asp Gly Ser Phe Phe Leu Tyr Ser Lys Leu Thr Val Asp
            675                 680                 685

Lys Ser Arg Trp Gln Gln Gly Asn Val Phe Ser Cys Ser Val Met His
    690                 695                 700

Glu Ala Leu His Asn His Tyr Thr Gln Lys Ser Leu Ser Leu Ser Pro
705                 710                 715                 720

Gly Lys
```

```
<210> SEQ ID NO 141
<211> LENGTH: 722
<212> TYPE: PRT
<213> ORGANISM: Artificial Sequence
<220> FEATURE:
<223> OTHER INFORMATION: Synthetic Construct

<400> SEQUENCE: 141
```

```
Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30

Tyr Met Ser Trp Val Arg Gln Ala Pro Gly Lys Gly Leu Asp Trp Val
        35                  40                  45

Ser Val Ile Ser Glu Ser Gly Gly Ser Thr Asn Tyr Ala Asp Ser Val
    50                  55                  60
```

___

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                    85                  90                  95

Ala Lys Gly Arg Phe Ser Thr Leu Ser Ser His Phe Phe Arg Ala Val
                100                 105                 110

Tyr Gly Met Asp Val Trp Gly Gln Gly Thr Ala Val Thr Val Ser Ser
            115                 120                 125

Ala Ser Thr Lys Gly Pro Ser Val Phe Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
        210                 215                 220

Lys Val Glu Pro Lys Ser Cys Gly Lys Thr Gly Gly Gly Ser Gly
225                 230                 235                 240

Gly Gly Gly Ser Gln Val Gln Leu Gln Gln Ser Gly Pro Gly Leu Val
                245                 250                 255

Lys Thr Ser Glu Thr Leu Ser Leu Thr Cys Thr Val Ser Gly Gly Ser
                260                 265                 270

Val Ser Asp Tyr Tyr Trp Ser Trp Ile Arg Gln Pro Pro Gly Lys Cys
            275                 280                 285

Leu Glu Trp Ile Gly Tyr Ile His Ser Ser Gly Ser Thr Asp Tyr Asn
    290                 295                 300

Pro Ser Leu Lys Ser Arg Leu Thr Ile Ser Gly Asp Ala Ala Lys Lys
305                 310                 315                 320

Gln Phe Ser Leu Lys Leu Ser Ser Val Thr Ala Ala Asp Thr Ala Leu
                325                 330                 335

Tyr Tyr Cys Ala Arg Ala Gln Gly Gly Ser Arg Arg Thr Leu Asp Tyr
            340                 345                 350

Trp Gly Gln Gly Thr Leu Val Thr Val Ser Ser Gly Gly Gly Gly Ser
        355                 360                 365

Gly Gly Gly Gly Ser Gly Gly Gly Gly Ser Gly Gly Gly Gly Ser Glu
    370                 375                 380

Ile Val Met Thr Gln Ser Pro Ser Thr Leu Ser Ala Ser Val Gly Asp
385                 390                 395                 400

Arg Val Ala Ile Thr Cys Arg Ala Ser Gln Thr Ile Ser Ser Tyr Leu
                405                 410                 415

Asn Trp Tyr Gln Leu Lys Pro Gly Lys Ala Pro Lys Leu Leu Ile Tyr
            420                 425                 430

Ala Ala Ser Ser Leu Gln Ser Gly Val Pro Ser Arg Phe Ser Gly Ser
        435                 440                 445

Gly Ser Gly Thr Asp Phe Thr Leu Thr Ile Ser Ser Leu Gln Pro Glu
        450                 455                 460

Asp Phe Ala Thr Tyr Tyr Cys Gln Gln Ser Tyr Ser Thr Pro Tyr Thr
465                 470                 475                 480

Phe Gly Cys Gly Thr Lys Val Asp Ile Lys Gly Gly Gly Gly Ser Gly

-continued

```
                 485                   490                   495
Gly Gly Gly Ser Cys Pro Pro Cys Pro Ala Pro Glu Leu Leu Gly Gly
             500                   505                   510

Pro Ser Val Phe Leu Phe Pro Pro Lys Pro Lys Asp Thr Leu Met Ile
             515                   520                   525

Ser Arg Thr Pro Glu Val Thr Cys Val Val Val Asp Val Ser His Glu
             530                   535                   540

Asp Pro Glu Val Lys Phe Asn Trp Tyr Val Asp Gly Val Glu Val His
545                   550                   555                   560

Asn Ala Lys Thr Lys Pro Arg Glu Glu Gln Tyr Asn Ser Thr Tyr Arg
                 565                   570                   575

Val Val Ser Val Leu Thr Val Leu His Gln Asp Trp Leu Asn Gly Lys
             580                   585                   590

Glu Tyr Lys Cys Lys Val Ser Asn Lys Ala Leu Pro Ala Pro Ile Glu
             595                   600                   605

Lys Thr Ile Ser Lys Ala Lys Gly Gln Pro Arg Glu Pro Gln Val Tyr
             610                   615                   620

Thr Leu Pro Pro Ser Arg Glu Glu Met Thr Lys Asn Gln Val Ser Leu
625                   630                   635                   640

Thr Cys Leu Val Lys Gly Phe Tyr Pro Ser Asp Ile Ala Val Glu Trp
                 645                   650                   655

Glu Ser Asn Gly Gln Pro Glu Asn Asn Tyr Lys Thr Thr Pro Pro Val
             660                   665                   670

Leu Asp Ser Asp Gly Ser Phe Phe Leu Tyr Ser Lys Leu Thr Val Asp
             675                   680                   685

Lys Ser Arg Trp Gln Gln Gly Asn Val Phe Ser Cys Ser Val Leu His
             690                   695                   700

Glu Ala Leu His Ser His Tyr Thr Gln Lys Ser Leu Ser Leu Ser Pro
705                   710                   715                   720

Gly Lys

<210> SEQ ID NO 142
<211> LENGTH: 733
<212> TYPE: PRT
<213> ORGANISM: Artificial Sequence
<220> FEATURE:
<223> OTHER INFORMATION: Synthetic Construct

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
             20                  25                  30

Tyr Met Ser Trp Val Arg Gln Ala Pro Gly Lys Gly Leu Asp Trp Val
             35                  40                  45

Ser Val Ile Ser Glu Ser Gly Gly Ser Thr Asn Tyr Ala Asp Ser Val
             50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                 85                  90                  95

Ala Lys Gly Arg Phe Ser Thr Leu Ser Ser His Phe Phe Arg Ala Val
             100                 105                 110

Tyr Gly Met Asp Val Trp Gly Gln Gly Thr Ala Val Thr Val Ser Ser
             115                 120                 125
```

-continued

```
Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Gly Gly Gly Ser Gly Gly Gly Gly
225                 230                 235                 240

Ser Gln Val Gln Leu Gln Gln Ser Gly Pro Gly Leu Val Lys Pro Ser
                245                 250                 255

Glu Thr Leu Ser Leu Thr Cys Thr Val Ser Gly Gly Pro Ile Thr Ser
            260                 265                 270

Ser Gly Asp Tyr Trp Gly Trp Ile Arg Gln Pro Pro Gly Lys Cys Leu
        275                 280                 285

Glu Leu Ile Gly Ser Ile His Asn Ser Gly Ser Thr Tyr Tyr Asn Pro
    290                 295                 300

Ser Leu Lys Gly Arg Val Thr Ile Ser Gly Asp Thr Ser Lys Asn Gln
305                 310                 315                 320

Ile Ser Leu Arg Leu Ser Ser Val Thr Ala Ala Asp Thr Ala Val Tyr
                325                 330                 335

Tyr Cys Ala Arg Gln Phe Gly Ser Glu Thr Tyr Tyr Asn Gly Ile Asp
            340                 345                 350

Pro Trp Gly Gln Gly Thr Leu Val Thr Val Ser Ser Gly Gly Gly Gly
        355                 360                 365

Ser Gly Gly Gly Gly Ser Gly Gly Gly Ser Gly Gly Gly Gly Ser
    370                 375                 380

Asp Ile Val Met Thr Gln Thr Pro Leu Ser Leu Pro Val Thr Pro Gly
385                 390                 395                 400

Glu Pro Ala Ser Ile Ser Cys Arg Ser Ser Gln Ser Leu Leu His Ser
                405                 410                 415

Asn Gly Tyr Asn Tyr Leu Asp Trp Tyr Leu Gln Lys Pro Gly Gln Ser
            420                 425                 430

Pro Gln Leu Leu Ile Tyr Leu Gly Ser Asn Arg Ala Ser Gly Val Pro
        435                 440                 445

Asp Arg Phe Ser Gly Ser Gly Ser Gly Thr Asp Phe Thr Leu Lys Ile
    450                 455                 460

Ser Arg Val Glu Ala Glu Asp Val Gly Val Tyr Tyr Cys Met Gln Ala
465                 470                 475                 480

Leu Gln Thr Pro Tyr Thr Phe Gly Cys Gly Thr Lys Leu Glu Ile Lys
                485                 490                 495

Gly Gly Gly Gly Ser Gly Gly Gly Gly Ser Asp Lys Thr His Thr Cys
            500                 505                 510

Pro Pro Cys Pro Ala Pro Glu Leu Leu Gly Gly Pro Ser Val Phe Leu
        515                 520                 525

Phe Pro Pro Lys Pro Lys Asp Thr Leu Met Ile Ser Arg Thr Pro Glu
    530                 535                 540
```

-continued

```
Val Thr Cys Val Val Val Asp Val Ser His Glu Asp Pro Glu Val Lys
545                 550                 555                 560

Phe Asn Trp Tyr Val Asp Gly Val Glu Val His Asn Ala Lys Thr Lys
                565                 570                 575

Pro Arg Glu Glu Gln Tyr Asn Ser Thr Tyr Arg Val Val Ser Val Leu
                580                 585                 590

Thr Val Leu His Gln Asp Trp Leu Asn Gly Lys Glu Tyr Lys Cys Lys
                595                 600                 605

Val Ser Asn Lys Ala Leu Pro Ala Pro Ile Glu Lys Thr Ile Ser Lys
                610                 615                 620

Ala Lys Gly Gln Pro Arg Glu Pro Gln Val Tyr Thr Leu Pro Pro Ser
625                 630                 635                 640

Arg Glu Glu Met Thr Lys Asn Gln Val Ser Leu Thr Cys Leu Val Lys
                645                 650                 655

Gly Phe Tyr Pro Ser Asp Ile Ala Val Glu Trp Glu Ser Asn Gly Gln
                660                 665                 670

Pro Glu Asn Asn Tyr Lys Thr Thr Pro Pro Val Leu Asp Ser Asp Gly
                675                 680                 685

Ser Phe Phe Leu Tyr Ser Lys Leu Thr Val Asp Lys Ser Arg Trp Gln
690                 695                 700

Gln Gly Asn Val Phe Ser Cys Ser Val Met His Glu Ala Leu His Asn
705                 710                 715                 720

His Tyr Thr Gln Lys Ser Leu Ser Leu Ser Pro Gly Lys
                725                 730

<210> SEQ ID NO 143
<211> LENGTH: 731
<212> TYPE: PRT
<213> ORGANISM: Artificial Sequence
<220> FEATURE:
<223> OTHER INFORMATION: Synthetic Construct

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
                20                  25                  30

Tyr Met Ser Trp Val Arg Gln Ala Pro Gly Lys Gly Leu Asp Trp Val
                35                  40                  45

Ser Val Ile Ser Glu Ser Gly Gly Ser Thr Asn Tyr Ala Asp Ser Val
                50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Leu Ser Ser His Phe Phe Arg Ala Val
                100                 105                 110

Tyr Gly Met Asp Val Trp Gly Gln Gly Thr Ala Val Thr Val Ser Ser
                115                 120                 125

Ala Ser Thr Lys Gly Pro Ser Val Phe Pro Leu Ala Pro Ser Ser Lys
130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175
```

-continued

```
Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
            210                 215                 220

Lys Val Glu Pro Lys Ser Cys Gly Lys Thr Gly Gly Gly Gly Ser Gly
225                 230                 235                 240

Gly Gly Gly Ser Gln Val Gln Leu Gln Gln Ser Gly Pro Gly Leu Val
            245                 250                 255

Lys Pro Ser Glu Thr Leu Ser Leu Thr Cys Thr Val Ser Gly Gly Pro
            260                 265                 270

Ile Thr Ser Ser Gly Asp Tyr Trp Gly Trp Ile Arg Gln Pro Pro Gly
            275                 280                 285

Lys Cys Leu Glu Leu Ile Gly Ser Ile His Asn Ser Gly Ser Thr Tyr
            290                 295                 300

Tyr Asn Pro Ser Leu Lys Gly Arg Val Thr Ile Ser Gly Asp Thr Ser
305                 310                 315                 320

Lys Asn Gln Ile Ser Leu Arg Leu Ser Ser Val Thr Ala Ala Asp Thr
            325                 330                 335

Ala Val Tyr Tyr Cys Ala Arg Gln Phe Gly Ser Glu Thr Tyr Tyr Asn
            340                 345                 350

Gly Ile Asp Pro Trp Gly Gln Gly Thr Leu Val Thr Val Ser Ser Gly
            355                 360                 365

Gly Gly Gly Ser Gly Gly Gly Gly Ser Gly Gly Gly Gly Ser Gly Gly
            370                 375                 380

Gly Gly Ser Asp Ile Val Met Thr Gln Thr Pro Leu Ser Leu Pro Val
385                 390                 395                 400

Thr Pro Gly Glu Pro Ala Ser Ile Ser Cys Arg Ser Ser Gln Ser Leu
            405                 410                 415

Leu His Ser Asn Gly Tyr Asn Tyr Leu Asp Trp Tyr Leu Gln Lys Pro
            420                 425                 430

Gly Gln Ser Pro Gln Leu Leu Ile Tyr Leu Gly Ser Asn Arg Ala Ser
            435                 440                 445

Gly Val Pro Asp Arg Phe Ser Gly Ser Gly Ser Gly Thr Asp Phe Thr
            450                 455                 460

Leu Lys Ile Ser Arg Val Glu Ala Glu Asp Val Gly Val Tyr Tyr Cys
465                 470                 475                 480

Met Gln Ala Leu Gln Thr Pro Tyr Thr Phe Gly Cys Gly Thr Lys Leu
            485                 490                 495

Glu Ile Lys Gly Gly Gly Gly Ser Gly Gly Gly Ser Cys Pro Pro
            500                 505                 510

Cys Pro Ala Pro Glu Leu Leu Gly Gly Pro Ser Val Phe Leu Phe Pro
            515                 520                 525

Pro Lys Pro Lys Asp Thr Leu Tyr Ile Thr Arg Glu Pro Glu Val Thr
            530                 535                 540

Cys Val Val Val Asp Val Ser His Glu Asp Pro Glu Val Lys Phe Asn
545                 550                 555                 560

Trp Tyr Val Asp Gly Val Glu Val His Asn Ala Lys Thr Lys Pro Arg
            565                 570                 575

Glu Glu Gln Tyr Asn Ser Thr Tyr Arg Val Val Ser Val Leu Thr Val
            580                 585                 590

Leu His Gln Asp Trp Leu Asn Gly Lys Glu Tyr Lys Cys Lys Val Ser
```

```
            595                 600                 605
Asn Lys Ala Leu Pro Ala Pro Ile Glu Lys Thr Ile Ser Lys Ala Lys
    610                 615                 620

Gly Gln Pro Arg Glu Pro Gln Val Tyr Thr Leu Pro Pro Ser Arg Glu
625                 630                 635                 640

Glu Met Thr Lys Asn Gln Val Ser Leu Thr Cys Leu Val Lys Gly Phe
                645                 650                 655

Tyr Pro Ser Asp Ile Ala Val Glu Trp Glu Ser Asn Gly Gln Pro Glu
                660                 665                 670

Asn Asn Tyr Lys Thr Thr Pro Pro Val Leu Asp Ser Asp Gly Ser Phe
                675                 680                 685

Phe Leu Tyr Ser Lys Leu Thr Val Asp Lys Ser Arg Trp Gln Gln Gly
    690                 695                 700

Asn Val Phe Ser Cys Ser Val Met His Glu Ala Leu His Asn His Tyr
705                 710                 715                 720

Thr Gln Lys Ser Leu Ser Leu Ser Pro Gly Lys
                725                 730

<210> SEQ ID NO 144
<211> LENGTH: 731
<212> TYPE: PRT
<213> ORGANISM: Artificial Sequence
<220> FEATURE:
<223> OTHER INFORMATION: Synthetic Construct

<400> SEQUENCE: 144

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30

Tyr Met Ser Trp Val Arg Gln Ala Pro Gly Lys Gly Leu Asp Trp Val
            35                  40                  45

Ser Val Ile Ser Glu Ser Gly Gly Ser Thr Asn Tyr Ala Asp Ser Val
        50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
            115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
    210                 215                 220

Lys Val Glu Pro Lys Ser Cys Gly Lys Thr Gly Gly Gly Gly Ser Gly
```

```
225              230              235              240

Gly Gly Gly Ser Gln Val Gln Leu Gln Gln Ser Gly Pro Gly Leu Val
                245              250              255

Lys Pro Ser Glu Thr Leu Ser Leu Thr Cys Thr Val Ser Gly Gly Pro
                260              265              270

Ile Thr Ser Ser Gly Asp Tyr Trp Gly Trp Ile Arg Gln Pro Pro Gly
                275              280              285

Lys Cys Leu Glu Leu Ile Gly Ser Ile His Asn Ser Gly Ser Thr Tyr
                290              295              300

Tyr Asn Pro Ser Leu Lys Gly Arg Val Thr Ile Ser Gly Asp Thr Ser
305              310              315              320

Lys Asn Gln Ile Ser Leu Arg Leu Ser Ser Val Thr Ala Ala Asp Thr
                325              330              335

Ala Val Tyr Tyr Cys Ala Arg Gln Phe Gly Ser Glu Thr Tyr Tyr Asn
                340              345              350

Gly Ile Asp Pro Trp Gly Gln Gly Thr Leu Val Thr Val Ser Ser Gly
                355              360              365

Gly Gly Gly Ser Gly Gly Gly Gly Ser Gly Gly Gly Ser Gly Gly
                370              375              380

Gly Gly Ser Asp Ile Val Met Thr Gln Thr Pro Leu Ser Leu Pro Val
385              390              395              400

Thr Pro Gly Glu Pro Ala Ser Ile Ser Cys Arg Ser Ser Gln Ser Leu
                405              410              415

Leu His Ser Asn Gly Tyr Asn Tyr Leu Asp Trp Tyr Leu Gln Lys Pro
                420              425              430

Gly Gln Ser Pro Gln Leu Leu Ile Tyr Leu Gly Ser Asn Arg Ala Ser
                435              440              445

Gly Val Pro Asp Arg Phe Ser Gly Ser Gly Ser Gly Thr Asp Phe Thr
                450              455              460

Leu Lys Ile Ser Arg Val Glu Ala Glu Asp Val Gly Val Tyr Tyr Cys
465              470              475              480

Met Gln Ala Leu Gln Thr Pro Tyr Thr Phe Gly Cys Gly Thr Lys Leu
                485              490              495

Glu Ile Lys Gly Gly Gly Ser Gly Gly Gly Ser Cys Pro Pro
                500              505              510

Cys Pro Ala Pro Glu Leu Leu Gly Gly Pro Ser Val Phe Leu Phe Pro
                515              520              525

Pro Lys Pro Lys Asp Thr Leu Met Ile Ser Arg Thr Pro Glu Val Thr
                530              535              540

Cys Val Val Val Asp Val Ser His Glu Asp Pro Glu Val Lys Phe Asn
545              550              555              560

Trp Tyr Val Asp Gly Val Glu Val His Asn Ala Lys Thr Lys Pro Arg
                565              570              575

Glu Glu Gln Tyr Asn Ser Thr Tyr Arg Val Val Ser Val Leu Thr Val
                580              585              590

Leu His Gln Asp Trp Leu Asn Gly Lys Glu Tyr Lys Cys Lys Val Ser
                595              600              605

Asn Lys Ala Leu Pro Ala Pro Ile Glu Lys Thr Ile Ser Lys Ala Lys
                610              615              620

Gly Gln Pro Arg Glu Pro Gln Val Tyr Thr Leu Pro Pro Ser Arg Glu
625              630              635              640

Glu Met Thr Lys Asn Gln Val Ser Leu Thr Cys Leu Val Lys Gly Phe
                645              650              655
```

-continued

```
Tyr Pro Ser Asp Ile Ala Val Glu Trp Glu Ser Asn Gly Gln Pro Glu
            660                 665                 670

Asn Asn Tyr Lys Thr Thr Pro Pro Val Leu Asp Ser Asp Gly Ser Phe
            675                 680                 685

Phe Leu Tyr Ser Lys Leu Thr Val Asp Lys Ser Arg Trp Gln Gln Gly
            690                 695                 700

Asn Val Phe Ser Cys Ser Val Leu His Glu Ala Leu His Ser His Tyr
705                 710                 715                 720

Thr Gln Lys Ser Leu Ser Leu Ser Pro Gly Lys
            725                 730

<210> SEQ ID NO 145
<211> LENGTH: 728
<212> TYPE: PRT
<213> ORGANISM: Artificial Sequence
<220> FEATURE:
<223> OTHER INFORMATION: Synthetic Construct

<400> SEQUENCE: 145

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30

Tyr Met Ser Trp Val Arg Gln Ala Pro Gly Lys Gly Leu Asp Trp Val
            35                  40                  45

Ser Val Ile Ser Glu Ser Gly Gly Ser Thr Asn Tyr Ala Asp Ser Val
            50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
            115                 120                 125

Ala Ser Thr Lys Gly Pro Ser Val Phe Pro Leu Ala Pro Ser Ser Lys
            130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
            210                 215                 220

Lys Val Glu Pro Lys Ser Cys Gly Gly Gly Ser Gly Gly Gly Gly
225                 230                 235                 240

Ser Gln Val Gln Leu Gln Gln Ser Gly Pro Gly Leu Val Lys Pro Ser
            245                 250                 255

Glu Thr Leu Ser Leu Thr Cys Thr Val Ser Gly Gly Pro Ile Thr Ser
            260                 265                 270

Ser Gly Asp Tyr Trp Gly Trp Ile Arg Gln Pro Pro Gly Lys Cys Leu
            275                 280                 285
```

```
Glu Leu Ile Gly Ser Ile His Asn Gln Gly Ser Thr Tyr Tyr Asn Pro
    290                 295                 300

Ser Leu Lys Gly Arg Val Thr Ile Ser Gly Asp Thr Ser Lys Asn Gln
305                 310                 315                 320

Ile Ser Leu Arg Leu Ser Ser Val Thr Ala Ala Asp Thr Ala Val Tyr
                325                 330                 335

Tyr Cys Ala Arg Gln Phe Gly Ser Glu Thr Tyr Tyr Thr Gly Ile Asp
            340                 345                 350

Pro Trp Gly Gln Gly Thr Leu Val Thr Val Ser Ser Gly Gly Gly Gly
            355                 360                 365

Ser Gly Gly Gly Gly Ser Gly Gly Gly Ser Gly Gly Gly Ser
    370                 375                 380

Asp Ile Val Met Thr Gln Thr Pro Leu Ser Leu Pro Val Thr Pro Gly
385                 390                 395                 400

Glu Pro Ala Ser Ile Ser Cys Arg Ser Ser Gln Ser Leu Leu His Ser
                405                 410                 415

Asn Gly Tyr Asn Tyr Leu Asp Trp Tyr Leu Gln Lys Pro Gly Gln Ser
                420                 425                 430

Pro Gln Leu Leu Ile Tyr Leu Gly Ser Asn Arg Ala Ser Gly Val Pro
            435                 440                 445

Asp Arg Phe Ser Gly Ser Gly Ser Gly Thr Asp Phe Thr Leu Lys Ile
    450                 455                 460

Ser Arg Val Glu Ala Glu Asp Val Gly Val Tyr Tyr Cys Met Gln Ala
465                 470                 475                 480

Leu Gln Thr Pro Tyr Thr Phe Gly Cys Gly Thr Lys Leu Glu Ile Lys
                485                 490                 495

Gly Gly Gly Gly Ser Gly Gly Gly Gly Ser Cys Pro Pro Cys Pro Ala
            500                 505                 510

Pro Glu Leu Leu Gly Gly Pro Ser Val Phe Leu Phe Pro Pro Lys Pro
    515                 520                 525

Lys Asp Thr Leu Met Ile Ser Arg Thr Pro Glu Val Thr Cys Val Val
    530                 535                 540

Val Asp Val Ser His Glu Asp Pro Glu Val Lys Phe Asn Trp Tyr Val
545                 550                 555                 560

Asp Gly Val Glu Val His Asn Ala Lys Thr Lys Pro Arg Glu Glu Gln
                565                 570                 575

Tyr Asn Ser Thr Tyr Arg Val Val Ser Val Leu Thr Val Leu His Gln
                580                 585                 590

Asp Trp Leu Asn Gly Lys Glu Tyr Lys Cys Lys Val Ser Asn Lys Ala
    595                 600                 605

Leu Pro Ala Pro Ile Glu Lys Thr Ile Ser Lys Ala Lys Gly Gln Pro
    610                 615                 620

Arg Glu Pro Gln Val Tyr Thr Leu Pro Pro Ser Arg Glu Glu Met Thr
625                 630                 635                 640

Lys Asn Gln Val Ser Leu Thr Cys Leu Val Lys Gly Phe Tyr Pro Ser
                645                 650                 655

Asp Ile Ala Val Glu Trp Glu Ser Asn Gly Gln Pro Glu Asn Asn Tyr
            660                 665                 670

Lys Thr Thr Pro Pro Val Leu Asp Ser Asp Gly Ser Phe Phe Leu Tyr
            675                 680                 685

Ser Lys Leu Thr Val Asp Lys Ser Arg Trp Gln Gln Gly Asn Val Phe
    690                 695                 700
```

Ser Cys Ser Val Leu His Glu Ala Leu His Ser His Tyr Thr Gln Lys
705                 710                 715                 720

Ser Leu Ser Leu Ser Pro Gly Lys
                725

<210> SEQ ID NO 146
<211> LENGTH: 731
<212> TYPE: PRT
<213> ORGANISM: Artificial Sequence
<220> FEATURE:
<223> OTHER INFORMATION: Synthetic Construct

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30

Tyr Met Ser Trp Val Arg Gln Ala Pro Gly Lys Gly Leu Asp Trp Val
        35                  40                  45

Ser Val Ile Ser Glu Ser Gly Gly Ser Thr Asn Tyr Ala Asp Ser Val
    50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
    210                 215                 220

Lys Val Glu Pro Lys Ser Cys Gly Lys Thr Gly Gly Gly Gly Ser Gly
225                 230                 235                 240

Gly Gly Gly Ser Gln Val Gln Leu Gln Gln Ser Gly Pro Gly Leu Val
            245                 250                 255

Lys Pro Ser Glu Thr Leu Ser Leu Thr Cys Thr Val Ser Gly Gly Pro
            260                 265                 270

Ile Thr Ser Ser Gly Asp Tyr Trp Gly Trp Ile Arg Gln Pro Pro Gly
        275                 280                 285

Lys Cys Leu Glu Leu Ile Gly Ser Ile His Asn Ser Gly Ser Thr Tyr
    290                 295                 300

Tyr Asn Pro Ser Leu Lys Gly Arg Val Thr Ile Ser Gly Asp Thr Ser
305                 310                 315                 320

Lys Asn Gln Ile Ser Leu Arg Leu Ser Ser Val Thr Ala Ala Asp Thr
            325                 330                 335

-continued

Ala Val Tyr Tyr Cys Ala Arg Gln Phe Gly Ser Glu Thr Tyr Tyr Asn
            340                 345                 350

Gly Ile Gln Pro Trp Gly Gln Gly Thr Leu Val Thr Val Ser Ser Gly
            355                 360                 365

Gly Gly Gly Ser Gly Gly Gly Gly Ser Gly Gly Gly Gly Ser Gly Gly
            370                 375                 380

Gly Gly Ser Asp Ile Val Met Thr Gln Thr Pro Leu Ser Leu Pro Val
385                 390                 395                 400

Thr Pro Gly Glu Pro Ala Ser Ile Ser Cys Arg Ser Ser Gln Ser Leu
                405                 410                 415

Leu His Ser Arg Gly Tyr Asn Tyr Leu Asp Trp Tyr Leu Gln Lys Pro
            420                 425                 430

Gly Gln Ser Pro Gln Leu Leu Ile Tyr Leu Gly Ser Asn Arg Ala Ser
            435                 440                 445

Gly Val Pro Asp Arg Phe Ser Gly Ser Gly Ser Gly Thr Asp Phe Thr
            450                 455                 460

Leu Lys Ile Ser Arg Val Glu Ala Glu Asp Val Gly Val Tyr Tyr Cys
465                 470                 475                 480

Met Gln Ala Leu Gln Thr Pro Tyr Thr Phe Gly Cys Gly Thr Lys Leu
                485                 490                 495

Glu Ile Lys Gly Gly Gly Gly Ser Gly Gly Gly Gly Ser Cys Pro Pro
            500                 505                 510

Cys Pro Ala Pro Glu Leu Leu Gly Gly Pro Ser Val Phe Leu Phe Pro
            515                 520                 525

Pro Lys Pro Lys Asp Thr Leu Met Ile Ser Arg Thr Pro Glu Val Thr
            530                 535                 540

Cys Val Val Val Asp Val Ser His Glu Asp Pro Glu Val Lys Phe Asn
545                 550                 555                 560

Trp Tyr Val Asp Gly Val Glu Val His Asn Ala Lys Thr Lys Pro Arg
                565                 570                 575

Glu Glu Gln Tyr Asn Ser Thr Tyr Arg Val Val Ser Val Leu Thr Val
            580                 585                 590

Leu His Gln Asp Trp Leu Asn Gly Lys Glu Tyr Lys Cys Lys Val Ser
            595                 600                 605

Asn Lys Ala Leu Pro Ala Pro Ile Glu Lys Thr Ile Ser Lys Ala Lys
            610                 615                 620

Gly Gln Pro Arg Glu Pro Gln Val Tyr Thr Leu Pro Pro Ser Arg Glu
625                 630                 635                 640

Glu Met Thr Lys Asn Gln Val Ser Leu Thr Cys Leu Val Lys Gly Phe
                645                 650                 655

Tyr Pro Ser Asp Ile Ala Val Glu Trp Glu Ser Asn Gly Gln Pro Glu
                660                 665                 670

Asn Asn Tyr Lys Thr Thr Pro Pro Val Leu Asp Ser Asp Gly Ser Phe
            675                 680                 685

Phe Leu Tyr Ser Lys Leu Thr Val Asp Lys Ser Arg Trp Gln Gln Gly
            690                 695                 700

Asn Val Phe Ser Cys Ser Val Leu His Glu Ala Leu His Ser His Tyr
705                 710                 715                 720

Thr Gln Lys Ser Leu Ser Leu Ser Pro Gly Lys
                725                 730

<210> SEQ ID NO 147
<211> LENGTH: 728
<212> TYPE: PRT

-continued

```
<213> ORGANISM: Artificial Sequence
<220> FEATURE:
<223> OTHER INFORMATION: Synthetic Construct

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
                20                  25                  30

Tyr Met Ser Trp Val Arg Gln Ala Pro Gly Lys Gly Leu Asp Trp Val
            35                  40                  45

Ser Val Ile Ser Glu Ser Gly Gly Ser Thr Asn Tyr Ala Asp Ser Val
        50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
            115                 120                 125

Ala Ser Thr Lys Gly Pro Ser Val Phe Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
        210                 215                 220

Lys Val Glu Pro Lys Ser Cys Gly Gly Gly Ser Gly Gly Gly Gly
225                 230                 235                 240

Ser Gln Val Gln Leu Gln Gln Ser Gly Pro Gly Leu Val Lys Pro Ser
                245                 250                 255

Glu Thr Leu Ser Leu Thr Cys Thr Val Ser Gly Gly Pro Ile Thr Ser
                260                 265                 270

Ser Gly Asp Tyr Trp Gly Trp Ile Arg Gln Pro Pro Gly Lys Cys Leu
            275                 280                 285

Glu Leu Ile Gly Ser Ile His Asn Gln Gly Ser Thr Tyr Tyr Asn Pro
        290                 295                 300

Ser Leu Lys Gly Arg Val Thr Ile Ser Gly Asp Thr Ser Lys Asn Gln
305                 310                 315                 320

Ile Ser Leu Arg Leu Ser Ser Val Thr Ala Ala Asp Thr Ala Val Tyr
                325                 330                 335

Tyr Cys Ala Arg Gln Phe Gly Ser Glu Thr Tyr Tyr Pro Gly Ile Asp
            340                 345                 350

Pro Trp Gly Gln Gly Thr Leu Val Thr Val Ser Ser Gly Gly Gly Gly
            355                 360                 365

Ser Gly Gly Gly Gly Ser Gly Gly Gly Gly Ser Gly Gly Gly Gly Ser
        370                 375                 380

Asp Ile Val Met Thr Gln Thr Pro Leu Ser Leu Pro Val Thr Pro Gly
```

-continued

```
385              390              395              400

Glu Pro Ala Ser Ile Ser Cys Arg Ser Ser Gln Ser Leu Leu His Ser
            405              410              415

Asn Gly Tyr Asn Tyr Leu Asp Trp Tyr Leu Gln Lys Pro Gly Gln Ser
            420              425          430

Pro Gln Leu Leu Ile Tyr Leu Gly Ser Asn Arg Ala Ser Gly Val Pro
        435              440              445

Asp Arg Phe Ser Gly Ser Gly Ser Gly Thr Asp Phe Thr Leu Lys Ile
    450              455              460

Ser Arg Val Glu Ala Glu Asp Val Gly Val Tyr Tyr Cys Met Gln Ala
465              470              475              480

Leu Gln Thr Pro Tyr Thr Phe Gly Cys Gly Thr Lys Leu Glu Ile Lys
            485              490              495

Gly Gly Gly Gly Ser Gly Gly Gly Ser Cys Pro Pro Cys Pro Ala
            500              505              510

Pro Glu Leu Leu Gly Gly Pro Ser Val Phe Leu Phe Pro Pro Lys Pro
            515              520              525

Lys Asp Thr Leu Met Ile Ser Arg Thr Pro Glu Val Thr Cys Val Val
    530              535              540

Val Asp Val Ser His Glu Asp Pro Glu Val Lys Phe Asn Trp Tyr Val
545              550              555              560

Asp Gly Val Glu Val His Asn Ala Lys Thr Lys Pro Arg Glu Glu Gln
            565              570              575

Tyr Asn Ser Thr Tyr Arg Val Val Ser Val Leu Thr Val Leu His Gln
            580              585              590

Asp Trp Leu Asn Gly Lys Glu Tyr Lys Cys Lys Val Ser Asn Lys Ala
            595              600              605

Leu Pro Ala Pro Ile Glu Lys Thr Ile Ser Lys Ala Lys Gly Gln Pro
    610              615              620

Arg Glu Pro Gln Val Tyr Thr Leu Pro Pro Ser Arg Glu Glu Met Thr
625              630              635              640

Lys Asn Gln Val Ser Leu Thr Cys Leu Val Lys Gly Phe Tyr Pro Ser
            645              650              655

Asp Ile Ala Val Glu Trp Glu Ser Asn Gly Gln Pro Glu Asn Asn Tyr
            660              665              670

Lys Thr Thr Pro Pro Val Leu Asp Ser Asp Gly Ser Phe Phe Leu Tyr
            675              680              685

Ser Lys Leu Thr Val Asp Lys Ser Arg Trp Gln Gln Gly Asn Val Phe
    690              695              700

Ser Cys Ser Val Leu His Glu Ala Leu His Ser His Tyr Thr Gln Lys
705              710              715              720

Ser Leu Ser Leu Ser Pro Gly Lys
            725
```

```
<210> SEQ ID NO 148
<211> LENGTH: 731
<212> TYPE: PRT
<213> ORGANISM: Artificial Sequence
<220> FEATURE:
<223> OTHER INFORMATION: Synthetic Construct

<400> SEQUENCE: 148

Glu Val Gln Leu Leu Glu Ser Gly Gly Gly Leu Val Gln Pro Gly Gly
1               5              10              15

Ser Leu Arg Leu Ser Cys Thr Ala Ser Gly Phe Thr Phe Ser Asp Asn
```

-continued

```
            20              25              30
Tyr Met Ser Trp Val Arg Gln Ala Pro Gly Lys Gly Leu Asp Trp Val
        35              40              45

Ser Val Ile Ser Glu Ser Gly Gly Ser Thr Asn Tyr Ala Asp Ser Val
    50              55              60

Lys Gly Arg Phe Ser Thr Ser Arg Asp Asn Ser Lys Ser Thr Leu Tyr
65              70              75              80

Leu Asp Met Asn Ser Leu Arg Ala Glu Asp Thr Ala Ile Tyr Tyr Cys
                85              90              95

Ala Lys Gly Arg Phe Ser Thr Leu Ser Ser His Phe Phe Arg Ala Val
            100             105             110

Tyr Gly Met Asp Val Trp Gly Gln Gly Thr Ala Val Thr Val Ser Ser
        115             120             125

Ala Ser Thr Lys Gly Pro Ser Val Phe Pro Leu Ala Pro Ser Ser Lys
    130             135             140

Ser Thr Ser Gly Gly Thr Ala Ala Leu Gly Cys Leu Val Lys Asp Tyr
145             150             155             160

Phe Pro Glu Pro Val Thr Val Ser Trp Asn Ser Gly Ala Leu Thr Ser
            165             170             175

Gly Val His Thr Phe Pro Ala Val Leu Gln Ser Ser Gly Leu Tyr Ser
        180             185             190

Leu Ser Ser Val Val Thr Val Pro Ser Ser Ser Leu Gly Thr Gln Thr
        195             200             205

Tyr Ile Cys Asn Val Asn His Lys Pro Ser Asn Thr Lys Val Asp Lys
    210             215             220

Lys Val Glu Pro Lys Ser Cys Gly Lys Thr Gly Gly Gly Gly Ser Gly
225             230             235             240

Gly Gly Gly Ser Gln Val Gln Leu Gln Gln Ser Gly Pro Gly Leu Val
            245             250             255

Lys Pro Ser Glu Thr Leu Ser Leu Thr Cys Thr Val Ser Gly Gly Pro
            260             265             270

Ile Thr Ser Ser Gly Asp Tyr Trp Gly Trp Ile Arg Gln Pro Pro Gly
        275             280             285

Lys Cys Leu Glu Leu Ile Gly Ser Ile His Asn Ser Gly Ser Thr Tyr
    290             295             300

Tyr Asn Pro Ser Leu Lys Gly Arg Val Thr Ile Ser Gly Asp Thr Ser
305             310             315             320

Lys Asn Gln Ile Ser Leu Arg Leu Ser Ser Val Thr Ala Ala Asp Thr
            325             330             335

Ala Val Tyr Tyr Cys Ala Arg Gln Phe Gly Ser Glu Thr Tyr Tyr Asn
            340             345             350

Gly Ile Gln Pro Trp Gly Gln Gly Thr Leu Val Thr Val Ser Ser Gly
        355             360             365

Gly Gly Gly Ser Gly Gly Gly Gly Ser Gly Gly Gly Ser Gly Gly
    370             375             380

Gly Gly Ser Asp Ile Val Met Thr Gln Thr Pro Leu Ser Leu Pro Val
385             390             395             400

Thr Pro Gly Glu Pro Ala Ser Ile Ser Cys Arg Ser Ser Gln Ser Leu
            405             410             415

Leu His Ser Arg Gly Tyr Asn Tyr Leu Asp Trp Tyr Leu Gln Lys Pro
            420             425             430

Gly Gln Ser Pro Gln Leu Leu Ile Tyr Leu Gly Ser Asn Arg Ala Ser
        435             440             445
```

```
Gly Val Pro Asp Arg Phe Ser Gly Ser Gly Ser Gly Thr Asp Phe Thr
    450                 455             460

Leu Lys Ile Ser Arg Val Glu Ala Glu Asp Val Gly Val Tyr Tyr Cys
465                 470             475             480

Met Gln Ala Leu Gln Thr Pro Tyr Thr Phe Gly Cys Gly Thr Lys Leu
                485             490             495

Glu Ile Lys Gly Gly Gly Gly Ser Gly Gly Gly Gly Ser Cys Pro Pro
            500             505             510

Cys Pro Ala Pro Glu Leu Leu Gly Gly Pro Ser Val Phe Leu Phe Pro
            515             520             525

Pro Lys Pro Lys Asp Thr Leu Tyr Ile Thr Arg Glu Pro Glu Val Thr
    530             535             540

Cys Val Val Val Asp Val Ser His Glu Asp Pro Glu Val Lys Phe Asn
545             550             555             560

Trp Tyr Val Asp Gly Val Glu Val His Asn Ala Lys Thr Lys Pro Arg
            565             570             575

Glu Glu Gln Tyr Asn Ser Thr Tyr Arg Val Val Ser Val Leu Thr Val
            580             585             590

Leu His Gln Asp Trp Leu Asn Gly Lys Glu Tyr Lys Cys Lys Val Ser
    595             600             605

Asn Lys Ala Leu Pro Ala Pro Ile Glu Lys Thr Ile Ser Lys Ala Lys
    610             615             620

Gly Gln Pro Arg Glu Pro Gln Val Tyr Thr Leu Pro Pro Ser Arg Glu
625             630             635             640

Glu Met Thr Lys Asn Gln Val Ser Leu Thr Cys Leu Val Lys Gly Phe
            645             650             655

Tyr Pro Ser Asp Ile Ala Val Glu Trp Glu Ser Asn Gly Gln Pro Glu
            660             665             670

Asn Asn Tyr Lys Thr Thr Pro Pro Val Leu Asp Ser Asp Gly Ser Phe
            675             680             685

Phe Leu Tyr Ser Lys Leu Thr Val Asp Lys Ser Arg Trp Gln Gln Gly
    690             695             700

Asn Val Phe Ser Cys Ser Val Met His Glu Ala Leu His Asn His Tyr
705             710             715             720

Thr Gln Lys Ser Leu Ser Leu Ser Pro Gly Lys
                725             730

<210> SEQ ID NO 149
<211> LENGTH: 718
<212> TYPE: PRT
<213> ORGANISM: Artificial Sequence
<220> FEATURE:
<223> OTHER INFORMATION: Synthetic Construct

<400> SEQUENCE: 149

Glu Val Gln Leu Leu Glu Ser Gly Gly Gly Leu Val Gln Pro Gly Gly
1               5               10              15

Ser Leu Arg Leu Ser Cys Thr Ala Ser Gly Phe Thr Phe Ser Asp Asn
            20              25              30

Tyr Met Ser Trp Val Arg Gln Ala Pro Gly Lys Gly Leu Asp Trp Val
            35              40              45

Ser Val Ile Ser Glu Ser Gly Gly Ser Thr Asn Tyr Ala Asp Ser Val
    50              55              60

Lys Gly Arg Phe Ser Thr Ser Arg Asp Asn Ser Lys Ser Thr Leu Tyr
65              70              75              80
```

Leu Asp Met Asn Ser Leu Arg Ala Glu Asp Thr Ala Ile Tyr Tyr Cys
            85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
            115                 120                 125

Ala Ser Thr Lys Gly Pro Ser Val Phe Pro Leu Ala Pro Ser Ser Lys
            130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
            210                 215                 220

Lys Val Glu Pro Lys Ser Cys Gly Gly Gly Ser Gly Gly Gly Gly
225                 230                 235                 240

Ser Gln Val Gln Leu Val Gln Ser Gly Ala Glu Val Lys Lys Pro Gly
                245                 250                 255

Ala Ser Val Lys Val Ser Cys Lys Ala Ser Gly Asp Thr Ser Thr Ile
            260                 265                 270

His Ser Val His Trp Val Arg Gln Ala Pro Gly Gln Cys Leu Glu Trp
            275                 280                 285

Met Gly Thr Ile Ile Ser Ser Gly Thr Thr Thr Tyr Ala Gln Ser
            290                 295                 300

Phe Gln Asp Arg Val Ser Met Thr Ile Asp Arg Ser Thr Ser Thr Gly
305                 310                 315                 320

Tyr Met Glu Leu Ser Ser Leu Arg Phe Glu Asp Thr Ala Val Tyr Tyr
                325                 330                 335

Cys Thr Thr Asp Gly Thr Ser Trp Gly Gln Gly Thr Leu Val Thr Val
            340                 345                 350

Ser Ser Gly Gly Gly Gly Ser Gly Gly Gly Gly Ser Gly Gly Gly Gly
            355                 360                 365

Ser Gly Gly Gly Gly Ser Asp Ile Gln Leu Thr Gln Ser Pro Ser Ser
            370                 375                 380

Val Ser Ala Ser Val Gly Asp Arg Val Thr Ile Ala Cys Arg Ala Ser
385                 390                 395                 400

Gln Gly Ile Ser Ser Trp Leu Ala Trp Tyr Gln Gln Lys Pro Gly Lys
                405                 410                 415

Ala Pro Lys Leu Leu Ile Tyr His Ala Ser Thr Leu Glu Ser Gly Val
                420                 425                 430

Pro Ser Arg Phe Ser Gly Ser Gly Ser Gly Thr Asp Phe Thr Leu Thr
                435                 440                 445

Ile Ser Ser Leu Gln Pro Glu Asp Phe Ala Thr Tyr Tyr Cys Leu Gln
            450                 455                 460

Ala Phe Ser Leu Pro His Thr Phe Gly Cys Gly Thr Lys Leu Glu Ile
465                 470                 475                 480

Lys Gly Gly Gly Gly Ser Gly Gly Gly Gly Ser Asp Lys Thr His Thr
                485                 490                 495

-continued

```
Cys Pro Pro Cys Pro Ala Pro Glu Leu Leu Gly Gly Pro Ser Val Phe
          500                 505                 510

Leu Phe Pro Pro Lys Pro Lys Asp Thr Leu Met Ile Ser Arg Thr Pro
          515                 520                 525

Glu Val Thr Cys Val Val Val Asp Val Ser His Glu Asp Pro Glu Val
          530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
          565                 570                 575

Leu Thr Val Leu His Gln Asp Trp Leu Asn Gly Lys Glu Tyr Lys Cys
          580                 585                 590

Lys Val Ser Asn Lys Ala Leu Pro Ala Pro Ile Glu Lys Thr Ile Ser
          595                 600                 605

Lys Ala Lys Gly Gln Pro Arg Glu Pro Gln Val Tyr Thr Leu Pro Pro
          610                 615                 620

Ser Arg Glu Glu Met Thr Lys Asn Gln Val Ser Leu Thr Cys Leu Val
625                 630                 635                 640

Lys Gly Phe Tyr Pro Ser Asp Ile Ala Val Glu Trp Glu Ser Asn Gly
          645                 650                 655

Gln Pro Glu Asn Asn Tyr Lys Thr Thr Pro Pro Val Leu Asp Ser Asp
          660                 665                 670

Gly Ser Phe Phe Leu Tyr Ser Lys Leu Thr Val Asp Lys Ser Arg Trp
          675                 680                 685

Gln Gln Gly Asn Val Phe Ser Cys Ser Val Met His Glu Ala Leu His
          690                 695                 700

Asn His Tyr Thr Gln Lys Ser Leu Ser Leu Ser Pro Gly Lys
705                 710                 715

<210> SEQ ID NO 150
<211> LENGTH: 716
<212> TYPE: PRT
<213> ORGANISM: Artificial Sequence
<220> FEATURE:
<223> OTHER INFORMATION: Synthetic Construct

<400> SEQUENCE: 150

Glu Val Gln Leu Leu Glu Ser Gly Gly Gly Leu Val Gln Pro Gly Gly
1                 5                   10                  15

Ser Leu Arg Leu Ser Cys Thr Ala Ser Gly Phe Thr Phe Ser Asp Asn
          20                  25                  30

Tyr Met Ser Trp Val Arg Gln Ala Pro Gly Lys Gly Leu Asp Trp Val
          35                  40                  45

Ser Val Ile Ser Glu Ser Gly Gly Ser Thr Asn Tyr Ala Asp Ser Val
          50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                    85                  90                  95

Ala Lys Gly Arg Phe Ser Thr Leu Ser Ser His Phe Phe Arg Ala Val
          100                 105                 110

Tyr Gly Met Asp Val Trp Gly Gln Gly Thr Ala Val Thr Val Ser Ser
          115                 120                 125

Ala Ser Thr Lys Gly Pro Ser Val Phe Pro Leu Ala Pro Ser Ser Lys
          130                 135                 140
```

-continued

```
Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Gly Lys Thr Gly Gly Gly Gly Ser Gly
225                 230                 235                 240

Gly Gly Gly Ser Gln Val Gln Leu Val Gln Ser Gly Ala Glu Val Lys
                245                 250                 255

Lys Pro Gly Ala Ser Val Lys Val Ser Cys Lys Ala Ser Gly Asp Thr
            260                 265                 270

Ser Thr Ile His Ser Val His Trp Val Arg Gln Ala Pro Gly Gln Cys
        275                 280                 285

Leu Glu Trp Met Gly Thr Ile Ile Ser Ser Gly Thr Thr Thr Thr Tyr
    290                 295                 300

Ala Gln Ser Phe Gln Asp Arg Val Ser Met Thr Ile Asp Arg Ser Thr
305                 310                 315                 320

Ser Thr Gly Tyr Met Glu Leu Ser Ser Leu Arg Phe Glu Asp Thr Ala
                325                 330                 335

Val Tyr Tyr Cys Thr Thr Asp Gly Thr Ser Trp Gly Gln Gly Thr Leu
            340                 345                 350

Val Thr Val Ser Ser Gly Gly Gly Gly Ser Gly Gly Gly Gly Ser Gly
        355                 360                 365

Gly Gly Gly Ser Gly Gly Gly Ser Asp Ile Gln Leu Thr Gln Ser
    370                 375                 380

Pro Ser Ser Val Ser Ala Ser Val Gly Asp Arg Val Thr Ile Ala Cys
385                 390                 395                 400

Arg Ala Ser Gln Gly Ile Ser Ser Trp Leu Ala Trp Tyr Gln Gln Lys
                405                 410                 415

Pro Gly Lys Ala Pro Lys Leu Leu Ile Tyr His Ala Ser Thr Leu Glu
            420                 425                 430

Ser Gly Val Pro Ser Arg Phe Ser Gly Ser Gly Ser Gly Thr Asp Phe
        435                 440                 445

Thr Leu Thr Ile Ser Ser Leu Gln Pro Glu Asp Phe Ala Thr Tyr Tyr
    450                 455                 460

Cys Leu Gln Ala Phe Ser Leu Pro His Thr Phe Gly Cys Gly Thr Lys
465                 470                 475                 480

Leu Glu Ile Lys Gly Gly Gly Gly Ser Gly Gly Gly Gly Ser Cys Pro
                485                 490                 495

Pro Cys Pro Ala Pro Glu Leu Leu Gly Gly Pro Ser Val Phe Leu Phe
            500                 505                 510

Pro Pro Lys Pro Lys Asp Thr Leu Tyr Ile Thr Arg Glu Pro Glu Val
            515                 520                 525

Thr Cys Val Val Val Asp Val Ser His Glu Asp Pro Glu Val Lys Phe
        530                 535                 540

Asn Trp Tyr Val Asp Gly Val Glu Val His Asn Ala Lys Thr Lys Pro
545                 550                 555                 560

Arg Glu Glu Gln Tyr Asn Ser Thr Tyr Arg Val Val Ser Val Leu Thr
```

-continued

```
                565                 570                 575
Val Leu His Gln Asp Trp Leu Asn Gly Lys Glu Tyr Lys Cys Lys Val
            580                 585                 590

Ser Asn Lys Ala Leu Pro Ala Pro Ile Glu Lys Thr Ile Ser Lys Ala
            595                 600                 605

Lys Gly Gln Pro Arg Glu Pro Gln Val Tyr Thr Leu Pro Pro Ser Arg
        610                 615                 620

Glu Glu Met Thr Lys Asn Gln Val Ser Leu Thr Cys Leu Val Lys Gly
625                 630                 635                 640

Phe Tyr Pro Ser Asp Ile Ala Val Glu Trp Glu Ser Asn Gly Gln Pro
                645                 650                 655

Glu Asn Asn Tyr Lys Thr Thr Pro Pro Val Leu Asp Ser Asp Gly Ser
            660                 665                 670

Phe Phe Leu Tyr Ser Lys Leu Thr Val Asp Lys Ser Arg Trp Gln Gln
            675                 680                 685

Gly Asn Val Phe Ser Cys Ser Val Met His Glu Ala Leu His Asn His
        690                 695                 700

Tyr Thr Gln Lys Ser Leu Ser Leu Ser Pro Gly Lys
705                 710                 715
```

```
<210> SEQ ID NO 151
<211> LENGTH: 716
<212> TYPE: PRT
<213> ORGANISM: Artificial Sequence
<220> FEATURE:
<223> OTHER INFORMATION: Synthetic Construct

<400> SEQUENCE: 151
```

```
Glu Val Gln Leu Leu Glu Ser Gly Gly Gly Leu Val Gln Pro Gly Gly
1                 5                 10                  15

Ser Leu Arg Leu Ser Cys Thr Ala Ser Gly Phe Thr Phe Ser Asp Asn
            20                  25                  30

Tyr Met Ser Trp Val Arg Gln Ala Pro Gly Lys Gly Leu Asp Trp Val
            35                  40                  45

Ser Val Ile Ser Glu Ser Gly Gly Ser Thr Asn Tyr Ala Asp Ser Val
        50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
            115                 120                 125

Ala Ser Thr Lys Gly Pro Ser Val Phe Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
```

-continued

```
           210              215              220

Lys Val Glu Pro Lys Ser Cys Gly Lys Thr Gly Gly Gly Ser Gly
225               230              235              240

Gly Gly Gly Ser Gln Val Gln Leu Val Gln Ser Gly Ala Glu Val Lys
              245              250              255

Lys Pro Gly Ala Ser Val Lys Val Ser Cys Lys Ala Ser Gly Asp Thr
              260              265              270

Ser Thr Ile His Ser Val His Trp Val Arg Gln Ala Pro Gly Gln Cys
              275              280              285

Leu Glu Trp Met Gly Thr Ile Ile Ser Ser Gly Thr Thr Thr Thr Tyr
              290              295              300

Ala Gln Ser Phe Gln Asp Arg Val Ser Met Thr Ile Asp Arg Ser Thr
305               310              315              320

Ser Thr Gly Tyr Met Glu Leu Ser Ser Leu Arg Phe Glu Asp Thr Ala
              325              330              335

Val Tyr Tyr Cys Thr Thr Asp Gly Thr Ser Trp Gly Gln Gly Thr Leu
              340              345              350

Val Thr Val Ser Ser Gly Gly Gly Gly Ser Gly Gly Gly Gly Ser Gly
              355              360              365

Gly Gly Gly Ser Gly Gly Gly Gly Ser Asp Ile Gln Leu Thr Gln Ser
              370              375              380

Pro Ser Ser Val Ser Ala Ser Val Gly Asp Arg Val Thr Ile Ala Cys
385               390              395              400

Arg Ala Ser Gln Gly Ile Ser Ser Trp Leu Ala Trp Tyr Gln Gln Lys
              405              410              415

Pro Gly Lys Ala Pro Lys Leu Leu Ile Tyr His Ala Ser Thr Leu Glu
              420              425              430

Ser Gly Val Pro Ser Arg Phe Ser Gly Ser Gly Ser Gly Thr Asp Phe
              435              440              445

Thr Leu Thr Ile Ser Ser Leu Gln Pro Glu Asp Phe Ala Thr Tyr Tyr
              450              455              460

Cys Leu Gln Ala Ser Ser Leu Pro His Thr Phe Gly Cys Gly Thr Lys
465               470              475              480

Leu Glu Ile Lys Gly Gly Gly Gly Ser Gly Gly Gly Gly Ser Cys Pro
              485              490              495

Pro Cys Pro Ala Pro Glu Leu Leu Gly Gly Pro Ser Val Phe Leu Phe
              500              505              510

Pro Pro Lys Pro Lys Asp Thr Leu Tyr Ile Thr Arg Glu Pro Glu Val
              515              520              525

Thr Cys Val Val Val Asp Val Ser His Glu Asp Pro Glu Val Lys Phe
              530              535              540

Asn Trp Tyr Val Asp Gly Val Glu Val His Asn Ala Lys Thr Lys Pro
545               550              555              560

Arg Glu Glu Gln Tyr Asn Ser Thr Tyr Arg Val Val Ser Val Leu Thr
              565              570              575

Val Leu His Gln Asp Trp Leu Asn Gly Lys Glu Tyr Lys Cys Lys Val
              580              585              590

Ser Asn Lys Ala Leu Pro Ala Pro Ile Glu Lys Thr Ile Ser Lys Ala
              595              600              605

Lys Gly Gln Pro Arg Glu Pro Gln Val Tyr Thr Leu Pro Pro Ser Arg
              610              615              620

Glu Glu Met Thr Lys Asn Gln Val Ser Leu Thr Cys Leu Val Lys Gly
625               630              635              640
```

Phe Tyr Pro Ser Asp Ile Ala Val Glu Trp Glu Ser Asn Gly Gln Pro
            645                 650                 655

Glu Asn Asn Tyr Lys Thr Thr Pro Pro Val Leu Asp Ser Asp Gly Ser
            660                 665                 670

Phe Phe Leu Tyr Ser Lys Leu Thr Val Asp Lys Ser Arg Trp Gln Gln
        675                 680                 685

Gly Asn Val Phe Ser Cys Ser Val Met His Glu Ala Leu His Asn His
    690                 695                 700

Tyr Thr Gln Lys Ser Leu Ser Leu Ser Pro Gly Lys
705                 710                 715

<210> SEQ ID NO 152
<211> LENGTH: 721
<212> TYPE: PRT
<213> ORGANISM: Artificial Sequence
<220> FEATURE:
<223> OTHER INFORMATION: Synthetic Construct

<400> SEQUENCE: 152

Glu Val Gln Leu Leu Glu Ser Gly Gly Gly Leu Val Gln Pro Gly Gly
1                   5                   10                  15

Ser Leu Arg Leu Ser Cys Thr Ala Ser Gly Phe Thr Phe Ser Asp Asn
            20                  25                  30

Tyr Met Ser Trp Val Arg Gln Ala Pro Gly Lys Gly Leu Asp Trp Val
        35                  40                  45

Ser Val Ile Ser Glu Ser Gly Gly Ser Thr Asn Tyr Ala Asp Ser Val
    50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Gly Lys Thr Gly Gly Gly Ser Gly
225                 230                 235                 240

Gly Gly Gly Ser Gln Val Gln Leu Val Gln Ser Gly Ala Glu Val Lys
                245                 250                 255

Lys Pro Gly Ala Ser Val Lys Val Ser Cys Lys Ala Ser Gly Asp Thr
            260                 265                 270

Ser Thr Ile His Ser Val His Trp Val Arg Gln Ala Pro Gly Gln Cys
    275                 280                 285

```
Leu Glu Trp Met Gly Thr Ile Ile Ser Ser Gly Thr Thr Thr Thr Tyr
    290                 295                 300

Ala Gln Ser Phe Gln Asp Arg Val Ser Met Thr Ile Asp Arg Ser Thr
305                 310                 315                 320

Ser Thr Gly Tyr Met Glu Leu Ser Ser Leu Arg Phe Glu Asp Thr Ala
                325                 330                 335

Val Tyr Tyr Cys Thr Thr Asp Gly Thr Ser Trp Gly Gln Gly Thr Leu
                340                 345                 350

Val Thr Val Ser Ser Gly Gly Gly Ser Gly Gly Gly Gly Ser Gly
                355                 360                 365

Gly Gly Gly Ser Gly Gly Gly Gly Ser Asp Ile Gln Leu Thr Gln Ser
    370                 375                 380

Pro Ser Ser Val Ser Ala Ser Val Gly Asp Arg Val Thr Ile Ala Cys
385                 390                 395                 400

Arg Ala Ser Gln Gly Ile Ser Ser Trp Leu Ala Trp Tyr Gln Gln Lys
                405                 410                 415

Pro Gly Lys Ala Pro Lys Leu Leu Ile Tyr His Ala Ser Thr Leu Glu
                420                 425                 430

Ser Gly Val Pro Ser Arg Phe Ser Gly Ser Gly Ser Gly Thr Asp Phe
                435                 440                 445

Thr Leu Thr Ile Ser Ser Leu Gln Pro Glu Asp Phe Ala Thr Tyr Tyr
    450                 455                 460

Cys Leu Gln Ala Lys Ser Leu Pro His Thr Phe Gly Cys Gly Thr Lys
465                 470                 475                 480

Leu Glu Ile Lys Gly Gly Gly Gly Ser Gly Gly Gly Ser Asp Lys
                485                 490                 495

Thr His Thr Cys Pro Pro Cys Pro Ala Pro Glu Leu Leu Gly Gly Pro
                500                 505                 510

Ser Val Phe Leu Phe Pro Pro Lys Pro Lys Asp Thr Leu Tyr Ile Thr
                515                 520                 525

Arg Glu Pro Glu Val Thr Cys Val Val Val Asp Val Ser His Glu Asp
    530                 535                 540

Pro Glu Val Lys Phe Asn Trp Tyr Val Asp Gly Val Glu Val His Asn
545                 550                 555                 560

Ala Lys Thr Lys Pro Arg Glu Glu Gln Tyr Asn Ser Thr Tyr Arg Val
                565                 570                 575

Val Ser Val Leu Thr Val Leu His Gln Asp Trp Leu Asn Gly Lys Glu
                580                 585                 590

Tyr Lys Cys Lys Val Ser Asn Lys Ala Leu Pro Ala Pro Ile Glu Lys
                595                 600                 605

Thr Ile Ser Lys Ala Lys Gly Gln Pro Arg Glu Pro Gln Val Tyr Thr
    610                 615                 620

Leu Pro Pro Ser Arg Glu Glu Met Thr Lys Asn Gln Val Ser Leu Thr
625                 630                 635                 640

Cys Leu Val Lys Gly Phe Tyr Pro Ser Asp Ile Ala Val Glu Trp Glu
                645                 650                 655

Ser Asn Gly Gln Pro Glu Asn Asn Tyr Lys Thr Thr Pro Pro Val Leu
                660                 665                 670

Asp Ser Asp Gly Ser Phe Phe Leu Tyr Ser Lys Leu Thr Val Asp Lys
                675                 680                 685

Ser Arg Trp Gln Gln Gly Asn Val Phe Ser Cys Ser Val Met His Glu
    690                 695                 700
```

-continued

```
Ala Leu His Asn His Tyr Thr Gln Lys Ser Leu Ser Leu Ser Pro Gly
705                 710                 715                 720

Lys

<210> SEQ ID NO 153
<211> LENGTH: 17
<212> TYPE: PRT
<213> ORGANISM: Artificial Sequence
<220> FEATURE:
<223> OTHER INFORMATION: Synthetic Construct

<400> SEQUENCE: 153

Glu Pro Lys Ser Asp Lys Thr Gly Gly Gly Gly Ser Gly Gly Gly Gly
1               5                   10                  15

Ser

<210> SEQ ID NO 154
<211> LENGTH: 18
<212> TYPE: PRT
<213> ORGANISM: Artificial Sequence
<220> FEATURE:
<223> OTHER INFORMATION: Synthetic Construct

<400> SEQUENCE: 154

Glu Pro Lys Ser Cys Gly Lys Thr Gly Gly Gly Ser Gly Gly Gly
1               5                   10                  15

Gly Ser

<210> SEQ ID NO 155
<211> LENGTH: 15
<212> TYPE: PRT
<213> ORGANISM: Artificial Sequence
<220> FEATURE:
<223> OTHER INFORMATION: Synthetic Construct

<400> SEQUENCE: 155

Glu Pro Lys Ser Cys Gly Gly Gly Gly Ser Gly Gly Gly Gly Ser
1               5                   10                  15

<210> SEQ ID NO 156
<211> LENGTH: 24
<212> TYPE: PRT
<213> ORGANISM: Artificial Sequence
<220> FEATURE:
<223> OTHER INFORMATION: Synthetic Construct

<400> SEQUENCE: 156

Gly Gly Gly Gly Ser Gly Gly Gly Gly Ser Glu Pro Lys Ser Asp Lys
1               5                   10                  15

Thr His Thr Cys Pro Pro Cys Pro
            20

<210> SEQ ID NO 157
<211> LENGTH: 15
<212> TYPE: PRT
<213> ORGANISM: Artificial Sequence
<220> FEATURE:
<223> OTHER INFORMATION: Synthetic Construct

<400> SEQUENCE: 157

Gly Gly Gly Gly Ser Gly Gly Gly Gly Ser Cys Pro Pro Cys Pro
1               5                   10                  15

<210> SEQ ID NO 158
```

```
<211> LENGTH: 20
<212> TYPE: PRT
<213> ORGANISM: Artificial Sequence
<220> FEATURE:
<223> OTHER INFORMATION: Synthetic Construct

<400> SEQUENCE: 158

Gly Gly Gly Gly Ser Gly Gly Gly Gly Ser Asp Lys Thr His Thr Cys
1               5                   10                  15

Pro Pro Cys Pro
            20

<210> SEQ ID NO 159
<211> LENGTH: 214
<212> TYPE: PRT
<213> ORGANISM: Artificial Sequence
<220> FEATURE:
<223> OTHER INFORMATION: Synthetic Construct

<400> SEQUENCE: 159

Glu Ile Val Met Thr Gln Ser Pro Ser Thr Leu Ser Ala Ser Val Gly
1               5                   10                  15

Asp Arg Val Ala Ile Thr Cys Arg Ala Ser Gln Thr Ile Ser Ser Tyr
            20                  25                  30

Leu Asn Trp Tyr Gln Leu Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 160
<211> LENGTH: 722
<212> TYPE: PRT
<213> ORGANISM: Artificial Sequence
<220> FEATURE:
<223> OTHER INFORMATION: Synthetic Construct

<400> SEQUENCE: 160

Gln Val Gln Leu Gln Gln Ser Gly Pro Gly Leu Val Lys Thr Ser Glu
1               5                   10                  15
```

-continued

```
Thr Leu Ser Leu Thr Cys Thr Val Ser Gly Gly Ser Val Ser Asp Tyr
         20                  25                  30

Tyr Trp Ser Trp Ile Arg Gln Pro Pro Gly Lys Gly Leu Glu Trp Ile
         35                  40                  45

Gly Tyr Ile His Ser Ser Gly Ser Thr Asp Tyr Asn Pro Ser Leu Lys
         50                  55                  60

Ser Arg Leu Thr Ile Ser Gly Asp Ala Ala Lys Lys Gln Phe Ser Leu
65                  70                  75                  80

Lys Leu Ser Ser Val Thr Ala Ala Asp Thr Ala Leu Tyr Tyr Cys Ala
                 85                  90                  95

Arg Ala Gln Gly Gly Ser Arg Arg Thr Leu Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Gly Lys
        210                 215                 220

Thr Gly Gly Gly Gly Ser Gly Gly Gly Gly Ser Glu Val Gln Leu Leu
225                 230                 235                 240

Glu Ser Gly Gly Gly Leu Val Gln Pro Gly Gly Ser Leu Arg Leu Ser
                245                 250                 255

Cys Thr Ala Ser Gly Phe Thr Phe Ser Asp Asn Tyr Met Ser Trp Val
            260                 265                 270

Arg Gln Ala Pro Gly Lys Cys Leu Asp Trp Val Ser Val Ile Ser Glu
            275                 280                 285

Ser Gly Gly Ser Thr Asn Tyr Ala Asp Ser Val Lys Gly Arg Phe Ser
        290                 295                 300

Thr Ser Arg Asp Asn Ser Lys Ser Thr Leu Tyr Leu Asp Met Asn Ser
305                 310                 315                 320

Leu Arg Ala Glu Asp Thr Ala Ile Tyr Tyr Cys Ala Lys Gly Arg Phe
                325                 330                 335

Ser Thr Leu Ser Ser His Phe Phe Arg Ala Val Tyr Gly Met Asp Val
            340                 345                 350

Trp Gly Gln Gly Thr Ala Val Thr Val Ser Ser Gly Gly Gly Gly Ser
            355                 360                 365

Gly Gly Gly Gly Ser Gly Gly Gly Gly Ser Gly Gly Gly Gly Ser Asp
        370                 375                 380

Ile Gln Leu Thr Gln Ser Pro Ser Ser Leu Ser Ala Ser Val Gly Asp
385                 390                 395                 400

Arg Val Thr Ile Thr Cys Arg Ala Ser Gln Gly Ile Ser Ser Tyr Leu
                405                 410                 415

Ala Trp Tyr Gln Gln Lys Pro Gly Lys Ala Pro Lys Leu Leu Ile Tyr
            420                 425                 430

Ala Ala Ser Thr Leu Gln Ser Gly Val Pro Ser Arg Phe Ser Gly Ser
```

```
                435                 440                 445
Gly Ser Gly Thr Asp Phe Thr Leu Thr Ile Ser Ser Leu Gln Pro Glu
    450                 455                 460

Asp Phe Ala Thr Tyr Tyr Cys Gln Gln Leu Ser Ser Tyr Pro Leu Thr
465                 470                 475                 480

Phe Gly Cys Gly Thr Lys Val Glu Ile Lys Gly Gly Gly Gly Ser Gly
                485                 490                 495

Gly Gly Gly Ser Cys Pro Pro Cys Pro Ala Pro Glu Leu Leu Gly Gly
                500                 505                 510

Pro Ser Val Phe Leu Phe Pro Pro Lys Pro Lys Asp Thr Leu Met Ile
                515                 520                 525

Ser Arg Thr Pro Glu Val Thr Cys Val Val Val Asp Val Ser His Glu
    530                 535                 540

Asp Pro Glu Val Lys Phe Asn Trp Tyr Val Asp Gly Val Glu Val His
545                 550                 555                 560

Asn Ala Lys Thr Lys Pro Arg Glu Glu Gln Tyr Asn Ser Thr Tyr Arg
                565                 570                 575

Val Val Ser Val Leu Thr Val Leu His Gln Asp Trp Leu Asn Gly Lys
                580                 585                 590

Glu Tyr Lys Cys Lys Val Ser Asn Lys Ala Leu Pro Ala Pro Ile Glu
                595                 600                 605

Lys Thr Ile Ser Lys Ala Lys Gly Gln Pro Arg Glu Pro Gln Val Tyr
                610                 615                 620

Thr Leu Pro Pro Ser Arg Glu Glu Met Thr Lys Asn Gln Val Ser Leu
625                 630                 635                 640

Thr Cys Leu Val Lys Gly Phe Tyr Pro Ser Asp Ile Ala Val Glu Trp
                645                 650                 655

Glu Ser Asn Gly Gln Pro Glu Asn Asn Tyr Lys Thr Thr Pro Pro Val
                660                 665                 670

Leu Asp Ser Asp Gly Ser Phe Phe Leu Tyr Ser Lys Leu Thr Val Asp
                675                 680                 685

Lys Ser Arg Trp Gln Gln Gly Asn Val Phe Ser Cys Ser Val Leu His
    690                 695                 700

Glu Ala Leu His Ser His Tyr Thr Gln Lys Ser Leu Ser Leu Ser Pro
705                 710                 715                 720

Gly Lys

<210> SEQ ID NO 161
<211> LENGTH: 128
<212> TYPE: PRT
<213> ORGANISM: Artificial Sequence
<220> FEATURE:
<223> OTHER INFORMATION: Synthetic Construct

<400> SEQUENCE: 161

Glu Val Gln Leu Leu Glu Ser Gly Gly Gly Leu Val Gln Pro Gly Gly
1                   5                   10                  15

Ser Leu Arg Leu Ser Cys Thr Ala Ser Gly Phe Thr Phe Ser Asp Asn
                20                  25                  30

Tyr Met Ser Trp Val Arg Gln Ala Pro Gly Lys Cys Leu Asp Trp Val
                35                  40                  45

Ser Val Ile Ser Glu Ser Gly Gly Ser Thr Asn Tyr Ala Asp Ser Val
    50                  55                  60

Lys Gly Arg Phe Ser Thr Ser Arg Asp Asn Ser Lys Ser Thr Leu Tyr
65                  70                  75                  80
```

-continued

Leu Asp Met Asn Ser Leu Arg Ala Glu Asp Thr Ala Ile Tyr Tyr Cys
                85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
        115                 120                 125

<210> SEQ ID NO 162
<211> LENGTH: 128
<212> TYPE: PRT
<213> ORGANISM: Artificial Sequence
<220> FEATURE:
<223> OTHER INFORMATION: Synthetic Construct

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30

His Met Ser Trp Val Arg Gln Ala Pro Gly Lys Cys Leu Asp Trp Val
        35                  40                  45

Ser Gly Ile Ser Glu Ser Gly Gly Ser Thr Asn Tyr Ala Asp Ser Val
    50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Ser Ser Ser His Phe Tyr Arg Ala Val
            100                 105                 110

Tyr Gly Met Asp Val Trp Gly Gln Gly Thr Ala Val Thr Val Ser Ser
        115                 120                 125

<210> SEQ ID NO 163
<211> LENGTH: 128
<212> TYPE: PRT
<213> ORGANISM: Artificial Sequence
<220> FEATURE:
<223> OTHER INFORMATION: Synthetic Construct

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30

His Met Ser Trp Val Arg Gln Ala Pro Gly Lys Cys Leu Asp Trp Val
        35                  40                  45

Ser Gly Ile Ser Glu Ser Gly Gly Ser Thr Asn Tyr Ala Asp Ser Val
    50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Asn Ser Ala His Phe Phe Arg Ala Val
            100                 105                 110

Tyr Gly Met Asp Val Trp Gly Gln Gly Thr Ala Val Thr Val Ser Ser
        115                 120                 125

<210> SEQ ID NO 164
<211> LENGTH: 128
<212> TYPE: PRT
<213> ORGANISM: Artificial Sequence
<220> FEATURE:
<223> OTHER INFORMATION: Synthetic Construct

<400> SEQUENCE: 164

```
Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Tyr
            20                  25                  30

Pro Met Ser Trp Val Arg Gln Ala Pro Gly Lys Cys Leu Asp Trp Val
        35                  40                  45

Ser Gly Ile Ser Glu Ser Gly Gly Ser Thr Asn Tyr Ala Asp Ser Val
    50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Asp Ser Ser His Phe Tyr Arg Ala Val
            100                 105                 110

Tyr Gly Met Asp Val Trp Gly Gln Gly Thr Ala Val Thr Val Ser Ser
        115                 120                 125
```

<210> SEQ ID NO 165
<211> LENGTH: 118
<212> TYPE: PRT
<213> ORGANISM: Artificial Sequence
<220> FEATURE:
<223> OTHER INFORMATION: Synthetic Construct

<400> SEQUENCE: 165

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Trp Met His Trp Val Arg Gln Ala Pro Gly Lys Cys Leu Val Trp Val
        35                  40                  45

Ser Arg Ile Asn Glu Asp Glu Thr Ser Ile Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Ala Glu Asp Thr Ala Val Tyr Tyr Cys
                85                  90                  95

Val Arg Asp Gly Pro Tyr Asp Ser Leu Asp Ile Trp Gly Gln Gly Thr
            100                 105                 110

Met Val Thr Val Ser Ser
        115
```

<210> SEQ ID NO 166
<211> LENGTH: 118
<212> TYPE: PRT
<213> ORGANISM: Artificial Sequence
<220> FEATURE:
<223> OTHER INFORMATION: Synthetic Construct

<400> SEQUENCE: 166

```
Gln Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Ser Phe Ser Ser Tyr
            20                  25                  30

Trp Met His Trp Val Arg Gln Ala Pro Gly Lys Cys Leu Val Trp Val
            35                  40                  45

Ser Arg Ile Asn Glu Asn Glu Gly Ser Ile Ser Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Ala Glu Asp Thr Ala Val Tyr Tyr Cys
                85                  90                  95

Val Arg Asp Gly Pro Tyr Asp Ala Leu Asp Ile Trp Gly Gln Gly Thr
            100                 105                 110

Met Val Thr Val Ser Ser
        115

<210> SEQ ID NO 167
<211> LENGTH: 118
<212> TYPE: PRT
<213> ORGANISM: Artificial Sequence
<220> FEATURE:
<223> OTHER INFORMATION: Synthetic Construct

<400> SEQUENCE: 167

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Trp Met His Trp Val Arg Gln Ala Pro Gly Lys Cys Leu Val Trp Val
            35                  40                  45

Ser Arg Ile Asn Glu Asp Glu Arg Ser Ile Ser Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Ala Glu Asp Thr Ala Val Tyr Tyr Cys
                85                  90                  95

Val Arg Asp Gly Pro Tyr Asp Ala Leu Asp Ile Trp Gly Gln Gly Thr
            100                 105                 110

Met Val Thr Val Ser Ser
        115

<210> SEQ ID NO 168
<211> LENGTH: 118
<212> TYPE: PRT
<213> ORGANISM: Artificial Sequence
<220> FEATURE:
<223> OTHER INFORMATION: Synthetic Construct

<400> SEQUENCE: 168

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Trp Met His Trp Val Arg Gln Ala Pro Gly Lys Cys Leu Val Trp Val
            35                  40                  45

Ser Arg Ile Asn Glu Asp Glu Arg Ser Ile Ser Tyr Ala Asp Ser Val
        50                  55                  60

Lys Gly Arg Phe Thr Ile Ser Arg Asp Asn Ala Lys Asn Thr Leu Tyr
```

-continued

```
65                  70                  75                  80

Leu Gln Met Asn Gly Leu Arg Ala Glu Asp Thr Ala Val Tyr Tyr Cys
                85                  90                  95

Val Arg Asp Gly Pro Tyr Asp Thr Leu Asp Ile Trp Gly Gln Gly Thr
                100                 105                 110

Met Val Thr Val Ser Ser
                115

<210> SEQ ID NO 169
<211> LENGTH: 118
<212> TYPE: PRT
<213> ORGANISM: Artificial Sequence
<220> FEATURE:
<223> OTHER INFORMATION: Synthetic Construct

<400> SEQUENCE: 169

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
                20                  25                  30

Trp Met His Trp Val Arg Gln Ala Pro Gly Lys Cys Leu Val Trp Val
            35                  40                  45

Ser Arg Ile Asn Glu Asn Glu Gly Ser Ile Ser Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Ala Glu Asp Thr Ala Val Tyr Tyr Cys
                85                  90                  95

Val Arg Asp Gly Pro Tyr Asp Thr Leu Asp Ile Trp Gly Gln Gly Thr
                100                 105                 110

Met Val Thr Val Ser Ser
                115

<210> SEQ ID NO 170
<211> LENGTH: 118
<212> TYPE: PRT
<213> ORGANISM: Artificial Sequence
<220> FEATURE:
<223> OTHER INFORMATION: Synthetic Construct

<400> SEQUENCE: 170

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
                20                  25                  30

Trp Met His Trp Val Arg Gln Ala Pro Gly Lys Cys Leu Val Trp Val
            35                  40                  45

Ser Arg Ile Asn Glu Asp Glu Arg Ser Ile Ser Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Ala Glu Asp Thr Ala Val Tyr Tyr Cys
                85                  90                  95

Val Arg Asp Gly Pro Tyr Asp Ser Leu Asp Ile Trp Gly Gln Gly Thr
                100                 105                 110

Met Val Thr Val Ser Ser
                115
```

```
<210> SEQ ID NO 171
<211> LENGTH: 118
<212> TYPE: PRT
<213> ORGANISM: Artificial Sequence
<220> FEATURE:
<223> OTHER INFORMATION: Synthetic Construct

<400> SEQUENCE: 171

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Trp Met His Trp Val Arg Gln Ala Pro Gly Lys Cys Leu Val Trp Val
        35                  40                  45

Ser Arg Ile Asn Glu Asn Glu Gly Ser Ile Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Ala Glu Asp Thr Ala Val Tyr Tyr Cys
                85                  90                  95

Val Arg Asp Gly Pro Tyr Asp Ser Leu Asp Ile Trp Gly Gln Gly Thr
            100                 105                 110

Met Val Thr Val Ser Ser
        115

<210> SEQ ID NO 172
<211> LENGTH: 118
<212> TYPE: PRT
<213> ORGANISM: Artificial Sequence
<220> FEATURE:
<223> OTHER INFORMATION: Synthetic Construct

<400> SEQUENCE: 172

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Arg Ser Tyr
            20                  25                  30

Trp Met His Trp Val Arg Gln Ala Pro Gly Lys Cys Leu Val Trp Val
        35                  40                  45

Ser Arg Ile Asn Glu Asp Glu Thr Ser Ile Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Ala Glu Asp Thr Ala Val Tyr Tyr Cys
                85                  90                  95

Ala Arg Asp Gly Pro Tyr Asp Ser Phe Asp Ile Trp Gly Gln Gly Thr
            100                 105                 110

Met Val Thr Val Ser Ser
        115

<210> SEQ ID NO 173
<211> LENGTH: 123
<212> TYPE: PRT
<213> ORGANISM: Artificial Sequence
<220> FEATURE:
<223> OTHER INFORMATION: Synthetic Construct

<400> SEQUENCE: 173

Gln Val Gln Leu Gln Gln Ser Gly Pro Gly Leu Val Lys Pro Ser Glu
```

-continued

```
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Cys Leu Glu
        35                  40                  45

Leu Ile Gly Ser Ile His Asn Gln Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Thr Gly Ile Asp Pro
            100                 105                 110

Trp Gly Gln Gly Thr Leu Val Thr Val Ser Ser
        115                 120
```

<210> SEQ ID NO 174
<211> LENGTH: 123
<212> TYPE: PRT
<213> ORGANISM: Artificial Sequence
<220> FEATURE:
<223> OTHER INFORMATION: Synthetic Construct

<400> SEQUENCE: 174

```
Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Cys Leu Glu
        35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Asn Gly Ile Gln Pro
            100                 105                 110

Trp Gly Gln Gly Thr Leu Val Thr Val Ser Ser
        115                 120
```

<210> SEQ ID NO 175
<211> LENGTH: 123
<212> TYPE: PRT
<213> ORGANISM: Artificial Sequence
<220> FEATURE:
<223> OTHER INFORMATION: Synthetic Construct

<400> SEQUENCE: 175

```
Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
            20                  25                  30

Gly Asp Tyr Trp Gly Trp Ile Arg Gln Pro Pro Gly Lys Cys Leu Glu
        35                  40                  45

Leu Ile Gly Ser Ile His Asn Gln Gly Ser Thr Tyr Tyr Asn Pro Ser
    50                  55                  60
```

-continued

```
Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Pro Gly Ile Asp Pro
            100                 105                 110

Trp Gly Gln Gly Thr Leu Val Thr Val Ser Ser
        115                 120

<210> SEQ ID NO 176
<211> LENGTH: 123
<212> TYPE: PRT
<213> ORGANISM: Artificial Sequence
<220> FEATURE:
<223> OTHER INFORMATION: Synthetic Construct

<400> SEQUENCE: 176

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Pro Ile Thr Ser Ser
                20                  25                  30

Gly Asp Tyr Trp Gly Trp Ile Arg Gln Pro Pro Gly Lys Cys Leu Glu
            35                  40                  45

Leu Ile Gly Ser Ile His Asn Ser Gly Ser Thr Tyr Tyr Asn Pro Ser
    50                  55                  60

Leu Lys Gly Arg Val Thr Ile Ser Gly Asp Thr Ser Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Gln Phe Gly Ser Glu Thr Tyr Tyr Asn Gly Ile Asp Pro
            100                 105                 110

Trp Gly Gln Gly Thr Leu Val Thr Val Ser Ser
        115                 120

<210> SEQ ID NO 177
<211> LENGTH: 119
<212> TYPE: PRT
<213> ORGANISM: Artificial Sequence
<220> FEATURE:
<223> OTHER INFORMATION: Synthetic Construct

<400> SEQUENCE: 177

Gln Val Gln Leu Gln Gln Ser Gly Pro Gly Leu Val Lys Thr Ser Glu
1               5                   10                  15

Thr Leu Ser Leu Thr Cys Thr Val Ser Gly Gly Ser Val Ser Asp Tyr
                20                  25                  30

Tyr Trp Ser Trp Ile Arg Gln Pro Pro Gly Lys Cys Leu Glu Trp Ile
            35                  40                  45

Gly Tyr Ile His Ser Ser Gly Ser Thr Asp Tyr Asn Pro Ser Leu Lys
    50                  55                  60

Ser Arg Leu Thr Ile Ser Gly Asp Ala Ala Lys Lys Gln Phe Ser Leu
65                  70                  75                  80

Asn Leu Ser Ser Val Thr Ala Ala Asp Thr Ala Leu Tyr Tyr Cys Ala
                85                  90                  95

Arg Ala Gln Gly Gly Ser Arg Arg Thr Leu Asp Tyr Trp Gly Gln Gly
            100                 105                 110

Thr Leu Val Thr Val Ser Ser
        115
```

```
<210> SEQ ID NO 178
<211> LENGTH: 119
<212> TYPE: PRT
<213> ORGANISM: Artificial Sequence
<220> FEATURE:
<223> OTHER INFORMATION: Synthetic Construct

<400> SEQUENCE: 178

Gln Val Gln Leu Gln Gln Ser Gly Pro Gly Leu Val Lys Thr Ser Glu
1               5                   10                  15

Thr Leu Ser Leu Thr Cys Thr Val Ser Gly Gly Ser Val Ser Asp Tyr
            20                  25                  30

Tyr Trp Ser Trp Ile Arg Gln Pro Pro Gly Lys Cys Leu Glu Trp Ile
        35                  40                  45

Gly Tyr Ile His Ser Ser Gly Ser Thr Asp Tyr Asn Pro Ser Leu Lys
    50                  55                  60

Ser Arg Leu Thr Ile Ser Gly Asp Ala Ala Lys Lys Gln Phe Ser Leu
65                  70                  75                  80

Lys Leu Ser Ser Val Thr Ala Ala Asp Thr Ala Leu Tyr Tyr Cys Ala
                85                  90                  95

Arg Ala Gln Gly Gly Ser Arg Arg Thr Leu Asp Tyr Trp Gly Gln Gly
            100                 105                 110

Thr Leu Val Thr Val Ser Ser
        115

<210> SEQ ID NO 179
<211> LENGTH: 113
<212> TYPE: PRT
<213> ORGANISM: Artificial Sequence
<220> FEATURE:
<223> OTHER INFORMATION: Synthetic Construct

<400> SEQUENCE: 179

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Ser Thr Ile His
            20                  25                  30

Ser Val His Trp Val Arg Gln Ala Pro Gly Gln Cys Leu Glu Trp Met
        35                  40                  45

Gly Thr Ile Ile Ser Ser Gly Thr Thr Thr Tyr Ala Gln Ser Phe
    50                  55                  60

Gln Asp Arg Val Ser Met Thr Ile Asp Arg Ser Thr Ser Thr Gly Tyr
65                  70                  75                  80

Met Glu Leu Ser Ser Leu Arg Phe Glu Asp Thr Ala Val Tyr Tyr Cys
                85                  90                  95

Thr Thr Asp Gly Asp Ser Trp Gly Gln Gly Thr Leu Val Thr Val Ser
            100                 105                 110

Ser

<210> SEQ ID NO 180
<211> LENGTH: 113
<212> TYPE: PRT
<213> ORGANISM: Artificial Sequence
<220> FEATURE:
<223> OTHER INFORMATION: Synthetic Construct

<400> SEQUENCE: 180

Gln Val Gln Leu Val Gln Ser Gly Ala Glu Val Lys Lys Pro Gly Ala
```

-continued

```
1               5               10              15

Ser Val Lys Val Ser Cys Lys Ala Ser Gly Asp Thr Ser Thr Ile His
            20              25              30

Ser Val His Trp Val Arg Gln Ala Pro Gly Gln Cys Leu Glu Trp Met
        35              40              45

Gly Thr Ile Ile Ser Ser Gly Thr Thr Thr Thr Tyr Ala Gln Ser Phe
    50              55              60

Gln Asp Arg Val Ser Met Thr Ile Asp Arg Ser Thr Ser Thr Gly Tyr
65              70              75              80

Met Glu Leu Ser Ser Leu Arg Phe Glu Asp Thr Ala Val Tyr Tyr Cys
            85              90              95

Thr Thr Asp Gly Thr Ser Trp Gly Gln Gly Thr Leu Val Thr Val Ser
            100             105             110

Ser
```

```
<210> SEQ ID NO 181
<211> LENGTH: 123
<212> TYPE: PRT
<213> ORGANISM: Artificial Sequence
<220> FEATURE:
<223> OTHER INFORMATION: Synthetic Construct

<400> SEQUENCE: 181
```

```
Gln Val Gln Leu Gln Glu Ser Gly Pro Gly Leu Val Lys Ser Ser Glu
1               5               10              15

Thr Leu Ser Leu Thr Cys Thr Val Ser Gly Asp Ser Ile Ser Ser Asp
            20              25              30

Ser Tyr Trp Gly Trp Ile Arg Gln Pro Pro Gly Lys Cys Leu Glu Trp
        35              40              45

Leu Ala Thr Ile Tyr Tyr Asp Gly Thr Thr Phe Tyr Asn Pro Ser Leu
    50              55              60

Arg Ser Arg Leu Ile Ile Ser Gly Asp Ala Ser Lys Lys Gln Phe Ser
65              70              75              80

Leu Arg Leu Ser Ser Val Thr Ala Ala Asp Thr Ala Ile Tyr Tyr Cys
            85              90              95

Ala Arg His Glu Ser Gly Gln Gln Leu Val Asn Asn Trp Phe Asp Pro
            100             105             110

Trp Gly Gln Gly Thr Val Val Thr Val Ser Ser
        115             120
```

```
<210> SEQ ID NO 182
<211> LENGTH: 107
<212> TYPE: PRT
<213> ORGANISM: Artificial Sequence
<220> FEATURE:
<223> OTHER INFORMATION: Synthetic Construct

<400> SEQUENCE: 182
```

```
Asp Ile Gln Leu Thr Gln Ser Pro Ser Ser Leu Ser Ala Ser Val Gly
1               5               10              15

Asp Arg Val Thr Ile Thr Cys Arg Ala Ser Gln Gly Ile Ser Ser Tyr
            20              25              30

Leu Ala Trp Tyr Gln Gln Lys Pro Gly Lys Ala Pro Lys Leu Leu Ile
        35              40              45

Tyr Ala Ala Ser Thr Leu Gln Ser Gly Val Pro Ser Arg Phe Ser Gly
    50              55              60

Ser Gly Ser Gly Thr Asp Phe Thr Leu Thr Ile Ser Ser Leu Gln Pro
```

```
65                  70                  75                  80

Glu Asp Phe Ala Thr Tyr Tyr Cys Gln Gln Leu Ser Ser Tyr Pro Leu
                    85                  90                  95

Thr Phe Gly Cys Gly Thr Lys Val Glu Ile Lys
            100                 105
```

<210> SEQ ID NO 183
<211> LENGTH: 107
<212> TYPE: PRT
<213> ORGANISM: Artificial Sequence
<220> FEATURE:
<223> OTHER INFORMATION: Synthetic Construct

<400> SEQUENCE: 183

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Ser Ser Tyr Pro Leu
                    85                  90                  95

Ser Phe Gly Cys Gly Thr Lys Val Glu Ile Lys
            100                 105
```

<210> SEQ ID NO 184
<211> LENGTH: 107
<212> TYPE: PRT
<213> ORGANISM: Artificial Sequence
<220> FEATURE:
<223> OTHER INFORMATION: Synthetic Construct

<400> SEQUENCE: 184

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln His Lys Pro Gly Gln Ala Pro Arg Leu Leu Ile
            35                  40                  45

Tyr Asp Ala Ser Ser Arg Ala Thr Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Leu
                    85                  90                  95

Thr Phe Gly Cys Gly Thr Lys Leu Glu Ile Lys
            100                 105
```

<210> SEQ ID NO 185
<211> LENGTH: 107
<212> TYPE: PRT
<213> ORGANISM: Artificial Sequence
<220> FEATURE:
<223> OTHER INFORMATION: Synthetic Construct

<400> SEQUENCE: 185

-continued

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Gly Val Arg Asn Asn
            20                  25                  30

Leu Ala Trp Tyr Gln His Lys Pro Gly Gln Ala Pro Arg Leu Leu Ile
        35                  40                  45

Tyr His Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Leu Gln Pro Ile
                85                  90                  95

Thr Phe Gly Cys Gly Thr Lys Leu Glu Ile Lys
            100                 105
```

<210> SEQ ID NO 186
<211> LENGTH: 107
<212> TYPE: PRT
<213> ORGANISM: Artificial Sequence
<220> FEATURE:
<223> OTHER INFORMATION: Synthetic Construct

<400> SEQUENCE: 186

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asn Val Lys Asn Asn
            20                  25                  30

Leu Ala Trp Tyr Gln His Lys Pro Gly Gln Ala Pro Arg Leu Leu Ile
        35                  40                  45

Tyr His Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Asn Glu Pro Ile
                85                  90                  95

Thr Phe Gly Cys Gly Thr Lys Leu Glu Ile Lys
            100                 105
```

<210> SEQ ID NO 187
<211> LENGTH: 112
<212> TYPE: PRT
<213> ORGANISM: Artificial Sequence
<220> FEATURE:
<223> OTHER INFORMATION: Synthetic Construct

<400> SEQUENCE: 187

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
```

-continued

```
                    85                  90                  95

Leu Gln Thr Pro Tyr Thr Phe Gly Cys Gly Thr Lys Leu Glu Ile Lys
            100                 105                 110

<210> SEQ ID NO 188
<211> LENGTH: 112
<212> TYPE: PRT
<213> ORGANISM: Artificial Sequence
<220> FEATURE:
<223> OTHER INFORMATION: Synthetic Construct

<400> SEQUENCE: 188

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Arg Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Cys Gly Thr Lys Leu Glu Ile Lys
            100                 105                 110

<210> SEQ ID NO 189
<211> LENGTH: 107
<212> TYPE: PRT
<213> ORGANISM: Artificial Sequence
<220> FEATURE:
<223> OTHER INFORMATION: Synthetic Construct

<400> SEQUENCE: 189

Glu Ile Val Met Thr Gln Ser Pro Ser Thr Leu Ser Ala Ser Val Gly
1               5                   10                  15

Asp Arg Val Ala Ile Thr Cys Arg Ala Ser Gln Thr Ile Ser Ser Tyr
            20                  25                  30

Leu Asn Trp Tyr Gln Leu Lys Pro Gly Lys Ala Pro Lys Leu Leu Ile
        35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Cys Gly Thr Lys Val Asp Ile Lys
            100                 105

<210> SEQ ID NO 190
<211> LENGTH: 107
<212> TYPE: PRT
<213> ORGANISM: Artificial Sequence
<220> FEATURE:
<223> OTHER INFORMATION: Synthetic Construct

<400> SEQUENCE: 190

Asp Ile Gln Leu Thr Gln Ser Pro Ser Ser Val Ser Ala Ser Val Gly
1               5                   10                  15
```

```
Asp Arg Val Thr Ile Ala Cys Arg Ala Ser Gln Gly Ile Ser Ser Trp
        20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Asn Ser Leu Pro His
                85                  90                  95

Thr Phe Gly Cys Gly Thr Lys Leu Glu Ile Lys
            100                 105

<210> SEQ ID NO 191
<211> LENGTH: 107
<212> TYPE: PRT
<213> ORGANISM: Artificial Sequence
<220> FEATURE:
<223> OTHER INFORMATION: Synthetic Construct

<400> SEQUENCE: 191

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
        20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Phe Ser Leu Pro His
                85                  90                  95

Thr Phe Gly Cys Gly Thr Lys Leu Glu Ile Lys
            100                 105

<210> SEQ ID NO 192
<211> LENGTH: 107
<212> TYPE: PRT
<213> ORGANISM: Artificial Sequence
<220> FEATURE:
<223> OTHER INFORMATION: Synthetic Construct

<400> SEQUENCE: 192

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
        20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Ser Ser Leu Pro His
                85                  90                  95

Thr Phe Gly Cys Gly Thr Lys Leu Glu Ile Lys
```

-continued

```
            100             105
```

```
<210> SEQ ID NO 193
<211> LENGTH: 107
<212> TYPE: PRT
<213> ORGANISM: Artificial Sequence
<220> FEATURE:
<223> OTHER INFORMATION: Synthetic Construct

<400> SEQUENCE: 193

Asp Ile Gln Leu Thr Gln Ser Pro Ser Ser Val Ser Ala Ser Val Gly
1               5                   10                  15

Asp Arg Val Thr Ile Ala Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr His Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Lys Ser Leu Pro His
                85                  90                  95

Thr Phe Gly Cys Gly Thr Lys Leu Glu Ile Lys
            100             105

<210> SEQ ID NO 194
<211> LENGTH: 107
<212> TYPE: PRT
<213> ORGANISM: Artificial Sequence
<220> FEATURE:
<223> OTHER INFORMATION: Synthetic Construct

<400> SEQUENCE: 194

Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Arg Leu Glu Pro
65                  70                  75                  80

Glu Asp Phe Ala Val Tyr Tyr Cys Gln Gln Ser Gly Asp Ser Leu Val
                85                  90                  95

Thr Phe Gly Cys Gly Thr Arg Leu Glu Ile Lys
            100             105

<210> SEQ ID NO 195
<211> LENGTH: 487
<212> TYPE: PRT
<213> ORGANISM: Artificial Sequence
<220> FEATURE:
<223> OTHER INFORMATION: Synthetic Construct

<400> SEQUENCE: 195

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30
```

```
Tyr Met Ser Trp Val Arg Gln Ala Pro Gly Lys Gly Leu Asp Trp Val
    35              40              45

Ser Val Ile Ser Glu Ser Gly Gly Ser Thr Asn Tyr Ala Asp Ser Val
    50              55              60

Lys Gly Arg Phe Ser Thr Ser Arg Asp Asn Ser Lys Ser Thr Leu Tyr
65              70              75              80

Leu Asp Met Asn Ser Leu Arg Ala Glu Asp Thr Ala Ile Tyr Tyr Cys
            85              90              95

Ala Lys Gly Arg Phe Ser Thr Leu Ser Ser His Phe Phe Arg Ala Val
            100             105             110

Tyr Gly Met Asp Val Trp Gly Gln Gly Thr Ala Val Thr Val Ser Ser
    115             120             125

Ala Ser Thr Lys Gly Pro Ser Val Phe Pro Leu Ala Pro Ser Ser Lys
    130             135             140

Ser Thr Ser Gly Gly Thr Ala Ala Leu Gly Cys Leu Val Lys Asp Tyr
145             150             155             160

Phe Pro Glu Pro Val Thr Val Ser Trp Asn Ser Gly Ala Leu Thr Ser
            165             170             175

Gly Val His Thr Phe Pro Ala Val Leu Gln Ser Ser Gly Leu Tyr Ser
            180             185             190

Leu Ser Ser Val Val Thr Val Pro Ser Ser Ser Leu Gly Thr Gln Thr
            195             200             205

Tyr Ile Cys Asn Val Asn His Lys Pro Ser Asn Thr Lys Val Asp Lys
    210             215             220

Lys Val Glu Pro Lys Ser Cys Gly Gly Gly Ser Gly Gly Gly Gly
225             230             235             240

Ser Gln Val Gln Leu Gln Gln Ser Gly Pro Gly Leu Val Lys Thr Ser
            245             250             255

Glu Thr Leu Ser Leu Thr Cys Thr Val Ser Gly Gly Ser Val Ser Asp
            260             265             270

Tyr Tyr Trp Ser Trp Ile Arg Gln Pro Pro Gly Lys Cys Leu Glu Trp
    275             280             285

Ile Gly Tyr Ile His Ser Ser Gly Ser Thr Asp Tyr Asn Pro Ser Leu
    290             295             300

Lys Ser Arg Leu Thr Ile Ser Gly Asp Ala Ala Lys Lys Gln Phe Ser
305             310             315             320

Leu Asn Leu Ser Ser Val Thr Ala Ala Asp Thr Ala Leu Tyr Tyr Cys
            325             330             335

Ala Arg Ala Gln Gly Gly Ser Arg Arg Thr Leu Asp Tyr Trp Gly Gln
            340             345             350

Gly Thr Leu Val Thr Val Ser Ser Gly Gly Gly Ser Gly Gly Gly
            355             360             365

Gly Ser Gly Gly Gly Gly Ser Gly Gly Gly Ser Glu Ile Val Met
    370             375             380

Thr Gln Ser Pro Ser Thr Leu Ser Ala Ser Val Gly Asp Arg Val Ala
385             390             395             400

Ile Thr Cys Arg Ala Ser Gln Thr Ile Ser Ser Tyr Leu Asn Trp Tyr
            405             410             415

Gln Leu Lys Pro Gly Lys Ala Pro Lys Leu Leu Ile Tyr Ala Ala Ser
            420             425             430

Ser Leu Gln Ser Gly Val Pro Ser Arg Phe Ser Gly Ser Gly Ser Gly
            435             440             445
```

-continued

```
Thr Asp Phe Thr Leu Thr Ile Ser Ser Leu Gln Pro Glu Asp Phe Ala
    450             455             460

Thr Tyr Tyr Cys Gln Gln Ser Tyr Ser Thr Pro Tyr Thr Phe Gly Cys
465             470             475             480

Gly Thr Lys Val Asp Ile Lys
            485

<210> SEQ ID NO 196
<211> LENGTH: 487
<212> TYPE: PRT
<213> ORGANISM: Artificial Sequence
<220> FEATURE:
<223> OTHER INFORMATION: Synthetic Construct

<400> SEQUENCE: 196

Glu Val Gln Leu Leu Glu Ser Gly Gly Gly Leu Val Gln Pro Gly Gly
1               5               10              15

Ser Leu Arg Leu Ser Cys Thr Ala Ser Gly Phe Thr Phe Ser Asp Asn
            20              25              30

Tyr Met Ser Trp Val Arg Gln Ala Pro Gly Lys Gly Leu Asp Trp Val
        35              40              45

Ser Val Ile Ser Glu Ser Gly Gly Ser Thr Asn Tyr Ala Asp Ser Val
    50              55              60

Lys Gly Arg Phe Ser Thr Ser Arg Asp Asn Ser Lys Ser Thr Leu Tyr
65              70              75              80

Leu Asp Met Asn Ser Leu Arg Ala Glu Asp Thr Ala Ile Tyr Tyr Cys
            85              90              95

Ala Lys Gly Arg Phe Ser Thr Leu Ser Ser His Phe Phe Arg Ala Val
            100             105             110

Tyr Gly Met Asp Val Trp Gly Gln Gly Thr Ala Val Thr Val Ser Ser
        115             120             125

Ala Ser Thr Lys Gly Pro Ser Val Phe Pro Leu Ala Pro Ser Ser Lys
    130             135             140

Ser Thr Ser Gly Gly Thr Ala Ala Leu Gly Cys Leu Val Lys Asp Tyr
145             150             155             160

Phe Pro Glu Pro Val Thr Val Ser Trp Asn Ser Gly Ala Leu Thr Ser
            165             170             175

Gly Val His Thr Phe Pro Ala Val Leu Gln Ser Ser Gly Leu Tyr Ser
        180             185             190

Leu Ser Ser Val Val Thr Val Pro Ser Ser Ser Leu Gly Thr Gln Thr
        195             200             205

Tyr Ile Cys Asn Val Asn His Lys Pro Ser Asn Thr Lys Val Asp Lys
    210             215             220

Lys Val Glu Pro Lys Ser Cys Gly Gly Gly Ser Gly Gly Gly Gly
225             230             235             240

Ser Gln Val Gln Leu Gln Gln Ser Gly Pro Gly Leu Val Lys Thr Ser
            245             250             255

Glu Thr Leu Ser Leu Thr Cys Thr Val Ser Gly Gly Ser Val Ser Asp
            260             265             270

Tyr Tyr Trp Ser Trp Ile Arg Gln Pro Pro Gly Lys Cys Leu Glu Trp
        275             280             285

Ile Gly Tyr Ile His Ser Ser Gly Ser Thr Asp Tyr Asn Pro Ser Leu
    290             295             300

Lys Ser Arg Leu Thr Ile Ser Gly Asp Ala Ala Lys Lys Gln Phe Ser
305             310             315             320
```

-continued

```
Leu Lys Leu Ser Ser Val Thr Ala Ala Asp Thr Ala Leu Tyr Tyr Cys
            325                 330                 335

Ala Arg Ala Gln Gly Gly Ser Arg Arg Thr Leu Asp Tyr Trp Gly Gln
            340                 345                 350

Gly Thr Leu Val Thr Val Ser Ser Gly Gly Gly Gly Ser Gly Gly Gly
            355                 360                 365

Gly Ser Gly Gly Gly Gly Ser Gly Gly Gly Gly Ser Glu Ile Val Met
    370                 375                 380

Thr Gln Ser Pro Ser Thr Leu Ser Ala Ser Val Gly Asp Arg Val Ala
385                 390                 395                 400

Ile Thr Cys Arg Ala Ser Gln Thr Ile Ser Ser Tyr Leu Asn Trp Tyr
            405                 410                 415

Gln Leu Lys Pro Gly Lys Ala Pro Lys Leu Leu Ile Tyr Ala Ala Ser
            420                 425                 430

Ser Leu Gln Ser Gly Val Pro Ser Arg Phe Ser Gly Ser Gly Ser Gly
            435                 440                 445

Thr Asp Phe Thr Leu Thr Ile Ser Ser Leu Gln Pro Glu Asp Phe Ala
    450                 455                 460

Thr Tyr Tyr Cys Gln Gln Ser Tyr Ser Thr Pro Tyr Thr Phe Gly Cys
465                 470                 475                 480

Gly Thr Lys Val Asp Ile Lys
            485
```

```
<210> SEQ ID NO 197
<211> LENGTH: 490
<212> TYPE: PRT
<213> ORGANISM: Artificial Sequence
<220> FEATURE:
<223> OTHER INFORMATION: Synthetic Construct

<400> SEQUENCE: 197
```

```
Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30

Tyr Met Ser Trp Val Arg Gln Ala Pro Gly Lys Gly Leu Asp Trp Val
            35                  40                  45

Ser Val Ile Ser Glu Ser Gly Gly Ser Thr Asn Tyr Ala Asp Ser Val
    50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
            85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
            115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
            165                 170                 175

Gly Val His Thr Phe Pro Ala Val Leu Gln Ser Ser Gly Leu Tyr Ser
            180                 185                 190
```

---

```
Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
        210                 215                 220

Lys Val Glu Pro Lys Ser Cys Gly Lys Thr Gly Gly Gly Gly Ser Gly
225                     230                 235                 240

Gly Gly Gly Ser Gln Val Gln Leu Gln Gln Ser Gly Pro Gly Leu Val
                245                 250                 255

Lys Thr Ser Glu Thr Leu Ser Leu Thr Cys Thr Val Ser Gly Gly Ser
                260                 265                 270

Val Ser Asp Tyr Tyr Trp Ser Trp Ile Arg Gln Pro Pro Gly Lys Cys
                275                 280                 285

Leu Glu Trp Ile Gly Tyr Ile His Ser Ser Gly Ser Thr Asp Tyr Asn
        290                 295                 300

Pro Ser Leu Lys Ser Arg Leu Thr Ile Ser Gly Asp Ala Ala Lys Lys
305                     310                 315                 320

Gln Phe Ser Leu Asn Leu Ser Ser Val Thr Ala Ala Asp Thr Ala Leu
                325                 330                 335

Tyr Tyr Cys Ala Arg Ala Gln Gly Gly Ser Arg Arg Thr Leu Asp Tyr
                340                 345                 350

Trp Gly Gln Gly Thr Leu Val Thr Val Ser Ser Gly Gly Gly Gly Ser
                355                 360                 365

Gly Gly Gly Gly Ser Gly Gly Gly Gly Ser Gly Gly Gly Gly Ser Glu
        370                 375                 380

Ile Val Met Thr Gln Ser Pro Ser Thr Leu Ser Ala Ser Val Gly Asp
385                     390                 395                 400

Arg Val Ala Ile Thr Cys Arg Ala Ser Gln Thr Ile Ser Ser Tyr Leu
                405                 410                 415

Asn Trp Tyr Gln Leu Lys Pro Gly Lys Ala Pro Lys Leu Leu Ile Tyr
                420                 425                 430

Ala Ala Ser Ser Leu Gln Ser Gly Val Pro Ser Arg Phe Ser Gly Ser
                435                 440                 445

Gly Ser Gly Thr Asp Phe Thr Leu Thr Ile Ser Ser Leu Gln Pro Glu
        450                 455                 460

Asp Phe Ala Thr Tyr Tyr Cys Gln Gln Ser Tyr Ser Thr Pro Tyr Thr
465                     470                 475                 480

Phe Gly Cys Gly Thr Lys Val Asp Ile Lys
                485                 490
```

```
<210> SEQ ID NO 198
<211> LENGTH: 490
<212> TYPE: PRT
<213> ORGANISM: Artificial Sequence
<220> FEATURE:
<223> OTHER INFORMATION: Synthetic Construct

<400> SEQUENCE: 198

Glu Val Gln Leu Leu Glu Ser Gly Gly Gly Leu Val Gln Pro Gly Gly
1                   5                   10                  15

Ser Leu Arg Leu Ser Cys Thr Ala Ser Gly Phe Thr Phe Ser Asp Asn
        20                  25                  30

Tyr Met Ser Trp Val Arg Gln Ala Pro Gly Lys Gly Leu Asp Trp Val
        35                  40                  45

Ser Val Ile Ser Glu Ser Gly Gly Ser Thr Asn Tyr Ala Asp Ser Val
        50                  55                  60
```

-continued

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                    85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
        180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Gly Lys Thr Gly Gly Gly Ser Gly
225                 230                 235                 240

Gly Gly Gly Ser Gln Val Gln Leu Gln Gln Ser Gly Pro Gly Leu Val
            245                 250                 255

Lys Thr Ser Glu Thr Leu Ser Leu Thr Cys Thr Val Ser Gly Gly Ser
            260                 265                 270

Val Ser Asp Tyr Tyr Trp Ser Trp Ile Arg Gln Pro Pro Gly Lys Cys
        275                 280                 285

Leu Glu Trp Ile Gly Tyr Ile His Ser Ser Gly Ser Thr Asp Tyr Asn
    290                 295                 300

Pro Ser Leu Lys Ser Arg Leu Thr Ile Ser Gly Asp Ala Ala Lys Lys
305                 310                 315                 320

Gln Phe Ser Leu Lys Leu Ser Ser Val Thr Ala Ala Asp Thr Ala Leu
            325                 330                 335

Tyr Tyr Cys Ala Arg Ala Gln Gly Gly Ser Arg Arg Thr Leu Asp Tyr
            340                 345                 350

Trp Gly Gln Gly Thr Leu Val Thr Val Ser Ser Gly Gly Gly Gly Ser
        355                 360                 365

Gly Gly Gly Gly Ser Gly Gly Gly Gly Ser Gly Gly Gly Gly Ser Glu
        370                 375                 380

Ile Val Met Thr Gln Ser Pro Ser Thr Leu Ser Ala Ser Val Gly Asp
385                 390                 395                 400

Arg Val Ala Ile Thr Cys Arg Ala Ser Gln Thr Ile Ser Ser Tyr Leu
                405                 410                 415

Asn Trp Tyr Gln Leu Lys Pro Gly Lys Ala Pro Lys Leu Leu Ile Tyr
        420                 425                 430

Ala Ala Ser Ser Leu Gln Ser Gly Val Pro Ser Arg Phe Ser Gly Ser
        435                 440                 445

Gly Ser Gly Thr Asp Phe Thr Leu Thr Ile Ser Ser Leu Gln Pro Glu
        450                 455                 460

Asp Phe Ala Thr Tyr Tyr Cys Gln Gln Ser Tyr Ser Thr Pro Tyr Thr
465                 470                 475                 480

Phe Gly Cys Gly Thr Lys Val Asp Ile Lys

-continued

```
                       485                    490

<210> SEQ ID NO 199
<211> LENGTH: 496
<212> TYPE: PRT
<213> ORGANISM: Artificial Sequence
<220> FEATURE:
<223> OTHER INFORMATION: Synthetic Construct

<400> SEQUENCE: 199

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30

Tyr Met Ser Trp Val Arg Gln Ala Pro Gly Lys Gly Leu Asp Trp Val
        35                  40                  45

Ser Val Ile Ser Glu Ser Gly Gly Ser Thr Asn Tyr Ala Asp Ser Val
    50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
    210                 215                 220

Lys Val Glu Pro Lys Ser Cys Gly Gly Gly Gly Ser Gly Gly Gly Gly
225                 230                 235                 240

Ser Gln Val Gln Leu Gln Gln Ser Gly Pro Gly Leu Val Lys Pro Ser
            245                 250                 255

Glu Thr Leu Ser Leu Thr Cys Thr Val Ser Gly Gly Pro Ile Thr Ser
            260                 265                 270

Ser Gly Asp Tyr Trp Gly Trp Ile Arg Gln Pro Pro Gly Lys Cys Leu
        275                 280                 285

Glu Leu Ile Gly Ser Ile His Asn Ser Gly Ser Thr Tyr Tyr Asn Pro
    290                 295                 300

Ser Leu Lys Gly Arg Val Thr Ile Ser Gly Asp Thr Ser Lys Asn Gln
305                 310                 315                 320

Ile Ser Leu Arg Leu Ser Ser Val Thr Ala Ala Asp Thr Ala Val Tyr
                325                 330                 335

Tyr Cys Ala Arg Gln Phe Gly Ser Glu Thr Tyr Tyr Asn Gly Ile Asp
            340                 345                 350

Pro Trp Gly Gln Gly Thr Leu Val Thr Val Ser Ser Gly Gly Gly Gly
```

-continued

```
                355                 360                 365

Ser Gly Gly Gly Gly Ser Gly Gly Gly Gly Ser Gly Gly Gly Gly Ser
    370                 375                 380

Asp Ile Val Met Thr Gln Thr Pro Leu Ser Leu Pro Val Thr Pro Gly
385                 390                 395                 400

Glu Pro Ala Ser Ile Ser Cys Arg Ser Ser Gln Ser Leu Leu His Ser
                    405                 410                 415

Asn Gly Tyr Asn Tyr Leu Asp Trp Tyr Leu Gln Lys Pro Gly Gln Ser
                420                 425                 430

Pro Gln Leu Leu Ile Tyr Leu Gly Ser Asn Arg Ala Ser Gly Val Pro
            435                 440                 445

Asp Arg Phe Ser Gly Ser Gly Ser Gly Thr Asp Phe Thr Leu Lys Ile
        450                 455                 460

Ser Arg Val Glu Ala Glu Asp Val Gly Val Tyr Tyr Cys Met Gln Ala
465                 470                 475                 480

Leu Gln Thr Pro Tyr Thr Phe Gly Cys Gly Thr Lys Leu Glu Ile Lys
                485                 490                 495
```

<210> SEQ ID NO 200
<211> LENGTH: 499
<212> TYPE: PRT
<213> ORGANISM: Artificial Sequence
<220> FEATURE:
<223> OTHER INFORMATION: Synthetic Construct

<400> SEQUENCE: 200

```
Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30

Tyr Met Ser Trp Val Arg Gln Ala Pro Gly Lys Gly Leu Asp Trp Val
        35                  40                  45

Ser Val Ile Ser Glu Ser Gly Gly Ser Thr Asn Tyr Ala Asp Ser Val
    50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
    210                 215                 220

Lys Val Glu Pro Lys Ser Cys Gly Lys Thr Gly Gly Gly Gly Ser Gly
```

-continued

```
225                 230                 235                 240

Gly Gly Gly Ser Gln Val Gln Leu Gln Gln Ser Gly Pro Gly Leu Val
                245                 250                 255

Lys Pro Ser Glu Thr Leu Ser Leu Thr Cys Thr Val Ser Gly Gly Pro
                260                 265                 270

Ile Thr Ser Ser Gly Asp Tyr Trp Gly Trp Ile Arg Gln Pro Pro Gly
                275                 280                 285

Lys Cys Leu Glu Leu Ile Gly Ser Ile His Asn Ser Gly Ser Thr Tyr
    290                 295                 300

Tyr Asn Pro Ser Leu Lys Gly Arg Val Thr Ile Ser Gly Asp Thr Ser
305                 310                 315                 320

Lys Asn Gln Ile Ser Leu Arg Leu Ser Ser Val Thr Ala Ala Asp Thr
                325                 330                 335

Ala Val Tyr Tyr Cys Ala Arg Gln Phe Gly Ser Glu Thr Tyr Tyr Asn
                340                 345                 350

Gly Ile Asp Pro Trp Gly Gln Gly Thr Leu Val Thr Val Ser Ser Gly
                355                 360                 365

Gly Gly Gly Ser Gly Gly Gly Gly Ser Gly Gly Gly Ser Gly Gly
    370                 375                 380

Gly Gly Ser Asp Ile Val Met Thr Gln Thr Pro Leu Ser Leu Pro Val
385                 390                 395                 400

Thr Pro Gly Glu Pro Ala Ser Ile Ser Cys Arg Ser Ser Gln Ser Leu
                405                 410                 415

Leu His Ser Asn Gly Tyr Asn Tyr Leu Asp Trp Tyr Leu Gln Lys Pro
                420                 425                 430

Gly Gln Ser Pro Gln Leu Leu Ile Tyr Leu Gly Ser Asn Arg Ala Ser
                435                 440                 445

Gly Val Pro Asp Arg Phe Ser Gly Ser Gly Ser Gly Thr Asp Phe Thr
    450                 455                 460

Leu Lys Ile Ser Arg Val Glu Ala Glu Asp Val Gly Val Tyr Tyr Cys
465                 470                 475                 480

Met Gln Ala Leu Gln Thr Pro Tyr Thr Phe Gly Cys Gly Thr Lys Leu
                485                 490                 495

Glu Ile Lys

<210> SEQ ID NO 201
<211> LENGTH: 496
<212> TYPE: PRT
<213> ORGANISM: Artificial Sequence
<220> FEATURE:
<223> OTHER INFORMATION: Synthetic Construct

<400> SEQUENCE: 201

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
                20                  25                  30

Tyr Met Ser Trp Val Arg Gln Ala Pro Gly Lys Gly Leu Asp Trp Val
            35                  40                  45

Ser Val Ile Ser Glu Ser Gly Gly Ser Thr Asn Tyr Ala Asp Ser Val
    50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95
```

-continued

```
Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
            115                 120                 125

Ala Ser Thr Lys Gly Pro Ser Val Phe Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
    210                 215                 220

Lys Val Glu Pro Lys Ser Cys Gly Gly Gly Ser Gly Gly Gly Gly
225                 230                 235                 240

Ser Gln Val Gln Leu Gln Gln Ser Gly Pro Gly Leu Val Lys Pro Ser
                245                 250                 255

Glu Thr Leu Ser Leu Thr Cys Thr Val Ser Gly Gly Pro Ile Thr Ser
                260                 265                 270

Ser Gly Asp Tyr Trp Gly Trp Ile Arg Gln Pro Pro Gly Lys Cys Leu
            275                 280                 285

Glu Leu Ile Gly Ser Ile His Asn Gln Gly Ser Thr Tyr Tyr Asn Pro
    290                 295                 300

Ser Leu Lys Gly Arg Val Thr Ile Ser Gly Asp Thr Ser Lys Asn Gln
305                 310                 315                 320

Ile Ser Leu Arg Leu Ser Ser Val Thr Ala Ala Asp Thr Ala Val Tyr
                325                 330                 335

Tyr Cys Ala Arg Gln Phe Gly Ser Glu Thr Tyr Tyr Thr Gly Ile Asp
            340                 345                 350

Pro Trp Gly Gln Gly Thr Leu Val Thr Val Ser Ser Gly Gly Gly Gly
            355                 360                 365

Ser Gly Gly Gly Gly Ser Gly Gly Gly Gly Ser Gly Gly Gly Gly Ser
    370                 375                 380

Asp Ile Val Met Thr Gln Thr Pro Leu Ser Leu Pro Val Thr Pro Gly
385                 390                 395                 400

Glu Pro Ala Ser Ile Ser Cys Arg Ser Ser Gln Ser Leu Leu His Ser
                405                 410                 415

Asn Gly Tyr Asn Tyr Leu Asp Trp Tyr Leu Gln Lys Pro Gly Gln Ser
            420                 425                 430

Pro Gln Leu Leu Ile Tyr Leu Gly Ser Asn Arg Ala Ser Gly Val Pro
        435                 440                 445

Asp Arg Phe Ser Gly Ser Gly Ser Gly Thr Asp Phe Thr Leu Lys Ile
    450                 455                 460

Ser Arg Val Glu Ala Glu Asp Val Gly Val Tyr Tyr Cys Met Gln Ala
465                 470                 475                 480

Leu Gln Thr Pro Tyr Thr Phe Gly Cys Gly Thr Lys Leu Glu Ile Lys
                485                 490                 495
```

<210> SEQ ID NO 202
<211> LENGTH: 499

```
<212> TYPE: PRT
<213> ORGANISM: Artificial Sequence
<220> FEATURE:
<223> OTHER INFORMATION: Synthetic Construct

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30

Tyr Met Ser Trp Val Arg Gln Ala Pro Gly Lys Gly Leu Asp Trp Val
        35                  40                  45

Ser Val Ile Ser Glu Ser Gly Gly Ser Thr Asn Tyr Ala Asp Ser Val
        50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
            115                 120                 125

Ala Ser Thr Lys Gly Pro Ser Val Phe Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
        210                 215                 220

Lys Val Glu Pro Lys Ser Cys Gly Lys Thr Gly Gly Gly Gly Ser Gly
225                 230                 235                 240

Gly Gly Gly Ser Gln Val Gln Leu Gln Gln Ser Gly Pro Gly Leu Val
            245                 250                 255

Lys Pro Ser Glu Thr Leu Ser Leu Thr Cys Thr Val Ser Gly Gly Pro
            260                 265                 270

Ile Thr Ser Ser Gly Asp Tyr Trp Gly Trp Ile Arg Gln Pro Pro Gly
            275                 280                 285

Lys Cys Leu Glu Leu Ile Gly Ser Ile His Asn Ser Gly Ser Thr Tyr
        290                 295                 300

Tyr Asn Pro Ser Leu Lys Gly Arg Val Thr Ile Ser Gly Asp Thr Ser
305                 310                 315                 320

Lys Asn Gln Ile Ser Leu Arg Leu Ser Ser Val Thr Ala Ala Asp Thr
            325                 330                 335

Ala Val Tyr Tyr Cys Ala Arg Gln Phe Gly Ser Glu Thr Tyr Tyr Asn
            340                 345                 350

Gly Ile Gln Pro Trp Gly Gln Gly Thr Leu Val Thr Val Ser Ser Gly
        355                 360                 365

Gly Gly Gly Ser Gly Gly Gly Gly Ser Gly Gly Gly Ser Gly Gly
        370                 375                 380
```

-continued

```
Gly Gly Ser Asp Ile Val Met Thr Gln Thr Pro Leu Ser Leu Pro Val
385             390             395             400

Thr Pro Gly Glu Pro Ala Ser Ile Ser Cys Arg Ser Ser Gln Ser Leu
            405             410             415

Leu His Ser Arg Gly Tyr Asn Tyr Leu Asp Trp Tyr Leu Gln Lys Pro
            420             425             430

Gly Gln Ser Pro Gln Leu Leu Ile Tyr Leu Gly Ser Asn Arg Ala Ser
        435             440             445

Gly Val Pro Asp Arg Phe Ser Gly Ser Gly Ser Gly Thr Asp Phe Thr
        450             455             460

Leu Lys Ile Ser Arg Val Glu Ala Glu Asp Val Gly Val Tyr Tyr Cys
465             470             475             480

Met Gln Ala Leu Gln Thr Pro Tyr Thr Phe Gly Cys Gly Thr Lys Leu
            485             490             495

Glu Ile Lys
```

<210> SEQ ID NO 203
<211> LENGTH: 496
<212> TYPE: PRT
<213> ORGANISM: Artificial Sequence
<220> FEATURE:
<223> OTHER INFORMATION: Synthetic Construct

<400> SEQUENCE: 203

```
Glu Val Gln Leu Leu Glu Ser Gly Gly Gly Leu Val Gln Pro Gly Gly
1               5               10              15

Ser Leu Arg Leu Ser Cys Thr Ala Ser Gly Phe Thr Phe Ser Asp Asn
            20              25              30

Tyr Met Ser Trp Val Arg Gln Ala Pro Gly Lys Gly Leu Asp Trp Val
        35              40              45

Ser Val Ile Ser Glu Ser Gly Gly Ser Thr Asn Tyr Ala Asp Ser Val
    50              55              60

Lys Gly Arg Phe Ser Thr Ser Arg Asp Asn Ser Lys Ser Thr Leu Tyr
65              70              75              80

Leu Asp Met Asn Ser Leu Arg Ala Glu Asp Thr Ala Ile Tyr Tyr Cys
            85              90              95

Ala Lys Gly Arg Phe Ser Thr Leu Ser Ser His Phe Phe Arg Ala Val
            100             105             110

Tyr Gly Met Asp Val Trp Gly Gln Gly Thr Ala Val Thr Val Ser Ser
        115             120             125

Ala Ser Thr Lys Gly Pro Ser Val Phe Pro Leu Ala Pro Ser Ser Lys
    130             135             140

Ser Thr Ser Gly Gly Thr Ala Ala Leu Gly Cys Leu Val Lys Asp Tyr
145             150             155             160

Phe Pro Glu Pro Val Thr Val Ser Trp Asn Ser Gly Ala Leu Thr Ser
            165             170             175

Gly Val His Thr Phe Pro Ala Val Leu Gln Ser Ser Gly Leu Tyr Ser
        180             185             190

Leu Ser Ser Val Val Thr Val Pro Ser Ser Ser Leu Gly Thr Gln Thr
        195             200             205

Tyr Ile Cys Asn Val Asn His Lys Pro Ser Asn Thr Lys Val Asp Lys
    210             215             220

Lys Val Glu Pro Lys Ser Cys Gly Gly Gly Ser Gly Gly Gly Gly
225             230             235             240

Ser Gln Val Gln Leu Gln Gln Ser Gly Pro Gly Leu Val Lys Pro Ser
```

-continued

```
                     245                 250                 255
Glu Thr Leu Ser Leu Thr Cys Thr Val Ser Gly Gly Pro Ile Thr Ser
                 260                 265                 270

Ser Gly Asp Tyr Trp Gly Trp Ile Arg Gln Pro Pro Gly Lys Cys Leu
             275                 280                 285

Glu Leu Ile Gly Ser Ile His Asn Gln Gly Ser Thr Tyr Tyr Asn Pro
         290                 295                 300

Ser Leu Lys Gly Arg Val Thr Ile Ser Gly Asp Thr Ser Lys Asn Gln
     305                 310                 315                 320

Ile Ser Leu Arg Leu Ser Ser Val Thr Ala Ala Asp Thr Ala Val Tyr
                 325                 330                 335

Tyr Cys Ala Arg Gln Phe Gly Ser Glu Thr Tyr Tyr Pro Gly Ile Asp
             340                 345                 350

Pro Trp Gly Gln Gly Thr Leu Val Thr Val Ser Ser Gly Gly Gly Gly
         355                 360                 365

Ser Gly Gly Gly Gly Ser Gly Gly Gly Gly Ser Gly Gly Gly Gly Ser
     370                 375                 380

Asp Ile Val Met Thr Gln Thr Pro Leu Ser Leu Pro Val Thr Pro Gly
 385                 390                 395                 400

Glu Pro Ala Ser Ile Ser Cys Arg Ser Ser Gln Ser Leu Leu His Ser
                 405                 410                 415

Asn Gly Tyr Asn Tyr Leu Asp Trp Tyr Leu Gln Lys Pro Gly Gln Ser
             420                 425                 430

Pro Gln Leu Leu Ile Tyr Leu Gly Ser Asn Arg Ala Ser Gly Val Pro
         435                 440                 445

Asp Arg Phe Ser Gly Ser Gly Ser Gly Thr Asp Phe Thr Leu Lys Ile
     450                 455                 460

Ser Arg Val Glu Ala Glu Asp Val Gly Val Tyr Tyr Cys Met Gln Ala
 465                 470                 475                 480

Leu Gln Thr Pro Tyr Thr Phe Gly Cys Gly Thr Lys Leu Glu Ile Lys
             485                 490                 495
```

<210> SEQ ID NO 204
<211> LENGTH: 481
<212> TYPE: PRT
<213> ORGANISM: Artificial Sequence
<220> FEATURE:
<223> OTHER INFORMATION: Synthetic Construct

<400> SEQUENCE: 204

```
Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
             20                  25                  30

Tyr Met Ser Trp Val Arg Gln Ala Pro Gly Lys Gly Leu Asp Trp Val
         35                  40                  45

Ser Val Ile Ser Glu Ser Gly Gly Ser Thr Asn Tyr Ala Asp Ser Val
     50                  55                  60

Lys Gly Arg Phe Ser Thr Ser Arg Asp Asn Ser Lys Ser Thr Leu Tyr
 65                  70                  75                  80

Leu Asp Met Asn Ser Leu Arg Ala Glu Asp Thr Ala Ile Tyr Tyr Cys
                 85                  90                  95

Ala Lys Gly Arg Phe Ser Thr Leu Ser Ser His Phe Phe Arg Ala Val
             100                 105                 110

Tyr Gly Met Asp Val Trp Gly Gln Gly Thr Ala Val Thr Val Ser Ser
```

-continued

```
               115                 120                 125
Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
                180                 185                 190

Leu Ser Ser Val Val Thr Val Pro Ser Ser Ser Leu Gly Thr Gln Thr
                195                 200                 205

Tyr Ile Cys Asn Val Asn His Lys Pro Ser Asn Thr Lys Val Asp Lys
    210                 215                 220

Lys Val Glu Pro Lys Ser Cys Gly Gly Gly Ser Gly Gly Gly Gly
225                 230                 235                 240

Ser Gln Val Gln Leu Val Gln Ser Gly Ala Glu Val Lys Lys Pro Gly
                245                 250                 255

Ala Ser Val Lys Val Ser Cys Lys Ala Ser Gly Asp Thr Ser Thr Ile
                260                 265                 270

His Ser Val His Trp Val Arg Gln Ala Pro Gly Gln Cys Leu Glu Trp
                275                 280                 285

Met Gly Thr Ile Ile Ser Ser Gly Thr Thr Thr Thr Tyr Ala Gln Ser
    290                 295                 300

Phe Gln Asp Arg Val Ser Met Thr Ile Asp Arg Ser Thr Ser Thr Gly
305                 310                 315                 320

Tyr Met Glu Leu Ser Ser Leu Arg Phe Glu Asp Thr Ala Val Tyr Tyr
                325                 330                 335

Cys Thr Thr Asp Gly Thr Ser Trp Gly Gln Gly Thr Leu Val Thr Val
                340                 345                 350

Ser Ser Gly Gly Gly Gly Ser Gly Gly Gly Gly Ser Gly Gly Gly Gly
                355                 360                 365

Ser Gly Gly Gly Gly Ser Asp Ile Gln Leu Thr Gln Ser Pro Ser Ser
    370                 375                 380

Val Ser Ala Ser Val Gly Asp Arg Val Thr Ile Ala Cys Arg Ala Ser
385                 390                 395                 400

Gln Gly Ile Ser Ser Trp Leu Ala Trp Tyr Gln Gln Lys Pro Gly Lys
                405                 410                 415

Ala Pro Lys Leu Leu Ile Tyr His Ala Ser Thr Leu Glu Ser Gly Val
                420                 425                 430

Pro Ser Arg Phe Ser Gly Ser Gly Ser Gly Thr Asp Phe Thr Leu Thr
                435                 440                 445

Ile Ser Ser Leu Gln Pro Glu Asp Phe Ala Thr Tyr Tyr Cys Leu Gln
    450                 455                 460

Ala Phe Ser Leu Pro His Thr Phe Gly Cys Gly Thr Lys Leu Glu Ile
465                 470                 475                 480

Lys
```

<210> SEQ ID NO 205
<211> LENGTH: 484
<212> TYPE: PRT
<213> ORGANISM: Artificial Sequence
<220> FEATURE:
<223> OTHER INFORMATION: Synthetic Construct

<400> SEQUENCE: 205

-continued

```
Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30

Tyr Met Ser Trp Val Arg Gln Ala Pro Gly Lys Gly Leu Asp Trp Val
        35                  40                  45

Ser Val Ile Ser Glu Ser Gly Gly Ser Thr Asn Tyr Ala Asp Ser Val
    50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
    210                 215                 220

Lys Val Glu Pro Lys Ser Cys Gly Lys Thr Gly Gly Gly Ser Gly
225                 230                 235                 240

Gly Gly Gly Ser Gln Val Gln Leu Val Gln Ser Gly Ala Glu Val Lys
            245                 250                 255

Lys Pro Gly Ala Ser Val Lys Val Ser Cys Lys Ala Ser Gly Asp Thr
            260                 265                 270

Ser Thr Ile His Ser Val His Trp Val Arg Gln Ala Pro Gly Gln Cys
            275                 280                 285

Leu Glu Trp Met Gly Thr Ile Ile Ser Ser Gly Thr Thr Thr Thr Tyr
    290                 295                 300

Ala Gln Ser Phe Gln Asp Arg Val Ser Met Thr Ile Asp Arg Ser Thr
305                 310                 315                 320

Ser Thr Gly Tyr Met Glu Leu Ser Ser Leu Arg Phe Glu Asp Thr Ala
            325                 330                 335

Val Tyr Tyr Cys Thr Thr Asp Gly Thr Ser Trp Gly Gln Gly Thr Leu
            340                 345                 350

Val Thr Val Ser Ser Gly Gly Gly Ser Gly Gly Gly Gly Ser Gly
            355                 360                 365

Gly Gly Gly Ser Gly Gly Gly Gly Ser Asp Ile Gln Leu Thr Gln Ser
    370                 375                 380

Pro Ser Ser Val Ser Ala Ser Val Gly Asp Arg Val Thr Ile Ala Cys
385                 390                 395                 400

Arg Ala Ser Gln Gly Ile Ser Ser Trp Leu Ala Trp Tyr Gln Gln Lys
                405                 410                 415
```

-continued

```
Pro Gly Lys Ala Pro Lys Leu Leu Ile Tyr His Ala Ser Thr Leu Glu
            420             425             430

Ser Gly Val Pro Ser Arg Phe Ser Gly Ser Gly Ser Gly Thr Asp Phe
            435             440             445

Thr Leu Thr Ile Ser Ser Leu Gln Pro Glu Asp Phe Ala Thr Tyr Tyr
    450             455             460

Cys Leu Gln Ala Phe Ser Leu Pro His Thr Phe Gly Cys Gly Thr Lys
465             470             475             480

Leu Glu Ile Lys

<210> SEQ ID NO 206
<211> LENGTH: 484
<212> TYPE: PRT
<213> ORGANISM: Artificial Sequence
<220> FEATURE:
<223> OTHER INFORMATION: Synthetic Construct

<400> SEQUENCE: 206

Glu Val Gln Leu Leu Glu Ser Gly Gly Gly Leu Val Gln Pro Gly Gly
1               5               10              15

Ser Leu Arg Leu Ser Cys Thr Ala Ser Gly Phe Thr Phe Ser Asp Asn
            20              25              30

Tyr Met Ser Trp Val Arg Gln Ala Pro Gly Lys Gly Leu Asp Trp Val
            35              40              45

Ser Val Ile Ser Glu Ser Gly Gly Ser Thr Asn Tyr Ala Asp Ser Val
    50              55              60

Lys Gly Arg Phe Ser Thr Ser Arg Asp Asn Ser Lys Ser Thr Leu Tyr
65              70              75              80

Leu Asp Met Asn Ser Leu Arg Ala Glu Asp Thr Ala Ile Tyr Tyr Cys
            85              90              95

Ala Lys Gly Arg Phe Ser Thr Leu Ser Ser His Phe Phe Arg Ala Val
            100             105             110

Tyr Gly Met Asp Val Trp Gly Gln Gly Thr Ala Val Thr Val Ser Ser
            115             120             125

Ala Ser Thr Lys Gly Pro Ser Val Phe Pro Leu Ala Pro Ser Ser Lys
    130             135             140

Ser Thr Ser Gly Gly Thr Ala Ala Leu Gly Cys Leu Val Lys Asp Tyr
145             150             155             160

Phe Pro Glu Pro Val Thr Val Ser Trp Asn Ser Gly Ala Leu Thr Ser
            165             170             175

Gly Val His Thr Phe Pro Ala Val Leu Gln Ser Ser Gly Leu Tyr Ser
            180             185             190

Leu Ser Ser Val Val Thr Val Pro Ser Ser Ser Leu Gly Thr Gln Thr
            195             200             205

Tyr Ile Cys Asn Val Asn His Lys Pro Ser Asn Thr Lys Val Asp Lys
    210             215             220

Lys Val Glu Pro Lys Ser Cys Gly Lys Thr Gly Gly Gly Gly Ser Gly
225             230             235             240

Gly Gly Gly Ser Gln Val Gln Leu Val Gln Ser Gly Ala Glu Val Lys
            245             250             255

Lys Pro Gly Ala Ser Val Lys Val Ser Cys Lys Ala Ser Gly Asp Thr
            260             265             270

Ser Thr Ile His Ser Val His Trp Val Arg Gln Ala Pro Gly Gln Cys
    275             280             285

Leu Glu Trp Met Gly Thr Ile Ile Ser Ser Gly Thr Thr Thr Thr Tyr
```

```
        290                 295                 300

Ala Gln Ser Phe Gln Asp Arg Val Ser Met Thr Ile Asp Arg Ser Thr
305                 310                 315                 320

Ser Thr Gly Tyr Met Glu Leu Ser Ser Leu Arg Phe Glu Asp Thr Ala
                325                 330                 335

Val Tyr Tyr Cys Thr Thr Asp Gly Thr Ser Trp Gly Gln Gly Thr Leu
                340                 345                 350

Val Thr Val Ser Ser Gly Gly Gly Ser Gly Gly Gly Gly Ser Gly
        355                 360                 365

Gly Gly Gly Ser Gly Gly Gly Gly Ser Asp Ile Gln Leu Thr Gln Ser
        370                 375                 380

Pro Ser Ser Val Ser Ala Ser Val Gly Asp Arg Val Thr Ile Ala Cys
385                 390                 395                 400

Arg Ala Ser Gln Gly Ile Ser Ser Trp Leu Ala Trp Tyr Gln Gln Lys
                405                 410                 415

Pro Gly Lys Ala Pro Lys Leu Leu Ile Tyr His Ala Ser Thr Leu Glu
                420                 425                 430

Ser Gly Val Pro Ser Arg Phe Ser Gly Ser Gly Ser Gly Thr Asp Phe
                435                 440                 445

Thr Leu Thr Ile Ser Ser Leu Gln Pro Glu Asp Phe Ala Thr Tyr Tyr
        450                 455                 460

Cys Leu Gln Ala Ser Ser Leu Pro His Thr Phe Gly Cys Gly Thr Lys
465                 470                 475                 480

Leu Glu Ile Lys

<210> SEQ ID NO 207
<211> LENGTH: 484
<212> TYPE: PRT
<213> ORGANISM: Artificial Sequence
<220> FEATURE:
<223> OTHER INFORMATION: Synthetic Construct

<400> SEQUENCE: 207

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asp Asn
            20                  25                  30

Tyr Met Ser Trp Val Arg Gln Ala Pro Gly Lys Gly Leu Asp Trp Val
        35                  40                  45

Ser Val Ile Ser Glu Ser Gly Gly Ser Thr Asn Tyr Ala Asp Ser Val
        50                  55                  60

Lys Gly Arg Phe Ser Thr Ser Arg Asp Asn Ser Lys Ser Thr Leu Tyr
65                  70                  75                  80

Leu Asp Met Asn Ser Leu Arg Ala Glu Asp Thr Ala Ile Tyr Tyr Cys
                85                  90                  95

Ala Lys Gly Arg Phe Ser Thr Leu Ser Ser His Phe Phe Arg Ala Val
            100                 105                 110

Tyr Gly Met Asp Val Trp Gly Gln Gly Thr Ala Val Thr Val Ser Ser
            115                 120                 125

Ala Ser Thr Lys Gly Pro Ser Val Phe Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
            165                 170                 175
```

-continued

```
Gly Val His Thr Phe Pro Ala Val Leu Gln Ser Ser Gly Leu Tyr Ser
            180             185             190

Leu Ser Ser Val Val Thr Val Pro Ser Ser Ser Leu Gly Thr Gln Thr
            195             200             205

Tyr Ile Cys Asn Val Asn His Lys Pro Ser Asn Thr Lys Val Asp Lys
            210             215             220

Lys Val Glu Pro Lys Ser Cys Gly Lys Thr Gly Gly Gly Gly Ser Gly
225                 230             235                 240

Gly Gly Gly Ser Gln Val Gln Leu Val Gln Ser Gly Ala Glu Val Lys
                245             250             255

Lys Pro Gly Ala Ser Val Lys Val Ser Cys Lys Ala Ser Gly Asp Thr
            260             265             270

Ser Thr Ile His Ser Val His Trp Val Arg Gln Ala Pro Gly Gln Cys
            275             280             285

Leu Glu Trp Met Gly Thr Ile Ile Ser Ser Gly Thr Thr Thr Thr Tyr
            290             295             300

Ala Gln Ser Phe Gln Asp Arg Val Ser Met Thr Ile Asp Arg Ser Thr
305                 310             315                 320

Ser Thr Gly Tyr Met Glu Leu Ser Ser Leu Arg Phe Glu Asp Thr Ala
            325             330             335

Val Tyr Tyr Cys Thr Thr Asp Gly Thr Ser Trp Gly Gln Gly Thr Leu
            340             345             350

Val Thr Val Ser Ser Gly Gly Gly Gly Ser Gly Gly Gly Gly Ser Gly
            355             360             365

Gly Gly Gly Ser Gly Gly Gly Gly Ser Asp Ile Gln Leu Thr Gln Ser
            370             375             380

Pro Ser Ser Val Ser Ala Ser Val Gly Asp Arg Val Thr Ile Ala Cys
385                 390             395                 400

Arg Ala Ser Gln Gly Ile Ser Ser Trp Leu Ala Trp Tyr Gln Gln Lys
            405             410             415

Pro Gly Lys Ala Pro Lys Leu Leu Ile Tyr His Ala Ser Thr Leu Glu
            420             425             430

Ser Gly Val Pro Ser Arg Phe Ser Gly Ser Gly Ser Gly Thr Asp Phe
            435             440             445

Thr Leu Thr Ile Ser Ser Leu Gln Pro Glu Asp Phe Ala Thr Tyr Tyr
            450             455             460

Cys Leu Gln Ala Lys Ser Leu Pro His Thr Phe Gly Cys Gly Thr Lys
465                 470             475                 480

Leu Glu Ile Lys

<210> SEQ ID NO 208
<211> LENGTH: 490
<212> TYPE: PRT
<213> ORGANISM: Artificial Sequence
<220> FEATURE:
<223> OTHER INFORMATION: Synthetic Construct

<400> SEQUENCE: 208

Gln Val Gln Leu Gln Gln Ser Gly Pro Gly Leu Val Lys Thr Ser Glu
1               5               10              15

Thr Leu Ser Leu Thr Cys Thr Val Ser Gly Gly Ser Val Ser Asp Tyr
            20              25              30

Tyr Trp Ser Trp Ile Arg Gln Pro Pro Gly Lys Gly Leu Glu Trp Ile
            35              40              45
```

-continued

```
Gly Tyr Ile His Ser Ser Gly Ser Thr Asp Tyr Asn Pro Ser Leu Lys
    50                  55                  60

Ser Arg Leu Thr Ile Ser Gly Asp Ala Ala Lys Lys Gln Phe Ser Leu
65                  70                  75                  80

Lys Leu Ser Ser Val Thr Ala Ala Asp Thr Ala Leu Tyr Tyr Cys Ala
                85                  90                  95

Arg Ala Gln Gly Gly Ser Arg Arg Thr Leu Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Gly Lys
    210                 215                 220

Thr Gly Gly Gly Gly Ser Gly Gly Gly Gly Ser Glu Val Gln Leu Leu
225                 230                 235                 240

Glu Ser Gly Gly Gly Leu Val Gln Pro Gly Gly Ser Leu Arg Leu Ser
                245                 250                 255

Cys Thr Ala Ser Gly Phe Thr Phe Ser Asp Asn Tyr Met Ser Trp Val
                260                 265                 270

Arg Gln Ala Pro Gly Lys Cys Leu Asp Trp Val Ser Val Ile Ser Glu
                275                 280                 285

Ser Gly Gly Ser Thr Asn Tyr Ala Asp Ser Val Lys Gly Arg Phe Ser
    290                 295                 300

Thr Ser Arg Asp Asn Ser Lys Ser Thr Leu Tyr Leu Asp Met Asn Ser
305                 310                 315                 320

Leu Arg Ala Glu Asp Thr Ala Ile Tyr Tyr Cys Ala Lys Gly Arg Phe
                325                 330                 335

Ser Thr Leu Ser Ser His Phe Phe Arg Ala Val Tyr Gly Met Asp Val
                340                 345                 350

Trp Gly Gln Gly Thr Ala Val Thr Val Ser Ser Gly Gly Gly Gly Ser
                355                 360                 365

Gly Gly Gly Gly Ser Gly Gly Gly Gly Ser Gly Gly Gly Gly Ser Asp
    370                 375                 380

Ile Gln Leu Thr Gln Ser Pro Ser Ser Leu Ser Ala Ser Val Gly Asp
385                 390                 395                 400

Arg Val Thr Ile Thr Cys Arg Ala Ser Gln Gly Ile Ser Ser Tyr Leu
                405                 410                 415

Ala Trp Tyr Gln Gln Lys Pro Gly Lys Ala Pro Lys Leu Leu Ile Tyr
                420                 425                 430

Ala Ala Ser Thr Leu Gln Ser Gly Val Pro Ser Arg Phe Ser Gly Ser
                435                 440                 445

Gly Ser Gly Thr Asp Phe Thr Leu Thr Ile Ser Ser Leu Gln Pro Glu
    450                 455                 460

Asp Phe Ala Thr Tyr Tyr Cys Gln Gln Leu Ser Ser Tyr Pro Leu Thr
```

-continued

```
465             470             475             480

Phe Gly Cys Gly Thr Lys Val Glu Ile Lys
                485             490

<210> SEQ ID NO 209
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = Ser or Arg

<400> SEQUENCE: 209

Arg Ala Ser Gln Gly Ile Xaa Ser Tyr Leu Ala
1               5               10

<210> SEQ ID NO 210
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ser, Asn, or Lys
<220> FEATURE:
<221> NAME/KEY: VARIANT
<222> LOCATION: 9
<223> OTHER INFORMATION: Xaa = Ser or Thr

<400> SEQUENCE: 210

Gln Gln Leu Xaa Ser Tyr Pro Leu Xaa
1               5

<210> SEQ ID NO 211
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Asp, Asn, Ile, Leu, or Val
<220> FEATURE:
<221> NAME/KEY: VARIANT
<222> LOCATION: 7
<223> OTHER INFORMATION: Xaa = Ser, Thr, Arg, Gly, or Asn

<400> SEQUENCE: 211

Arg Ile Asn Glu Xaa Glu Xaa Ser Ile Ser Tyr Ala Asp Ser Val Lys
1               5               10              15

Gly

<210> SEQ ID NO 212
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Asn, Gly, Asp, or Ser
<220> FEATURE:
<221> NAME/KEY: VARIANT
```

-continued

```
<222> LOCATION: 7
<223> OTHER INFORMATION: Xaa = Lys, Arg, Ser, Asn, or Thr
<220> FEATURE:
<221> NAME/KEY: VARIANT
<222> LOCATION: 8
<223> OTHER INFORMATION: Xaa = Asn, Gly, Ser, or Asp

<400> SEQUENCE: 212

Arg Ala Ser Gln Xaa Val Xaa Xaa Asn Leu Ala
1               5               10

<210> SEQ ID NO 213
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp, Asn, His, or Ala

<400> SEQUENCE: 213

Xaa Ala Ser Ser Arg Ala Thr
1               5

<210> SEQ ID NO 214
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser, Thr, Glu, His, Asn, Ala, Asp, Met,
     or Leu
<220> FEATURE:
<221> NAME/KEY: VARIANT
<222> LOCATION: 6
<223> OTHER INFORMATION: Xaa = Ser, Gln, Glu, Thr, Asp, Gly, His, Leu,
     Asn, Val, or Tyr
<220> FEATURE:
<221> NAME/KEY: VARIANT
<222> LOCATION: 8
<223> OTHER INFORMATION: Xaa = Ile, Leu, or Val

<400> SEQUENCE: 214

Gln Gln Tyr Gly Xaa Xaa Pro Xaa Thr
1               5
```

1

COMBINATIONS OF ANTIBODIES AND BISPECIFIC ANTIBODIES COMPRISING ANTIGEN-BINDING SPECIFICALLY RECOGNIZING *PSEUDOMONAS* PCRV AND PSL

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 202011036860_SEQLIST.TXT, date recorded: Nov. 3, 2020, size: 276 KB).

FIELD OF THE APPLICATION

This application pertains to bispecific antibodies that specifically recognize PcrV and/or Psl from *Pseudomonas aeruginosa*, pharmaceutical compositions comprising antigen-binding molecules specifically recognizing non-overlapping epitopes of *Pseudomonas* PcrV and/or antigen-binding molecules specifically recognizing Psl from *Pseudomonas aeruginosa*, as well as methods of manufacture and uses thereof, including methods of treating and preventing *Pseudomonas* infections.

BACKGROUND OF THE APPLICATION

*Pseudomonas aeruginosa* is an obligately aerobic gram-negative *bacillus* being widely existing in the natural world. Although its pathogenicity is usually low, it is a pathogen that causes opportunistic infections, often occurring in patients suffering from various pre-existing diseases such as cancer, diabetes, immunodeficiency diseases and patients administered with pharmaceuticals exhibiting immune-inhibitory action. Patients with breached skin mucous membrane are prone to *P. aeruginosa* infections while it also poses considerable risk to patients with chronic structural lung diseases (such as COPD or cystic fibrosis). *P. aeruginosa* may often cause pneumonia, urinary tract infection, sepsis and the like, and often leading to severe results. Up to 10% of nosocomial infections are attributed to *P. aeruginosa*, with mortality rates approaching 40% in patients with *P. aeruginosa* bacteremia. In clinical fields, *P. aeruginosa* infection is considered as one of the most difficult infections to be treated not only because *P. aeruginosa* has inherently low sensitivity to existent antibiotics, but also because of its high tendency to acquire resistance to various antibiotics. Thus the strategy of developing an arsenal of antibiotics has limited merits in combating *P. aeruginosa* infections.

*Pseudomonas aeruginosa* is a major cause of hospital-acquired infections, particularly in mechanically ventilated patients, and it is the leading cause of death in cystic fibrosis patients. A key virulence factor associated with disease severity is the *P. aeruginosa* type III secretion system (T3SS), which injects bacterial toxins directly into the cytoplasm of host cells. High cytotoxicity of *Pseudomonas aeruginosa* is exerted by injection of toxin into a eukaryotic cell via a type III exotoxin secretion system (T3SS). PcrV is a protein of 294 residues (NCBI Accession No. AAC45935, SEQ ID NO: 71) constituting the type III exotoxin secretion system, and an operon sequence encoding the same is open to the public (U.S. Pat. No. 6,551,795, Yahr, T. L. et al., *J. Bacteriol.*, 1997, vol. 179, p. 7165). The PcrV protein, located at the tip of the T3SS injectisome complex, is required for T3SS function and is a well-validated target in animal models of immunoprophylactic strategies targeting *P. aeruginosa*. The *P. aeruginosa* T3SS is a well-validated target for intervention in infections caused by this opportunistic pathogen. Both active vaccination with T3SS component proteins and passive immunotherapy targeting PcrV strongly attenuate *P. aeruginosa* disease in animal models. Since control for PcrV can possibly lead a therapeutic means in controlling *Pseudomonas aeruginosa* infection (T. Sawa et al., *Nature Medicine*, 1999, vol. 5, p. 392), polyclonal antibodies (Shime N et al., *J. Immunol.* 2001, vol. 167, p. 5880, Imamura Y et al., *Eur. Respir. J.*, 2007, Vol. 29, p. 965) and monoclonal antibodies (WO2002064161A2, Karine Faure et al., *J. Immune. Based. Therapies and Vaccines*, 2003, Vol. 1, Dara W. Frank et al., *J. Infect. Disease*, 2002, Vol. 186, p. 64) against PcrV having neutralizing activity are reported. However, polyclonal antibodies are difficult to be humanized and to be used as pharmaceutical compositions because of the difficulty in improving antigenicity. An antibody against PcrV, designated V2L2-MD, is described in Warrener et al., 2014, *Antimicrob. Agents Chemother.*, 58, 4384-4391. A pegylated Fab fragment of an anti-PcrV Mab, based on the PcrV-specific mouse monoclonal antibody MAb166, is inactive for preventing *P. aeruginosa* respiratory infections in mechanically ventilated patients. While effective in blocking *P. aeruginosa* T3SS in vitro, MAb166 requires relatively high antibody doses for protection in animal models. The present application provides novel anti-PcrV mAbs that showed potent inhibition of PcrV in vitro and in vivo.

One key component of the *P. aeruginosa* biofilm matrix is the polysaccharide Psl, which is produced by proteins encoded within the polysaccharide synthesis locus. Psl is both cell-free and surface-associated. The structure of cell-free Psl is composed of a repeating pentasaccharide of D-mannose, L-rhamnose, and D-glucose. Since Psl serves both a structural and protective function during biofilm formation, and is also known to protect biofilms form antibiotics, by chemical binding, and from the immune system by an unknown mechanism, it may be an ideal target for novel therapeutic options (Ray VA. et al. Anti-Psl Targeting of *Pseudomonas aeruginosa* Biofilms for Neutrophil-Mediated Disruption. *Sci Rep.* 2017). Human monoclonal antibodies (mAbs) targeting Psl, for example, Wapr-001, Wapr-016, Cam-003 or its derivative, Ps10096 were described in (DiGiandomenico, A. et al. Identification of broadly protective human antibodies to *Pseudomonas aeruginosa* exopolysaccharide Psl by phenotypic screening. *J Exp Med* 209, 1273-1287; Valerie A. Ray, et al, Anti-Psl targeting of *Pseudomonas aeruginosa* biofilms for neutrophil mediated disruption, *Scientific Reports* 7, Article number: 16065(2017)). MedI3902 (also known as MEDI3902) is a bivalent, bispecific human immunoglobulin G1(IgG1) kappa monoclonal antibody (mAb) that selectively binds to PcrV proteins and Psl exopolysaccharides on the surface of *Pseudomonas aeruginosa*. MedI3902 is highly protective in the *Pseudomonas aeruginosa* murine infection model. See, e.g., PCT publication Nos. WO2013/070615, WO2014/074528, PCT application Nos. PCT/US2015/029063, and PCT application No. PCT/US 2015/036576.

The disclosures of all publications, patents, patent applications and published patent applications referred to herein are hereby incorporated herein by reference in their entirety.

BRIEF SUMMARY OF THE APPLICATION

The present application provides bispecific molecules specifically recognizing *Pseudomonas* PcrV and specifically recognizing *Pseudomonas* Psl, bispecific molecules specifically recognizing non-overlapping epitopes of *Pseudomonas* PcrV, and pharmaceutical compositions comprising antigen binding proteins specifically recognizing non-overlapping epitopes of *Pseudomonas* PcrV and/or antigen binding proteins specifically recognizing Psl. Also provided are methods of use thereof for preventing and treating *Pseudomonas* infections.

In one aspect, the present application provides a bispecific molecule comprising a first antigen-binding domain specifically recognizing *Pseudomonas* PcrV, and a second antigen-binding domain specifically recognizing *Pseudomonas* Psl, wherein the first antigen-binding domain comprises: (a) heavy chain variable domain ($V_H$) comprising a heavy chain complementarity determining region (HC-CDR) 1 comprising $DX_1X_2MS$ (SEQ ID NO: 20), wherein $X_1$ is N or Y, and $X_2$ is Y, H or P; an HC-CDR2 comprising $X_1$ISESGGSTNYADSVKG (SEQ ID NO: 15), wherein $X_1$ is V or G; and an HC-CDR3 comprising $GRFSTX_1SX_2HFX_3RAVYGMDV$ (SEQ ID NO: 21), wherein $X_1$ is L, S, N or D, $X_2$ is S or A, $X_3$ is F or Y; and a light chain variable domain ($V_L$) comprising a light chain complementarity determining region (LC-CDR) 1 comprising RASQGISSYLA (SEQ ID NO: 10); an LC-CDR2 comprising AASTLQS (SEQ ID NO: 11), and an LC-CDR3 comprising $QQLSSYPLX_1$ (SEQ ID NO: 19), wherein $X_1$ is S or T; or (b) a $V_H$ comprising a HC-CDR1 comprising SYWMH (SEQ ID NO: 22); an HC-CDR2 comprising $RINEX_1EX_2SISYADSVKG$ (SEQ ID NO: 44), wherein $X_1$ is D or N, and $X_2$ is T, G or R; and an HC-CDR3 comprising $DGPYDX_1X_2DI$ (SEQ ID NO: 45), wherein $X_1$ is S, A, or T, and $X_2$ is F or L; and a $V_L$ comprising an LC-CDR1 comprising $RASQX_1VX_2X_3NLA$ (SEQ ID NO: 46), wherein $X_1$ is S, G or N, $X_2$ is S, R or K and $X_3$ is S or N; an LC-CDR2 comprising $X_1$ASSRAT (SEQ ID NO: 42), wherein $X_1$ is D or H, and an LC-CDR3 comprising $QQYGX_1X_2PX_3T$ (SEQ ID NO: 47), wherein $X_1$ is S, L or N, $X_2$ is S, Q or E and $X_3$ is L or I; or (c) a $V_H$ comprising an HC-CDR1 comprising $X_1X_2X_3MS$ (SEQ ID NO: 17), wherein $X_1$ is D or S, $X_2$ is Y or N, and $X_3$ is P, H, Y or S; an HC-CDR2 comprising $X_1$ISESGGSTX$_2$X$_3$ADSVKG (SEQ ID NO: 18), wherein $X_1$ is G or V; $X_2$ is N or Y; and $X_3$ is D or Y; and an HC-CDR3 comprising $GRFX_1X_2X_3X_4X_5X_6FX_7RAVYGMDV$ (SEQ ID NO: 38), wherein $X_1$ is S or C, $X_2$ is T, G, D, Y, Q or A, $X_3$ is S, D, N, E, L, A, or Y, $X_4$ is S, T, Y, or A, $X_5$ is S, H, Q, A, R, K, G, E, Y or D, $X_6$ is H or C, and $X_7$ is F or Y; and a $V_L$ comprising an LC-CDR1 comprising $RASQGIX_1SYLA$ (SEQ ID NO: 209), wherein $X_1$ is S or R; an LC-CDR2 comprising AASTLQS (SEQ ID NO: 11); and an LC-CDR3 comprising $QQLX_1SYPLX_2$ (SEQ ID NO: 210), wherein $X_1$ is S, N or K, and $X_2$ is S or T; or (d) a $V_H$ comprising an HC-CDR1 comprising SYWMH (SEQ ID NO: 22); an HC-CDR2 comprising $RINEX_1EX_2SISYADSVKG$ (SEQ ID NO: 211), wherein $X_1$ is D, N, I, L or V, $X_2$ is S, T, R, G or N; and an HC-CDR3 comprising $DGPYDX_1X_2DI$ (SEQ ID NO: 45), wherein $X_1$ is S, A or T, $X_2$ is F or L; and a $V_L$ comprising an LC-CDR1 comprising $RASQX_1VX_2X_3NLA$ (SEQ ID NO: 212), wherein $X_1$ is N, G, D or S, $X_2$ is K, R, S, N or T, $X_3$ is N, G, S or D; an LC-CDR2 comprising $X_1$ASSRAT (SEQ ID NO: 213), wherein $X_1$ is D, N, H or A; and an LC-CDR3 comprising $QQYGX_1X_2PX_3T$ (SEQ ID NO: 214), wherein $X_1$ is S, T, E, H, N, A, D, M or L, $X_2$ is S, Q, E, T, D, G, H, L, N, V or Y, and $X_3$ is I, L or V. In some embodiments, the second antigen-binding domain comprises: (a) a $V_H$ comprising a HC-CDR1 comprising SSGDYWG (SEQ ID NO: 48); an HC-CDR2 comprising $SIHNX_1GSTYYNPSLKG$ (SEQ ID NO: 81), wherein $X_1$ is S or Q; and an HC-CDR3 comprising $QFGSETYYX_1GIX_2P$ (SEQ ID NO: 82), wherein $X_1$ is T, N or P, and $X_2$ is D or Q; and a $V_L$ comprising an LC-CDR1 comprising $RSSQSLLHSX_1GYNYLD$ (SEQ ID NO: 83), wherein $X_1$ is N or R; an LC-CDR2 comprising LGSNRAS (SEQ ID NO: 70), and an LC-CDR3 comprising MQALQTPYT (SEQ ID NO: 74); or (b) a $V_H$ comprising a HC-CDR1 comprising IHSVH (SEQ ID NO: 50); an HC-CDR2 comprising TIISSGTTTTYAQSFQD (SEQ ID NO: 55); and an HC-CDR3 comprising $DGX_1S$ (SEQ ID NO: 84), wherein $X_1$ is D or T; and a $V_L$ comprising an LC-CDR1 comprising RASQGISSWLA (SEQ ID NO: 68); an LC-CDR2 comprising HASTLES (SEQ ID NO: 72), and an LC-CDR3 comprising $LQAX_1SLPHT$ (SEQ ID NO: 85), wherein $X_1$ is N, F, S or K; or (c) a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75; or (d) a $V_H$ comprising an HC-CDR1 comprising the amino acid sequence of SEQ ID NO: 51, an HC-CDR2 comprising the amino acid sequence of SEQ ID NO: 56, and an HC-CDR3 comprising the amino acid sequence of SEQ ID NO: 64; and a $V_L$ comprising: an LC-CDR1 comprising the amino acid sequence of SEQ ID NO: 69, an LC-CDR2 comprising the amino acid sequence of SEQ ID NO: 73, and an LC-CDR3 comprising the amino acid sequence of SEQ ID NO: 80.

In one aspect, there is provided a bispecific molecule comprising a first antigen-binding domain specifically recognizing *Pseudomonas* PcrV, and a second antigen-binding domain specifically recognizing *Pseudomonas* Psl, wherein the second antigen-binding domain comprises: (a) a $V_H$ comprising a HC-CDR1 comprising SSGDYWG (SEQ ID NO: 48); an HC-CDR2 comprising $SIHNX_1GSTYYNPSLKG$ (SEQ ID NO: 81), wherein $X_1$ is S or Q; and an HC-CDR3 comprising $QFGSETYYX_1GIX_2P$ (SEQ ID NO: 82), wherein $X_1$ is T, N or P, and $X_2$ is D or Q; and a $V_L$ comprising an LC-CDR1 comprising $RSSQSLLHSX_1GYNYLD$ (SEQ ID NO: 83), wherein $X_1$ is N or R; an LC-CDR2 comprising LGSNRAS (SEQ ID NO: 70), and an LC-CDR3 comprising MQALQTPYT (SEQ ID NO: 74); or (b) a $V_H$ comprising a HC-CDR1 comprising IHSVH (SEQ ID NO: 50); an HC-CDR2 comprising TIISSGTTTTYAQSFQD (SEQ ID NO: 55); and an HC-CDR3 comprising $DGX_1S$ (SEQ ID NO: 84), wherein $X_1$ is D or T; and a $V_L$ comprising an LC-CDR1 comprising RASQGISSWLA (SEQ ID NO: 68); an LC-CDR2 comprising HASTLES (SEQ ID NO: 72), and an LC-CDR3 comprising $LQAX_1SLPHT$ (SEQ ID NO: 85), wherein $X_1$ is N, F, S or K; or (c) a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75; or (d) a $V_H$ comprising an HC-CDR1 comprising the amino acid sequence of SEQ ID NO: 51, an HC-CDR2 comprising the amino acid sequence of SEQ ID NO: 56, and an HC-CDR3 comprising the amino acid sequence of SEQ ID NO: 64; and a $V_L$ comprising: an LC-CDR1 comprising the amino acid sequence of SEQ ID NO: 69, an LC-CDR2 comprising the amino acid sequence of SEQ ID NO: 73, and an LC-CDR3 comprising the amino acid sequence of SEQ ID NO: 80.

In some embodiments, the first antigen-binding domain comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12. In some embodiments, the first antigen-binding domain comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13. In some embodiments, the first antigen-binding domain comprises: a $V_H$ comprising an HC-CDR1 comprising the amino acid sequence SEQ ID NO: 22, an HC-CDR2 comprising the amino acid sequence of SEQ ID NO: 23, and an HC-CDR3 comprising the amino acid sequence of SEQ ID NO: 26; and a $V_L$ comprising: an LC-CDR1 comprising the amino acid sequence of SEQ ID NO: 30, an LC-CDR2 comprising the amino acid sequence of SEQ ID NO: 33, and an LC-CDR3 comprising the amino acid sequence of SEQ ID NO: 35. In some embodiments, the first antigen-binding domain comprises: a $V_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 27; and a $V_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36.

In some embodiments, the second antigen-binding domain comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the second antigen-binding domain comprises: a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 62; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 76.

In some embodiments according to any one of the bispecific molecules described herein, the first antigen-binding domain comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; and the second antigen-binding domain comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the first antigen-binding domain comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; and the second antigen-binding domain comprises: a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75. In some embodiments, the first antigen-binding domain comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; and the second antigen-binding domain comprises: a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 62; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 76.

In some embodiments, the first antigen-binding domain comprises: a $V_H$ comprising the amino acid sequence of SEQ ID NO: 91 or 161 and a $V_L$ comprising the amino acid sequence of SEQ ID NO: 112 or 182; and the second antigen-binding domain comprises: a $V_H$ comprising the amino acid sequence of SEQ ID NO: 103 or 173 and a $V_L$ comprising the amino acid sequence of SEQ ID NO: 117 or 187. In some embodiments, the first antigen-binding domain comprises: a $V_H$ comprising the amino acid sequence of SEQ ID NO: 91 or 161 and a $V_L$ comprising the amino acid sequence of SEQ ID NO: 112 or 182; and the second antigen-binding domain comprises: a $V_H$ comprising the amino acid sequence of SEQ ID NO: 109 or 179 and a $V_L$ comprising the amino acid sequence of SEQ ID NO: 120 or 190. In some embodiments, the first antigen-binding domain comprises: a $V_H$ comprising the amino acid sequence of SEQ ID NO: 91 or 161 and a $V_L$ comprising the amino acid sequence of SEQ ID NO: 112 or 182; and the second antigen-binding domain comprises: a $V_H$ comprising the amino acid sequence of SEQ ID NO: 107 or 177 and a $V_L$ comprising the amino acid sequence of SEQ ID NO: 119 or 189.

In some embodiments, the first antigen-binding domain is an Fab arm specifically recognizing PcrV, the second antigen-binding domain is a single-chain variable fragment (scFv) specifically recognizing Psl, wherein the molecule further comprises an Fc region comprising CH2 and CH3 domains; and the scFv is interconnected to the Fab arm via a first polypeptide linker (L1) and to the Fc region via a second polypeptide linker (L2); and wherein the bispecific molecule is bivalent for binding to each of PcrV and Psl. In some embodiments, the first antigen-binding domain is a single-chain variable fragment (scFv) specifically recognizing PcrV, the second antigen-binding domain is an Fab arm specifically recognizing Psl, wherein the molecule further comprises an Fc region comprising CH2 and CH3 domains; and the scFv is interconnected to the Fab arm via a first polypeptide linker (L1) and to the Fc region via a second polypeptide linker (L2); and wherein the bispecific molecule is bivalent for binding to each of PcrV and Psl. In some embodiments, the bispecific molecule comprises: the amino acid sequence of SEQ ID NO: 135-136 or 159; and/or the amino acid sequence of any one of SEQ ID NOs: 195-208.

In some embodiments, the bispecific molecule comprises a Fc region, wherein the Fc region is selected from the group consisting of an Fc region from an IgG1, IgG2, IgG3, IgG4, IgA, IgM, IgE, and IgD. In some embodiments, the Fc region comprises a variant Fc region. In some embodiments, the Fc region is aglycosylated. In some embodiments, the Fc region is deglycosylated. In some embodiments, the Fc region has reduced fucosylation or is afucosylated. In some embodiments, the variant Fc region comprises a substitution at position 297. In some embodiments, the substitution at position 297 is 297Q. In some embodiments, the variant Fc region comprises a substitution at one or more of positions 239, 282, 289, 297, 312, 324, 330, 335, 337, 339, 356, 359, 361, 383, 384, 398, 400, 440, 422, and 442, as numbered by the EU index.

In some embodiments, the bispecific molecule comprises a chimeric heavy chain comprising the amino acid sequence of any one of SEQ ID NOs:137-152 and 160 and/or a light chain comprising the amino acid sequence of SEQ ID NO: 135, 136 or 159.

In one aspect, there is provided a pharmaceutical composition comprising: (i) an antigen-binding protein specifically recognizing a first epitope on *Pseudomonas* PcrV and (ii) an antigen-binding protein specifically recognizing a second epitope on *Pseudomonas* PcrV and/or an antigen-binding protein specifically recognizing *Pseudomonas* Psl; wherein the antigen-binding protein recognizing the first epitope on *Pseudomonas* PcrV comprises: (a) a heavy chain variable domain ($V_H$) comprising a heavy chain complementarity determining region (HC-CDR) 1 comprising $DX_1X_2MS$ (SEQ ID NO: 20), wherein $X_1$ is N or Y, and $X_2$ is Y, H or P; an HC-CDR2 comprising $X_1$ISESGGSTNYADSVKG (SEQ ID NO: 15), wherein $X_1$ is V or G; and an HC-CDR3 comprising $GRFSTX_1SX_2HFX_3RAVYGMDV$ (SEQ ID NO: 21), wherein $X_1$ is L, S, N or D, $X_2$ is S or A, $X_3$ is F or Y; and a light chain variable domain ($V_L$) comprising a light chain complementarity determining region (LC-CDR) 1 comprising RASQGISSYLA (SEQ ID NO: 10); an LC-CDR2 comprising AASTLQS (SEQ ID NO: 11), and an LC-CDR3 comprising $QQLSSYPLX_1$(SEQ ID NO: 19), wherein $X_1$ is S or T; or (b) a $V_H$ comprising a HC-CDR1 comprising SYWMH (SEQ ID NO: 22); an HC-CDR2 comprising $RINEX_1EX_2SISYADSVKG$ (SEQ ID NO: 44), wherein $X_1$ is D or N, and $X_2$ is T, G or R; and an HC-CDR3 comprising $DGPYDX_1X_2DI$ (SEQ ID NO: 45), wherein $X_1$ is S, A, or T, and $X_2$ is F or L; and a $V_L$ comprising an LC-CDR1 comprising $RASQX_1VX_2X_3NLA$ (SEQ ID NO: 46), wherein $X_1$ is S, G or N, $X_2$ is S, R or K and $X_3$ is S or N; an LC-CDR2 comprising $X_1$ASSRAT (SEQ ID NO: 42), wherein $X_1$ is D or H, and an LC-CDR3 comprising $QQYGX_1X_2PX_3T$ (SEQ ID NO: 47), wherein $X_1$ is S, L or N, $X_2$ is S, Q or E and $X_3$ is L or I; or (c) a $V_H$ comprising an HC-CDR1 comprising $X_1X_2X_3MS$ (SEQ ID NO: 17), wherein $X_1$ is D or S, $X_2$ is Y or N, and $X_3$ is P, H, Y or S; an HC-CDR2 comprising $X_1$ISESGGSTX$_2$X$_3$ADSVKG (SEQ ID NO: 18), wherein $X_1$ is G or V; $X_2$ is N or Y; and $X_3$ is D or Y; and an HC-CDR3 comprising $GRFX_1X_2X_3X_4X_5X_6FX_7RAVYGMDV$ (SEQ ID NO: 38), wherein $X_1$ is S or C, $X_2$ is T, G, D, Y, Q or A, $X_3$ is S, D, N, E, L, A, or Y, $X_4$ is S, T, Y, or A, $X_5$ is S, H, Q, A, R, K, G, E, Y or D, $X_6$ is H or C, and $X_7$ is F or Y; and a $V_L$ comprising an LC-CDR1 comprising $RASQGIX_1SYLA$ (SEQ ID NO: 209), wherein $X_1$ is S or R; an LC-CDR2 comprising AASTLQS (SEQ ID NO: 11); and an LC-CDR3 comprising $QQLX_1SYPLX_2$ (SEQ ID NO: 210), wherein $X_1$ is S, N or K, and $X_2$ is S or T; or (d) a $V_H$ comprising an HC-CDR1 comprising SYWMH (SEQ ID NO: 22); an HC-CDR2 comprising $RINEX_1EX_2SISYADSVKG$ (SEQ ID NO: 211), wherein $X_1$ is D, N, I, L or V, $X_2$ is S, T, R, G or N; and an HC-CDR3 comprising $DGPYDX_1X_2DI$ (SEQ ID NO: 45), wherein $X_1$ is S, A or T, $X_2$ is F or L; and a $V_L$ comprising an LC-CDR1 comprising $RASQX_1VX_2X_3NLA$ (SEQ ID NO: 212), wherein $X_1$ is N, G, D or S, $X_2$ is K, R, S, N or T, $X_3$ is N, G, S or D; an LC-CDR2 comprising $X_1$ASSRAT (SEQ ID NO: 213), wherein $X_1$ is D, N, H or A; and an LC-CDR3 comprising $QQYGX_1X_2PX_3T$ (SEQ ID NO: 214), wherein $X_1$ is S, T, E, H, N, A, D, M or L, $X_2$ is S, Q, E, T, D, G, H, L, N, V or Y, and $X_3$ is I, L or V.

In one aspect, there is provided a method of treating and/or preventing a disease or condition in an individual in need thereof, comprising administering to the individual an effective amount of (i) an antigen-binding protein specifically recognizing a first epitope on *Pseudomonas* PcrV and (ii) an antigen-binding protein specifically recognizing a second epitope on *Pseudomonas* PcrV and/or an antigen-binding protein specifically recognizing *Pseudomonas* Psl; wherein the antigen-binding protein specifically recognizing the first epitope on *Pseudomonas* PcrV comprises: (a) a heavy chain variable domain ($V_H$) comprising a heavy chain complementarity determining region (HC-CDR) 1 comprising $DX_1X_2MS$ (SEQ ID NO: 20), wherein $X_1$ is N or Y, and $X_2$ is Y, H or P; an HC-CDR2 comprising $X_1$ISESGGSTNYADSVKG (SEQ ID NO: 15), wherein $X_1$ is V or G; and an HC-CDR3 comprising $GRFSTX_1SX_2HFX_3RAVYGMDV$ (SEQ ID NO: 21), wherein $X_1$ is L, S, N or D, $X_2$ is S or A, $X_3$ is F or Y; and a light chain variable domain ($V_L$) comprising a light chain complementarity determining region (LC-CDR) 1 comprising RASQGISSYLA (SEQ ID NO: 10); an LC-CDR2 comprising AASTLQS (SEQ ID NO: 11), and an LC-CDR3 comprising $QQLSSYPLX_1$(SEQ ID NO: 19), wherein $X_1$ is S or T; or (b) a $V_H$ comprising a HC-CDR1 comprising SYWMH (SEQ ID NO: 22); an HC-CDR2 comprising $RINEX_1EX_2SISYADSVKG$ (SEQ ID NO: 44), wherein $X_1$ is D or N, and $X_2$ is T, G or R; and an HC-CDR3 comprising $DGPYDX_1X_2DI$ (SEQ ID NO: 45), wherein $X_1$ is S, A, or T, and $X_2$ is F or L; and a $V_L$ comprising an LC-CDR1 comprising RASQX$_1$VX$_2$X$_3$NLA (SEQ ID NO: 46), wherein X$_1$ is S, G or N, X$_2$ is S, R or K and X$_3$ is S or N; an LC-CDR2 comprising X$_1$ASSRAT (SEQ ID NO: 42), wherein X$_1$ is D or H, and an LC-CDR3 comprising QQYGX$_1$X$_2$PX$_3$T (SEQ ID NO: 47), wherein X$_1$ is S, L or N, X$_2$ is S, Q or E and X$_3$ is L or I; or (c) a V$_H$ comprising an HC-CDR1 comprising X$_1$X$_2$X$_3$MS (SEQ ID NO: 17), wherein X$_1$ is D or S, X$_2$ is Y or N, and X$_3$ is P, H, Y or S; an HC-CDR2 comprising X$_1$ISESGGSTX$_2$X$_3$ADSVKG (SEQ ID NO: 18), wherein X$_1$ is G or V; X$_2$ is N or Y; and X$_3$ is D or Y; and an HC-CDR3 comprising GRFX$_1$X$_2$X$_3$X$_4$X$_5$X$_6$FX$_7$RAVYGMDV (SEQ ID NO: 38), wherein X$_1$ is S or C, X$_2$ is T, G, D, Y, Q or A, X$_3$ is S, D, N, E, L, A, or Y, X$_4$ is S, T, Y, or A, X$_5$ is S, H, Q, A, R, K, G, E, Y or D, X$_6$ is H or C, and X$_7$ is F or Y; and a V$_L$ comprising an LC-CDR1 comprising RASQGIX$_1$SYLA (SEQ ID NO: 209), wherein X$_1$ is S or R; an LC-CDR2 comprising AASTLQS (SEQ ID NO: 11); and an LC-CDR3 comprising QQLX$_1$SYPLX$_2$ (SEQ ID NO: 210), wherein X$_1$ is S, N or K, and X$_2$ is S or T; or (d) a V$_H$ comprising an HC-CDR1 comprising SYWMH (SEQ ID NO: 22); an HC-CDR2 comprising RINEX$_1$EX$_2$SISYADSVKG (SEQ ID NO: 211), wherein X$_1$ is D, N, I, L or V, X$_2$ is S, T, R, G or N; and an HC-CDR3 comprising DGPYDX$_1$X$_2$DI (SEQ ID NO: 45), wherein X$_1$ is S, A or T, X$_2$ is F or L; and a V$_L$ comprising an LC-CDR1 comprising RASQX$_1$VX$_2$X$_3$NLA (SEQ ID NO: 212), wherein X$_1$ is N, G, D or S, X$_2$ is K, R, S, N or T, X$_3$ is N, G, S or D; an LC-CDR2 comprising X$_1$ASSRAT (SEQ ID NO: 213), wherein X$_1$ is D, N, H or A; and an LC-CDR3 comprising QQYGX$_1$X$_2$PX$_3$T (SEQ ID NO: 214), wherein X$_1$ is S, T, E, H, N, A, D, M or L, X$_2$ is S, Q, E, T, D, G, H, L, N, V or Y, and X$_3$ is I, L or V.

In some embodiments, the antigen-binding protein specifically recognizing the second epitope on *Pseudomonas* PcrV comprises: (a) a V$_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a V$_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13; or (b) a V$_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a V$_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; or (c) a V$_H$ comprising an HC-CDR1 comprising the amino acid sequence SEQ ID NO: 22, an HC-CDR2 comprising the amino acid sequence of SEQ ID NO: 23, and an HC-CDR3 comprising the amino acid sequence of SEQ ID NO: 26; and a V$_L$ comprising: an LC-CDR1 comprising the amino acid sequence of SEQ ID NO: 30, an LC-CDR2 comprising the amino acid sequence of SEQ ID NO: 33, and an LC-CDR3 comprising the amino acid sequence of SEQ ID NO: 35; or (d) a V$_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 27; and a V$_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36.

In some embodiments, the antigen-binding protein specifically recognizing *Pseudomonas* Psl comprises: (a) a V$_H$ comprising a HC-CDR1 comprising SSGDYWG (SEQ ID NO: 48); an HC-CDR2 comprising SIHNX$_1$GSTYYNPSLKG (SEQ ID NO: 81), wherein X$_1$ is S or Q; and an HC-CDR3 comprising QFGSETYYX$_1$GIX$_2$P (SEQ ID NO: 82), wherein X$_1$ is T, N or P, and X$_2$ is D or Q; and a V$_L$ comprising an LC-CDR1 comprising RSSQSLLHSX$_1$GYNYLD (SEQ ID NO: 83), wherein X$_1$ is N or R; an LC-CDR2 comprising LGSNRAS (SEQ ID NO: 70), and an LC-CDR3 comprising MQALQTPYT (SEQ ID NO: 74); or (b) a V$_H$ comprising a HC-CDR1 comprising IHSVH (SEQ ID NO: 50); an HC-CDR2 comprising TIISSGTTTTYAQSFQD (SEQ ID NO: 55); and an HC-CDR3 comprising DGX$_1$S (SEQ ID NO: 84), wherein X$_1$ is D or T; and a V$_L$ comprising an LC-CDR1 comprising RASQGISSWLA (SEQ ID NO: 68); an LC-CDR2 comprising HASTLES (SEQ ID NO: 72), and an LC-CDR3 comprising LQAX$_1$SLPHT (SEQ ID NO: 85), wherein X$_1$ is N, F, S or K; or (c) a V$_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a V$_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75; or (d) a V$_H$ comprising an HC-CDR1 comprising the amino acid sequence of SEQ ID NO: 51, an HC-CDR2 comprising the amino acid sequence of SEQ ID NO: 56, and an HC-CDR3 comprising the amino acid sequence of SEQ ID NO: 64; and a V$_L$ comprising: an LC-CDR1 comprising the amino acid sequence of SEQ ID NO: 69, an LC-CDR2 comprising the amino acid sequence of SEQ ID NO: 73, and an LC-CDR3 comprising the amino acid sequence of SEQ ID NO: 80.

In one aspect, there is provided a pharmaceutical composition comprising: (i) an antigen-binding protein specifically recognizing *Pseudomonas* Psl and (ii) an antigen-binding protein specifically recognizing a first epitope on *Pseudomonas* PcrV and/or an antigen-binding protein specifically recognizing a second epitope on *Pseudomonas* PcrV, wherein the antigen-binding protein specifically recognizing *Pseudomonas* Psl comprises: (a) a V$_H$ comprising a HC-CDR1 comprising SSGDYWG (SEQ ID NO: 48); an HC-CDR2 comprising SIHNX$_1$GSTYYNPSLKG (SEQ ID NO: 81), wherein X$_1$ is S or Q; and an HC-CDR3 comprising QFGSETYYX$_1$GIX$_2$P (SEQ ID NO: 82), wherein X$_1$ is T, N or P, and X$_2$ is D or Q; and a V$_L$ comprising an LC-CDR1 comprising RSSQSLLHSX$_1$GYNYLD (SEQ ID NO: 83), wherein X$_1$ is N or R; an LC-CDR2 comprising LGSNRAS (SEQ ID NO: 70), and an LC-CDR3 comprising MQALQTPYT (SEQ ID NO: 74); or (b) a V$_H$ comprising a HC-CDR1 comprising IHSVH (SEQ ID NO: 50); an HC-CDR2 comprising TIISSGTTTTYAQSFQD (SEQ ID NO: 55); and an HC-CDR3 comprising DGX$_1$S (SEQ ID NO: 84), wherein X$_1$ is D or T; and a V$_L$ comprising an LC-CDR1 comprising RASQGISSWLA (SEQ ID NO: 68); an LC-CDR2 comprising HASTLES (SEQ ID NO: 72), and an LC-CDR3 comprising LQAX$_1$SLPHT (SEQ ID NO: 85), wherein X$_1$ is N, F, S or K; or (c) a V$_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a V$_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75; or (d) a $V_H$ comprising an HC-CDR1 comprising the amino acid sequence of SEQ ID NO: 51, an HC-CDR2 comprising the amino acid sequence of SEQ ID NO: 56, and an HC-CDR3 comprising the amino acid sequence of SEQ ID NO: 64; and a $V_L$ comprising: an LC-CDR1 comprising the amino acid sequence of SEQ ID NO: 69, an LC-CDR2 comprising the amino acid sequence of SEQ ID NO: 73, and an LC-CDR3 comprising the amino acid sequence of SEQ ID NO: 80.

In one aspect, there is provided a method of treating and/or preventing a disease or condition in an individual in need thereof, comprising administering to the individual an effective amount of: (i) an antigen-binding protein specifically recognizing *Pseudomonas* Psl and (ii) an antigen-binding protein specifically recognizing a first epitope on *Pseudomonas* PcrV and/or an antigen-binding protein specifically recognizing a second epitope on *Pseudomonas* PcrV, wherein the antigen-binding protein specifically recognizing *Pseudomonas* Psl comprises: (a) a $V_H$ comprising a HC-CDR1 comprising SSGDYWG (SEQ ID NO: 48); an HC-CDR2 comprising SIHNX$_1$GSTYYNPSLKG (SEQ ID NO: 81), wherein X$_1$ is S or Q; and an HC-CDR3 comprising QFGSETYYX$_1$GIX$_2$P (SEQ ID NO: 82), wherein X$_1$ is T, N or P, and X$_2$ is D or Q; and a $V_L$ comprising an LC-CDR1 comprising RSSQSLLHSX$_1$GYNYLD (SEQ ID NO: 83), wherein X$_1$ is N or R; an LC-CDR2 comprising LGSNRAS (SEQ ID NO: 70), and an LC-CDR3 comprising MQALQTPYT (SEQ ID NO: 74); or (b) a $V_H$ comprising a HC-CDR1 comprising IHSVH (SEQ ID NO: 50); an HC-CDR2 comprising TIISSGTTTTYAQSFQD (SEQ ID NO: 55); and an HC-CDR3 comprising DGX$_1$S (SEQ ID NO: 84), wherein X$_1$ is D or T; and a $V_L$ comprising an LC-CDR1 comprising RASQGISSWLA (SEQ ID NO: 68); an LC-CDR2 comprising HASTLES (SEQ ID NO: 72), and an LC-CDR3 comprising LQAX$_1$SLPHT (SEQ ID NO: 85), wherein X$_1$ is N, F, S or K; or (c) a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75; or (d) a $V_H$ comprising an HC-CDR1 comprising the amino acid sequence of SEQ ID NO: 51, an HC-CDR2 comprising the amino acid sequence of SEQ ID NO: 56, and an HC-CDR3 comprising the amino acid sequence of SEQ ID NO: 64; and a $V_L$ comprising: an LC-CDR1 comprising the amino acid sequence of SEQ ID NO: 69, an LC-CDR2 comprising the amino acid sequence of SEQ ID NO: 73, and an LC-CDR3 comprising the amino acid sequence of SEQ ID NO: 80.

In some embodiments, the antigen-binding protein specifically recognizing the first epitope on *Pseudomonas* PcrV comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13.

In some embodiments, the antigen-binding protein specifically recognizing the first epitope on *Pseudomonas* PcrV comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12. In some embodiments, the antigen-binding protein specifically recognizing the first epitope on *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 23, and an HC-CDR3 comprising the amino acid sequence of SEQ ID NO: 26; and a $V_L$ comprising: an LC-CDR1 comprising the amino acid sequence of SEQ ID NO: 30, an LC-CDR2 comprising the amino acid sequence of SEQ ID NO: 33, and an LC-CDR3 comprising the amino acid sequence of SEQ ID NO: 35. In some embodiments, the antigen-binding protein specifically recognizing the second epitope on *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 27; and a $V_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36).

In some embodiments, the antigen-binding protein specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the antigen-binding protein specifically recognizing *Pseudomonas* Psl comprises: a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 62; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 76.

In some embodiments, the antigen-binding protein specifically recognizing the first epitope on *Pseudomonas* PcrV comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; and the antigen-binding protein specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74.

In some embodiments, the antigen-binding protein specifically recognizing the first epitope on *Pseudomonas* PcrV comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; and the antigen-binding protein specifically recognizing *Pseudomonas* Psl comprises: a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75.

In some embodiments, the antigen-binding protein specifically recognizing the first epitope on *Pseudomonas* PcrV comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13; and the antigen-binding protein specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74.

In some embodiments, the antigen-binding protein specifically recognizing the first epitope on *Pseudomonas* PcrV comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; the antigen-binding protein specifically recognizing the second epitope on *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 27; and a $V_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36; and the antigen-binding protein specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74.

In some embodiments, the antigen-binding protein specifically recognizing the first epitope on *Pseudomonas* PcrV comprises: a $V_H$ comprising the amino acid sequence of SEQ ID NO: 91 and a $V_L$ comprising the amino acid sequence of SEQ ID NO: 112; and the antigen-binding protein specifically recognizing *Pseudomonas* Psl comprises: a $V_H$ comprising the amino acid sequence of SEQ ID NO: 103 and a $V_L$ comprising the amino acid sequence of SEQ ID NO: 117. In some embodiments, the antigen-binding protein specifically recognizing the first epitope on *Pseudomonas* PcrV comprises: a $V_H$ comprising the amino acid sequence of SEQ ID NO: 92 and a $V_L$ comprising the amino acid sequence of SEQ ID NO: 113; and the antigen-binding protein specifically recognizing *Pseudomonas* Psl comprises: a $V_H$ comprising the amino acid sequence of SEQ ID NO: 103 and a $V_L$ comprising the amino acid sequence of SEQ ID NO: 117. In some embodiments, the antigen-binding protein specifically recognizing the first epitope on *Pseudomonas* PcrV comprises: a $V_H$ comprising the amino acid sequence of SEQ ID NO: 91 and a $V_L$ comprising the amino acid sequence of SEQ ID NO: 112; and the antigen-binding protein specifically recognizing *Pseudomonas* Psl comprises: a $V_H$ comprising the amino acid sequence of SEQ ID NO: 107 and a $V_L$ comprising the amino acid sequence of SEQ ID NO: 119. In some embodiments, the antigen-binding protein specifically recognizing the first epitope on *Pseudomonas* PcrV comprises: a $V_H$ comprising the amino acid sequence of SEQ ID NO: 91 and a $V_L$ comprising the amino acid sequence of SEQ ID NO: 112; the antigen-binding protein specifically recognizing the second epitope on *Pseudomonas* PcrV comprises: a $V_H$ comprising the amino acid sequence of SEQ ID NO: 96 and a $V_L$ comprising the amino acid sequence of SEQ ID NO: 115; and the antigen-binding protein specifically recognizing *Pseudomonas* Psl comprises: a $V_H$ comprising the amino acid sequence of SEQ ID NO: 103 and a $V_L$ comprising the amino acid sequence of SEQ ID NO: 117.

In some embodiments, the antigen-binding protein specifically recognizing the first epitope on *Pseudomonas* PcrV, the antigen-binding protein specifically recognizing the second epitope on *Pseudomonas* PcrV and/or the antigen-binding protein specifically recognizing *Pseudomonas* Psl are administered concurrently. In some embodiments, the antigen-binding protein specifically recognizing the first epitope on *Pseudomonas* PcrV, the antigen-binding protein specifically recognizing the second epitope on *Pseudomonas* PcrV and/or the antigen-binding protein specifically recognizing *Pseudomonas* Psl are administered consecutively.

In some embodiments, the ratio by molar mass of the antigen-binding protein specifically recognizing *Pseudomonas* Psl and the antigen-binding protein specifically recognizing the first epitope on *Pseudomonas* PcrV is any one of about 5:1, 4:1, 3:1, 2:1, 1:1, 1:2, 1:3, 1:4 or 1:5. In some embodiments, the ratio by molar mass of the antigen-binding protein specifically recognizing *Pseudomonas* Psl and the antigen-binding protein specifically recognizing the first epitope on *Pseudomonas* PcrV is about 2:1 or 1:1. In some embodiments, the ratio by molar mass of the antigen-binding protein specifically recognizing the first epitope on *Pseudomonas* PcrV and the antigen-binding protein specifically recognizing the second epitope on *Pseudomonas* PcrV is any one of about 5:1, 4:1, 3:1, 2:1, 1:1, 1:2, 1:3, 1:4 or 1:5. In some embodiments, the ratio by molar mass of the antigen-binding protein specifically recognizing the first epitope on *Pseudomonas* PcrV and the antigen-binding protein specifically recognizing the second epitope on *Pseudomonas* PcrV is about 2:1 or 1:1. In some embodiments, the ratio by molar mass of the first antigen-binding protein specifically recognizing the first epitope on *Pseudomonas* PcrV, the second antigen-binding protein specifically recognizing the second epitope on *Pseudomonas* PcrV and the antigen-binding protein specifically recognizing *Pseudomonas* Psl is about 1:1:1 or 1:1:2.

In some embodiments, there are provided methods of treating and/or preventing a disease or condition in an individual in need thereof, comprising administering to the individual an effective amount of any one of the pharmaceutical compositions and/or bispecific molecules described herein. In some embodiments, there are provided the use of any one of the bispecific molecules described herein for the preparation of pharmaceutical compositions for treating a disease or condition in an individual in need.

In some embodiments, according to any one of the methods described herein, the disease or condition is a pathogenic infection. In some embodiments, the infection is a gram-negative bacterium infection. In some embodiments, the bacterium is *Pseudomonas aeruginosa*. In some embodiments, the disease or condition comprises one or more symptoms caused by *Pseudomonas aeruginosa* infection. In some embodiments, the symptom comprises one or more of fever, chills, fatigues, muscle and joint pain, swelling of joints, headache, diarrhea, skin rashes, pus in wounds, bacteremia, acute pneumonia, intraperitoneal infection, respiratory tract infections, septic shock, suppurative arthritis, enteritis, skin and soft tissue infections, urinary tract infections, intestinal infections, ulcerative keratitis, chronic suppurative otitis media, mastoiditis, sinusitis, or endocarditis.

In some embodiments, there is provided isolated nucleic acid molecule(s) that encodes any one of the antigen-binding proteins recognizing PcrV, antigen-binding proteins recognizing Psl, and bispecific molecules described above. In some embodiments, there is provided a vector comprising any one of the nucleic acid molecules described above. In some embodiments, there is provided a host cell comprising any one of antigen-binding proteins or bispecific molecules described above, any one of the nucleic acid molecules described above, or any one of the vectors described above. In some embodiments, there is provided a method of producing an anti-PcrV antibody, an anti-Psl antibody, or a bispecific molecule recognizing PcrV and/or Psl, comprising: a) culturing any one of the host cells described above under conditions effective to express the anti-PcrV antibody, the anti-Psl antibody, or the bispecific molecule recognizing PcrV and/or PSL; and b) obtaining the expressed anti-PcrV antibody, anti-Psl antibody, or bispecific molecule recognizing PcrV and/or Psl from the host cell.

Also provided are pharmaceutical compositions, kits and articles of manufacture comprising any one of the bispecific molecules, anti-PcrV and/or anti-Psl antibodies, nucleic acids, vectors, isolated host cells described above.

DETAILED DESCRIPTION OF THE APPLICATION

Figure 1A:
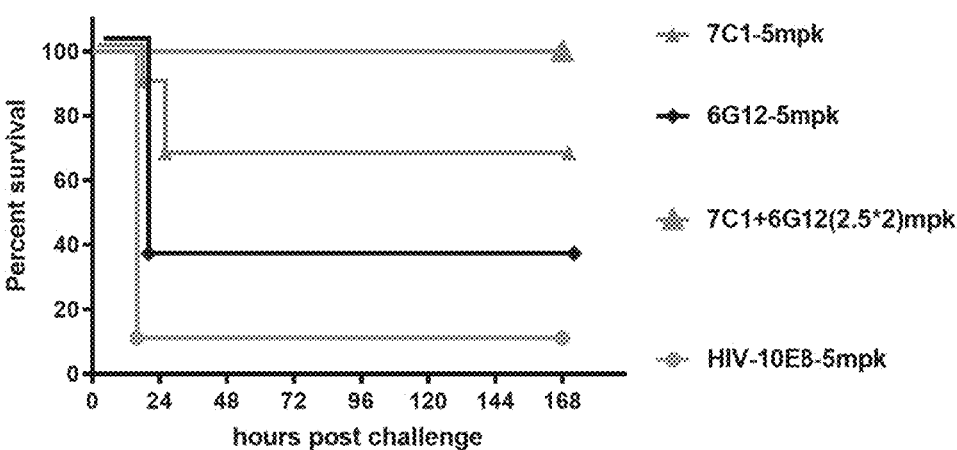
FIGS. 1A and 1B show the ability of the combination of anti-PcrV antibodies recognizing non-overlapping epitopes (7C1 and 6G12) to improve survival in a mouse intraperitoneal infection model at double the lethal dose (2×LD90) of *P. aeruginosa* inoculation compared to the each anti-PcrV antibody alone.

The present application in one aspect provides bispecific molecules specifically recognizing PcrV and/or Psl. The present application in one aspect provides combinations of antigen-binding proteins specifically recognizing PcrV and/or antigen-binding proteins specifically recognizing Psl. By using a combination of selections on scFv phage libraries, affinity maturation and appropriately designed biochemical and biological assays, we have identified highly potent antigen-binding proteins that bind to PcrV and to highly potent antibody molecules that bind to Psl. The results herein indicate that combinations of these antigen-binding moieties, either as (i) a combination in a pharmaceutical composition or (ii) a bispecific antibody can inhibit the action of red blood cell and A549 cell lysis by *Pseudomonas aeruginosa* in an additive or synergistic manner, and provide stronger therapeutic and prophylactic in vivo protection against *Pseudomonas aeruginosa* compared to the single antibody molecules alone.

Also provided are nucleic acids encoding the PcrV- and Psl-binding proteins and domains, the bispecific molecules, compositions comprising the PcrV- and Psl-binding proteins or the bispecific molecules, and methods of making and using the PcrV- and Psl-binding proteins and the bispecific molecules.

Definitions

As used herein, "treatment" or "treating" is an approach for obtaining beneficial or desired results, including clinical results. For purposes of this application, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., systemic spread of a pathogen) of the disease, preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of infection (such as, for example, host cell lysis or necrosis). The methods of the application contemplate any one or more of these aspects of treatment.

The term "prevent," and similar words such as "prevented," "preventing," "prevention" or "prophylactic" etc., indicate an approach for preventing, inhibiting, or reducing the likelihood of the occurrence or recurrence of, a disease or condition, e.g., a pathogenic infection. It also refers to delaying the occurrence or recurrence of a disease or condition, or delaying the occurrence or recurrence of the symptoms of a disease or condition. As used herein, "prevention" and similar words also includes reducing the intensity, effect, symptoms and/or burden of a disease or condition prior to occurrence or recurrence of the disease or condition. As used herein, "prevention" and similar words also includes reducing the risk and susceptibility to occurrence or recurrence of the disease or condition, e.g., a pathogenic infection.

As used herein, the term "antigen binding protein" refers in its broadest sense to a protein comprising a moiety that specifically binds to an antigen or target. Examples of antigen binding proteins are antibodies and antibody fragments.

The term "antibody" herein is used in the broadest sense and encompasses a variety of antibody structures, including, but not limited to, monoclonal antibodies, polyclonal antibodies, monospecific, multispecific antibodies (e.g., bispecific antibodies), full-length antibodies and antigen-binding fragments thereof, so long as they exhibit the desired antigen binding activity. A full-length antibody comprises two heavy chains and two light chains. The variable regions of the light and heavy chains are responsible for antigen binding. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of $\alpha$, $\delta$, $\varepsilon$, $\gamma$, and $\mu$ heavy chains, respectively. Several of the major antibody classes are divided into subclasses such as IgG1 ($\gamma$1 heavy chain), IgG2 ($\gamma$2 heavy chain), IgG3 ($\gamma$3 heavy chain), IgG4 ($\gamma$4 heavy chain), IgA1 ($\alpha$1 heavy chain), or IgA2 ($\alpha$2 heavy chain).

The term "antigen-binding fragment" as used herein includes an antibody fragment including, for example, a diabody, a Fab, a Fab', a F(ab')$_2$, an Fv fragment, a disulfide stabilized Fv fragment (dsFv), a (dsFv)2, a bispecific dsFv (dsFv-dsFv'), a disulfide stabilized diabody (ds diabody), a single-chain Fv (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment also includes a fusion protein comprising the antibody fragment described above. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

The term "bispecific antibody" as used herein refers to an antibody having binding specificity to two different antigen or epitopes in one molecule. Bispecific antibody is produced through a process that involves design of the intact molecule, synthesis and cloning of the nucleotide sequences for each domain, expression in mammalian cells and purification of the final product.

The term "antigen-binding domain" as used herein refers to the portion of an antigen binding molecule that specifically binds to an antigen. More specifically, the term "antigen-binding domain" refers to a portion of an antibody that comprises a region that specifically binds to and is complementary to a portion or all of an antigen. In the case of large antigens, the antigen binding molecule may bind only a specific part of the antigen, which part is called an epitope. The antigen-binding domain may be provided by, for example, one or more variable domains (also referred to as variable regions). Preferably, the antigen-binding domain comprises an antibody light chain variable domain ($V_L$) and an antibody heavy chain variable domain ($V_H$). In one aspect, the antigen-binding domain is capable of binding its antigen and blocking or partially blocking the function of said antigen. Antigen-binding domains that specifically bind PcrV or Psl include antibodies and fragments thereof as further defined herein.

The term "epitope" as used herein refers to the specific group of atoms or amino acids on an antigen to which an antibody or antibody moiety binds. Two antibodies or anti-body moieties may bind the same epitope within an antigen if they exhibit competitive binding for the antigen.

As used herein, a first antibody "competes" for binding to a target PcrV with a second antibody when the first antibody inhibits target PcrV binding of the second antibody by at least about 50% (such as at least about any of 55%, 60%, 65%, 70%, 75%, 80%, 85%, 90%, 95%, 98% or 99%) in the presence of an equimolar concentration of the first antibody, or vice versa. A high throughput process for "binning" antibodies based upon their cross-competition is described in PCT Publication No. WO 03/48731.

As used herein, the term "specifically binds," "specifically recognizing," or "is specific for" refers to measurable and reproducible interactions, such as binding between a target and an antibody, that is determinative of the presence of the target in the presence of a heterogeneous population of molecules, including biological molecules. For example, an antibody that specifically recognizes a target (which can be an epitope) is an antibody that binds to this target with greater affinity, avidity, more readily, and/or with greater duration than its bindings to other targets. In some embodiments, an antibody that specifically recognizes an antigen reacts with one or more antigenic determinants of the antigen with a binding affinity that is at least about 10 times its binding affinity for other targets.

An "isolated" antibody as used herein refers to an antibody that (1) is not associated with proteins found in nature, (2) is free of other proteins from the same source, (3) is expressed by a cell from a different species, or, (4) does not occur in nature.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

As used herein, the term "CDR" or "complementarity determining region" is intended to mean the non-contiguous antigen combining sites found within the variable region of both heavy and light chain polypeptides. These particular regions have been described by Kabat et al., *J. Biol. Chem.* 252:6609-6616 (1977); Kabat et al., U.S. Dept. of Health and Human Services, "*Sequences of proteins of immunological interest*" (1991); Chothia et al., *J. Mol. Biol.* 196: 901-917 (1987); Al-Lazikani B. et al., *J. Mol. Biol.,* 273: 927-948 (1997); MacCallum et al., *J. Mol. Biol.* 262:732-745 (1996); *Abhinandan and Martin, Mol. Immunol.,* 45: 3832-3839 (2008); Lefranc M. P. et al., *Dev. Comp. Immunol.,* 27: 55-77 (2003); and Honegger and Plackthun, *J. Mol. Biol.,* 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison. CDR prediction algorithms and interfaces are known in the art, including, for example, Abhinandan and Martin, *Mol. Immunol.,* 45: 3832-3839 (2008); Ehrenmann F. et al., *Nucleic Acids Res.,* 38: D301-D307 (2010); and Adolf-Bryfogle J. et al., *Nucleic Acids Res.,* 43: D432-D438 (2015). *The contents of the references* cited in this paragraph are incorporated herein by reference in their entireties for use in the present application and for possible inclusion in one or more claims herein.

TABLE 1

CDR DEFINITIONS

| | Kabat[1] | Chothia[2] | MacCallum[3] | IMGT[4] | AHo[5] |
|---|---|---|---|---|---|
| $V_H$ CDR1 | 31-35 | 26-32 | 30-35 | 27-38 | 25-40 |
| $V_H$ CDR2 | 50-65 | 53-55 | 47-58 | 56-65 | 58-77 |
| $V_H$ CDR3 | 95-102 | 96-101 | 93-101 | 105-117 | 109-137 |
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The term "chimeric antibodies" refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this application (see U.S. Pat. No. 4,816,567; and Morrison et al., *Proc. Natl. Acad. Sci. USA,* 81:6851-6855 (1984)).

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$ domains which enables the scFv to form the desired structure for antigen binding. For a review of scFv, see Pluckthun in *The Pharmacology of Monoclonal Antibodies,* vol. 113, Rosenburg and Moore eds., Springer-Verlag, New York, pp. 269-315 (1994).

The term "diabodies" refers to small antibody fragments prepared by constructing scFv fragments (see preceding paragraph) typically with short linkers (such as about 5 to about 10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" scFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA,* 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skilled in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., *Nucleic Acids Research* 32(5):1792-1797, 2004; Edgar, R. C., *BMC Bioinformatics* 5(1):113, 2004).

The terms "Fc receptor" or "FcR" are used to describe a receptor that binds to the Fc region of an antibody. In some embodiments, an FcR of this application is one that binds an IgG antibody (a γ receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234 (1997)). The term includes allotypes, such as FcγRIIIA allotypes: FcγRIIIA-Phe158, FcγRIIIA-Val158, FcγRIIA-R131 and/or FcγRIIA-H131. FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "FcRn" refers to the neonatal Fc receptor (FcRn). FcRn is structurally similar to major histocompatibility complex (MHC) and consists of an α-chain noncovalently bound to β2-microglobulin. The multiple functions of the neonatal Fc receptor FcRn are reviewed in Ghetie and Ward (2000) *Annu. Rev. Immunol.* 18, 739-766. FcRn plays a role in the passive delivery of immunoglobulin IgGs from mother to young and the regulation of serum IgG levels. FcRn can act as a salvage receptor, binding and transporting pinocytosed IgGs in intact form both within and across cells, and rescuing them from a default degradative pathway.

The "CH1 domain" of a human IgG heavy chain constant region usually extends from about amino acid 118 to about amino acid 215 (EU numbering system).

"Hinge region" is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" comprises the stretch of residues C-terminal to a CH2 domain in an Fc region (i.e. from about amino acid residue 341 to the C-terminal end of an antibody sequence, typically at amino acid residue 446 or 447 of an IgG).

A "functional Fc fragment" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art.

An antibody with a variant IgG Fc with "altered" FcR binding affinity or ADCC activity is one which has either enhanced or diminished FcR binding activity (e.g., FcγR or FcRn) and/or ADCC activity compared to a parent polypeptide or to a polypeptide comprising a native sequence Fc region. The variant Fc which "exhibits increased binding" to an FcR binds at least one FcR with higher affinity (e.g., lower apparent Kd or IC$_{50}$ value) than the parent polypeptide or a native sequence IgG Fc. According to some embodiments, the improvement in binding compared to a parent polypeptide is about 3-fold, such as about any of 5, 10, 25, 50, 60, 100, 150, 200, or up to 500-fold, or about 25% to 1000% improvement in binding. The polypeptide variant which "exhibits decreased binding" to an FcR, binds at least one FcR with lower affinity (e.g., higher apparent Kd or higher IC$_{50}$ value) than a parent polypeptide. The decrease in binding compared to a parent polypeptide may be about 40% or more decrease in binding.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (USA) 95:652-656 (1998).

The polypeptide comprising a variant Fc region which "exhibits increased ADCC" or mediates ADCC in the presence of human effector cells more effectively than a polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using any in vitro ADCC assay known in the art, such as assays or methods for determining ADCC activity, e.g., in an animal model etc. In some embodiments, the variant is from about 5-fold to about 100-fold, e.g. from about 25 to about 50-fold, more effective at mediating ADCC than the wild type Fc (or parent polypeptide).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed. Polypeptide variants with altered Fc region amino acid sequences and increased or decreased C1q binding capability are described in U.S. Pat. No. 6,194, 551B1 and WO99/51642. The contents of those patent publications are specifically incorporated herein by reference. See also, Idusogie et al. *J. Immunol.* 164: 4178-4184 (2000).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

An "effective amount" of an antibody or composition as disclosed herein, is an amount sufficient to carry out a specifically stated purpose. An "effective amount" can be determined empirically and by known methods relating to the stated purpose.

The term "therapeutically effective amount" refers to an amount of an antibody or composition as disclosed herein, effective to "treat" a disease or disorder in an individual. In the case of *P. aeruginosa* infection, the therapeutically effective amount of the antibody or composition as disclosed herein can reduce the number of infected cells; inhibit (i.e., slow to some extent and preferably stop) the spread of infection; and/or relieve to some extent one or more of the symptoms associated with the infection. To the extent the antibody or composition as disclosed herein can prevent *P. aeruginosa* growth and/or kill *P. aeruginosa* in an infection, the antibody can be cytostatic and/or cytotoxic. In some embodiments, the therapeutically effective amount is an amount that inhibits infection in a patient. In some embodiments, the therapeutically effective amount is an amount that completely eradicates infection in a patient.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug Administration.

It is understood that embodiments of the application described herein include "consisting of" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat infection of type X means the method is used to treat infection of types other than X.

As used herein and in the appended claims, the singular forms "a," "or," and "the" include plural referents unless the context clearly dictates otherwise.

Bispecific Antibodies Recognizing *Pseudomonas* PcrV and *Pseudomonas* Psl

In one aspect, the present application provides a bispecific molecule comprising a first antigen-binding domain specifically recognizing *Pseudomonas* PcrV, and a second antigen-binding domain specifically recognizing *Pseudomonas* Psl.

In some embodiments, the first antigen-binding domain specifically recognizing *Pseudomonas* PcrV comprises: (a) a heavy chain variable domain ($V_H$) comprising a heavy chain complementarity determining region (HC-CDR) 1 comprising $DX_1X_2MS$ (SEQ ID NO: 20), wherein $X_1$ is N or Y, and $X_2$ is Y, H or P; an HC-CDR2 comprising $X_1ISESGGSTNYADSVKG$ (SEQ ID NO: 15), wherein $X_1$ is V or G; and an HC-CDR3 comprising $GRFSTX_1SX_2HFX_3RAVYGMDV$ (SEQ ID NO: 21), wherein $X_1$ is L, S, N or D, $X_2$ is S or A, $X_3$ is F or Y; and a light chain variable domain ($V_L$) comprising a light chain complementarity determining region (LC-CDR) 1 comprising RASQGISSYLA (SEQ ID NO: 10); an LC-CDR2 comprising AASTLQS (SEQ ID NO: 11), and an LC-CDR3 comprising $QQLSSYPLX_1$ (SEQ ID NO: 19), wherein $X_1$ is S or T; or (b) a $V_H$ comprising an HC-CDR1 comprising $X_1X_2X_3MS$ (SEQ ID NO: 17), wherein $X_1$ is D or S, $X_2$ is Y or N, and $X_3$ is P, H, Y or S; an HC-CDR2 comprising $X_1ISESGGSTX_2X_3ADSVKG$ (SEQ ID NO: 18), wherein $X_1$ is G or V; $X_2$ is N or Y; and $X_3$ is D or Y; and an HC-CDR3 comprising $GRFX_1X_2X_3X_4X_5X_6FX_7RAVYGMDV$ (SEQ ID NO: 38), wherein $X_1$ is S or C, $X_2$ is T, G, D, Y, Q or A, $X_3$ is S, D, N, E, L, A, or Y, $X_4$ is S, T, Y, or A, $X_5$ is S, H, Q, A, R, K, G, E, Y or D, $X_6$ is H or C, and $X_7$ is F or Y; and a $V_L$ comprising an LC-CDR1 comprising $RASQGIX_1SYLA$ (SEQ ID NO: 209), wherein $X_1$ is S or R; an LC-CDR2 comprising AASTLQS (SEQ ID NO: 11); and an LC-CDR3 comprising $QQLX_1SYPLX_2$ (SEQ ID NO: 210), wherein $X_1$ is S, N or K, and $X_2$ is S or T.

In some embodiments, the first antigen-binding domain specifically recognizing *Pseudomonas* PcrV comprises: (a) a $V_H$ comprising a HC-CDR1 comprising $DNX_1MS$ (SEQ ID NO: 14), wherein $X_1$ is Y or H; an HC-CDR2 comprising $X_1ISESGGSTNYADSVKG$ (SEQ ID NO: 15), wherein $X_1$ is V or G; and an HC-CDR3 comprising $GRFSTX_1SSHFX_2RAVYGMDV$ (SEQ ID NO: 16), wherein $X_1$ is L or S, $X_2$ is F or Y; and a $V_L$ comprising an LC-CDR1 comprising RASQGISSYLA (SEQ ID NO: 10); an LC-CDR2 comprising AASTLQS (SEQ ID NO: 11), and an LC-CDR3 comprising $QQLSSYPLX_1$ (SEQ ID NO: 19), wherein $X_1$ is S or T.

In some embodiments, the first antigen-binding domain specifically recognizing *Pseudomonas* PcrV comprises: (a) a $V_H$ comprising an HC-CDR1 comprising SYWMH (SEQ ID NO: 22); an HC-CDR2 comprising $RINEX_1EX_2SISYADSVKG$ (SEQ ID NO: 44), wherein $X_1$ is D or N, and $X_2$ is T, G or R; and an HC-CDR3 comprising $DGPYDX_1X_2DI$ (SEQ ID NO: 45), wherein $X_1$ is S, A, or T, and $X_2$ is F or L; and a $V_L$ Comprising an LC-CDR1 comprising $RASQX_1VX_2X_3NLA$ (SEQ ID NO: 46), wherein $X_1$ is S, G or N, $X_2$ is S, R or K and $X_3$ is S or N; an LC-CDR2 comprising $X_1ASSRAT$ (SEQ ID NO: 42), wherein $X_1$ is D or H, and an LC-CDR3 comprising $QQYGX_1X_2PX_3T$ (SEQ ID NO: 47), wherein $X_1$ is S, L or N, $X_2$ is S, Q or E and $X_3$ is L or I; or (b) a $V_H$ comprising an HC-CDR1 comprising SYWMH (SEQ ID NO: 22); an HC-CDR2 comprising $RINEX_1EX_2SISYADSVKG$ (SEQ ID NO: 211), wherein $X_1$ is D, N, I, L or V, $X_2$ is S, T, R, G or N; and an HC-CDR3 comprising DGPYDX$_1$X$_2$DI (SEQ ID NO: 45), wherein $X_1$ is S, A or T, $X_2$ is F or L; and a $V_L$ comprising an LC-CDR1 comprising RASQX$_1$VX$_2$X$_3$NLA (SEQ ID NO: 212), wherein $X_1$ is N, G, D or S, $X_2$ is K, R, S, N or T, $X_3$ is N, G, S or D; an LC-CDR2 comprising X$_1$ASSRAT (SEQ ID NO: 213), wherein $X_1$ is D, N, H or A; and an LC-CDR3 comprising QQYGX$_1$X$_2$PX$_3$T (SEQ ID NO: 214), wherein $X_1$ is S, T, E, H, N, A, D, M or L, $X_2$ is S, Q, E, T, D, G, H, L, N, V or Y, and $X_3$ is I, L or V.

In some embodiments, the first antigen-binding domain specifically recognizing *Pseudomonas* PcrV comprises: (a) a $V_H$ comprising a HC-CDR1 comprising SYWMH (SEQ ID NO: 22); an HC-CDR2 comprising RINEX$_1$EX$_2$SISYADSVKG (SEQ ID NO: 39), wherein $X_1$ is D or N, $X_2$ is T or G; and an HC-CDR3 comprising DGPYDX$_1$LDI (SEQ ID NO: 40), wherein $X_1$ is S or A; and a $V_L$ comprising an LC-CDR1 comprising RASQX$_1$VX$_2$X$_3$NLA (SEQ ID NO: 41), wherein $X_1$ is S or G, $X_2$ is S or R and $X_3$ is S or N; an LC-CDR2 comprising X$_1$ASSRAT (SEQ ID NO: 42), wherein $X_1$ is D or H, and an LC-CDR3 comprising QQYGX$_1$X$_2$PX$_3$T (SEQ ID NO: 43), wherein $X_1$ is S or L, $X_2$ is S or Q and $X_3$ is L or I.

In some embodiments, the second antigen-binding domain specifically recognizing *Pseudomonas* Psl comprises: a $V_H$ comprising an HC-CDR1 comprising SSGDYWG (SEQ ID NO: 48); an HC-CDR2 comprising SIHNX$_1$GSTYYNPSLKG (SEQ ID NO: 81), wherein $X_1$ is S or Q; and an HC-CDR3 comprising QFGSETYYX$_1$GIX$_2$P (SEQ ID NO: 82), wherein $X_1$ is T, N or P, and $X_2$ is D or Q; and a $V_L$ comprising an LC-CDR1 comprising RSSQSLLHSX$_1$GYNYLD (SEQ ID NO: 83), wherein $X_1$ is N or R; an LC-CDR2 comprising LGSNRAS (SEQ ID NO: 70), and an LC-CDR3 comprising MQALQTPYT (SEQ ID NO: 74). In some embodiments, the second antigen-binding domain specifically recognizing *Pseudomonas* Psl comprises: a $V_H$ comprising an HC-CDR1 comprising SSGDYWG (SEQ ID NO: 48); an HC-CDR2 comprising SIHNX$_1$GSTYYNPSLKG (SEQ ID NO: 125), wherein $X_1$ is S, K or Q; and an HC-CDR3 comprising QFGSETYYX$_1$GIX$_2$P (SEQ ID NO: 126), wherein $X_1$ is N, S, V, T or P, and $X_2$ is D, Y, C, H, S, R, A, E, G, K, W, V, or Q; and a $V_L$ comprising an LC-CDR1 comprising RSSQSLLHSX$_1$GYNYLD (SEQ ID NO: 127), wherein $X_1$ is N, A, V, F, R, G, H, Q, W or P; an LC-CDR2 comprising LGSNRAS (SEQ ID NO: 70), and an LC-CDR3 comprising MQALQTP X$_1$T (SEQ ID NO: 128), wherein $X_1$ is R or Y.

In some embodiments, the second antigen-binding domain specifically recognizing *Pseudomonas* Psl comprises: a $V_H$ comprising an HC-CDR1 comprising IHSVH (SEQ ID NO: 50); an HC-CDR2 comprising TIISSGTTT-TYAQSFQD (SEQ ID NO: 55); and an HC-CDR3 comprising DGX$_1$S (SEQ ID NO: 84), wherein $X_1$ is D or T; and a $V_L$ comprising an LC-CDR1 comprising RASQGISSWLA (SEQ ID NO: 68); an LC-CDR2 comprising HASTLES (SEQ ID NO: 72), and an LC-CDR3 comprising LQAX$_1$SLPHT (SEQ ID NO: 85), wherein $X_1$ is N, F, S or K. In some embodiments, the second antigen-binding domain specifically recognizing *Pseudomonas* Psl comprises: a $V_H$ comprising an HC-CDR1 comprising IHSVH (SEQ ID NO: 50); an HC-CDR2 comprising TIISSGTTT-TYAQSFQD (SEQ ID NO: 55); and an HC-CDR3 comprising X$_1$X$_2$X$_3$X$_4$(SEQ ID NO: 129), wherein $X_1$ is D, Y, or N, wherein $X_2$ is G or A, wherein $X_3$ is D or T and wherein $X_4$ is S, A or T; and a $V_L$ comprising an LC-CDR1 comprising RASQGISSWLA (SEQ ID NO: 68); an LC-CDR2 comprising HASTLES (SEQ ID NO: 72) and an LC-CDR3 comprising LQAX$_1$SLPHT (SEQ ID NO: 130), wherein $X_1$ is N, D, Y, F, P, G, K, H, A, C, E, Q, R, S, T, V, W or L.

In some embodiments, the first antigen-binding domain specifically recognizing *Pseudomonas* PcrV comprises: a $V_H$ comprising an HC-CDR1 comprising the amino acid sequence of any one of SEQ ID NOs: 1-3, an HC-CDR2 comprising the amino acid sequence of SEQ ID NO: 4 or 5, and an HC-CDR3 comprising the amino acid sequence of any one of SEQ ID NOs: 6-9; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12 or 13.

In some embodiments, the first antigen-binding domain specifically recognizing *Pseudomonas* PcrV comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12. In some embodiments, the first antigen-binding domain specifically recognizing *Pseudomonas* PcrV comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13. In some embodiments, the first antigen-binding domain specifically recognizing *Pseudomonas* PcrV comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 8; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12. In some embodiments, the first antigen-binding domain specifically recognizing *Pseudomonas* PcrV comprises: a $V_H$ comprising an HC-CDR1 comprising the amino acid sequence SEQ ID NO: 3, an HC-CDR2 comprising the amino acid sequence of SEQ ID NO: 5, and an HC-CDR3 comprising the amino acid sequence of SEQ ID NO: 9; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13.

In some embodiments, the first antigen-binding domain specifically recognizing *Pseudomonas* PcrV comprises: a $V_H$ comprising an HC-CDR1 comprising the amino acid sequence of SEQ ID NO: 22, an HC-CDR2 comprising the amino acid sequence of any one of SEQ ID NOs: 23-25, and an HC-CDR3 comprising the amino acid sequence of any one of SEQ ID NOs: 26-29; and a $V_L$ comprising: an LC-CDR1 comprising the amino acid sequence of any one of SEQ ID NOs: 30-32, an LC-CDR2 comprising the amino acid sequence of SEQ ID NO: 33 or 34, and an LC-CDR3 comprising the amino acid sequence of any one of SEQ ID NOs: 35-37.

In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 23, and an HC-CDR3 comprising the amino acid sequence of SEQ ID NO: 26; and a $V_L$ comprising: an LC-CDR1 comprising the amino acid sequence of SEQ ID NO: 30, an LC-CDR2 comprising the amino acid sequence of SEQ ID NO: 33, and an LC-CDR3 comprising the amino acid sequence of SEQ ID NO: 35. In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 27; and a $V_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36. In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 25, and an HC-CDR3 comprising the amino acid sequence of SEQ ID NO: 27; and a $V_L$ comprising: an LC-CDR1 comprising the amino acid sequence of SEQ ID NO: 32, an LC-CDR2 comprising the amino acid sequence of SEQ ID NO: 34, and an LC-CDR3 comprising the amino acid sequence of SEQ ID NO: 37. In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 25, and an HC-CDR3 comprising the amino acid sequence of SEQ ID NO: 28; and a $V_L$ comprising: an LC-CDR1 comprising the amino acid sequence of SEQ ID NO: 32, an LC-CDR2 comprising the amino acid sequence of SEQ ID NO: 34, and an LC-CDR3 comprising the amino acid sequence of SEQ ID NO: 37. In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 28; and a $V_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36. In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 25, and an HC-CDR3 comprising the amino acid sequence of SEQ ID NO: 26; and a $V_L$ comprising: an LC-CDR1 comprising the amino acid sequence of SEQ ID NO: 32, an LC-CDR2 comprising the amino acid sequence of SEQ ID NO: 34, and an LC-CDR3 comprising the amino acid sequence of SEQ ID NO: 37. In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 26; and a $V_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36. In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 23, and an HC-CDR3 comprising the amino acid sequence of SEQ ID NO: 29; and a $V_L$ comprising: an LC-CDR1 comprising the amino acid sequence of SEQ ID NO: 30, an LC-CDR2 comprising the amino acid sequence of SEQ ID NO: 33, and an LC-CDR3 comprising the amino acid sequence of SEQ ID NO: 35.

In some embodiments, the second antigen-binding domain specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NOs: 52 or 53, and an HC-CDR3 comprising the amino acid sequence of any one of SEQ ID NOs: 57-60; and a $V_L$ comprising: an LC-CDR1 comprising the amino acid sequence of SEQ ID NO: 65 or 66, an LC-CDR2 comprising the amino acid sequence of SEQ ID NO: 70, and an LC-CDR3 comprising the amino acid sequence of SEQ ID NO: 74.

In some embodiments, the second antigen-binding domain specifically recognizing *Pseudomonas* Psl comprises: a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 62 or 63; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of any one of SEQ ID NOs: 76-79.

In some embodiments, the second antigen-binding domain specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the second antigen-binding domain specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 53, and an HC-CDR3 comprising the amino acid sequence of SEQ ID NO: 58; and a $V_L$ comprising: an LC-CDR1 comprising the amino acid sequence of SEQ ID NO: 66, an LC-CDR2 comprising the amino acid sequence of SEQ ID NO: 70, and an LC-CDR3 comprising the amino acid sequence of SEQ ID NO: 74. In some embodiments, the second antigen-binding domain specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 59; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the second antigen-binding domain specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 53; and an HC-CDR3 comprising the amino acid sequence of SEQ ID NO: 60; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the second antigen-binding domain specifically recognizing *Pseudomonas* Psl comprises: a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75. In some embodiments, the second antigen-binding domain specifically recognizing *Pseudomonas* Psl comprises: a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 62; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 76. In some embodiments, the second antigen-binding domain specifically recognizing *Pseudomonas* Psl comprises: a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 63; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 77. In some embodiments, the second antigen-binding domain specifically recognizing *Pseudomonas* Psl comprises: a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 63; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 78. In some embodiments, the second antigen-binding domain specifically recognizing *Pseudomonas* Psl comprises: a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 63; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 79. In some embodiments, the second antigen-binding domain specifically recognizing *Pseudomonas* Psl comprises: a $V_H$ comprising an HC-CDR1 comprising the amino acid sequence of SEQ ID NO: 51, an HC-CDR2 comprising the amino acid sequence of SEQ ID NO: 56, and an HC-CDR3 comprising the amino acid sequence of SEQ ID NO: 64; and a $V_L$ comprising: an LC-CDR1 comprising the amino acid sequence of SEQ ID NO: 69, an LC-CDR2 comprising the amino acid sequence of SEQ ID NO: 73, and an LC-CDR3 comprising the amino acid sequence of SEQ ID NO: 80.

In some embodiments, the first antigen-binding domain specifically recognizing *Pseudomonas* PcrV comprises a $V_H$ comprising the amino acid sequence of SEQ ID NO: 91 or 161 and a $V_L$ comprising the amino acid sequence of SEQ ID NO: 112 or 182. In some embodiments, the first antigen-binding domain specifically recognizing *Pseudomonas* PcrV comprises a $V_H$ comprising an HC-CDR1, an HC-CDR2 and an HC-CDR3 of the $V_H$ comprising the amino acid sequence of SEQ ID NO: 91 or 161; and a $V_L$ Comprising an LC-CDR1, an LC-CDR2, and an LC-CDR3 of the $V_L$ comprising the amino acid sequence of SEQ ID NO: 112 or 182.

In some embodiments, the first antigen-binding domain specifically recognizing *Pseudomonas* PcrV comprises a $V_H$ comprising the amino acid sequence of SEQ ID NO: 92 or 162 and a $V_L$ comprising the amino acid sequence of SEQ ID NO: 113 or 183. In some embodiments, the first antigen-binding domain specifically recognizing *Pseudomonas* PcrV comprises a $V_H$ comprising an HC-CDR1, an HC-CDR2 and an HC-CDR3 of the $V_H$ comprising the amino acid sequence of SEQ ID NO: 92; or 162 and a $V_L$ Comprising an LC-CDR1, an LC-CDR2, and an LC-CDR3 of the $V_L$ comprising the amino acid sequence of SEQ ID NO: 113 or 183.

In some embodiments, the first antigen-binding domain specifically recognizing *Pseudomonas* PcrV comprises a $V_H$ comprising the amino acid sequence of SEQ ID NO: 93 or 163 and a $V_L$ comprising the amino acid sequence of SEQ ID NO: 112 or 182. In some embodiments, the first antigen-binding domain specifically recognizing *Pseudomonas* PcrV comprises a $V_H$ comprising an HC-CDR1, an HC-CDR2 and an HC-CDR3 of the $V_H$ comprising the amino acid sequence of SEQ ID NO: 93 or 163; and a $V_L$ Comprising an LC-CDR1, an LC-CDR2, and an LC-CDR3 of the $V_L$ comprising the amino acid sequence of SEQ ID NO: 112 or 182.

In some embodiments, the first antigen-binding domain specifically recognizing *Pseudomonas* PcrV comprises a $V_H$ comprising the amino acid sequence of SEQ ID NO: 94 or 164 and a $V_L$ comprising the amino acid sequence of SEQ ID NO: 113 or 183. In some embodiments, the first antigen-binding domain specifically recognizing *Pseudomonas* PcrV comprises a $V_H$ comprising an HC-CDR1, an HC-CDR2 and an HC-CDR3 of the $V_H$ comprising the amino acid sequence of SEQ ID NO: 94 or 164; and a $V_L$ Comprising an LC-CDR1, an LC-CDR2, and an LC-CDR3 of the $V_L$ comprising the amino acid sequence of SEQ ID NO: 113 or 183.

In some embodiments, the first antigen-binding domain specifically recognizing *Pseudomonas* PcrV comprises a $V_H$ comprising the amino acid sequence of SEQ ID NO: 95 or 165 and a $V_L$ comprising the amino acid sequence of SEQ ID NO: 114 or 184. In some embodiments, the first antigen-binding domain specifically recognizing *Pseudomonas* PcrV comprises a $V_H$ comprising an HC-CDR1, an HC-CDR2 and an HC-CDR3 of the $V_H$ comprising the amino acid sequence of SEQ ID NO: 95 or 165; and a $V_L$ Comprising an LC-CDR1, an LC-CDR2, and an LC-CDR3 of the $V_L$ comprising the amino acid sequence of SEQ ID NO: 114 or 184.

In some embodiments, the first antigen-binding domain specifically recognizing *Pseudomonas* PcrV comprises a $V_H$ comprising the amino acid sequence of SEQ ID NO: 96 or 166 and a $V_L$ comprising the amino acid sequence of SEQ ID NO: 115 or 185. In some embodiments, the first antigen-binding domain specifically recognizing *Pseudomonas* PcrV comprises a $V_H$ comprising an HC-CDR1, an HC-CDR2 and an HC-CDR3 of the $V_H$ comprising the amino acid sequence of SEQ ID NO: 96 or 166; and a $V_L$ Comprising an LC-CDR1, an LC-CDR2, and an LC-CDR3 of the $V_L$ comprising the amino acid sequence of SEQ ID NO: 115 or 185.

In some embodiments, the first antigen-binding domain specifically recognizing *Pseudomonas* PcrV comprises a $V_H$ comprising the amino acid sequence of SEQ ID NO: 97 or 167 and a $V_L$ comprising the amino acid sequence of SEQ ID NO: 116 or 186. In some embodiments, the first antigen-binding domain specifically recognizing *Pseudomonas* PcrV comprises a $V_H$ comprising an HC-CDR1, an HC-CDR2 and an HC-CDR3 of the $V_H$ comprising the amino acid sequence of SEQ ID NO: 97 or 167; and a $V_L$ Comprising an LC-CDR1, an LC-CDR2, and an LC-CDR3 of the $V_L$ comprising the amino acid sequence of SEQ ID NO: 116 or 186.

In some embodiments, the first antigen-binding domain specifically recognizing *Pseudomonas* PcrV comprises a $V_H$ comprising the amino acid sequence of SEQ ID NO: 98 or 168 and a $V_L$ comprising the amino acid sequence of SEQ ID NO: 116 or 186. In some embodiments, the first antigen-binding domain specifically recognizing *Pseudomonas* PcrV comprises a $V_H$ comprising an HC-CDR1, an HC-CDR2 and an HC-CDR3 of the $V_H$ comprising the amino acid sequence of SEQ ID NO: 98 or 168; and a $V_L$ Comprising an LC-CDR1, an LC-CDR2, and an LC-CDR3 of the $V_L$ comprising the amino acid sequence of SEQ ID NO: 116 or 186.

In some embodiments, the first antigen-binding domain specifically recognizing *Pseudomonas* PcrV comprises a $V_H$ comprising the amino acid sequence of SEQ ID NO: 99 or 169 and a $V_L$ comprising the amino acid sequence of SEQ ID NO: 115 or 185. In some embodiments, the first antigen-binding domain specifically recognizing *Pseudomonas* PcrV comprises a $V_H$ comprising an HC-CDR1, an HC-CDR2 and an HC-CDR3 of the $V_H$ comprising the amino acid sequence of SEQ ID NO: 99 or 169; and a $V_L$ Comprising an LC-CDR1, an LC-CDR2, and an LC-CDR3 of the $V_L$ comprising the amino acid sequence of SEQ ID NO: 115 or 185.

In some embodiments, the first antigen-binding domain specifically recognizing *Pseudomonas* PcrV comprises a $V_H$ comprising the amino acid sequence of SEQ ID NO: 100 or 170 and a $V_L$ comprising the amino acid sequence of SEQ ID NO: 116 or 186. In some embodiments, the first antigen-binding domain specifically recognizing *Pseudomonas* PcrV comprises a $V_H$ comprising an HC-CDR1, an HC-CDR2 and an HC-CDR3 of the $V_H$ comprising the amino acid sequence of SEQ ID NO: 100 or 170; and a $V_L$ comprising an LC-CDR1, an LC-CDR2, and an LC-CDR3 of the $V_L$ comprising the amino acid sequence of SEQ ID NO: 116 or 186.

In some embodiments, the first antigen-binding domain specifically recognizing *Pseudomonas* PcrV comprises a $V_H$ comprising the amino acid sequence of SEQ ID NO: 101 or 171 and a $V_L$ comprising the amino acid sequence of SEQ ID NO: 115 or 185. In some embodiments, the first antigen-binding domain specifically recognizing *Pseudomonas* PcrV comprises a $V_H$ comprising an HC-CDR1, an HC-CDR2 and an HC-CDR3 of the $V_H$ comprising the amino acid sequence of SEQ ID NO: 101 or 171; and a $V_L$ comprising an LC-CDR1, an LC-CDR2, and an LC-CDR3 of the $V_L$ comprising the amino acid sequence of SEQ ID NO: 115 or 185.

In some embodiments, the first antigen-binding domain specifically recognizing *Pseudomonas* PcrV comprises a $V_H$ comprising the amino acid sequence of SEQ ID NO: 102 or 172 and a $V_L$ comprising the amino acid sequence of SEQ ID NO: 114 or 184. In some embodiments, the first antigen-binding domain specifically recognizing *Pseudomonas* PcrV comprises a $V_H$ comprising an HC-CDR1, an HC-CDR2 and an HC-CDR3 of the $V_H$ comprising the amino acid sequence of SEQ ID NO: 102 or 172; and a $V_L$ comprising an LC-CDR1, an LC-CDR2, and an LC-CDR3 of the $V_L$ comprising the amino acid sequence of SEQ ID NO: 114 or 184.

In some embodiments, the second antigen-binding domain specifically recognizing *Pseudomonas* Psl comprises a $V_H$ comprising the amino acid sequence of SEQ ID NO: 103 or 173 and a $V_L$ comprising the amino acid sequence of SEQ ID NO: 117 or 187. In some embodiments, the second antigen-binding domain specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 103 or 173; and a $V_L$ comprising an LC-CDR1, an LC-CDR2, and an LC-CDR3 of the $V_L$ comprising the amino acid sequence of SEQ ID NO: 117 or 187.

In some embodiments, the second antigen-binding domain specifically recognizing *Pseudomonas* Psl comprises a $V_H$ comprising the amino acid sequence of SEQ ID NO: 104 or 174 and a $V_L$ comprising the amino acid sequence of SEQ ID NO: 118 or 188. In some embodiments, the second antigen-binding domain specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 104 or 174 and a $V_L$ comprising an LC-CDR1, an LC-CDR2, and an LC-CDR3 of the $V_L$ comprising the amino acid sequence of SEQ ID NO: 118 or 188.

In some embodiments, the second antigen-binding domain specifically recognizing *Pseudomonas* Psl comprises a $V_H$ comprising the amino acid sequence of SEQ ID NO: 105 or 175 and a $V_L$ comprising the amino acid sequence of SEQ ID NO: 117 or 187. In some embodiments, the second antigen-binding domain specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 105 or 175; and a $V_L$ comprising an LC-CDR1, an LC-CDR2, and an LC-CDR3 of the $V_L$ comprising the amino acid sequence of SEQ ID NO: 117 or 187.

In some embodiments, the second antigen-binding domain specifically recognizing *Pseudomonas* Psl comprises a $V_H$ comprising the amino acid sequence of SEQ ID NO: 106 or 176 and a $V_L$ comprising the amino acid sequence of SEQ ID NO: 117 or 187. In some embodiments, the second antigen-binding domain specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 106 or 176; and a $V_L$ comprising an LC-CDR1, an LC-CDR2, and an LC-CDR3 of the $V_L$ comprising the amino acid sequence of SEQ ID NO: 117 or 187.

In some embodiments, the second antigen-binding domain specifically recognizing *Pseudomonas* Psl comprises a $V_H$ comprising the amino acid sequence of SEQ ID NO: 107 or 177 and a $V_L$ comprising the amino acid sequence of SEQ ID NO: 119 or 189. In some embodiments, the second antigen-binding domain specifically recognizing *Pseudomonas* Psl comprises a V$_H$ comprising an HC-CDR1, an HC-CDR2 and an HC-CDR3 of the V$_H$ comprising the amino acid sequence of SEQ ID NO: 107 or 177 and a V$_L$ comprising an LC-CDR1, an LC-CDR2, and an LC-CDR3 of the V$_L$ comprising the amino acid sequence of SEQ ID NO: 119 or 189.

In some embodiments, the second antigen-binding domain specifically recognizing *Pseudomonas* Psl comprises a V$_H$ comprising the amino acid sequence of SEQ ID NO: 108 or 178 and a V$_L$ comprising the amino acid sequence of SEQ ID NO: 119 or 189. In some embodiments, the second antigen-binding domain specifically recognizing *Pseudomonas* Psl comprises a V$_H$ comprising an HC-CDR1, an HC-CDR2 and an HC-CDR3 of the V$_H$ comprising the amino acid sequence of SEQ ID NO: 108 or 178; and a V$_L$ comprising an LC-CDR1, an LC-CDR2, and an LC-CDR3 of the V$_L$ comprising the amino acid sequence of SEQ ID NO: 119 or 189.

In some embodiments, the second antigen-binding domain specifically recognizing *Pseudomonas* Psl comprises a V$_H$ comprising the amino acid sequence of SEQ ID NO: 109 or 179 and a V$_L$ comprising the amino acid sequence of SEQ ID NO: 120 or 190. In some embodiments, the second antigen-binding domain specifically recognizing *Pseudomonas* Psl comprises a V$_H$ comprising an HC-CDR1, an HC-CDR2 and an HC-CDR3 of the V$_H$ comprising the amino acid sequence of SEQ ID NO: 109 or 179; and a V$_L$ comprising an LC-CDR1, an LC-CDR2, and an LC-CDR3 of the V$_L$ comprising the amino acid sequence of SEQ ID NO: 120 or 190.

In some embodiments, the second antigen-binding domain specifically recognizing *Pseudomonas* Psl comprises a V$_H$ comprising the amino acid sequence of SEQ ID NO: 110 or 180 and a V$_L$ comprising the amino acid sequence of SEQ ID NO: 121 or 191. In some embodiments, the second antigen-binding domain specifically recognizing *Pseudomonas* Psl comprises a V$_H$ comprising an HC-CDR1, an HC-CDR2 and an HC-CDR3 of the V$_H$ comprising the amino acid sequence of SEQ ID NO: 110 or 180; and a V$_L$ comprising an LC-CDR1, an LC-CDR2, and an LC-CDR3 of the V$_L$ comprising the amino acid sequence of SEQ ID NO: 121 or 191.

In some embodiments, the second antigen-binding domain specifically recognizing *Pseudomonas* Psl comprises a V$_H$ comprising the amino acid sequence of SEQ ID NO: 110 or 180 and a V$_L$ comprising the amino acid sequence of SEQ ID NO: 122 or 192. In some embodiments, the second antigen-binding domain specifically recognizing *Pseudomonas* Psl comprises a V$_H$ comprising an HC-CDR1, an HC-CDR2 and an HC-CDR3 of the V$_H$ comprising the amino acid sequence of SEQ ID NO: 110 or 180; and a V$_L$ comprising an LC-CDR1, an LC-CDR2, and an LC-CDR3 of the V$_L$ comprising the amino acid sequence of SEQ ID NO: 122 or 192.

In some embodiments, the second antigen-binding domain specifically recognizing *Pseudomonas* Psl comprises a V$_H$ comprising the amino acid sequence of SEQ ID NO: 110 or 180 and a V$_L$ comprising the amino acid sequence of SEQ ID NO: 123 or 193. In some embodiments, the second antigen-binding domain specifically recognizing *Pseudomonas* Psl comprises a V$_H$ comprising an HC-CDR1, an HC-CDR2 and an HC-CDR3 of the V$_H$ comprising the amino acid sequence of SEQ ID NO: 110 or 180; and a V$_L$ comprising an LC-CDR1, an LC-CDR2, and an LC-CDR3 of the V$_L$ comprising the amino acid sequence of SEQ ID NO: 123 or 193.

In some embodiments, the second antigen-binding domain specifically recognizing *Pseudomonas* Psl comprises a V$_H$ comprising the amino acid sequence of SEQ ID NO: 111 or 181 and a V$_L$ comprising the amino acid sequence of SEQ ID NO: 124 or 194. In some embodiments, the second antigen-binding domain specifically recognizing *Pseudomonas* Psl comprises a V$_H$ comprising an HC-CDR1, an HC-CDR2 and an HC-CDR3 of the V$_H$ comprising the amino acid sequence of SEQ ID NO: 111 or 181; and a V$_L$ comprising an LC-CDR1, an LC-CDR2, and an LC-CDR3 of the V$_L$ comprising the amino acid sequence of SEQ ID NO: 124 or 194.

In some embodiments, there is provided a bispecific molecule comprising a first antigen-binding domain specifically recognizing *Pseudomonas* PcrV, and a second antigen-binding domain specifically recognizing *Pseudomonas* Psl, wherein the first antigen-binding domain comprises: (a) a V$_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a V$_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; or (b) a V$_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a V$_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13; or (c) a V$_H$ comprising an HC-CDR1 comprising the amino acid sequence SEQ ID NO: 22, an HC-CDR2 comprising the amino acid sequence of SEQ ID NO: 23, and an HC-CDR3 comprising the amino acid sequence of SEQ ID NO: 26; and a V$_L$ comprising: an LC-CDR1 comprising the amino acid sequence of SEQ ID NO: 30, an LC-CDR2 comprising the amino acid sequence of SEQ ID NO: 33, and an LC-CDR3 comprising the amino acid sequence of SEQ ID NO: 35; or (d) a V$_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 27; and a V$_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36.

In some embodiments, there is provided a bispecific molecule comprising a first antigen-binding domain specifically recognizing *Pseudomonas* PcrV, and a second antigen-binding domain specifically recognizing *Pseudomonas* Psl, wherein the second antigen-binding domain comprises: (a) a V$_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a V$_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74; or (b) a V$_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75; or (c) a $V_H$ comprising an HC-CDR1 comprising the amino acid sequence of SEQ ID NO: 51, an HC-CDR2 comprising the amino acid sequence of SEQ ID NOs 56, and an HC-CDR3 comprising the amino acid sequence of SEQ ID NO: 64; and a $V_L$ comprising: an LC-CDR1 comprising the amino acid sequence of SEQ ID NO: 69, an LC-CDR2 comprising the amino acid sequence of SEQ ID NO: 73, and an LC-CDR3 comprising the amino acid sequence of SEQ ID NO: 80.

In some embodiments, there is provided a bispecific molecule comprising a first antigen-binding domain specifically recognizing *Pseudomonas* PcrV, and a second antigen-binding domain specifically recognizing *Pseudomonas* Psl, wherein the first antigen-binding domain comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; and wherein the second antigen-binding domain comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74.

In some embodiments, there is provided a bispecific molecule comprising a first antigen-binding domain specifically recognizing *Pseudomonas* PcrV, and a second antigen-binding domain specifically recognizing *Pseudomonas* Psl, wherein the first antigen-binding domain comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; and wherein the second antigen-binding domain comprises: a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75.

In some embodiments, there is provided a bispecific molecule comprising a first antigen-binding domain specifically recognizing *Pseudomonas* PcrV, and a second antigen-binding domain specifically recognizing *Pseudomonas* Psl, wherein the first antigen-binding domain comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13; and wherein the second antigen-binding domain comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74.

In some embodiments, there is provided a bispecific molecule comprising a first antigen-binding domain specifically recognizing *Pseudomonas* PcrV, and a second antigen-binding domain specifically recognizing *Pseudomonas* Psl, wherein the first antigen-binding domain comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13; and wherein the second antigen-binding domain comprises: a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75.

In some embodiments according to any one of the bispecific molecules described herein, the first antigen-binding domain is a single-chain variable fragment (scFv) specifically recognizing *Pseudomonas* PcrV, the second antigen-binding domain is an Fab arm specifically recognizing *Pseudomonas* Psl, wherein the molecule further comprises an Fc region comprising CH2 and CH3 domains; and wherein the scFv is interconnected to the Fab arm via a first polypeptide linker (L1) and to the Fc region via a second polypeptide linker (L2). In some embodiments, the molecule is bivalent for binding to each of PcrV and Psl.

In some embodiments according to any one of the bispecific molecules described herein, the first antigen-binding domain is an Fab arm specifically recognizing PcrV, the second antigen-binding domain is a single-chain variable fragment (scFv) specifically recognizing Psl, wherein the molecule further comprises an Fc region comprising CH2 and CH3 domains; and wherein the scFv is interconnected to the Fab arm via a first polypeptide linker (L1) and to the Fc region via a second polypeptide linker (L2). In some embodiments, the molecule is the bispecific molecule that is bivalent for binding to each of PcrV and Psl.

In some embodiments according to any one of the bispecific molecules described herein, the antigen-binding domain of the single-chain variable fragment (scFv) specifically recognizing PcrV or Psl comprises engineered cysteine mutations, a disulfide-stabilized bispecific antibody was obtained by introducing two cysteine mutations at the $V_H$ and $V_L$ interface.

Figure 6:
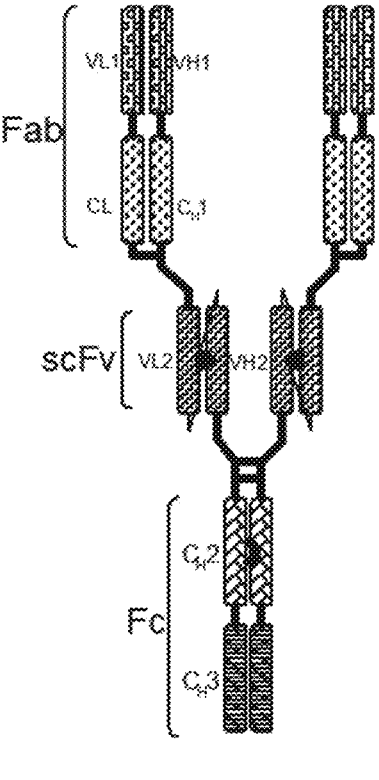
FIG. 6 shows an exemplary bispecific antibody recognizing PcrV and Psl, or recognizing two non-overlapping epitopes on PcrV.

Linkers may be used to join domains and/or regions of the chimeric heavy chain of the bispecific molecule into a contiguous molecule. In some embodiments, the bispecific molecule includes at least two linker polypeptides, L1 and L2. In some embodiments, the bispecific molecule may include additional linkers, such as a flexible linker interconnecting the variable heavy and light chains of an scFv. In some embodiments, the bispecific molecule may include additional linkers, such as a flexible linker interconnecting the variable heavy and light chains of an scFv and other linkers that connect other binding units to the core structure of the bispecific molecule. Examples of additional binding units connected to the bispecific molecule core structure are depicted in FIG. 6.

An exemplary, non-limiting example of a linker is a polypeptide chain comprising at least 4 residues. Portions of such linkers may be flexible, hydrophilic and have little or no secondary structure of their own (linker portions or flexible linker portions). Linkers of at least 4 amino acids may be used to join domains and/or regions that are positioned near to one another after the molecule has assembled. Longer linkers may also be used. In some embodiments, linkers may be about any one of: 1, 2, 3, 4, 5, 6, 7, 8, 9, 10, 11, 12, 13, 14, 15, 16, 17, 18, 19, 20, 25, 30, 35, 40, 45, 50, 100, 125, 150, 175 or 200 residues. When multiple linkers are used to interconnect portions of the molecule, the linkers may be the same or different (e.g., the same or different length and/or amino acid sequence).

In some aspects, the polypeptide linker comprises or consists of a Gly-Ser linker. As used herein, the term "Gly-Ser linker" refers to a peptide that consists of glycine and serine residues. An exemplary Gly-Ser linker comprises an amino acid sequence of the formula $(Gly_4Ser)_n$, wherein n is a positive integer (e.g., 1, 2, 3, 4, 5, 6, 7, 8, 9 or 10). A preferred Gly-Ser linker is $(Gly_4Ser)_2$ and $(Gly_4Ser)_4$. Another exemplary Gly-Ser linker is $(Gly_4Ser)_3$. In yet other aspects, two or more Gly-Ser linker are incorporated in series in a polypeptide linker. In some aspects, the polypeptide linker comprises at least a portion of a hinge region (e.g., derived from an IgG1, IgG2, IgG3, or IgG4 molecule) and a series of Gly-Ser amino acid residues (e.g., a Gly-Ser linker such as $(Gly_4Ser)_n$).

In some embodiments, L1 and/or L2 include both a hinge portion and a linker portion, such as a linker portion comprising a Gly-Ser linker. In other aspects, L1 and/or L2 include only a hinge portion or only a linker portion, such as a Gly-Ser linker. In some embodiments, L1 and L2 include a Gly-Ser linker portion. In certain aspects, the Gly-Ser linker portion of L1 and L2 is the same length, whereas in other aspects, the Gly-Ser linker portion of L1 and L2 are different lengths. When a bispecific molecule comprises an scFv, the heavy and light chains of the scFv may be connected by a flexible linker. In some embodiments, this flexible linker generally does not include a hinge portion, but rather, is a Gly-Ser linker or other flexible linker. The length and amino acid sequence of a flexible linker interconnecting domains of an scFv may be selected and optimized.

In some embodiments, the bispecific molecule comprises a binding unit 1 (BU1) and a binding unit 2 (BU2). In some embodiments, BU1 comprises a Fab domain. In some embodiments, BU2 comprises a scFv. In some embodiments, the polypeptide linker (for example L1 and/or L2) comprises a Gly-Ser or all Gly linker and a portion or modified portion of a hinge domain. In some aspects, the polypeptide linker (L1) connecting BU1 (e.g. the Fab domain) to the other binding domain BU2 (e.g. the scFv) of the bispecific molecule comprises the amino acid sequence EPKSDKTGGGGSGGGGS (SEQ ID NO: 153) or EPKSCGKTGGGGSGGGGS (SEQ ID NO: 154) or EPKSCGGGGSGGGGS (SEQ ID NO: 155) In some aspects the polypeptide linker (L2) connecting BD2 to the Fc domain of the bispecific molecule comprises the amino acid sequence GGGGSGGGGSEPKSDKTHTCPPCP (SEQ ID NO: 156) or GGGGSGGGGSCPPCP (SEQ ID NO: 157) or GGGGSGGGGSDKTHTCPPCP (SEQ ID NO: 158).

Regardless of the polypeptide linker used to interconnect binding unit 1 to binding unit 2 and binding unit 2 to Fc (e.g., L1 and L2), the bispecific molecule may optionally comprise additional polypeptide linkers. The lengths and sequence of such additional polypeptide linkers are independently selected. For example, the bispecific molecule may further comprise a flexible polypeptide linker (L3) interconnecting the variable heavy and light chains of a scFv ($V_{HSCFV}$ and $V_{LSCFV}$). This flexible polypeptide linker may comprise a gly-ser linker. Generally, this linker does not include a hinge portion. In some embodiments, this flexible polypeptide linker (L3) interconnecting the variable heavy and light chains of the scFv comprises the sequence of GGGGSGGGGSGGGGSGGGG (SEQ ID NO: 87).

In some embodiments, the bispecific molecules of the present disclosure comprise two heavy-light chain pairs. In some embodiments, the polypeptide sequence of the bispecific molecule chimeric heavy chain may comprise a polypeptide sequence comprising an antibody heavy chain variable domain 1 (VH1), a polypeptide sequence comprising an antibody heavy chain constant domain 1 (CH1), a polypeptide sequence comprising a first polypeptide linker (L1), a polypeptide sequence comprising a binding unit 2 (BU2) that binds to a second epitope, a polypeptide sequence comprising a second polypeptide linker (L2), and a polypeptide sequence comprising an Fc domain. In some aspects, the Fc domain comprises a CH2 domain and a CH3 domain. In some embodiments, the chimeric heavy chain of the bispecific molecule may comprise polypeptide sequences in the following orientation from N-terminus to C-terminus: VH1-CH1-L1-BU$_2$-L2-CH2-CH3. The polypeptide sequence of the light chain of the bispecific molecule may comprise a light chain variable domain 1 (VL1) and a light chain constant domain (CL). In some embodiments, the light chain of the bispecific molecule may comprise polypeptide sequence in the following orientation from N-terminus to C-terminus: VL1-CL. In some embodiments, VH1, VL1, CH1 and CL are used to denote portions of binding unit 1 (BU1) that binds the first epitope. In certain embodiments, one or more additional binding units (e.g., scFvs) are present at the N-terminal and/or C-terminal ends of the core of the bispecific molecule. In some embodiments, one or more additional binding units (e.g., scFvs) are present within the hinge. Thus, the heavy chain of the bispecific molecule may comprise an extended core and have polypeptide sequences in the following orientation from N-terminus to C-terminus: VH1-CH1-L1-(BU)$_n$-L2-CH2-CH3 where n>1. In some embodiments, the bispecific molecule comprises a CH1 comprising the amino acid sequence of SEQ ID No: 134. In some embodiments, the bispecific molecule comprises a CH2-CH3 comprising the amino acid sequence of SEQ ID NO: 131, 132, or 133. In some embodiments, the bispecific molecule comprises a CH2-CH3 comprising one or more substitutions in position 22, 24, 26 according to the amino acid sequence of SEQ ID NO: 131. In some embodiments, the bispecific molecule comprises a CH2-CH3 comprising one or more substitutions of M22Y, S24T, T26E according to the amino acid sequence of SEQ ID NO: 131. In some embodiments, the bispecific molecule comprises a CH2-CH3 comprising one or more substitutions in position 198, 204 according to the amino acid sequence of SEQ ID NO:

131. In some embodiments, the bispecific molecule comprises a CH2-CH3 comprising one or more substitutions of M198L, N204S according to the amino acid sequence of SEQ ID NO: 131.

In some embodiments, where the binding unit 2 (BU2) is an scFv, the bispecific molecule chimeric heavy chain may comprise a polypeptide sequence comprising an antibody heavy chain variable domain (VH1), a polypeptide sequence comprising an antibody heavy chain constant domain 1 (CH1), a polypeptide sequence comprising a first polypeptide linker (L1), a polypeptide sequence comprising an antibody light chain variable domain (VL2), a polypeptide sequence comprising a flexible linker (L3), a polypeptide sequence comprising an antibody heavy chain variable domain (VH2), a polypeptide sequence comprising a second polypeptide linker (L2), and a polypeptide sequence comprising an antibody Fc domain. In some embodiments, the chimeric heavy chain of the bispecific molecule may comprise polypeptide sequences in the following orientation from N-terminus to C-terminus: VH1-CH1-L1-VL2-L3-VH2-L2-Fc. The chimeric heavy chain is a polypeptide chain comprising an amino acid sequence (e.g., the amino acid sequence of each of the polypeptide domains). Alternatively, in some embodiments, the chimeric heavy chain of the bispecific molecule may comprise polypeptide sequences in the following orientation from N-terminus to C-terminus: VH1-CH1-L1-VH2-L3-VL2-L2-Fc. The chimeric heavy chain is a polypeptide chain comprising an amino acid sequence (e.g., the amino acid sequence of each of the polypeptide domains). Note that VH1, VL1, CH1 and CL are used to denote portions of binding unit 1, with VH1 and VL1 denoting that portion that binds the first epitope. VH2 and VL2 is used to denote portions of binding unit 2 that bind the second epitope. In certain embodiments, one or more additional binding units (e.g., scFvs) are present at the N-terminal and/or C-terminal ends of the core of the bispecific molecule. In other aspects, one or more additional binding units (e.g., scFvs) are present within the hinge. The antibody heavy chain variable regions comprised within the successive scFv are denoted as VH3, VH4, VH5, and the corresponding antibody light chain variable regions within the successive scFv are denoted as VL3, VL4, VL5. In some embodiments, the bispecific molecule comprises a CH1 comprising the amino acid sequence of SEQ ID No: 134. In some embodiments, the bispecific molecule comprises a CH2-CH3 comprising the amino acid sequence of SEQ ID NO: 131, 132, or 133. In some embodiments, the bispecific molecule comprises a CH2-CH3 comprising one or more substitutions in position 22, 24, 26 according to the amino acid sequence of SEQ ID NO: 131. In some embodiments, the bispecific molecule comprises a CH2-CH3 comprising one or more substitutions of M22Y, S24T, T26E according to the amino acid sequence of SEQ ID NO: 131. In some embodiments, the bispecific molecule comprises a CH2-CH3 comprising one or more substitutions in position 198, 204 according to the amino acid sequence of SEQ ID NO: 131. In some embodiments, the bispecific molecule comprises a CH2-CH3 comprising one or more substitutions of M198L, N204S according to the amino acid sequence of SEQ ID NO: 131.

In some embodiments, chimeric heavy chain of the bispecific molecule may comprise polypeptide sequences in the following orientation from N-terminus to C-terminus: VH1-CH1-L1-BU$_2$-L2-CH2-CH3. In some embodiments, the light chain of the bispecific molecule may comprise polypeptide sequence in the following orientation from N-terminus to C-terminus: VL1-CL. In some embodiments, the bispecific molecule comprises a chimeric heavy chain comprising the amino acid sequence of SEQ ID NO: 137 and a light chain comprising the amino acid sequence of SEQ ID NO: 135. In some embodiments, the bispecific molecule comprises a chimeric heavy chain comprising the amino acid sequence of SEQ ID NO: 139 and a light chain comprising the amino acid sequence of SEQ ID NO: 135.

In some embodiments, chimeric heavy chain of the bispecific molecule may comprise polypeptide sequences in the following orientation from N-terminus to C-terminus: VH1-CH1-L1-BU$_2$-L2-CH2-CH3. In some embodiments, the light chain of the bispecific molecule may comprise polypeptide sequence in the following orientation from N-terminus to C-terminus: VL1-CL. In some embodiments, the bispecific molecule comprises a chimeric heavy chain comprising the amino acid sequence of SEQ ID NO: 138 and a light chain comprising the amino acid sequence of SEQ ID NO: 135. In some embodiments, the bispecific molecule comprises a chimeric heavy chain comprising the amino acid sequence of SEQ ID NO: 140 and a light chain comprising the amino acid sequence of SEQ ID NO: 135. In some embodiments, the bispecific molecule comprises a chimeric heavy chain comprising the amino acid sequence of SEQ ID NO: 141 and a light chain comprising the amino acid sequence of SEQ ID NO: 135.

In some embodiments, chimeric heavy chain of the bispecific molecule may comprise polypeptide sequences in the following orientation from N-terminus to C-terminus: VH1-CH1-L1-BU$_2$-L2-CH2-CH3. In some embodiments, the light chain of the bispecific molecule may comprise polypeptide sequence in the following orientation from N-terminus to C-terminus: VL1-CL. In some embodiments, the bispecific molecule comprises a chimeric heavy chain comprising the amino acid sequence of SEQ ID NO: 140 and a light chain comprising the amino acid sequence of SEQ ID NO: 136. In some embodiments, the bispecific molecule comprises a chimeric heavy chain comprising the amino acid sequence of SEQ ID NO: 141 and a light chain comprising the amino acid sequence of SEQ ID NO: 136. In some embodiments, the bispecific molecule comprises a chimeric heavy chain comprising the amino acid sequence of SEQ ID NO: 142 and a light chain comprising the amino acid sequence of SEQ ID NO: 136.

In some embodiments, chimeric heavy chain of the bispecific molecule may comprise polypeptide sequences in the following orientation from N-terminus to C-terminus: VH1-CH1-L1-BU$_2$-L2-CH2-CH3. In some embodiments, the light chain of the bispecific molecule may comprise polypeptide sequence in the following orientation from N-terminus to C-terminus: VL1-CL. In some embodiments, the bispecific molecule comprises a chimeric heavy chain comprising the amino acid sequence of SEQ ID NO: 142 and a light chain comprising the amino acid sequence of SEQ ID NO: 135. In some embodiments, the bispecific molecule comprises a chimeric heavy chain comprising the amino acid sequence of SEQ ID NO: 143 and a light chain comprising the amino acid sequence of SEQ ID NO: 135. In some embodiments, the bispecific molecule comprises a chimeric heavy chain comprising the amino acid sequence of SEQ ID NO: 144 and a light chain comprising the amino acid sequence of SEQ ID NO: 135.

In some embodiments, chimeric heavy chain of the bispecific molecule may comprise polypeptide sequences in the following orientation from N-terminus to C-terminus: VH1-CH1-L1-BU$_2$-L2-CH2-CH3. In some embodiments, the light chain of the bispecific molecule may comprise polypeptide sequence in the following orientation from N-terminus to C-terminus: VL1-CL. In some embodiments, the bispecific molecule comprises a chimeric heavy chain comprising the amino acid sequence of SEQ ID NO: 148 and a light chain comprising the amino acid sequence of SEQ ID NO: 135. In some embodiments, the bispecific molecule comprises a chimeric heavy chain comprising the amino acid sequence of SEQ ID NO: 146 and a light chain comprising the amino acid sequence of SEQ ID NO: 135.

In some embodiments, chimeric heavy chain of the bispecific molecule may comprise polypeptide sequences in the following orientation from N-terminus to C-terminus: VH1-CH1-L1-BU$_2$-L2-CH2-CH3. In some embodiments, the light chain of the bispecific molecule may comprise polypeptide sequence in the following orientation from N-terminus to C-terminus: VL1-CL. In some embodiments, the bispecific molecule comprises a chimeric heavy chain comprising the amino acid sequence of SEQ ID NO: 145 and a light chain comprising the amino acid sequence of SEQ ID NO: 135. In some embodiments, the bispecific molecule comprises a chimeric heavy chain comprising the amino acid sequence of SEQ ID NO: 147 and a light chain comprising the amino acid sequence of SEQ ID NO: 135.

In some embodiments, chimeric heavy chain of the bispecific molecule may comprise polypeptide sequences in the following orientation from N-terminus to C-terminus: VH1-CH1-L1-BU$_2$-L2-CH2-CH3. In some embodiments, the light chain of the bispecific molecule may comprise polypeptide sequence in the following orientation from N-terminus to C-terminus: VL1-CL. In some embodiments, the bispecific molecule comprises a chimeric heavy chain comprising the amino acid sequence of SEQ ID NO: 149 and a light chain comprising the amino acid sequence of SEQ ID NO: 135. In some embodiments, the bispecific molecule comprises a chimeric heavy chain comprising the amino acid sequence of SEQ ID NO: 150 and a light chain comprising the amino acid sequence of SEQ ID NO: 135. In some embodiments, the bispecific molecule comprises a chimeric heavy chain comprising the amino acid sequence of SEQ ID NO: 151 and a light chain comprising the amino acid sequence of SEQ ID NO: 135. In some embodiments, the bispecific molecule comprises a chimeric heavy chain comprising the amino acid sequence of SEQ ID NO: 152 and a light chain comprising the amino acid sequence of SEQ ID NO: 135.

In some embodiments, chimeric heavy chain of the bispecific molecule may comprise polypeptide sequences in the following orientation from N-terminus to C-terminus: VH1-CH1-L1-BU$_2$-L2-CH2-CH3. In some embodiments, the light chain of the bispecific molecule may comprise polypeptide sequence in the following orientation from N-terminus to C-terminus: VL1-CL. In some embodiments, the bispecific molecule comprises a chimeric heavy chain comprising the amino acid sequence of SEQ ID NO: 159 and a light chain comprising the amino acid sequence of SEQ ID NO: 160.

In some embodiments, chimeric heavy chain of the bispecific molecule may comprise polypeptide sequences in the following orientation from N-terminus to C-terminus: VH1-CH1-L1-BU$_2$-L2-CH2-CH3. In some embodiments, the light chain of the bispecific molecule may comprise polypeptide sequence in the following orientation from N-terminus to C-terminus: VL1-CL.

Exemplary antibody sequences are shown in Tables 2-6, wherein the CDR numbering is according to the EU index of Kabat. Those skilled in the art will recognize that many algorithms are known for prediction of CDR positions and for delimitation of antibody heavy chain and light chain variable regions. Anti-PcrV, anti-Psl antibodies or bispecific antibodies that specifically recognizing *Pseudomonas* PcrV and/or Psl comprising CDRs, V$_H$ and/or V$_L$ sequences from antibodies described herein, but based on prediction algorithms other than those exemplified in the tables below, are within the scope of this invention. The anti-PcrV or anti-Psl antibody sequences of our company patent with international application No. PCT/CN2020/100592, PCT/CN2020/093702 and PCT/CN2020/107666 were incorporated here in this invention.

TABLE 2

Exemplary antigen-binding domain CDR sequences

| Name | CDR H1 | CDR H2 | CDR H3 |
|---|---|---|---|
| 7B1 | DNYMS (SEQ ID NO: 1) | VISESGGSTNYADSVKG (SEQ ID NO: 4) | GRFSTLSSHFFRAVYGMDV (SEQ ID NO: 6) |
| 7C1 | DNHMS (SEQ ID NO: 2) | GISESGGSTNYADSVKG (SEQ ID NO: 5) | GRFSTSSSHFYRAVYGMDV (SEQ ID NO: 7) |
| Composite 1 | DNX1MS (SEQ ID NO: 14) wherein X1 is Y or H | X$_1$ISESGGSTNYADSVKG (SEQ ID NO: 15) wherein X$_1$ is V or G | GRFSTX$_1$SSHFX$_2$RAVYGMDV (SEQ ID NO: 16) wherein X$_1$ is L or S, and X$_2$ is F or Y |
| 8C1 | DNHMS (SEQ ID NO: 2) | GISESGGSTNYADSVKG (SEQ ID NO: 5) | GRFSTNSAHFFRAVYGMDV (SEQ ID NO: 8) |
| 6D10 | DYPMS (SEQ ID NO: 3) | GISESGGSTNYADSVKG (SEQ ID NO: 5) | GRFSTDSSHFYRAVYGMDV (SEQ ID NO: 9) |
| Composite 2 | DX$_1$X$_2$MS (SEQ ID NO: 20) Wherein X$_1$ is N or Y, and X$_2$ is Y, H or P | X$_1$ISESGGSTNYADSVKG (SEQ ID NO: 15) wherein X$_1$ is V or G | GRFSTX$_1$SX$_2$HFX$_3$RAVYGMDV (SEQ ID NO: 21) wherein X$_1$ is L, S, N or D, and X$_2$ is S or A, X$_3$ is F or Y |
| 6G12 | SYWMH (SEQ ID NO: 22) | RINEDETSISYADSVKG (SEQ ID NO: 23) | DGPYDSLDI (SEQ ID NO: 26) |
| 9C7 | SYWMH (SEQ ID NO: 22) | RINENEGSISYADSVKG (SEQ ID NO: 24) | DGPYDALDI (SEQ ID NO: 27) |

TABLE 2-continued

Exemplary antigen-binding domain CDR sequences

| Composite 3 | SYWMH<br>(SEQ ID NO: 22) | RINEX₁EX₂SISYADSVKG<br>(SEQ ID NO: 39)<br>wherein X₁ is D or N, and<br>X₂ is T or G | DGPYDX₁LDI<br>(SEQ ID NO: 40)<br>wherein X₁ is S or A |
|---|---|---|---|
| 5F3 | SYWMH<br>(SEQ ID NO: 22) | RINEDERSISYADSVKG<br>(SEQ ID NO: 25) | DGPYDALDI<br>(SEQ ID NO: 27) |
| 7H5 | SYWMH<br>(SEQ ID NO: 22) | RINEDERSISYADSVKG<br>(SEQ ID NO: 25) | DGPYDTLDI<br>(SEQ ID NO: 28) |
| 11E9 | SYWMH<br>(SEQ ID NO: 22) | RINENEGSISYADSVKG<br>(SEQ ID NO: 24) | DGPYDTLDI<br>(SEQ ID NO: 28) |
| 6G4 | SYWMH<br>(SEQ ID NO: 22) | RINEDERSISYADSVKG<br>(SEQ ID NO: 25) | DGPYDSLDI<br>(SEQ ID NO: 26) |
| 10D8 | SYWMH<br>(SEQ ID NO: 22) | RINENEGSISYADSVKG<br>(SEQ ID NO: 24) | DGPYDSLDI<br>(SEQ ID NO: 26) |
| PA49 | SYWMH<br>(SEQ ID NO: 22) | RINEDETSISYADSVKG<br>(SEQ ID NO: 23) | DGPYDSFDI<br>(SEQ ID NO: 29) |
| Composite 4 | SYWMH<br>(SEQ ID NO: 22) | RINEX₁EX₂SISYADSVKG<br>(SEQ ID NO: 44)<br>wherein X₁ is D or N, and<br>X₂ is T, G or R | DGPYDX₁X₂DI<br>(SEQ ID NO: 45)<br>wherein X₁ is S, A, or T,<br>and X₂ is F or L |
| P59 | SSGDYWG<br>(SEQ ID NO: 48) | SIHNQGSTYYNPSLKG<br>(SEQ ID NO: 52) | QFGSETYYTGIDP<br>(SEQ ID NO: 57) |
| P5921 | SSGDYWG<br>(SEQ ID NO: 48) | SIHNSGSTYYNPSLKG<br>(SEQ ID NO: 53) | QFGSETYYNGIQP<br>(SEQ ID NO: 58) |
| P5923 | SSGDYWG<br>(SEQ ID NO: 48) | SIHNQGSTYYNPSLKG<br>(SEQ ID NO: 52) | QFGSETYYPGIDP<br>(SEQ ID NO: 59) |
| P5925 | SSGDYWG<br>(SEQ ID NO: 48) | SIHNSGSTYYNPSLKG<br>(SEQ ID NO: 53) | QFGSETYYNGIDP<br>(SEQ ID NO: 60) |
| Composite 5 | SSGDYWG<br>(SEQ ID NO: 48) | SIHNX₁GSTYYNPSLKG<br>(SEQ ID NO: 81)<br>wherein X₁ is S or Q | QFGSETYYX₁GIX₂P<br>(SEQ ID NO: 82)<br>wherein X₁ is T, N or P,<br>and X₂ is D or Q |
| 3F12 | DYYWS<br>(SEQ ID NO: 49) | YIHSSGSTDYNPSLKS<br>(SEQ ID NO: 54) | AQGGSRRTLDY<br>(SEQ ID NO: 61) |
| 3F1201 | DYYWS<br>(SEQ ID NO: 49) | YIHSSGSTDYNPSLKS<br>(SEQ ID NO: 54) | AQGGSRRTLDY<br>(SEQ ID NO: 61) |
| 7H9 | IHSVH<br>(SEQ ID NO: 50) | TIISSGTTTTYAQSFQD<br>(SEQ ID NO: 55) | DGDS<br>(SEQ ID NO: 62) |
| 7H923 | IHSVH<br>(SEQ ID NO: 50) | TIISSGTTTTYAQSFQD<br>(SEQ ID NO: 55) | DGTS<br>(SEQ ID NO: 63) |
| 7H924 | IHSVH<br>(SEQ ID NO: 50) | TIISSGTTTTYAQSFQD<br>(SEQ ID NO: 55) | DGTS<br>(SEQ ID NO: 63) |
| 7H925 | IHSVH<br>(SEQ ID NO: 50) | TIISSGTTTTYAQSFQD<br>(SEQ ID NO: 55) | DGTS<br>(SEQ ID NO: 63) |
| Composite 6 | IHSVH<br>(SEQ ID NO: 50) | TIISSGTTTTYAQSFQD<br>(SEQ ID NO: 55) | DGX₁S<br>(SEQ ID NO: 84)<br>wherein X₁ is D or T |
| 6G7 | SDSYWG<br>(SEQ ID NO: 51) | TIYYDGTTFYNPSLRS<br>(SEQ ID NO: 56) | HESGQQLVNNWFDP<br>(SEQ ID NO: 64) |

| Name | CDR L1 | CDR L2 | CDR L3 |
|---|---|---|---|
| 7B1 | RASQGISSYLA<br>(SEQ ID NO: 10) | AASTLQS<br>(SEQ ID NO: 11) | QQLSSYPLT<br>(SEQ ID NO: 12) |
| 7C1 | RASQGISSYLA<br>(SEQ ID NO: 10) | AASTLQS<br>(SEQ ID NO: 11) | QQLSSYPLS<br>(SEQ ID NO: 13) |

TABLE 2-continued

Exemplary antigen-binding domain CDR sequences

| | | | |
|---|---|---|---|
| Composite 7 | RASQGISSYLA<br>(SEQ ID NO: 10) | AASTLQS<br>(SEQ ID NO: 11) | QQLSSYPLX₁<br>(SEQ ID NO: 19)<br>wherein X₁ is S or T |
| 8C1 | RASQGISSYLA<br>(SEQ ID NO: 10) | AASTLQS<br>(SEQ ID NO: 11) | QQLSSYPLT<br>(SEQ ID NO: 12) |
| 6D10 | RASQGISSYLA<br>(SEQ ID NO: 10) | AASTLQS<br>(SEQ ID NO: 11) | QQLSSYPLS<br>(SEQ ID NO: 13) |
| Composite 8 | RASQGISSYLA<br>(SEQ ID NO: 10) | AASTLQS<br>(SEQ ID NO: 11) | QQLSSYPLX₁<br>(SEQ ID NO: 19)<br>wherein X₁ is S or T |
| 6G12 | RASQSVSSNLA<br>(SEQ ID NO: 30) | DASSRAT<br>(SEQ ID NO: 33) | QQYGSSPLT<br>(SEQ ID NO: 35) |
| 9C7 | RASQGVRNNLA<br>(SEQ ID NO: 31) | HASSRAT<br>(SEQ ID NO: 34) | QQYGLQPIT<br>(SEQ ID NO: 36) |
| Composite 9 | RASQX₁VX₂X₃NLA<br>(SEQ ID NO: 41)<br>wherein X₁ is S or G,<br>X₂ is S or R and X₃ is<br>S or N | X₁ASSRAT<br>(SEQ ID NO: 42)<br>wherein X₁ is D or H | QQYGX₁X₂PX₃T<br>(SEQ ID NO: 43)<br>wherein X₁ is S or L, X₂ is<br>S or Q and X₃ is L or I |
| 5F3 | RASQNVKNNLA<br>(SEQ ID NO: 32) | HASSRAT<br>(SEQ ID NO: 34) | QQYGNEPIT<br>(SEQ ID NO: 37) |
| 7H5 | RASQNVKNNLA<br>(SEQ ID NO: 32) | HASSRAT<br>(SEQ ID NO: 34) | QQYGNEPIT<br>(SEQ ID NO: 37) |
| 11E9 | RASQGVRNNLA<br>(SEQ ID NO: 31) | HASSRAT<br>(SEQ ID NO: 34) | QQYGLQPIT<br>(SEQ ID NO: 36) |
| 6G4 | RASQNVKNNLA<br>(SEQ ID NO: 32) | HASSRAT<br>(SEQ ID NO: 34) | QQYGNEPIT<br>(SEQ ID NO: 37) |
| 10D8 | RASQGVRNNLA<br>(SEQ ID NO: 31) | HASSRAT<br>(SEQ ID NO: 34) | QQYGLQPIT<br>(SEQ ID NO: 36) |
| PA49 | RASQSVSSNLA<br>(SEQ ID NO: 30) | DASSRAT<br>(SEQ ID NO: 33) | QQYGSSPLT<br>(SEQ ID NO: 35) |
| Composite 10 | RASQX₁VX₂X₃NLA<br>(SEQ ID NO: 46)<br>wherein X₁ is S, G or<br>N, X₂ is S, R or K and<br>X₃ is S or N | X₁ASSRAT<br>(SEQ ID NO: 42)<br>wherein X₁ is D or H | QQYGX₁X₂PX₃T<br>(SEQ ID NO: 47)<br>wherein X₁ is S, L or N, X₂<br>is S, Q or E and X₃ is L or I |
| P59 | RSSQSLLHSNGYNYLD<br>(SEQ ID NO: 65) | LGSNRAS<br>(SEQ ID NO: 70) | MQALQTPYT<br>(SEQ ID NO: 74) |
| P5921 | RSSQSLLHSRGYNYLD<br>(SEQ ID NO: 66) | LGSNRAS<br>(SEQ ID NO: 70) | MQALQTPYT<br>(SEQ ID NO: 74) |
| P5923 | RSSQSLLHSNGYNYLD<br>(SEQ ID NO: 65) | LGSNRAS<br>(SEQ ID NO: 70) | MQALQTPYT<br>(SEQ ID NO: 74) |
| P5925 | RSSQSLLHSNGYNYLD<br>(SEQ ID NO: 65) | LGSNRAS<br>(SEQ ID NO: 70) | MQALQTPYT<br>(SEQ ID NO: 74) |
| Composite 11 | RSSQSLLHSX₁GYNYLD<br>(SEQ ID NO: 83)<br>wherein X₁ is N or R | LGSNRAS<br>(SEQ ID NO: 70) | MQALQTPYT<br>(SEQ ID NO: 74) |
| 3F12 | RASQTISSYLN<br>(SEQ ID NO: 67) | AASSLQS<br>(SEQ ID NO: 71) | QQSYSTPYT<br>(SEQ ID NO: 75) |
| 3F1201 | RASQTISSYLN<br>(SEQ ID NO: 67) | AASSLQS<br>(SEQ ID NO: 71) | QQSYSTPYT<br>(SEQ ID NO: 75) |
| 7H9 | RASQGISSWLA<br>(SEQ ID NO: 68) | HASTLES<br>(SEQ ID NO: 72) | LQANSLPHT<br>(SEQ ID NO: 76) |
| 7H923 | RASQGISSWLA<br>(SEQ ID NO: 68) | HASTLES<br>(SEQ ID NO: 72) | LQAFSLPHT<br>(SEQ ID NO: 77) |

TABLE 2-continued

Exemplary antigen-binding domain CDR sequences

| 7H924 | RASQGISSWLA (SEQ ID NO: 68) | HASTLES (SEQ ID NO: 72) | LQASSLPHT (SEQ ID NO: 78) |
|---|---|---|---|
| 7H925 | RASQGISSWLA (SEQ ID NO: 68) | HASTLES (SEQ ID NO: 72) | LQAKSLPHT (SEQ ID NO: 79) |
| Composite 12 | RASQGISSWLA (SEQ ID NO: 68) | HASTLES (SEQ ID NO: 72) | LQAX$_1$SLPHT (SEQ ID NO: 85) wherein X$_1$ is N, F, S or K |
| 6G7 | RASQSVSSNLA (SEQ ID NO: 69) | GASTRAT (SEQ ID NO: 73) | QQSGDSLVT (SEQ ID NO: 80) |

TABLE 3

Exemplary V$_H$ and V$_L$ sequences

| SEQ ID NO | Description | V$_H$ Sequence |
|---|---|---|
| 91 | 7B1 V$_H$ | EVQLLESGGGLVQPGGSLRLSCTASGFTFSDNYMSWVRQAPGKGLDWVSVISESGG STNYADSVKGRFSTSRDNSKSTLYLDMNSLRAEDTAIYYCAKGRFSTLSSHFFRAVY GMDVWGQGTAVTVSS (SEQ ID NO: 91) |
| 92 | 7C1 V$_H$ | EVQLLESGGGLVQPGGSLRLSCTASGFTFSDNHMSWVRQAPGKGLDWVSGISESGG STNYADSVKGRFSTSRDNSKSTLYLDMNSLRAEDTAIYYCAKGRESTSSSHFYRAVY GMDVWGQGTAVTVSS (SEQ ID NO: 92) |
| 93 | 8C1 V$_H$ | EVQLLESGGGLVQPGGSLRLSCTASGFTFSDNHMSWVRQAPGKGLDWVSGISESGG STNYADSVKGRFSTSRDNSKSTLYLDMNSLRAEDTAIYYCAKGRESTNSAHFFRAV YGMDVWGQGTAVTVSS (SEQ ID NO: 93) |
| 94 | 6D10 V$_H$ | EVQLLESGGGLVQPGGSLRLSCTASGFTFSDYPMSWVRQAPGKGLDWVSGISESGG STNYADSVKGRFSTSRDNSKSTLYLDMNSLRAEDTAIYYCAKGRFSTDSSHFYRAV YGMDVWGQGTAVTVSS (SEQ ID NO: 94) |
| 95 | 6G12 V$_H$ | QVQLVESGGGLVQPGGSLRLSCAASGFSFSSYWMHWVRQAPGKGLVWVSRINEDE TSISYADSVKGRFTISRDNAKNTLYLQMNGLRAEDTAVYYCVRDGPYDSLDIWGQG TMVTVSS (SEQ ID NO: 95) |
| 96 | 9C7 V$_H$ | QVQLVESGGGLVQPGGSLRLSCAASGFSFSSYWMHWVRQAPGKGLVWVSRINENE GSISY ADSVKGRFTISRDNAKNTLYLQMNGLRAEDTAVYYCVRDGPYDALDIWGQ GTMVTVSS (SEQ ID NO: 96) |
| 97 | 5F3 V$_H$ | QVQLVESGGGLVQPGGSLRLSCAASGFSFSSYWMHWVRQAPGKGLVWVSRINEDE RSISYADSVKGRFTISRDNAKNTLYLQMNGLRAEDTAVYYCVRDGPYDALDIWGQ GTMVTVSS (SEQ ID NO: 97) |
| 98 | 7H5 V$_H$ | QVQLVESGGGLVQPGGSLRLSCAASGFSFSSYWMHWVRQAPGKGLVWVSRINEDE RSISYADSVKGRFTISRDNAKNTLYLQMNGLRAEDTAVYYCVRDGPYDTLDIWGQG TMVTVSS (SEQ ID NO: 98) |
| 99 | 11E9 V$_H$ | QVQLVESGGGLVQPGGSLRLSCAASGFSFSSYWMHWVRQAPGKGLVWVSRINENE GSISY ADSVKGRFTISRDNAKNTLYLQMNGLRAEDTAVYYCVRDGPYDTLDIWGQG TMVTVSS (SEQ ID NO: 99) |
| 100 | 6G4 V$_H$ | QVQLVESGGGLVQPGGSLRLSCAASGFSFSSYWMHWVRQAPGKGLVWVSRINEDE RSISYADSVKGRFTISRDNAKNTLYLQMNGLRAEDTAVYYCVRDGPYDSLDIWGQG TMVTVSS (SEQ ID NO: 100) |
| 101 | 10D8 V$_H$ | QVQLVESGGGLVQPGGSLRLSCAASGFSFSSYWMHWVRQAPGKGLVWVSRINENE GSISYADSVKGRFTISRDNAKNTLYLQMNGLRAEDTAVYYCVRDGPYDSLDIWGQG TMVTVSS (SEQ ID NO: 101) |
| 102 | PA49 V$_H$ | QVQLVESGGGLVQPGGSLRLSCAASGFSFRSYWMHWVRQAPGKGLVWVSRINEDE TSISYADSVKGRFTISRDNAKNTLYLQMNGLRAEDTAVYYCARDGPYDSFDIWGQG TMVTVSS (SEQ ID NO: 102) |
| 103 | P59 V$_H$ | QVQLQQSGPGLVKPSETLSLTCTVSGGPITSSGDYWGWIRQPPGKGLELIGSIHNQGS TYYNPSLKGRVTISGDTSKNQISLRLSSVTAADTAVYYCARQFGSETYYTGIDPWGQ GTLVTVSS (SEQ ID NO: 103) |

TABLE 3-continued

Exemplary V$_H$ and V$_L$ sequences

| 104 | P5921 V$_H$ | QVQLQQSGPGLVKPSETLSLTCTVSGGPITSSGDYWGWIRQPPGKGLELIGSIHNSGS TYYNPSLKGRVTISGDTSKNQISLRLSSVTAADTAVYYCARQFGSETYYNGIQPWGQ GTLVTVSS (SEQ ID NO: 104) |
|---|---|---|
| 105 | P5923 V$_H$ | QVQLQQSGPGLVKPSETLSLTCTVSGGPITSSGDYWGWIRQPPGKGLELIGSIHNQGS TYYNPSLKGRVTISGDTSKNQISLRLSSVTAADTAVYYCARQFGSETYYPGIDPWGQ GTLVTVSS (SEQ ID NO: 105) |
| 106 | P5925 V$_H$ | QVQLQQSGPGLVKPSETLSLTCTVSGGPITSSGDYWGWIRQPPGKGLELIGSIHNSGS TYYNPSLKGRVTISGDTSKNQISLRLSSVTAADTAVYYCARQFGSETYYNGIDPWGQ GTLVTVSS (SEQ ID NO: 106) |
| 107 | 3F12 V$_H$ | QVQLQQSGPGLVKTSETLSLTCTVSGGSVSDYYWSWIRQPPGKGLEWIGYIHSSGST DYNPSLKSRLTISGDAAKKQFSLNLSSVTAADTALYYCARAQGGSRRTLDYWGQGT LVTVSS (SEQ ID NO: 107) |
| 108 | 3F1201 V$_H$ | QVQLQQSGPGLVKTSETLSLTCTVSGGSVSDYYWSWIRQPPGKGLEWIGYIHSSGST DYNPSLKSRLTISGDAAKKQFSLKLSSVTAADTALYYCARAQGGSRRTLDYWGQGT LVTVSS (SEQ ID NO: 108) |
| 109 | 7H9 V$_H$ | QVQLVQSGAEVKKPGASVKVSCKASGDTSTIHSVHWVRQAPGQGLEWMGTIISSGT TTTYAQSFQDRVSMTIDRSTSTGYMELSSLRFEDTAVYYCTTDGDSWGQGTLVTVS S (SEQ ID NO: 109) |
| 110 | 7H923 V$_H$<br>7H924 V$_H$<br>7H925 V$_H$ | QVQLVQSGAEVKKPGASVKVSCKASGDTSTIHSVHWVRQAPGQGLEWMGTIISSGT TTTYAQSFQDRVSMTIDRSTSTGYMELSSLRFEDTAVYYCTTDGTSWGQGTLVTVSS (SEQ ID NO: 110) |
| 111 | 6G7 V$_H$ | QVQLQESGPGLVKSSETLSLTCTVSGDSISSDSYWGWIRQPPGKGLEWLATIYYDGT TFYNPSLRSRLIISGDASKKQFSLRLSSVTAADTAIYYCARHESGQQLVNNWFDPWG QGTVVTVSS (SEQ ID NO: 111) |
| 161 | 7B1 V$_H$<br>Cysteine variant | EVQLLESGGGLVQPGGSLRLSCTASGFTFSDNYMSWVRQAPGKCLDWVSVISESGG STNYADSVKGRFSTSRDNSKSTLYLDMNSLRAEDTAIYYCAKGRFSTLSSHFFRAVY GMDVWGQGTAVTVSS |
| 162 | 7C1 V$_H$<br>Cysteine variant | EVQLLESGGGLVQPGGSLRLSCTASGFTFSDNHMSWVRQAPGKCLDWVSGISESGG STNYADSVKGRFSTSRDNSKSTLYLDMNSLRAEDTAIYYCAKGRFSTSSSHFYRAVY GMDVWGQGTAVTVSS |
| 163 | 8C1 V$_H$<br>Cysteine variant | EVQLLESGGGLVQPGGSLRLSCTASGFTFSDNHMSWVRQAPGKCLDWVSGISESGG STNYADSVKGRFSTSRDNSKSTLYLDMNSLRAEDTAIYYCAKGRFSTNSAHFFRAV YGMDVWGQGTAVTVSS |
| 164 | 6D10 V$_H$<br>Cysteine variant | EVQLLESGGGLVQPGGSLRLSCTASGFTFSDYPMSWVRQAPGKCLDWVSGISESGG STNYADSVKGRFSTSRDNSKSTLYLDMNSLRAEDTAIYYCAKGRFSTDSSHFYRAV YGMDVWGQGTAVTVSS |
| 165 | 6G12 V$_H$<br>Cysteine variant | QVQLVESGGGLVQPGGSLRLSCAASGFSFSSYWMHWVRQAPGKCLVWVSRINEDE TSISYADSVKGRFTISRDNAKNTLYLQMNGLRAEDTAVYYCVRDGPYDSLDIWGQG TMVTVSS |
| 166 | 9C7 V$_H$<br>Cysteine variant | QVQLVESGGGLVQPGGSLRLSCAASGFSFSSYWMHWVRQAPGKCLVWVSRINENE GSISYADSVKGRFTISRDNAKNTLYLQMNGLRAEDTAVYYCVRDGPYDALDIWGQ GTMVTVSS |
| 167 | 5F3 V$_H$<br>Cysteine variant | QVQLVESGGGLVQPGGSLRLSCAASGFSFSSYWMHWVRQAPGKCLVWVSRINEDE RSISYADSVKGRFTISRDNAKNTLYLQMNGLRAEDTAVYYCVRDGPYDALDIWGQ GTMVTVSS |
| 168 | 7H5 V$_H$<br>Cysteine variant | QVQLVESGGGLVQPGGSLRLSCAASGFSFSSYWMHWVRQAPGKCLVWVSRINEDE RSISYADSVKGRFTISRDNAKNTLYLQMNGLRAEDTAVYYCVRDGPYDTLDIWGQG TMVTVSS |
| 169 | 11E9 V$_H$<br>Cysteine variant | QVQLVESGGGLVQPGGSLRLSCAASGFSFSSYWMHWVRQAPGKCLVWVSRINENE GSISYADSVKGRFTISRDNAKNTLYLQMNGLRAEDTAVYYCVRDGPYDTLDIWGQG TMVTVSS |
| 170 | 6G4 V$_H$<br>Cysteine variant | QVQLVESGGGLVQPGGSLRLSCAASGFSFSSYWMHWVRQAPGKCLVWVSRINEDE RSISYADSVKGRFTISRDNAKNTLYLQMNGLRAEDTAVYYCVRDGPYDSLDIWGQG TMVTVSS |
| 171 | 10D8 V$_H$<br>Cysteine variant | QVQLVESGGGLVQPGGSLRLSCAASGFSFSSYWMHWVRQAPGKCLVWVSRINENE GSISYADSVKGRFTISRDNAKNTLYLQMNGLRAEDTAVYYCVRDGPYDSLDIWGQG TMVTVSS |

TABLE 3-continued

Exemplary V$_H$ and V$_L$ sequences

| 172 | PA49 V$_H$ Cysteine variant | QVQLVESGGGLVQPGGSLRLSCAASGFSFRSYWMHWVRQAPGKCL VWVSRINEDE TSISYADSVKGRFTISRDNAKNTLYLQMNGLRAEDTAVYYCARDGPYDSFDIWGQG TMVTVSS |
| 173 | P59 V$_H$ Cysteine variant | QVQLQQSGPGLVKPSETLSLTCTVSGGPITSSGDYWGWIRQPPGKCLELIGSIHNQGS TYYNPSLKGRVTISGDTSKNQISLRLSSVTAADTAVYYCARQFGSETYYTGIDPWGQ GTLVTVSS |
| 174 | P5921 V$_H$ Cysteine variant | QVQLQQSGPGLVKPSETLSLTCTVSGGPITSSGDYWGWIRQPPGKCLELIGSIHNSGS TYYNPSLKGRVTISGDTSKNQISLRLSSVTAADTAVYYCARQFGSETYYNGIQPWGQ GTLVTVSS |
| 175 | P5923 V$_H$ Cysteine variant | QVQLQQSGPGLVKPSETLSLTCTVSGGPITSSGDYWGWIRQPPGKCLELIGSIHNQGSN TYYNPSLKGRVTISGDTSKNQISLRLSSVTAADTAVYYCARQFGSETYYPGIDPWGQ GTLVTVSS |
| 176 | P5925 V$_H$ Cysteine variant | QVQLQQSGPGLVKPSETLSLTCTVSGGPITSSGDYWGWIRQPPGKCLELIGSIHNSGS TYYNPSLKGRVTISGDTSKNQISLRLSSVTAADTAVYYCARQFGSETYYNGIDPWGQ GTLVTVSS |
| 177 | 3F12 V$_H$ Cysteine variant | QVQLQQSGPGLVKTSETLSLTCTVSGGSVSDYYWSWIRQPPGKCLEWIGYIHSSGST DYNPSLKSRLTISGDAAKKQFSLNLSSVTAADTALYYCARAQGGSRRTLDYWGQGT LVTVSS |
| 178 | 3F1201 V$_H$ Cysteine variant | QVQLQQSGPGLVKTSETLSLTCTVSGGSVSDYYWSWIRQPPGKCLEWIGYIHSSGST DYNPSLKSRLTISGDAAKKQFSLKLSSVTAADTALYYCARAQGGSRRTLDYWGQGT LVTVSS |
| 179 | 7H9 V$_H$ Cysteine variant | QVQLVQSGAEVKKPGASVKVSCKASGDTSTIHSVHWVRQAPGQCLEWMGTIISSGT TTTYAQSFQDRVSMTIDRSTSTGYMELSSLRFEDTAVYYCTTDGDSWGQGTLVTVS S |
| 180 | 7H923 V$_H$ 7H924 V$_H$ 7H925 V$_H$ Cysteine variants | QVQLVQSGAEVKKPGASVKVSCKASGDTSTIHSVHWVRQAPGQCLEWMGTIISSGT TTTYAQSFQDRVSMTIDRSTSTGYMELSSLRFEDTAVYYCTTDGTSWGQGTLVTVSS |
| 181 | 6G7 V$_H$ Cysteine variant | QVQLQESGPGLVKSSETLSLTCTVSGDSISSDSYWGWIRQPPGKCLEWLATIYYDGT TFYNPSLRSRLIISGDASKKQFSLRLSSVTAADTAIYYCARHESGQQLVNNWFDPWG QGTVVTVSS |

| SEQ ID NO | Description | V$_L$ Sequence |
| --- | --- | --- |
| 112 | 7B1 V$_L$ 8C1 V$_L$ | DIQLTQSPSSLSASVGDRVTITCRASQGISSYLAWYQQKPGKAPKLLIYAASTLQSGV PSRFSGSGSGTDFTLTISSLQPEDFATYYCQQLSSYPLTFGGGTKVEIK (SEQ ID NO: 112) |
| 113 | 7C1 V$_L$ 6D10 V$_L$ | DIQLTQSPSSLSASVGDRVTITCRASQGISSYLAWYQQKPGKAPKLLIYAASTLQSGV PSRFSGSGSGTDFTLTISSLQPEDFATYYCQQLSSYPLSFGGGTKVEIK (SEQ ID NO: 113) |
| 114 | 6G12 V$_L$ PA49 V$_L$ | EIVMTQSPATLSVSPGERATLSCRASQSVSSNLAWYQHKPGQAPRLLIYDASSRATGI PDRFSGSGSGTDFTLTISRLEPEDFAVYYCQQYGSSPLTFGGGTKLEIK (SEQ ID NO: 114) |
| 115 | 9C7 V$_L$ 11E9 V$_L$ 10D8 V$_L$ | EIVMTQSPATLSVSPGERATLSCRASQGVRNNLAWYQHKPGQAPRLLIYHASSRATG IPDRFSGSGSGTDFTLTISRLEPEDFAVYYCQQYGLQPITFGGGTKLEIK (SEQ ID NO: 115) |
| 116 | 5F3 V$_L$ 6G4 V$_L$ 7H5 V$_L$ | EIVMTQSPATLSVSPGERATLSCRASQNVKNNLAWYQHKPGQAPRLLIYHASSRAT GIPDRFSGSGSGTDFTLTISRLEPEDFAVYYCQQYGNEPITFGGGTKLEIK (SEQ ID NO: 116) |
| 117 | P59 V$_L$ P5923 V$_L$ P5925 V$_L$ | DIVMTQTPLSLPVTPGEPASISCRSSQSLLHSNGYNYLDWYLQKPGQSPQLLIYLGSN RASGVPDRFSGSGSGTDFTLKISRVEAEDVGVYYCMQALQTPYTFGQGTKLEIK (SEQ ID NO: 117) |
| 118 | P5921 V$_L$ | DIVMTQTPLSLPVTPGEPASISCRSSQSLLHSRGYNYLDWYLQKPGQSPQLLIYLGSN RASGVPDRFSGSGSGTDFTLKISRVEAEDVGVYYCMQALQTPYTFGQGTKLEIK (SEQ ID NO: 118) |
| 119 | 3F12 V$_L$ 3F1201 V$_L$ | EIVMTQSPSTLSASVGDRVAITCRASQTISSYLNWYQKPGKAPKLLIYAASSLQSGV PSRFSGSGSGTDFTLTISSLQPEDFATYYCQQSYSTPYTFGQGTKVDIK (SEQ ID NO: 119) |

TABLE 3-continued

| | | Exemplary $V_H$ and $V_L$ sequences |
|---|---|---|
| 120 | 7H9 $V_L$ | DIQLTQSPSSVSASVGDRVTIACRASQGISSWLAWYQQKPGKAPKLLIYHASTLESG VPSRFSGSGSGTDFTLTISSLQPEDFATYYCLQANSLPHTFGQGTKLEIK (SEQ ID NO: 120) |
| 121 | 7H923 $V_L$ | DIQLTQSPSSVSASVGDRVTIACRASQGISSWLAWYQQKPGKAPKLLIYHASTLESG VPSRFSGSGSGTDFTLTISSLQPEDFATYYCLQAFSLPHTFGQGTKLEIK (SEQ ID NO: 121) |
| 122 | 7H924 $V_L$ | DIQLTQSPSSVSASVGDRVTIACRASQGISSWLAWYQQKPGKAPKLLIYHASTLESG VPSRFSGSGSGTDFTLTISSLQPEDFATYYCLQASSLPHTFGQGTKLEIK (SEQ ID NO: 122) |
| 123 | 7H925 $V_L$ | DIQLTQSPSSVSASVGDRVTIACRASQGISSWLAWYQQKPGKAPKLLIYHASTLESG VPSRFSGSGSGTDFTLTISSLQPEDFATYYCLQAKSLPHTFGQGTKLEIK (SEQ ID NO: 123) |
| 124 | 6G7 $V_L$ | ETTLTQSPATLSVSPGERATLSCRASQSVSSNLAWYQQKPGQAPRLLIYGASTRATGI PARFSGSGSGTEFTLTISRLEPEDFAVYYCQQSGDSLVTFGQGTRLEIK (SEQ ID NO: 124) |
| 182 | 7B1 $V_L$ 8C1 $V_L$ Cysteine variants | DIQLTQSPSSLSASVGDRVTITCRASQGISSYLAWYQQKPGKAPKLLIYAASTLQSGV PSRFSGSGSGTDFTLTISSLQPEDFATYYCQQLSSYPLTFGCGTKVEIK |
| 183 | 7C1 $V_L$ 6D10 $V_L$ Cysteine variants | DIQLTQSPSSLSASVGDRVTITCRASQGISSYLAWYQQKPGKAPKLLIYAASTLQSGV PSRFSGSGSGTDFTLTISSLQPEDFATYYCQQLSSYPLSFGCGTKVEIK |
| 184 | 6G12 $V_L$ PA49 $V_L$ Cysteine variants | EIVMTQSPATLSVSPGERATLSCRASQSVSSNLAWYQHKPGQAPRLLIYDASSRATGI PDRFSGSGSGTDFTLTISRLEPEDFAVYYCQQYGSSPLTFGCGTKLEIK |
| 185 | 9C7 $V_L$ 11E9 $V_L$ 10D8 $V_L$ Cysteine variants | EIVMTQSPATLSVSPGERATLSCRASQGVRNNLAWYQHKPGQAPRLLIYHASSRATG IPDRFSGSGSGTDFTLTISRLEPEDFAVYYCQQYGLQPITFGCGTKLEIK |
| 186 | 5F3 $V_L$ 6G4 $V_L$ 7H5 $V_L$ Cysteine variants | EIVMTQSPATLSVSPGERATLSCRASQNVKNNLAWYQHKPGQAPRLLIYHASSRAT GIPDRFSGSGSGTDFTLTISRLEPEDFAVYYCQQYGNEPITFGCGTKLEIK |
| 187 | P59 $V_L$ P5923 $V_L$ P5925 $V_L$ Cysteine variants | DIVMTQTPLSLPVTPGEPASISCRSSQSLLHSNGYNYLDWYLQKPGQSPQLLIYLGSN RASGVPDRFSGSGSGTDFTLKISRVEAEDVGVYYCMQALQTPYTFGCGTKLEIK |
| 188 | P5921 $V_L$ Cysteine variant | DIVMTQTPLSLPVTPGEPASISCRSSQSLLHSRGYNYLDWYLQKPGQSPQLLIYLGSN RASGVPDRFSGSGSGTDFTLKISRVEAEDVGVYYCMQALQTPYTFGCGTKLEIK |
| 189 | 3F12 $V_L$ 3F1201 $V_L$ Cysteine variants | EIVMTQSPSTLSASVGDRVAITCRASQTISSYLNWYQLKPGKAPKLLIYAASSLQSGV PSRFSGSGSGTDFTLTISSLQPEDFATYYCQQSYSTPYTFGCGTKVDIK |
| 190 | 7H9 $V_L$ Cysteine variant | DIQLTQSPSSVSASVGDRVTIACRASQGISSWLAWYQQKPGKAPKLLIYHASTLESG VPSRFSGSGSGTDFTLTISSLQPEDFATYYCLQANSLPHTFGCGTKLEIK |
| 191 | 7H923 $V_L$ Cysteine variant | DIQLTQSPSSVSASVGDRVTIACRASQGISSWLAWYQQKPGKAPKLLIYHASTLESG VPSRFSGSGSGTDFTLTISSLQPEDFATYYCLQAFSLPHTFGCGTKLEIK |
| 192 | 7H924 $V_L$ Cysteine variant | DIQLTQSPSSVSASVGDRVTIACRASQGISSWLAWYQQKPGKAPKLLIYHASTLESG VPSRFSGSGSGTDFTLTISSLQPEDFATYYCLQASSLPHTFGCGTKLEIK |
| 193 | 7H925 $V_L$ Cysteine variant | DIQLTQSPSSVSASVGDRVTIACRASQGISSWLAWYQQKPGKAPKLLIYHASTLESG VPSRFSGSGSGTDFTLTISSLQPEDFATYYCLQAKSLPHTFGCGTKLEIK |

TABLE 3-continued

| Exemplary V_H and V_L sequences | | |
|---|---|---|
| 194 | 6G7 V_L Cysteine variant | ETTLTQSPATLSVSPGERATLSCRASQSVSSNLAWYQQKPGQAPRLLIYGASTRATGI PARFSGSGSGTEFTLTISRLEPEDFAVYYCQQSGDSLVTFGCGTRLEIK |

TABLE 4

Exemplary Sequences

| SEQ ID NO: | Description | Sequence |
|---|---|---|
| 86 | Full-length PcrV | MEVRNLNAARELFLDELLAASAAPASAEQEELLALLRSERIVLAHAGQPLSEAQ VLKALAWLLAANPSAPPGQGLEVLREVLQARRQPGAQWDLREFLVSAYFSLHG RLDEDVIGVYKDVLQTQDGKRKALLDELKALTAELKVYSVIQSQINAALSAKQG IRIDAGGIDLVDPTLYGYAVGDPRWKDSPEYALLSNLDTFSGKLSIKDFLSGSPK QSGELKGLSDEYPFEKDNNPVGNFATTVSDRSRPLNDKVNEKTTLLNDTSSRYN SAVEALNRFIQKYDSVLRDILSAI |
| 88 | Light chain constant region | RTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |
| 89 | IgG1 heavy chain constant region | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHTCP PCPAPELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPEN NYKTTPPVLDSDGSFFLYSKLTVDKSRWQQGNVFSCSVMHEALHNHYTQKSLS LSPGK |
| 90 | IgG4 heavy chain constant region | ASTKGPSVFPLAPCSRSTSESTAALGCLVKDYFPEPVTVSWNSGALTSGVHTFPA VLQSSGLYSLSSVVTVPSSSLGTKTYTCNVDHKPSNTKVDKRVESKYGPPCPSCP APEFLGGPSVFLFPPKPKDTLMISRTPEVTCVVVDVSQEDPEVQFNWYVDGVEV HNAKTKPREEQFNSTYRVVSVLTVLHQDWLNGKEYKCKVSNKGLPSSIEKTISK AKGQPREPQVYTLPPSQEEMTKNQVSLTCLVKGFYPSDIAVEWESNGQPENNYK TTPPVLDSDGSFFLYSRLTVDKSRWQEGNVFSCSVMHEALHNHYTQKSLSLSLG K |

TABLE 5

Exemplary Sequences Linker sequences

| SEQ ID NO: | Sequence |
|---|---|
| 87 | GGGGSGGGGSGGGGSGGGG |
| 153 | EPKSDKTGGGGSGGGGS |
| 154 | EPKSCGKTGGGGSGGGGS |
| 155 | EPKSCGGGGSGGGGS |

TABLE 5-continued

Exemplary Sequences Linker sequences

| SEQ ID NO: | Sequence |
|---|---|
| 156 | GGGGSGGGGSEPKSDKTHTCPPCP |
| 157 | GGGGSGGGGSCPPCP |
| 158 | GGGGSGGGGSDKTHTCPPCP |

TABLE 6

Exemplary Bispecific molecule sequences

| CH2-CH3 (original) | APELLGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSDGSFFLYSKLT VDKSRWQQGNVFSCSVMHEALHNHYTQKSLSLSPGK (SEQ ID NO: 131) |
|---|---|
| CH2-CH3 (mut 1) | APELLGGPSVFLFPPKPKDTLYITREPEVTCVVVDVSHEDPEVKFNWYVDGVEVHNAKTK PREEQYNSTYRVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSDGSFFLYSKLT VDKSRWQQGNVFSCSVMHEALHNHYTQKSLSLSPGK (SEQ ID NO: 132) |
| CH2-CH3 (mut 2) | APELLGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSDGSFFLYSKLT VDKSRWQQGNVFSCSVLHEALHSHYTQKSLSLSPGK (SEQ ID NO: 133) |

TABLE 6-continued

Exemplary Bispecific molecule sequences

| | |
|---|---|
| CH1 | ASTKGPSVFPLAPSSKSTSGGTAALGCLVKDYFPEPVTVSWNSGALTSGVHTFPAVLQSSG<br>LYSLSSVVTVPSSSLGTQTYICNVNHKPSNTKVDKKV (SEQ ID NO: 134) |
| 7B1-VL-CL | DIQLTQSPSSLSASVGDRVTITCRASQGISSYLAWYQQKPGKAPKLLIYAASTLQSGVPSRF<br>SGSGSGTDFTLTISSLQPEDFATYYCQQLSSYPLTFGGGTKVEIKRTVAAPSVFIFPPSDEQL<br>KSGTASVVCLLNNFYPREAKVQWKVDNALQSGNSQESVTEQDSKDSTYSLSSTLTLSKAD<br>YEKHKVYACEVTHQGLSSPVTKSFNRGEC (SEQ ID NO: 135) |
| 7C1-VL-CL | DIQLTQSPSSLSASVGDRVTITCRASQGISSYLAWYQQKPGKAPKLLIYAASTLQSGVPSRF<br>SGSGSGTDFTLTISSLQPEDFATYYCQQLSSYPLSFGGGTKVEIKRTVAAPSVFIFPPSDEQL<br>KSGTASVVCLLNNFYPREAKVQWKVDNALQSGNSQESVTEQDSKDSTYSLSSTLTLSKAD<br>YEKHKVYACEVTHQGLSSPVTKSFNRGEC (SEQ ID NO: 136) |
| Chimeric-STS7B112-<br>heavy chain | EVQLLESGGGLVQPGGSLRLSCTASGFTFSDNYMSWVRQAPGKGLDWVSVISESGGSTNY<br>ADSVKGRFSTSRDNSKSTLYLDMNSLRAEDTAIYYCAKGRFSTLSSHFFRAVYGMDVWG<br>QGTAVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCGGGGSGGGGS<br>QVQLQQSGPGLVKTSETLSLTCTVSGGSVSDYYWSWIRQPPGKCLEWIGYIHSSGSTDYNP<br>SLKSRLTISGDAAKKQFSLNLSSVTAADTALYYCARAQGGSRRTLDYWGQGTLVTVSSGG<br>GGSGGGGSGGGGSGGGGSEIVMTQSPSTLSASVGDRVAITCRASQTISSYLNWYQLKPGK<br>APKLLIYAASSLQSGVPSRFSGSGSGTDFTLTISSLQPEDFATYYCQQSYSTPYTFGCGTKV<br>DIKGGGGSGGGGSDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKEYKCKVSNK<br>ALPAPIEKTISKAKGQPREPQVYTLPPSREEMTKNQVSLTCLVKGFYPSDIAVEWESNGQPE<br>NNYKTTPPVLDSDGSFFLYSKLTVDKSRWQQGNVFSCSVMHEALHNHYTQKSLSLSPGK<br>(SEQ ID NO: 137) |
| Chimeric-STS7B11201-<br>heavy chain | EVQLLESGGGLVQPGGSLRLSCTASGFTFSDNYMSWVRQAPGKGLDWVSVISESGGSTNY<br>ADSVKGRFSTSRDNSKSTLYLDMNSLRAEDTAIYYCAKGRFSTLSSHFFRAVYGMDVWG<br>QGTAVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCGGGGSGGGGS<br>QVQLQQSGPGLVKTSETLSLTCTVSGGSVSDYYWSWIRQPPGKCLEWIGYIHSSGSTDYNP<br>SLKSRLTISGDAAKKQFSLKLSSVTAADTALYYCARAQGGSRRTLDYWGQGTLVTVSSGG<br>GGSGGGGSGGGGSGGGGSEIVMTQSPSTLSASVGDRVAITCRASQTISSYLNWYQLKPGK<br>APKLLIYAASSLQSGVPSRFSGSGSGTDFTLTISSLQPEDFATYYCQQSYSTPYTFGCGTKV<br>DIKGGGGSGGGGSDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKEYKCKVSNK<br>ALPAPIEKTISKAKGQPREPQVYTLPPSREEMTKNQVSLTCLVKGFYPSDIAVEWESNGQPE<br>NNYKTTPPVLDSDGSFFLYSKLTVDKSRWQQGNVFSCSVMHEALHNHYTQKSLSLSPGK<br>(SEQ ID NO: 138) |
| Chimeric-<br>STS7B112M-heavy<br>chain | EVQLLESGGGLVQPGGSLRLSCTASGFTFSDNYMSWVRQAPGKGLDWVSVISESGGSTNY<br>ADSVKGRFSTSRDNSKSTLYLDMNSLRAEDTAIYYCAKGRFSTLSSHFFRAVYGMDVWG<br>QGTAVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCgktGGGGSGGGG<br>GSQVQLQQSGPGLVKTSETLSLTCTVSGGSVSDYYWSWIRQPPGKCLEWIGYIHSSGSTDY<br>NPSLKSRLTISGDAAKKQFSLNLSSVTAADTALYYCARAQGGSRRTLDYWGQGTLVTVSS<br>GGGGSGGGGSGGGGSGGGGSEIVMTQSPSTLSASVGDRVAITCRASQTISSYLNWYQLKP<br>GKAPKLLIYAASSLQSGVPSRFSGSGSGTDFTLTISSLQPEDFATYYCQQSYSTPYTFGCGT<br>KVDIKGGGGSGGGGSCPPCPAPELLGGPSVFLFPPKPKDTLYITREPEVTCVVVDVSHEDPE<br>VKFNWYVDGVEVHNAKTKPREEQYNSTYRVVSVLTVLHQDWLNGKEYKCKVSNKALP<br>APIEKTISKAKGQPREPQVYTLPPSREEMTKNQVSLTCLVKGFYPSDIAVEWESNGQPENN<br>YKTTPPVLDSDGSFFLYSKLTVDKSRWQQGNVFSCSVMHEALHNHYTQKSLSLSPGK<br>(SEQ ID NO: 139) |
| Chimeric-<br>STS7B11201M-heavy<br>chain | EVQLLESGGGLVQPGGSLRLSCTASGFTFSDNYMSWVRQAPGKGLDWVSVISESGGSTNY<br>ADSVKGRFSTSRDNSKSTLYLDMNSLRAEDTAIYYCAKGRFSTLSSHFFRAVYGMDVWG<br>QGTAVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCgktGGGGSGGGG<br>GSQVQLQQSGPGLVKTSETLSLTCTVSGGSVSDYYWSWIRQPPGKCLEWIGYIHSSGSTDY<br>NPSLKSRLTISGDAAKKQFSLKLSSVTAADTALYYCARAQGGSRRTLDYWGQGTLVTVSS<br>GGGGGGGGSGGGGSGGGGSEIVMTQSPSTLSASVGDRVAITCRASQTISSYLNWYQLKP<br>GKAPKLLIYAASSLQSGVPSRFSGSGSGTDFTLTISSLQPEDFATYYCQQSYSTPYTFGCGT<br>KVDIKGGGGSGGGGSCPPCPAPELLGGPSVFLFPPKPKDTLYITREPEVTCVVVDVSHEDPE<br>VKFNWYVDGVEVHNAKTKPREEQYNSTYRVVSVLTVLHQDWLNGKEYKCKVSNKALP<br>APIEKTISKAKGQPREPQVYTLPPSREEMTKNQVSLTCLVKGFYPSDIAVEWESNGQPENN<br>YKTTPPVLDSDGSFFLYSKLTVDKSRWQQGNVFSCSVMHEALHNHYTQKSLSLSPGK<br>(SEQ ID NO: 140) |
| Chimeric-<br>STS7B11201S-heavy<br>chain | EVQLLESGGGLVQPGGSLRLSCTASGFTFSDNYMSWVRQAPGKGLDWVSVISESGGSTNY<br>ADSVKGRFSTSRDNSKSTLYLDMNSLRAEDTAIYYCAKGRFSTLSSHFFRAVYGMDVWG<br>QGTAVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCgktGGGGSGGGG<br>GSQVQLQQSGPGLVKTSETLSLTCTVSGGSVSDYYWSWIRQPPGKCLEWIGYIHSSGSTDY<br>NPSLKSRLTISGDAAKKQFSLKLSSVTAADTALYYCARAQGGSRRTLDYWGQGTLVTVSS<br>GGGGSGGGGSGGGGSGGGGSEIVMTQSPSTLSASVGDRVAITCRASQTISSYLNWYQLKP<br>GKAPKLLIYAASSLQSGVPSRFSGSGSGTDFTLTISSLQPEDFATYYCQQSYSTPYTFGCGT<br>KVDIKGGGGSGGGGSCPPCPAPELLGGPSVFLFPPKPKDTLMISRTPEVTCVVVDVSHEDP |

TABLE 6-continued

Exemplary Bispecific molecule sequences

| | |
|---|---|
| | EVKFNWYVDGVEVHNAKTKPREEQYNSTYRVVSVLTVLHQDWLNGKEYKCKVSNKALP APIEKTISKAKGQPREPQVYTLPPSREEMTKNQVSLTCLVKGFYPSDIAVEWESNGQPENN YKTTPPVLDSDGSFFLYSKLTVDKSRWQQGNVFSCSVLHEALHSHYTQKSLSLSPGK (SEQ ID NO: 141) |
| Chimeric-STS7B15925-heavy chain | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCGGGGSGGGGS QVQLQQSGPGLVKPSETLSLTCTVSGGPITSSGDYWGWIRQPPGKCLELIGSIHNSGSTYYN PSLKGRVTISGDTSKNQISLRLSSVTAADTAVYYCARQFGSETYYNGIDPWGQGTLVTVSS GGGGSGGGGSGGGGSGGGGSDIVMTQTPLSLPVTPGEPASISCRSSQSLLHSNGYNYLDW YLQKPGQSPQLLIYLGSNRASGVPDRFSGSGSGTDFTLKISRVEAEDVGVYYCMQALQTPY TFGCGTKLEIKGGGGSGGGGSDKTHTCPPCPAPELLGGPSVFLFPPKPKDTLMISRTPEVTC VVVDVSHEDPEVKFNWYVDGVEVHNAKTKPREEQYNSTYRVVSVLTVLHQDWLNGKE YKCKVSNKALPAPIEKTISKAKGQPREPQVYTLPPSREEMTKNQVSLTCLVKGFYPSDIAV EWESNGQPENNYKTTPPVLDSDGSFFLYSKLTVDKSRWQQGNVFSCSVMHEALHNHYTQ KSLSLSPGK (SEQ ID NO: 142) |
| Chimeric-STS7B15925M-heavy chain | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCgktGGGGSGGGG GSQVQLQQSGPGLVKPSETLSLTCTVSGGPITSSGDYWGWIRQPPGKCLELIGSIHNSGSTY YNPSLKGRVTISGDTSKNQISLRLSSVTAADTAVYYCARQFGSETYYNGIDPWGQGTLVT VSSGGGGSGGGGSGGGGSGGGGSDIVMTQTPLSLPVTPGEPASISCRSSQSLLHSNGYNYL DWYLQKPGQSPQLLIYLGSNRASGVPDRFSGSGSGTDFTLKISRVEAEDVGVYYCMQALQ TPYTFGCGTKLEIKGGGGSGGGGSCPPCPAPELLGGPSVFLFPPKPKDTLYITREPEVTCVV VDVSHEDPEVKFNWYVDGVEVHNAKTKPREEQYNSTYRVVSVLTVLHQDWLNGKEYKC KVSNKALPAPIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEALHNHYTQKSL SLSPGK (SEQ ID NO: 143) |
| Chimeric-STS7B15925S-heavy chain | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCgktGGGGSGGGG GSQVQLQQSGPGLVKPSETLSLTCTVSGGPITSSGDYWGWIRQPPGKCLELIGSIHNSGSTY YNPSLKGRVTISGDTSKNQISLRLSSVTAADTAVYYCARQFGSETYYNGIDPWGQGTLVT VSSGGGGSGGGGSGGGGSGGGGSDIVMTQTPLSLPVTPGEPASISCRSSQSLLHSNGYNYL DWYLQKPGQSPQLLIYLGSNRASGVPDRFSGSGSGTDFTLKISRVEAEDVGVYYCMQALQ TPYTFGCGTKLEIKGGGGSGGGGSCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKC KVSNKALPAPIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVLHEALHSHYTQKSLS LSPGK (SEQ ID NO: 144) |
| Chimeric-STS7B159S-heavy chain | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCGGGGSGGGGS QVQLQQSGPGLVKPSETLSLTCTVSGGPITSSGDYWGWIRQPPGKCLELIGSIHNQGSTYY NPSLKGRVTISGDTSKNQISLRLSSVTAADTAVYYCARQFGSETYYTGIDPWGQGTLVTVS SGGGGSGGGGSGGGGSGGGGSDIVMTQTPLSLPVTPGEPASISCRSSQSLLHSNGYNYLD WYLQKPGQSPQLLIYLGSNRASGVPDRFSGSGSGTDFTLKISRVEAEDVGVYYCMQALQT PYTFGCGTKLEIKGGGGSGGGGSCPPCPAPELLGGPSVFLFPPKPKDTLMISRTPEVTCVVV DVSHEDPEVKFNWYVDGVEVHNAKTKPREEQYNSTYRVVSVLTVLHQDWLNGKEYKCK VSNKALPAPIEKTISKAKGQPREPQVYTLPPSREEMTKNQVSLTCLVKGFYPSDIAVEWES NGQPENNYKTTPPVLDSDGSFFLYSKLTVDKSRWQQGNVFSCSVLHEALHSHYTQKSLSL SPGK (SEQ ID NO: 145) |
| Chimeric-STS7B15921S-heavy chain | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCgktGGGGSGGGG GSQVQLQQSGPGLVKPSETLSLTCTVSGGPITSSGDYWGWIRQPPGKCLELIGSIHNSGSTY YNPSLKGRVTISGDTSKNQISLRLSSVTAADTAVYYCARQFGSETYYNGIQPWGQGTLVT VSSGGGGSGGGGSGGGGSGGGGSDIVMTQTPLSLPVTPGEPASISCRSSQSLLHSRGYNYL DWYLQKPGQSPQLLIYLGSNRASGVPDRFSGSGSGTDFTLKISRVEAEDVGVYYCMQALQ TPYTFGCGTKLEIKGGGGSGGGGSCPPCPAPELLGGPSVFLFPPKPKDTLMISRTPEVTCVV VDVSHEDPEVKFNWYVDGVEVHNAKTKPREEQYNSTYRVVSVLTVLHQDWLNGKEYKC KVSNKALPAPIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVLHEALHSHYTQKSLS LSPGK (SEQ ID NO: 146) |

TABLE 6-continued

Exemplary Bispecific molecule sequences

| | |
|---|---|
| Chimeric-STS7B15923S-heavy chain | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCGGGGSGGGGS QVQLQQSGPGLVKPSETLSLTCTVSGGPITSSGDYWGWIRQPPGKCLELIGSIHNQGSTYY NPSLKGRVTISGDTSKNQISLRLSSVTAADTAVYYCARQFGSETYYPGIDPWGQGTLVTVS SGGGGSGGGGSGGGGSGGGGSDIVMTQTPLSLPVTPGEPASISCRSSQSLLHSNGYNYLD WYLQKPGQSPQLLIYLGSNRASGVPDRFSGSGSGTDFTLKISRVEAEDVGVYYCMQALQT PYTFGCGTKLEIKGGGGSGGGGSCPPCPAPELLGGPSVFLFPPKPKDTLMISRTPEVTCVVV DVSHEDPEVKFNWYVDGVEVHNAKTKPREEQYNSTYRVVSVLTVLHQDWLNGKEYKCK VSNKALPAPIEKTISKAKGQPREPQVYTLPPSREEMTKNQVSLTCLVKGFYPSDIAVEWES NGQPENNYKTTPPVLDSDGSFFLYSKLTVDKSRWQQGNVFSCSVLHEALHSHYTQKSLSL SPGK (SEQ ID NO: 147) |
| Chimeric-STS7B15921M-heavy chain | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCgktGGGGSGGG GSQVQLQQSGPGLVKPSETLSLTCTVSGGPITSSGDYWGWIRQPPGKCLELIGSIHNSGSTY YNPSLKGRVTISGDTSKNQISLRLSSVTAADTAVYYCARQFGSETYYNGIQPWGQGTLVT VSSGGGGSGGGGSGGGGSGGGGSDIVMTQTPLSLPVTPGEPASISCRSSQSLLHSRGYNYL DWYLQKPGQSPQLLIYLGSNRASGVPDRFSGSGSGTDFTLKISRVEAEDVGVYYCMQALQ TPYTFGCGTKLEIKGGGGSGGGGSCPPCPAPELLGGPSVFLFPPKPKDTLYITREPEVTCVV VDVSHEDPEVKFNWYVDGVEVHNAKTKPREEQYNSTYRVVSVLTVLHQDWLNGKEYKC KVSNKALPAPIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEALHNHYTQKSL SLSPGK (SEQ ID NO: 148) |
| Chimeric-STS7B1H9-heavy chain | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCGGGGSGGGGS QVQLVQSGAEVKKPGASVKVSCKASGDTSTIHSVHWVRQAPGQCLEWMGTIISSGTTTTY AQSFQDRVSMTIDRSTSTGYMELSSLRFEDTAVYYCTTDGTSWGQGTLVTVSSGGGGSGG GGSGGGGSGGGGSDIQLTQSPSSVSASVGDRVTIACRASQGISSWLAWYQQKPGKAPKLLI YHASTLESGVPSRFSGSGSGTDFTLTISSLQPEDFATYYCLQAFSLPHTFGCGTKLEIKGGG GSGGGGSDKTHTCPPCPAPELLGGPSVFLFPPKPKDTLMISRTPEVTCVVVDVSHEDPEVK FNWYVDGVEVHNAKTKPREEQYNSTYRVVSVLTVLHQDWLNGKEYKCKVSNKALPAPI EKTISKAKGQPREPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLSLSPGK (SEQ ID NO: 149) |
| Chimeric-STS7B1H923M-heavy chain | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCgktGGGGSGGG GSQVQLVQSGAEVKKPGASVKVSCKASGDTSTIHSVHWVRQAPGQCLEWMGTIISSGTTT TYAQSFQDRVSMTIDRSTSTGYMELSSLRFEDTAVYYCTTDGTSWGQGTLVTVSSGGGGS GGGGSGGGGSGGGGSDIQLTQSPSSVSASVGDRVTIACRASQGISSWLAWYQQKPGKAPK LLIYHASTLESGVPSRFSGSGSGTDFTLTISSLQPEDFATYYCLQAFSLPHTFGCGTKLEIKG GGGSGGGGSCPPCPAPELLGGPSVFLFPPKPKDTLYITREPEVTCVVVDVSHEDPEVKFNW YVDGVEVHNAKTKPREEQYNSTYRVVSVLTVLHQDWLNGKEYKCKVSNKALPAPIEKTI SKAKGQPREPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPGK (SEQ ID NO: 150) |
| Chimeric-STS7B1H924M-heavy chain | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCgktGGGGSGGG GSQVQLVQSGAEVKKPGASVKVSCKASGDTSTIHSVHWVRQAPGQCLEWMGTIISSGTTT TYAQSFQDRVSMTIDRSTSTGYMELSSLRFEDTAVYYCTTDGTSWGQGTLVTVSSGGGGS GGGGSGGGGSGGGGSDIQLTQSPSSVSASVGDRVTIACRASQGISSWLAWYQQKPGKAPK LLIYHASTLESGVPSRFSGSGSGTDFTLTISSLQPEDFATYYCLQASSLPHTFGCGTKLEIKG GGGSGGGGSCPPCPAPELLGGPSVFLFPPKPKDTLYITREPEVTCVVVDVSHEDPEVKFNW YVDGVEVHNAKTKPREEQYNSTYRVVSVLTVLHQDWLNGKEYKCKVSNKALPAPIEKTI SKAKGQPREPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPGK (SEQ ID NO: 151) |
| Chimeric-STS7B1H925M-heavy chain | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCgktGGGGSGGG GSQVQLVQSGAEVKKPGASVKVSCKASGDTSTIHSVHWVRQAPGQCLEWMGTIISSGTTT TYAQSFQDRVSMTIDRSTSTGYMELSSLRFEDTAVYYCTTDGTSWGQGTLVTVSSGGGGS GGGGSGGGGSGGGGSDIQLTQSPSSVSASVGDRVTIACRASQGISSWLAWYQQKPGKAPK |

TABLE 6-continued

Exemplary Bispecific molecule sequences

|  |  |
|---|---|
|  | LLIYHASTLESGVPSRFSGSGSGTDFTLTISSLQPEDFATYYCLQAKSLPHTFGCGTKLEIKG<br>GGGSGGGGSDKTHTCPPCPAPELLGGPSVFLFPPKPKDTLYITREPEVTCVVVDVSHEDPE<br>VKFNWYVDGVEVHNAKTKPREEQYNSTYRVVSVLTVLHQDWLNGKEYKCKVSNKALP<br>APIEKTISKAKGQPREPQVYTLPPSREEMTKNQVSLTCLVKGFYPSDIAVEWESNGQPENN<br>YKTTPPVLDSDGSFFLYSKLTVDKSRWQQGNVFSCSVMHEALHNHYTQKSLSLSPGK<br>(SEQ ID NO: 152) |
| 3F1201-VL-CL | EIVMTQSPSTLSASVGDRVAITCRASQTISSYLNWYQLKPGKAPKLLIYAASSLQSGVPSRF<br>SGSGSGTDFTLTISSLQPEDFATYYCQQSYSTPYTFGQGTKVDIKRTVAAPSVFIFPPSDEQL<br>KSGTASVVCLLNNFYPREAKVQWKVDNALQSGNSQESVTEQDSKDSTYSLSSTLTLSKAD<br>YEKHKVYACEVTHQGLSSPVTKSFNRGEC (SEQ ID NO: 159) |
| Chimeric-STS12017B1S-<br>heavy chain | QVQLQQSGPGLVKTSETLSLTCTVSGGSVSDYYWSWIRQPPGKGLEWIGYIHSSGSTDYNP<br>SLKSRLTISGDAAKKQFSLKLSSVTAADTALYYCARAQGGSRRTLDYWGQGTLVTVSSAS<br>TKGPSVFPLAPSSKSTSGGTAALGCLVKDYFPEPVTVSWNSGALTSGVHTFPAVLQSSGLY<br>SLSSVVTVPSSSLGTQTYICNVNHKPSNTKVDKKVEPKSCGKTGGGGGGGGSEVQLLES<br>GGGLVQPGGSLRLSCTASGFTFSDNYMSWVRQAPGKCLDWVSVISESGGSTNYADSVKG<br>RFSTSRDNSKSTLYLDMNSLRAEDTAIYYCAKGRFSTLSSHFFRAVYGMDVWGQGTAVT<br>VSSGGGGSGGGGSGGGGSGGGGSDIQLTQSPSSLSASVGDRVTITCRASQGISSYLAWYQQ<br>KPGKAPKLLIYAASTLQSGVPSRFSGSGSGTDFTLTISSLQPEDFATYYCQQLSSYPLTFGCG<br>TKVEIKGGGGSGGGGSCPPCPAPELLGGPSVFLFPPKPKDTLMISRTPEVTCVVVDVSHEDP<br>EVKFNWYVDGVEVHNAKTKPREEQYNSTYRVVSVLTVLHQDWLNGKEYKCKVSNKALP<br>APIEKTISKAKGQPREPQVYTLPPSREEMTKNQVSLTCLVKGFYPSDIAVEWESNGQPENN<br>YKTTPPVLDSDGSFFLYSKLTVDKSRWQQGNVFSCSVLHEALHSHYTQKSLSLSPGK<br>(SEQ ID NO: 160) |
| Chimeric-STS7B112-<br>heavy chain with the<br>sequence of<br>VH-CH1-upper<br>hinge/linker-scFv<br>(VH-linker-VL) | EVQLLESGGGLVQPGGSLRLSCTASGFTFSDNYMSWVRQAPGKGLDWVSVISESGGSTNY<br>ADSVKGRFSTSRDNSKSTLYLDMNSLRAEDTAIYYCAKGRFSTLSSHFFRAVYGMDVWG<br>QGTAVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCGGGGSGGGGS<br>QVQLQQSGPGLVKTSETLSLTCTVSGGSVSDYYWSWIRQPPGKCLEWIGYIHSSGSTDYNP<br>SLKSRLTISGDAAKKQFSLNLSSVTAADTALYYCARAQGGSRRTLDYWGQGTLVTVSSGG<br>GGSGGGGSGGGGSGGGGSEIVMTQSPSTLSASVGDRVAITCRASQTISSYLNWYQLKPG<br>APKLLIYAASSLQSGVPSRFSGSGSGTDFTLTISSLQPEDFATYYCQQSYSTPYTFGCGTKV<br>DIK<br>(SEQ ID NO: 195) |
| Chimeric-STS7B11201-<br>heavy chain with<br>the sequence of<br>VH-CH1-upper<br>hinge/linker-scFv<br>(VH-linker-VL) | EVQLLESGGGLVQPGGSLRLSCTASGFTFSDNYMSWVRQAPGKGLDWVSVISESGGSTNY<br>ADSVKGRFSTSRDNSKSTLYLDMNSLRAEDTAIYYCAKGRFSTLSSHFFRAVYGMDVWG<br>QGTAVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCGGGGSGGGGS<br>QVQLQQSGPGLVKTSETLSLTCTVSGGSVSDYYWSWIRQPPGKCLEWIGYIHSSGSTDYNP<br>SLKSRLTISGDAAKKQFSLKLSSVTAADTALYYCARAQGGSRRTLDYWGQGTLVTVSSGG<br>GGSGGGGSGGGGSGGGGSEIVMTQSPSTLSASVGDRVAITCRASQTISSYLNWYQLKPG<br>APKLLIYAASSLQSGVPSRFSGSGSGTDFTLTISSLQPEDFATYYCQQSYSTPYTFGCGTKV<br>DIK<br>(SEQ ID NO: 196) |
| Chimeric-STS7B112M-<br>heavy chain with<br>the sequence of<br>VH-CH1-upper<br>hinge/linker-scFv<br>(VH-linker-VL) | EVQLLESGGGLVQPGGSLRLSCTASGFTFSDNYMSWVRQAPGKGLDWVSVISESGGSTNY<br>ADSVKGRFSTSRDNSKSTLYLDMNSLRAEDTAIYYCAKGRFSTLSSHFFRAVYGMDVWG<br>QGTAVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCgktGGGGSGGG<br>GSQVQLQQSGPGLVKTSETLSLTCTVSGGSVSDYYWSWIRQPPGKCLEWIGYIHSSGSTDY<br>NPSLKSRLTISGDAAKKQFSLNLSSVTAADTALYYCARAQGGSRRTLDYWGQGTLVTVSS<br>GGGGSGGGGSGGGGSGGGGSGGGGSEIVMTQSPSTLSASVGDRVAITCRASQTISSYLNWYQLKP<br>GKAPKLLIYAASSLQSGVPSRFSGSGSGTDFTLTISSLQPEDFATYYCQQSYSTPYTFGCGT<br>KVDIK<br>(SEQ ID NO: 197) |
| Chimeric-STS7B11201M-<br>heavy chain with the<br>sequence of<br>VH-CH1-upper<br>hinge/linker-scFv<br>(VH-linker-VL) | EVQLLESGGGLVQPGGSLRLSCTASGFTFSDNYMSWVRQAPGKGLDWVSVISESGGSTNY<br>ADSVKGRFSTSRDNSKSTLYLDMNSLRAEDTAIYYCAKGRFSTLSSHFFRAVYGMDVWG<br>QGTAVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCgktGGGGSGGG<br>GSQVQLQQSGPGLVKTSETLSLTCTVSGGSVSDYYWSWIRQPPGKCLEWIGYIHSSGSTDY<br>NPSLKSRLTISGDAAKKQFSLKLSSVTAADTALYYCARAQGGSRRTLDYWGQGTLVTVSS<br>GGGGSGGGGSGGGGSGGGGSEIVMTQSPSTLSASVGDRVAITCRASQTISSYLNWYQLKP<br>GKAPKLLIYAASSLQSGVPSRFSGSGSGTDFTLTISSLQPEDFATYYCQQSYSTPYTFGCGT<br>KVDIK<br>(SEQ ID NO: 198) |

TABLE 6-continued

Exemplary Bispecific molecule sequences

| Chimeric-STS7B11201S-heavy chain with the sequence of VH-CH1-upper hinge/linker-scFv (VH-linker-VL) | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCGKTGGGGSGG GGSQVQLQQSGPGLVKTSETLSLTCTVSGGSVSDYYWSWIRQPPGKCLEWIGYIHSSGSTD YNPSLKSRLTISGDAAKKQFSLKLSSVTAADTALYYCARAQGGSRRTLDYWGQGTLVTVS SGGGGSGGGGSGGGGSGGGGSEIVMTQSPSTLSASVGDRVAITCRASQTISSYLNWYQLK PGKAPKLLIYAASSLQSGVPSRFSGSGSGTDFTLTISSLQPEDFATYYCQQSYSTPYTFGCGT KVDIK (SEQ ID NO: 198) |
|---|---|
| Chimeric-STS7B15925-heavy chain with the sequence of VH-CH1-upper hinge/linker-scFv (VH-linker-VL) | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCGGGGSGGGGS QVQLQQSGPGLVKPSETLSLTCTVSGGPITSSGDYWGWIRQPPGKCLELIGSIHNSGSTYYN PSLKGRVTISGDTSKNQISLRLSSVTAADTAVYYCARQFGSETYYNGIDPWGQGTL VTVSS GGGGSGGGGSGGGGSGGGGSDIVMTQTPLSLPVTPGEPASISCRSSQSLLHSNGYNYLDW YLQKPGQSPQLLIYLGSNRASGVPDRFSGSGSGTDFTLKISRVEAEDVGVYYCMQALQTPY TFGCGTKLEIK (SEQ ID NO: 199) |
| Chimeric-STS7B15925M-heavy chain with the sequence of VH-CH1-upper hinge/linker-scFv (VH-linker-VL) | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCgktGGGGSGGG GSQVQLQQSGPGLVKPSETLSLTCTVSGGPITSSGDYWGWIRQPPGKCLELIGSIHNSGSTY YNPSLKGRVTISGDTSKNQISLRLSSVTAADTAVYYCARQFGSETYYNGIDPWGQGTLVT VSSGGGGSGGGGSGGGGSGGGGSDIVMTQTPLSLPVTPGEPASISCRSSQSLLHSNGYNYL DWYLQKPGQSPQLLIYLGSNRASGVPDRFSGSGSGTDFTLKISRVEAEDVGVYYCMQALQ TPYTFGCGTKLEIK (SEQ ID NO: 200) |
| Chimeric-STS7B15925S-heavy chain with the sequence of VH-CH1-upper hinge/linker-scFv (VH-linker-VL) | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCgktGGGGSGGG GSQVQLQQSGPGLVKPSETLSLTCTVSGGPITSSGDYWGWIRQPPGKCLELIGSIHNSGSTY YNPSLKGRVTISGDTSKNQISLRLSSVTAADTAVYYCARQFGSETYYNGIDPWGQGTLVT VSSGGGGSGGGGSGGGGSGGGGSDIVMTQTPLSLPVTPGEPASISCRSSQSLLHSNGYNYL DWYLQKPGQSPQLLIYLGSNRASGVPDRFSGSGSGTDFTLKISRVEAEDVGVYYCMQALQ TPYTFGCGTKLEIK (SEQ ID NO: 200) |
| Chimeric-STS7B159S-heavy chain with the sequence of VH-CH1-upper hinge/linker-scFv (VH-linker-VL) | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCGGGGSGGGGS QVQLQQSGPGLVKPSETLSLTCTVSGGPITSSGDYWGWIRQPPGKCLELIGSIHNQGSTYY NPSLKGRVTISGDTSKNQISLRLSSVTAADTAVYYCARQFGSETYYTGIDPWGQGTLVTVS SGGGGSGGGGSGGGGSGGGGSDIVMTQTPLSLPVTPGEPASISCRSSQSLLHSNGYNYLD WYLQKPGQSPQLLIYLGSNRASGVPDRFSGSGSGTDFTLKISRVEAEDVGVYYCMQALQT PYTFGCGTKLEIK (SEQ ID NO: 201) |
| Chimeric-STS7B15921S-heavy chain with the sequence of VH-CH1-upper hinge/linker-scFv (VH-linker-VL) | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCgktGGGGSGGG GSQVQLQQSGPGLVKPSETLSLTCTVSGGPITSSGDYWGWIRQPPGKCLELIGSIHNSGSTY YNPSLKGRVTISGDTSKNQISLRLSSVTAADTAVYYCARQFGSETYYNGIQPWGQGTLVT VSSGGGGSGGGGSGGGGSGGGGSDIVMTQTPLSLPVTPGEPASISCRSSQSLLHSRGYNYL DWYLQKPGQSPQLLIYLGSNRASGVPDRFSGSGSGTDFTLKISRVEAEDVGVYYCMQALQ TPYTFGCGTKLEIK (SEQ ID NO: 202) |
| Chimeric-STS7B15923S-heavy chain with the sequence of VH-CH1-upper hinge/linker-scFv (VH-linker-VL) | EVQLLESGGGLVQPGGSLRLSCTASGFTFSDNYMSWVRQAPGKGLDWVSVISESGGSTNY ADSVKGRFSTSRDNSKSTLYLDMNSLRAEDTAIYYCAKGRFSTLSSHFFRAVYGMDVWG QGTAVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCGGGGSGGGGS QVQLQQSGPGLVKPSETLSLTCTVSGGPITSSGDYWGWIRQPPGKCLELIGSIHNQGSTYY NPSLKGRVTISGDTSKNQISLRLSSVTAADTAVYYCARQFGSETYYPGIDPWGQGTL VTVS SGGGGSGGGGSGGGGSGGGGSDIVMTQTPLSLPVTPGEPASISCRSSQSLLHSNGYNYLD WYLQKPGQSPQLLIYLGSNRASGVPDRFSGSGSGTDFTLKISRVEAEDVGVYYCMQALQT PYTFGCGTKLEIK (SEQ ID NO: 203) |

TABLE 6-continued

Exemplary Bispecific molecule sequences

| | |
|---|---|
| Chimeric-STS7B15921M-<br>heavy chain with<br>the sequence of<br>VH-CH1-upper<br>hinge/linker-scFv<br>(VH-linker-VL) | EVQLLESGGGLVQPGGSLRLSCTASGFTFSDNYMSWVRQAPGKGLDWVSVISESGGSTNY<br>ADSVKGRFSTSRDNSKSTLYLDMNSLRAEDTAIYYCAKGRFSTLSSHFFRAVYGMDVWG<br>QGTAVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCgktGGGGSGGG<br>GSQVQLQQSGPGLVKPSETLSLTCTVSGGPITSSGDYWGWIRQPPGKCLELIGSIHNSGSTY<br>YNPSLKGRVTISGDTSKNQISLRLSSVTAADTAVYYCARQFGSETYYNGIQPWGQGTLVT<br>VSSGGGGSGGGGSGGGGSGGGGSDIVMTQTPLSLPVTPGEPASISCRSSQSLLHSRGYNYL<br>DWYLQKPGQSPQLLIYLGSNRASGVPDRFSGSGSGTDFTLKISRVEAEDVGVYYCMQALQ<br>TPYTFGCGTKLEIK<br>(SEQ ID NO: 202) |
| Chimeric-STS7B1H9-<br>heavy chain with the<br>sequence of<br>VH-CH1-upper<br>hinge/linker-scFv<br>(VH-linker-VL) | EVQLLESGGGLVQPGGSLRLSCTASGFTFSDNYMSWVRQAPGKGLDWVSVISESGGSTNY<br>ADSVKGRFSTSRDNSKSTLYLDMNSLRAEDTAIYYCAKGRFSTLSSHFFRAVYGMDVWG<br>QGTAVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCGGGGSGGGGS<br>QVQLVQSGAEVKKPGASVKVSCKASGDTSTIHSVHWVRQAPGQCLEWMGTIISSGTTTTY<br>AQSFQDRVSMTIDRSTSTGYMELSSLRFEDTAVYYCTTDGTSWGQGTLVTVSSGGGGSGG<br>GGSGGGGSGGGGSDIQLTQSPSSVSASVGDRVTIACRASQGISSWLAWYQQKPGKAPKLLI<br>YHASTLESGVPSRFSGSGSGTDFTLTISSLQPEDFATYYCLQAFSLPHTFGCGTKLEIK<br>(SEQ ID NO: 204) |
| Chimeric-STS7B1H923M-<br>heavy chain with<br>the sequence of<br>VH-CH1-upper<br>hinge/linker-scFv<br>(VH-linker-VL) | EVQLLESGGGLVQPGGSLRLSCTASGFTFSDNYMSWVRQAPGKGLDWVSVISESGGSTNY<br>ADSVKGRFSTSRDNSKSTLYLDMNSLRAEDTAIYYCAKGRESTLSSHFFRAVYGMDVWG<br>QGTAVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCgktGGGGSGGG<br>GSQVQLVQSGAEVKKPGASVKVSCKASGDTSTIHSVHWVRQAPGQCLEWMGTIISSGTTT<br>TYAQSFQDRVSMTIDRSTSTGYMELSSLRFEDTAVYYCTTDGTSWGQGTLVTVSSGGGGS<br>GGGGSGGGGSGGGGSDIQLTQSPSSVSASVGDRVTIACRASQGISSWLAWYQQKPGKAPK<br>LLIYHASTLESGVPSRFSGSGSGTDFTLTISSLQPEDFATYYCLQAFSLPHTFGCGTKLEIK<br>(SEQ ID NO: 205) |
| Chimeric-STS7B1H924M-<br>heavy chain with<br>the sequence of<br>VH-CH1-upper<br>hinge/linker-scFv<br>(VH-linker-VL) | EVQLLESGGGLVQPGGSLRLSCTASGFTFSDNYMSWVRQAPGKGLDWVSVISESGGSTNY<br>ADSVKGRFSTSRDNSKSTLYLDMNSLRAEDTAIYYCAKGRFSTLSSHFFRAVYGMDVWG<br>QGTAVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCgktGGGGSGGG<br>GSQVQLVQSGAEVKKPGASVKVSCKASGDTSTIHSVHWVRQAPGQCLEWMGTIISSGTTT<br>TYAQSFQDRVSMTIDRSTSTGYMELSSLRFEDTAVYYCTTDGTSWGQGTLVTVSSGGGGS<br>GGGGSGGGGSGGGGSDIQLTQSPSSVSASVGDRVTIACRASQGISSWLAWYQQKPGKAPK<br>LLIYHASTLESGVPSRFSGSGSGTDFTLTISSLQPEDFATYYCLQASSLPHTFGCGTKLEIK<br>(SEQ ID NO: 206) |
| Chimeric-STS7B1H925M-<br>heavy chain with<br>the sequence of<br>VH-CH1-upper<br>hinge/linker-scFv<br>(VH-linker-VL) | EVQLLESGGGLVQPGGSLRLSCTASGFTFSDNYMSWVRQAPGKGLDWVSVISESGGSTNY<br>ADSVKGRFSTSRDNSKSTLYLDMNSLRAEDTAIYYCAKGRFSTLSSHFFRAVYGMDVWG<br>QGTAVTVSSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCgktGGGGSGGG<br>GSQVQLVQSGAEVKKPGASVKVSCKASGDTSTIHSVHWVRQAPGQCLEWMGTIISSGTTT<br>TYAQSFQDRVSMTIDRSTSTGYMELSSLRFEDTAVYYCTTDGTSWGQGTLVTVSSGGGGS<br>GGGGSGGGGSGGGGSDIQLTQSPSSVSASVGDRVTIACRASQGISSWLAWYQQKPGKAPK<br>LLIYHASTLESGVPSRFSGSGSGTDFTLTISSLQPEDFATYYCLQAKSLPHTFGCGTKLEIK<br>(SEQ ID NO: 207) |
| Chimeric-STS12017B1S-<br>heavy chain with<br>the sequence of<br>VH-CH1-upper<br>hinge/linker-scFv<br>(VH-linker-VL) | QVQLQQSGPGLVKTSETLSLTCTVSGGSVSDYYWSWIRQPPGKGLEWIGYIHSSGSTDYNP<br>SLKSRLTISGDAAKKQFSLKLSSVTAADTALYYCARAQGGSRRTLDYWGQGTLVTVSSAS<br>TKGPSVFPLAPSSKSTSGGTAALGCLVKDYFPEPVTVSWNSGALTSGVHTFPAVLQSSGLY<br>SLSSVVTVPSSSLGTQTYICNVNHKPSNTKVDKKVEPKSCGKTGGGGSGGGGSEVQLLES<br>GGGLVQPGGSLRLSCTASGFTFSDNYMSWVRQAPGKCLDWVSVISESGGSTNYADSVKG<br>RFSTSRDNSKSTLYLDMNSLRAEDTAIYYCAKGRFSTLSSHFFRAVYGMDVWGQGTAVT<br>VSSGGGGSGGGGSGGGGSGGGGSDIQLTQSPSSLSASVGDRVTITCRASQGISSYLAWYQQ<br>KPGKAPKLLIYAASTLQSGVPSRFSGSGSGTDFTLTISSLQPEDFATYYCQQLSSYPLTFGCG<br>TKVEIK<br>(SEQ ID NO: 208) |

Combination of Antibodies Recognizing *Pseudomonas* PcrV and *Pseudomonas* Psl

In one aspect, the present application provides a pharmaceutical composition comprising (i) an antigen-binding protein specifically recognizing a first epitope on *Pseudomonas* PcrV and (ii) an antigen-binding protein specifically recognizing a second epitope on *Pseudomonas* PcrV and/or an antigen-binding protein specifically recognizing *Pseudomonas* Psl.

In some embodiments, there is provided a pharmaceutical composition comprising (i) an antigen-binding protein specifically recognizing a first epitope on *Pseudomonas* PcrV and (ii) an antigen-binding protein specifically recognizing a second epitope on *Pseudomonas* PcrV and/or an antigen-binding protein specifically recognizing *Pseudomonas* Psl, wherein: the antigen-binding protein specifically recognizing the first epitope on *Pseudomonas* PcrV comprises: (a) a heavy chain variable domain (V$_H$) comprising a heavy chain complementarity determining region (HC-CDR) 1 comprising DX$_1$X$_2$MS (SEQ ID NO: 20), wherein X$_1$ is N or Y, and X$_2$ is Y, H or P; an HC-CDR2 comprising X$_1$ISESGGSTNYADSVKG (SEQ ID NO: 15), wherein X$_1$ is V or G; and an HC-CDR3 comprising GRFSTX$_1$SX$_2$HFX$_3$RAVYGMDV (SEQ ID NO: 21), wherein $X_1$ is L, S, N or D, $X_2$ is S or A, $X_3$ is F or Y; and a light chain variable domain ($V_L$) comprising a light chain complementarity determining region (LC-CDR) 1 comprising RASQGISSYLA (SEQ ID NO: 10); an LC-CDR2 comprising AASTLQS (SEQ ID NO: 11), and an LC-CDR3 comprising QQLSSYPLX$_1$(SEQ ID NO: 19), wherein $X_1$ is S or T; or (b) a $V_H$ comprising an HC-CDR1 comprising $X_1X_2X_3$MS (SEQ ID NO: 17), wherein $X_1$ is D or S, $X_2$ is Y or N, and $X_3$ is P, H, Y or S; an HC-CDR2 comprising $X_1$ISESGGSTX$_2$X$_3$ADSVKG (SEQ ID NO: 18), wherein $X_1$ is G or V; $X_2$ is N or Y; and $X_3$ is D or Y; and an HC-CDR3 comprising GRFX$_1$X$_2$X$_3$X$_4$X$_5$X$_6$FX$_7$RAVYGMDV (SEQ ID NO: 38), wherein $X_1$ is S or C, $X_2$ is T, G, D, Y, Q or A, $X_3$ is S, D, N, E, L, A, or Y, $X_4$ is S, T, Y, or A, $X_5$ is S, H, Q, A, R, K, G, E, Y or D, $X_6$ is H or C, and $X_7$ is F or Y; and a $V_L$ comprising an LC-CDR1 comprising RASQGIX$_1$SYLA (SEQ ID NO: 209), wherein $X_1$ is S or R; an LC-CDR2 comprising AASTLQS (SEQ ID NO: 11); and an LC-CDR3 comprising QQLX$_1$SYPLX$_2$ (SEQ ID NO: 210), wherein $X_1$ is S, N or K, and $X_2$ is S or T.

In some embodiments, there is provided a pharmaceutical composition comprising (i) an antigen-binding protein specifically recognizing *Pseudomonas* Psl and (ii) an antigen-binding protein specifically recognizing a first epitope on *Pseudomonas* PcrV and/or an antigen-binding protein specifically recognizing a second epitope on *Pseudomonas* PcrV, wherein: the antigen-binding protein specifically recognizing *Pseudomonas* Psl comprises: (a) a $V_H$ comprising a HC-CDR1 comprising SSGDYWG (SEQ ID NO: 48); an HC-CDR2 comprising SIHNX$_1$GSTYYNPSLKG (SEQ ID NO: 81), wherein $X_1$ is S or Q; and an HC-CDR3 comprising QFGSETYYX$_1$GIX$_2$P (SEQ ID NO: 82), wherein $X_1$ is T, N or P, and $X_2$ is D or Q; and a $V_L$ comprising an LC-CDR1 comprising RSSQSLLHSX$_1$GYNYLD (SEQ ID NO: 83), wherein $X_1$ is N or R; an LC-CDR2 comprising LGSNRAS (SEQ ID NO: 70), and an LC-CDR3 comprising MQALQTPYT (SEQ ID NO: 74); or (b) a $V_H$ comprising a HC-CDR1 comprising IHSVH (SEQ ID NO: 50); an HC-CDR2 comprising TIISSGTTTTYAQSFQD (SEQ ID NO: 55); and an HC-CDR3 comprising DGX$_1$S (SEQ ID NO: 84), wherein $X_1$ is D or T; and a $V_L$ comprising an LC-CDR1 comprising RASQGISSWLA (SEQ ID NO: 68); an LC-CDR2 comprising HASTLES (SEQ ID NO: 72), and an LC-CDR3 comprising LQAX$_1$SLPHT (SEQ ID NO: 85), wherein $X_1$ is N, F, S or K; or (c) a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75; or (d) a $V_H$ comprising an HC-CDR1 comprising the amino acid sequence of SEQ ID NO: 51, an HC-CDR2 comprising the amino acid sequence of SEQ ID NOs 56, and an HC-CDR3 comprising the amino acid sequence of SEQ ID NO: 64; and a $V_L$ comprising: an LC-CDR1 comprising the amino acid sequence of SEQ ID NO: 69, an LC-CDR2 comprising the amino acid sequence of SEQ ID NO: 73, and an LC-CDR3 comprising the amino acid sequence of SEQ ID NO: 80.

In some embodiments, the antigen-binding protein specifically recognizing the first epitope on *Pseudomonas* PcrV comprises: (a) a heavy chain variable domain ($V_H$) comprising a heavy chain complementarity determining region (HC-CDR) 1 comprising DX$_1$X$_2$MS (SEQ ID NO: 20), wherein $X_1$ is N or Y, and $X_2$ is Y, H or P; an HC-CDR2 comprising X$_1$ISESGGSTNYADSVKG (SEQ ID NO: 15), wherein $X_1$ is V or G; and an HC-CDR3 comprising GRFSTX$_1$SX$_2$HFX$_3$RAVYGMDV (SEQ ID NO: 21), wherein $X_1$ is L, S, N or D, $X_2$ is S or A, $X_3$ is F or Y; and a light chain variable domain ($V_L$) comprising a light chain complementarity determining region (LC-CDR) 1 comprising RASQGISSYLA (SEQ ID NO: 10); an LC-CDR2 comprising AASTLQS (SEQ ID NO: 11), and an LC-CDR3 comprising QQLSSYPLX$_1$(SEQ ID NO: 19), wherein $X_1$ is S or T. In some embodiments, the antigen-binding protein specifically recognizing the first epitope on *Pseudomonas* PcrV comprises: a $V_H$ comprising a HC-CDR1 comprising DNX$_1$MS (SEQ ID NO: 14), wherein $X_1$ is Y or H; an HC-CDR2 comprising X$_1$ISESGGSTNYADSVKG (SEQ ID NO: 15), wherein $X_1$ is V or G; and an HC-CDR3 comprising GRFSTX$_1$SSHFX$_2$RAVYGMDV (SEQ ID NO: 16), wherein $X_1$ is L or S, $X_2$ is F or Y; and a $V_L$ comprising an LC-CDR1 comprising RASQGISSYLA (SEQ ID NO: 10); an LC-CDR2 comprising AASTLQS (SEQ ID NO: 11), and an LC-CDR3 comprising QQLSSYPLX$_1$(SEQ ID NO: 19), wherein $X_1$ is S or T.

In some embodiments, the antigen-binding protein specifically recognizing the first epitope on *Pseudomonas* PcrV comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12. In some embodiments, the antigen-binding protein specifically recognizing the first epitope on *Pseudomonas* PcrV comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13. In some embodiments, the antigen-binding protein specifically recognizing the first epitope on *Pseudomonas* PcrV comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 8; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12. In some embodiments the antigen-binding protein specifically recognizing the first epitope on *Pseudomonas* PcrV comprises: a $V_H$ comprising an HC-CDR1 comprising the amino acid sequence SEQ ID NO: 3, an HC-CDR2 comprising the amino acid sequence of SEQ ID NO: 5, and an HC-CDR3 comprising the amino acid sequence of SEQ ID NO: 9; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13.

In some embodiments, the antigen-binding protein specifically recognizing the second epitope on *Pseudomonas* PcrV comprises: (a) a $V_H$ comprising an HC-CDR1 comprising SYWMH (SEQ ID NO: 22); an HC-CDR2 comprising RINEX$_1$EX$_2$SISYADSVKG (SEQ ID NO: 44), wherein X$_1$ is D or N, and X$_2$ is T, G or R; and an HC-CDR3 comprising DGPYDX$_1$X$_2$DI (SEQ ID NO: 45), wherein X$_1$ is S, A, or T, and X$_2$ is F or L; and a V$_L$ comprising an LC-CDR1 comprising RASQX$_1$VX$_2$X$_3$NLA (SEQ ID NO: 46), wherein X$_1$ is S, G or N, X$_2$ is S, R or K and X$_3$ is S or N; an LC-CDR2 comprising X$_1$ASSRAT (SEQ ID NO: 42), wherein X$_1$ is D or H, and an LC-CDR3 comprising QQYGX$_1$X$_2$PX$_3$T (SEQ ID NO: 47), wherein X$_1$ is S, L or N, X$_2$ is S, Q or E and X$_3$ is L or I; or (b) a V$_H$ comprising an HC-CDR1 comprising SYWMH (SEQ ID NO: 22); an HC-CDR2 comprising RINEX$_1$EX$_2$SISYADSVKG (SEQ ID NO: 211), wherein X$_1$ is D, N, I, L or V, X$_2$ is S, T, R, G or N; and an HC-CDR3 comprising DGPYDX$_1$X$_2$DI (SEQ ID NO: 45), wherein X$_1$ is S, A or T, X$_2$ is F or L; and a V$_L$ comprising an LC-CDR1 comprising RASQX$_1$VX$_2$X$_3$NLA (SEQ ID NO: 212), wherein X$_1$ is N, G, D or S, X$_2$ is K, R, S, N or T, X$_3$ is N, G, S or D; an LC-CDR2 comprising X$_1$ASSRAT (SEQ ID NO: 213), wherein X$_1$ is D, N, H or A; and an LC-CDR3 comprising QQYGX$_1$X$_2$PX$_3$T (SEQ ID NO: 214), wherein X$_1$ is S, T, E, H, N, A, D, M or L, X$_2$ is S, Q, E, T, D, G, H, L, N, V or Y, and X$_3$ is I, L or V. In some embodiments, the antigen-binding protein specifically recognizing the second epitope on *Pseudomonas* PcrV comprises: a V$_H$ comprising a HC-CDR1 comprising SYWMH (SEQ ID NO: 22); an HC-CDR2 comprising RINEX$_1$EX$_2$SISYADSVKG (SEQ ID NO: 39), wherein X$_1$ is D or N, X$_2$ is T or G; and an HC-CDR3 comprising DGPYDX$_1$LDI (SEQ ID NO: 40), wherein X$_1$ is S or A; and a V$_L$ comprising an LC-CDR1 comprising RASQX$_1$VX$_2$X$_3$NLA (SEQ ID NO: 41), wherein X$_1$ is S or G, X$_2$ is S or R and X$_3$ is S or N; an LC-CDR2 comprising X$_1$ASSRAT (SEQ ID NO: 42), wherein X$_1$ is D or H, and an LC-CDR3 comprising QQYGX$_1$X$_2$PX$_3$T (SEQ ID NO: 43), wherein X$_1$ is S or L, X$_2$ is S or Q and X$_3$ is L or I.

In some embodiments, the antigen-binding protein specifically recognizing the second epitope on *Pseudomonas* PcrV comprises: a V$_H$ comprising an HC-CDR1 comprising the amino acid sequence of SEQ ID NO: 22, an HC-CDR2 comprising the amino acid sequence of any one of SEQ ID NOs: 23-25, and an HC-CDR3 comprising the amino acid sequence of any one of SEQ ID NOs: 26-29; and a V$_L$ comprising: an LC-CDR1 comprising the amino acid sequence of any one of SEQ ID NOs: 30-32, an LC-CDR2 comprising the amino acid sequence of SEQ ID NO: 33 or 34, and an LC-CDR3 comprising the amino acid sequence of any one of SEQ ID NOs: 35-37.

In some embodiments, the antigen-binding protein specifically recognizing the second epitope on *Pseudomonas* PcrV comprises: a V$_H$ comprising an HC-CDR1 comprising the amino acid sequence SEQ ID NO: 22, an HC-CDR2 comprising the amino acid sequence of SEQ ID NO: 23, and an HC-CDR3 comprising the amino acid sequence of SEQ ID NO: 26; and a V$_L$ comprising: an LC-CDR1 comprising the amino acid sequence of SEQ ID NO: 30, an LC-CDR2 comprising the amino acid sequence of SEQ ID NO: 33, and an LC-CDR3 comprising the amino acid sequence of SEQ ID NO: 35. In some embodiments, the antigen-binding protein specifically recognizing the second epitope on *Pseudomonas* PcrV comprises: a V$_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 27; and a V$_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36. In some embodiments, the antigen-binding protein specifically recognizing the second epitope on *Pseudomonas* PcrV comprises: a V$_H$ comprising an HC-CDR1 comprising the amino acid sequence SEQ ID NO: 22, an HC-CDR2 comprising the amino acid sequence of SEQ ID NO: 25, and an HC-CDR3 comprising the amino acid sequence of SEQ ID NO: 27; and a V$_L$ comprising: an LC-CDR1 comprising the amino acid sequence of SEQ ID NO: 32, an LC-CDR2 comprising the amino acid sequence of SEQ ID NO: 34, and an LC-CDR3 comprising the amino acid sequence of SEQ ID NO: 37. In some embodiments, the antigen-binding protein specifically recognizing the second epitope on *Pseudomonas* PcrV comprises: a V$_H$ comprising an HC-CDR1 comprising the amino acid sequence SEQ ID NO: 22, an HC-CDR2 comprising the amino acid sequence of SEQ ID NO: 25, and an HC-CDR3 comprising the amino acid sequence of SEQ ID NO: 28; and a V$_L$ Comprising: an LC-CDR1 comprising the amino acid sequence of SEQ ID NO: 32, an LC-CDR2 comprising the amino acid sequence of SEQ ID NO: 34, and an LC-CDR3 comprising the amino acid sequence of SEQ ID NO: 37. In some embodiments, the antigen-binding protein specifically recognizing the second epitope on *Pseudomonas* PcrV comprises: a V$_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 28; and a V$_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36. In some embodiments, the antigen-binding protein specifically recognizing the second epitope on *Pseudomonas* PcrV comprises: a V$_H$ comprising an HC-CDR1 comprising the amino acid sequence SEQ ID NO: 22, an HC-CDR2 comprising the amino acid sequence of SEQ ID NO: 25, and an HC-CDR3 comprising the amino acid sequence of SEQ ID NO: 26; and a V$_L$ comprising: an LC-CDR1 comprising the amino acid sequence of SEQ ID NO: 32, an LC-CDR2 comprising the amino acid sequence of SEQ ID NO: 34, and an LC-CDR3 comprising the amino acid sequence of SEQ ID NO: 37. In some embodiments, the antigen-binding protein specifically recognizing the second epitope on *Pseudomonas* PcrV comprises: a V$_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 26; and a V$_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36. In some embodiments, the antigen-binding protein specifically recognizing the second epitope on *Pseudomonas* PcrV comprises: a V$_H$ comprising an HC-CDR1 comprising the amino acid sequence SEQ ID NO: 22, an HC-CDR2 comprising the amino acid sequence of SEQ ID NO: 23, and an HC-CDR3 comprising the amino acid sequence of SEQ ID NO: 29; and a V$_L$ comprising: an LC-CDR1 comprising the amino acid sequence of SEQ ID NO: 30, an LC-CDR2 comprising the amino acid sequence of SEQ ID NO: 33, and an LC-CDR3 comprising the amino acid sequence of SEQ ID NO: 35.

In some embodiments, the antigen-binding protein specifically recognizing *Pseudomonas* Psl comprises: a V$_H$ comprising an HC-CDR1 comprising SSGDYWG (SEQ ID NO: 48); an HC-CDR2 comprising SIHNX$_1$GSTYYNPSLKG (SEQ ID NO: 81), wherein X$_1$ is S or Q; and an HC-CDR3 comprising QFGSETYYX$_1$GIX$_2$P (SEQ ID NO: 82), wherein X$_1$ is T, N or P, and X$_2$ is D or Q; and a V$_L$ comprising an LC-CDR1 comprising RSSQSLLHSX$_1$GYNYLD (SEQ ID NO: 83), wherein X$_1$ is N or R; an LC-CDR2 comprising LGSNRAS (SEQ ID NO: 70), and an LC-CDR3 comprising MQALQTPYT (SEQ ID NO: 74). In some embodiments, the second antigen-binding domain specifically recognizing *Pseudomonas* Psl comprises: (a) a V$_H$ comprising an HC-CDR1 comprising SSGDYWG (SEQ ID NO: 48); an HC-CDR2 comprising SIHNX$_1$GSTYYNPSLKG (SEQ ID NO: 125), wherein X$_1$ is S, K or Q; and an HC-CDR3 comprising QFGSETYYX$_1$GIX$_2$P (SEQ ID NO: 126), wherein X$_1$ is N, S, V, T or P, and X$_2$ is D, Y, C, H, S, R, A, E, G, K, W, V, or Q; and a V$_L$ comprising an LC-CDR1 comprising RSSQSLLHSX$_1$GYNYLD (SEQ ID NO: 127), wherein X$_1$ is N, A, V, F, R, G, H, Q, W or P; an LC-CDR2 comprising LGSNRAS (SEQ ID NO: 70), and an LC-CDR3 comprising MQALQTP X$_1$T (SEQ ID NO: 128), wherein X$_1$ is R or Y.

In some embodiments, the antigen-binding protein specifically recognizing *Pseudomonas* Psl comprises: a V$_H$ comprising an HC-CDR1 comprising IHSVH (SEQ ID NO: 50); an HC-CDR2 comprising TIISSGTTTTYAQSFQD (SEQ ID NO: 55); and an HC-CDR3 comprising DGX$_1$S (SEQ ID NO: 84), wherein X$_1$ is D or T; and a V$_L$ comprising an LC-CDR1 comprising RASQGISSWLA (SEQ ID NO: 68); an LC-CDR2 comprising HASTLES (SEQ ID NO: 72), and an LC-CDR3 comprising LQAX$_1$SLPHT (SEQ ID NO: 85), wherein X$_1$ is N, F, S or K. In some embodiments, the second antigen-binding domain specifically recognizing *Pseudomonas* Psl comprises: (a) a V$_H$ comprising an HC-CDR1 comprising IHSVH (SEQ ID NO: 50); an HC-CDR2 comprising TIISSGTTTTYAQSFQD (SEQ ID NO: 55); and an HC-CDR3 comprising X$_1$X$_2$X$_3$X$_4$(SEQ ID NO: 129), wherein X$_1$ is D, Y, or N, wherein X$_2$ is G or A, wherein X$_3$ is D or T and wherein X$_4$ is S, A or T; and a V$_L$ comprising an LC-CDR1 comprising RASQGISSWLA (SEQ ID NO: 68); an LC-CDR2 comprising HASTLES (SEQ ID NO: 72) and an LC-CDR3 comprising LQAX$_1$SLPHT (SEQ ID NO: 130), wherein X$_1$ is N, D, Y, F, P, G, K, H, A, C, E, Q, R, S, T, V, W or L. In some embodiments, the antigen-binding protein specifically recognizing *Pseudomonas* Psl comprises: a V$_H$ comprising an HC-CDR1 comprising the amino acid sequence of SEQ ID NO: 48, an HC-CDR2 comprising the amino acid sequence of SEQ ID NOs: 52 or 53, and an HC-CDR3 comprising the amino acid sequence of any one of SEQ ID NOs: 57-60; and a V$_L$ comprising: an LC-CDR1 comprising the amino acid sequence of SEQ ID NO: 65 or 66, an LC-CDR2 comprising the amino acid sequence of SEQ ID NO: 70, and an LC-CDR3 comprising the amino acid sequence of SEQ ID NO: 74. In some embodiments, the antigen-binding protein specifically recognizing *Pseudomonas* Psl comprises: a V$_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 62 or 63; and a V$_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of any one of SEQ ID NOs: 76-79.

In some embodiments, the antigen-binding protein specifically recognizing *Pseudomonas* Psl comprises: a V$_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a V$_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the antigen-binding protein specifically recognizing *Pseudomonas* Psl comprises: a V$_H$ comprising an HC-CDR1 comprising the amino acid sequence of SEQ ID NO: 48, an HC-CDR2 comprising the amino acid sequence of SEQ ID NO: 53, and an HC-CDR3 comprising the amino acid sequence of SEQ ID NO: 58; and a V$_L$ comprising: an LC-CDR1 comprising the amino acid sequence of SEQ ID NO: 66, an LC-CDR2 comprising the amino acid sequence of SEQ ID NO: 70, and an LC-CDR3 comprising the amino acid sequence of SEQ ID NO: 74. In some embodiments, the antigen-binding protein specifically recognizing *Pseudomonas* Psl comprises: a V$_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 59; and a V$_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the antigen-binding protein specifically recognizing *Pseudomonas* Psl comprises: a V$_H$ comprising an HC-CDR1 comprising the amino acid sequence of SEQ ID NO: 48, an HC-CDR2 comprising the amino acid sequence of SEQ ID NO: 53; and an HC-CDR3 comprising the amino acid sequence of SEQ ID NO: 60; and a V$_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the antigen-binding protein specifically recognizing *Pseudomonas* Psl comprises: a V$_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a V$_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75. In some embodiments, the antigen-binding protein specifically recognizing *Pseudomonas* Psl comprises: a V$_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 62; and a V$_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 76. In some embodiments, the antigen-binding protein specifically recognizing *Pseudomonas* Psl comprises: a V$_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 63; and a V$_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 77. In some embodiments, the antigen-binding protein specifically recognizing *Pseudomonas* Psl comprises: a V$_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 63; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 78. In some embodiments, the antigen-binding protein specifically recognizing *Pseudomonas* Psl comprises: a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 63; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 79. In some embodiments, the antigen-binding protein specifically recognizing *Pseudomonas* Psl comprises: a $V_H$ comprising an HC-CDR1 comprising the amino acid sequence of SEQ ID NO: 51, an HC-CDR2 comprising the amino acid sequence of SEQ ID NOs 56, and an HC-CDR3 comprising the amino acid sequence of SEQ ID NO: 64; and a $V_L$ comprising: an LC-CDR1 comprising the amino acid sequence of SEQ ID NO: 69, an LC-CDR2 comprising the amino acid sequence of SEQ ID NO: 73, and an LC-CDR3 comprising the amino acid sequence of SEQ ID NO: 80.

In some embodiments, the antigen-binding protein specifically recognizing the first epitope on *Pseudomonas* PcrV comprises a $V_H$ comprising the amino acid sequence of SEQ ID NO: 91 and a $V_L$ comprising the amino acid sequence of SEQ ID NO: 112. In some embodiments, the antigen-binding protein specifically recognizing the first epitope on *Pseudomonas* PcrV comprises a $V_H$ comprising an HC-CDR1, an HC-CDR2 and an HC-CDR3 of the $V_H$ comprising the amino acid sequence of SEQ ID NO: 91; and a $V_L$ comprising an LC-CDR1, an LC-CDR2, and an LC-CDR3 of the $V_L$ comprising the amino acid sequence of SEQ ID NO: 112.

In some embodiments, antigen-binding protein specifically recognizing the first epitope on *Pseudomonas* PcrV comprises a $V_H$ comprising the amino acid sequence of SEQ ID NO: 92 and a $V_L$ comprising the amino acid sequence of SEQ ID NO: 113. In some embodiments, the antigen-binding protein specifically recognizing the first epitope on *Pseudomonas* PcrV comprises a $V_H$ comprising an HC-CDR1, an HC-CDR2 and an HC-CDR3 of the $V_H$ comprising the amino acid sequence of SEQ ID NO: 92; and a $V_L$ comprising an LC-CDR1, an LC-CDR2, and an LC-CDR3 of the $V_L$ comprising the amino acid sequence of SEQ ID NO: 113.

In some embodiments, antigen-binding protein specifically recognizing the first epitope on *Pseudomonas* PcrV comprises a $V_H$ comprising the amino acid sequence of SEQ ID NO: 93 and a $V_L$ comprising the amino acid sequence of SEQ ID NO: 112. In some embodiments, the antigen-binding protein specifically recognizing the first epitope on *Pseudomonas* PcrV comprises a $V_H$ comprising an HC-CDR1, an HC-CDR2 and an HC-CDR3 of the $V_H$ comprising the amino acid sequence of SEQ ID NO: 93; and a $V_L$ comprising an LC-CDR1, an LC-CDR2, and an LC-CDR3 of the $V_L$ comprising the amino acid sequence of SEQ ID NO: 112.

In some embodiments, the antigen-binding protein specifically recognizing the first epitope on *Pseudomonas* PcrV comprises a $V_H$ comprising the amino acid sequence of SEQ ID NO: 94 and a $V_L$ comprising the amino acid sequence of SEQ ID NO: 113. In some embodiments, the antigen-binding protein specifically recognizing the first epitope on *Pseudomonas* PcrV comprises a $V_H$ comprising an HC-CDR1, an HC-CDR2 and an HC-CDR3 of the $V_H$ comprising the amino acid sequence of SEQ ID NO: 94; and a $V_L$ comprising an LC-CDR1, an LC-CDR2, and an LC-CDR3 of the $V_L$ comprising the amino acid sequence of SEQ ID NO: 113.

In some embodiments, the antigen-binding protein specifically recognizing the second epitope on *Pseudomonas* PcrV comprises a $V_H$ comprising the amino acid sequence of SEQ ID NO: 95 and a $V_L$ comprising the amino acid sequence of SEQ ID NO: 114. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 95; and a $V_L$ comprising an LC-CDR1, an LC-CDR2, and an LC-CDR3 of the $V_L$ comprising the amino acid sequence of SEQ ID NO: 114.

In some embodiments, the antigen-binding protein specifically recognizing the second epitope on *Pseudomonas* PcrV comprises a $V_H$ comprising the amino acid sequence of SEQ ID NO: 96 and a $V_L$ comprising the amino acid sequence of SEQ ID NO: 115. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 96; and a $V_L$ comprising an LC-CDR1, an LC-CDR2, and an LC-CDR3 of the $V_L$ comprising the amino acid sequence of SEQ ID NO: 115.

In some embodiments, the antigen-binding protein specifically recognizing the second epitope on *Pseudomonas* PcrV comprises a $V_H$ comprising the amino acid sequence of SEQ ID NO: 97 and a $V_L$ comprising the amino acid sequence of SEQ ID NO: 116. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 97; and a $V_L$ comprising an LC-CDR1, an LC-CDR2, and an LC-CDR3 of the $V_L$ comprising the amino acid sequence of SEQ ID NO: 116.

In some embodiments, the antigen-binding protein specifically recognizing the second epitope on *Pseudomonas* PcrV comprises a $V_H$ comprising the amino acid sequence of SEQ ID NO: 98 and a $V_L$ comprising the amino acid sequence of SEQ ID NO: 116. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 98; and a $V_L$ comprising an LC-CDR1, an LC-CDR2, and an LC-CDR3 of the $V_L$ comprising the amino acid sequence of SEQ ID NO: 116.

In some embodiments, the antigen-binding protein specifically recognizing the second epitope on *Pseudomonas* PcrV comprises a $V_H$ comprising the amino acid sequence of SEQ ID NO: 99 and a $V_L$ comprising the amino acid sequence of SEQ ID NO: 115. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 99; and a $V_L$ comprising an LC-CDR1, an LC-CDR2, and an LC-CDR3 of the $V_L$ comprising the amino acid sequence of SEQ ID NO: 115.

In some embodiments, the antigen-binding protein specifically recognizing the second epitope on *Pseudomonas* PcrV comprises a $V_H$ comprising the amino acid sequence of SEQ ID NO: 100 and a $V_L$ comprising the amino acid sequence of SEQ ID NO: 116. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 100; and a $V_L$ comprising an LC-CDR1, an LC-CDR2, and an LC-CDR3 of the $V_L$ comprising the amino acid sequence of SEQ ID NO: 116.

In some embodiments, the antigen-binding protein specifically recognizing the second epitope on *Pseudomonas* PcrV comprises a $V_H$ comprising the amino acid sequence of SEQ ID NO: 101 and a $V_L$ comprising the amino acid sequence of SEQ ID NO: 115. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 101; and a $V_L$ comprising an LC-CDR1, an LC-CDR2, and an LC-CDR3 of the $V_L$ comprising the amino acid sequence of SEQ ID NO: 115.

In some embodiments, the antigen-binding protein specifically recognizing the second epitope on *Pseudomonas* PcrV comprises a $V_H$ comprising the amino acid sequence of SEQ ID NO: 102 and a $V_L$ comprising the amino acid sequence of SEQ ID NO: 114. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 102; and a $V_L$ comprising an LC-CDR1, an LC-CDR2, and an LC-CDR3 of the $V_L$ comprising the amino acid sequence of SEQ ID NO: 114.

In some embodiments, the antigen-binding protein specifically recognizing *Pseudomonas* Psl comprises a $V_H$ comprising the amino acid sequence of SEQ ID NO: 103 and a $V_L$ comprising the amino acid sequence of SEQ ID NO: 117. In some embodiments, the antigen-binding protein specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 103; and a $V_L$ comprising an LC-CDR1, an LC-CDR2, and an LC-CDR3 of the $V_L$ comprising the amino acid sequence of SEQ ID NO: 117.

In some embodiments, the antigen-binding protein specifically recognizing *Pseudomonas* Psl comprises a $V_H$ comprising the amino acid sequence of SEQ ID NO: 104 and a $V_L$ comprising the amino acid sequence of SEQ ID NO: 118. In some embodiments, the antigen-binding protein specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 104 and a $V_L$ comprising an LC-CDR1, an LC-CDR2, and an LC-CDR3 of the $V_L$ comprising the amino acid sequence of SEQ ID NO: 118.

In some embodiments, the antigen-binding protein specifically recognizing *Pseudomonas* Psl comprises a $V_H$ comprising the amino acid sequence of SEQ ID NO: 105 and a $V_L$ comprising the amino acid sequence of SEQ ID NO: 117. In some embodiments, the antigen-binding protein specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 105; and a $V_L$ comprising an LC-CDR1, an LC-CDR2, and an LC-CDR3 of the $V_L$ comprising the amino acid sequence of SEQ ID NO: 117.

In some embodiments, the antigen-binding protein specifically recognizing *Pseudomonas* Psl comprises a $V_H$ comprising the amino acid sequence of SEQ ID NO: 106 and a $V_L$ comprising the amino acid sequence of SEQ ID NO: 117. In some embodiments, the antigen-binding protein specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 106; and a $V_L$ comprising an LC-CDR1, an LC-CDR2, and an LC-CDR3 of the $V_L$ comprising the amino acid sequence of SEQ ID NO: 117.

In some embodiments, the antigen-binding protein specifically recognizing *Pseudomonas* Psl comprises a $V_H$ comprising the amino acid sequence of SEQ ID NO: 107 and a $V_L$ comprising the amino acid sequence of SEQ ID NO: 119. In some embodiments, the antigen-binding protein specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 107 and a $V_L$ comprising an LC-CDR1, an LC-CDR2, and an LC-CDR3 of the $V_L$ comprising the amino acid sequence of SEQ ID NO: 119.

In some embodiments, the antigen-binding protein specifically recognizing *Pseudomonas* Psl comprises a $V_H$ comprising the amino acid sequence of SEQ ID NO: 108 and a $V_L$ comprising the amino acid sequence of SEQ ID NO: 119. In some embodiments, the antigen-binding protein specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 108; and a $V_L$ comprising an LC-CDR1, an LC-CDR2, and an LC-CDR3 of the $V_L$ comprising the amino acid sequence of SEQ ID NO: 119.

In some embodiments, the antigen-binding protein specifically recognizing *Pseudomonas* Psl comprises a $V_H$ comprising the amino acid sequence of SEQ ID NO: 109 and a $V_L$ comprising the amino acid sequence of SEQ ID NO: 120. In some embodiments, the antigen-binding protein specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 109; and a $V_L$ comprising an LC-CDR1, an LC-CDR2, and an LC-CDR3 of the $V_L$ comprising the amino acid sequence of SEQ ID NO: 120.

In some embodiments, the antigen-binding protein specifically recognizing *Pseudomonas* Psl comprises a $V_H$ comprising the amino acid sequence of SEQ ID NO: 110 and a $V_L$ comprising the amino acid sequence of SEQ ID NO: 121. In some embodiments, the antigen-binding protein specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 110; and a $V_L$ comprising an LC-CDR1, an LC-CDR2, and an LC-CDR3 of the $V_L$ comprising the amino acid sequence of SEQ ID NO: 121.

In some embodiments, the antigen-binding protein specifically recognizing *Pseudomonas* Psl comprises a $V_H$ comprising the amino acid sequence of SEQ ID NO: 110 and a $V_L$ comprising the amino acid sequence of SEQ ID NO: 122. In some embodiments, the antigen-binding protein specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 110; and a $V_L$ comprising an LC-CDR1, an LC-CDR2, and an LC-CDR3 of the $V_L$ comprising the amino acid sequence of SEQ ID NO: 122.

In some embodiments, the antigen-binding protein specifically recognizing *Pseudomonas* Psl comprises a $V_H$ comprising the amino acid sequence of SEQ ID NO: 110 and a $V_L$ comprising the amino acid sequence of SEQ ID NO: 123. In some embodiments, the antigen-binding protein specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 110; and a $V_L$ comprising an LC-CDR1, an LC-CDR2, and an LC-CDR3 of the $V_L$ comprising the amino acid sequence of SEQ ID NO: 123.

In some embodiments, the antigen-binding protein specifically recognizing *Pseudomonas* Psl comprises a $V_H$ comprising the amino acid sequence of SEQ ID NO: 111 and a $V_L$ comprising the amino acid sequence of SEQ ID NO: 124. In some embodiments, the antigen-binding protein specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 111; and a $V_L$ comprising an LC-CDR1, an LC-CDR2, and an LC-CDR3 of the $V_L$ comprising the amino acid sequence of SEQ ID NO: 124.

In some embodiments, wherein the pharmaceutical composition comprises (i) an antigen-binding protein specifically recognizing *Pseudomonas* Psl and (ii) an antigen-binding protein specifically recognizing a first epitope on *Pseudomonas* PcrV and/or an antigen-binding protein specifically recognizing a second epitope on *Pseudomonas* PcrV, the ratio by molar mass of the antigen-binding protein specifically recognizing *Pseudomonas* Psl to the antigen-binding protein specifically recognizing the first epitope on *Pseudomonas* PcrV is about any one of: 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or 1:20. In some embodiments, the ratio by molar mass of the antigen-binding protein specifically recognizing *Pseudomonas* Psl to the antigen-binding protein specifically recognizing the first epitope on *Pseudomonas* PcrV is about any one of: 5:1, 4:1, 3:1, 2:1, 1:1, 1:2, 1:3, 1:4 or 1:5. In some embodiments, the ratio by molar mass of the antigen-binding protein specifically recognizing *Pseudomonas* Psl to the antigen-binding protein specifically recognizing the first epitope on *Pseudomonas* PcrV is about 2:1 or about 1:1.

In some embodiments, wherein the pharmaceutical composition comprises (i) an antigen-binding protein specifically recognizing *Pseudomonas* Psl and (ii) an antigen-binding protein specifically recognizing a first epitope on *Pseudomonas* PcrV and/or an antigen-binding protein specifically recognizing a second epitope on *Pseudomonas* PcrV, the ratio by molar mass of the antigen-binding protein specifically recognizing *Pseudomonas* Psl to the antigen-binding protein specifically recognizing the second epitope on *Pseudomonas* PcrV is about any one of: 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or 1:20. In some embodiments, the ratio by molar mass of the antigen-binding protein specifically recognizing *Pseudomonas* Psl to the antigen-binding protein specifically recognizing the second epitope on *Pseudomonas* PcrV is about any one of: 5:1, 4:1, 3:1, 2:1, 1:1, 1:2, 1:3, 1:4 or 1:5. In some embodiments, the ratio by molar mass of the antigen-binding protein specifically recognizing *Pseudomonas* Psl to the antigen-binding protein specifically recognizing the second epitope on *Pseudomonas* PcrV is about 2:1 or about 1:1.

In some embodiments, wherein the pharmaceutical composition comprises (i) an antigen-binding protein specifically recognizing a first epitope on *Pseudomonas* PcrV and (ii) an antigen-binding protein specifically recognizing a second epitope on *Pseudomonas* PcrV and/or an antigen-binding protein specifically recognizing *Pseudomonas* Psl, the ratio by molar mass of the antigen-binding protein specifically recognizing the first epitope on *Pseudomonas* PcrV to the antigen-binding protein specifically recognizing the second epitope on *Pseudomonas* PcrV is about any one of: 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or 1:20. In some embodiments, the ratio by molar mass of the antigen-binding protein specifically recognizing the first epitope on *Pseudomonas* PcrV to the antigen-binding protein specifically recognizing the second epitope on *Pseudomonas* PcrV is about any one of: 5:1, 4:1, 3:1, 2:1, 1:1, 1:2, 1:3, 1:4 or 1:5. In some embodiments, the ratio by molar mass of the antigen-binding protein specifically recognizing the first epitope on *Pseudomonas* PcrV to the antigen-binding protein specifically recognizing the second epitope on *Pseudomonas* PcrV is about 1:1.

In some embodiments, wherein the pharmaceutical composition comprises (i) an antigen-binding protein specifically recognizing a first epitope on *Pseudomonas* PcrV and (ii) an antigen-binding protein specifically recognizing a second epitope on *Pseudomonas* PcrV and/or an antigen-binding protein specifically recognizing *Pseudomonas* Psl, the ratio by molar mass of the antigen-binding protein specifically recognizing the first epitope on *Pseudomonas* PcrV to the antigen-binding protein specifically recognizing a first epitope on *Pseudomonas* PcrV is about any one of: 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or 1:20. In some embodiments, the ratio by molar mass of the antigen-binding protein specifically recognizing the first epitope on *Pseudomonas* PcrV to the antigen-binding protein specifically recognizing the antigen-binding protein specifically recognizing *Pseudomonas* Psl is about any one of: 5:1, 4:1, 3:1, 2:1, 1:1, 1:2, 1:3, 1:4 or 1:5. In some embodiments, the ratio by molar mass of the antigen-binding protein specifically recognizing the first epitope on *Pseudomonas* PcrV to the antigen-binding protein specifically recognizing *Pseudomonas* Psl is about 1:1 or about 1:2.

In some embodiments, there is provided a pharmaceutical composition comprising an antigen-binding protein specifically recognizing a first epitope on *Pseudomonas* PcrV and an antigen-binding protein specifically recognizing *Pseudomonas* PSL, wherein the antigen-binding protein specifically recognizing the first epitope on *Pseudomonas* PcrV comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ Comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; and wherein the antigen-binding protein specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the ratio by molar mass of the antigen-binding protein specifically recognizing the first epitope on *Pseudomonas* PcrV to the antigen-binding protein specifically recognizing *Pseudomonas* Psl is about 1:1 or about 1:2.

In some embodiments, there is provided a pharmaceutical composition comprising an antigen-binding protein specifically recognizing a first epitope on *Pseudomonas* PcrV and an antigen-binding protein specifically recognizing *Pseudomonas* PSL, wherein the antigen-binding protein specifically recognizing the first epitope on *Pseudomonas* PcrV comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ Comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; and wherein the antigen-binding protein specifically recognizing *Pseudomonas* Psl comprises: a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75. In some embodiments, the ratio by molar mass of the antigen-binding protein specifically recognizing the first epitope on *Pseudomonas* PcrV to the antigen-binding protein specifically recognizing *Pseudomonas* Psl is about 1:1 or about 1:2.

In some embodiments, there is provided a pharmaceutical composition comprising an antigen-binding protein specifically recognizing a first epitope on *Pseudomonas* PcrV and an antigen-binding protein specifically recognizing *Pseudomonas* PSL, wherein the antigen-binding protein specifically recognizing the first epitope on *Pseudomonas* PcrV comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13; and wherein the antigen-binding protein specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the ratio by molar mass of the antigen-binding protein specifically recognizing the first epitope on *Pseudomonas* PcrV to the antigen-binding protein specifically recognizing *Pseudomonas* Psl is about 1:1 or about 1:2.

In some embodiments, there is provided a pharmaceutical composition comprising an antigen-binding protein specifically recognizing a first epitope on *Pseudomonas* PcrV and an antigen-binding protein specifically recognizing *Pseudomonas* Psl, wherein the antigen-binding protein specifically recognizing the first epitope on *Pseudomonas* PcrV comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ Comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13; and wherein the antigen-binding protein specifically recognizing *Pseudomonas* Psl comprises: a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75. In some embodiments, the ratio by molar mass of the antigen-binding protein specifically recognizing the first epitope on *Pseudomonas* PcrV to the antigen-binding protein specifically recognizing *Pseudomonas* Psl is about 1:1 or about 1:2.

In some embodiments, there is provided a pharmaceutical composition comprising an antigen-binding protein specifically recognizing a first epitope on *Pseudomonas* PcrV, an antigen-binding protein specifically recognizing a second epitope on *Pseudomonas* PcrV and an antigen-binding protein specifically recognizing *Pseudomonas* Psl, wherein the antigen-binding protein specifically recognizing the first epitope on *Pseudomonas* PcrV comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; wherein the antigen-binding protein specifically recognizing the second epitope on *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 27; and a $V_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36; and wherein the antigen-binding protein specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the ratio by molar mass of the antigen-binding protein specifically recognizing the first epitope on *Pseudomonas* PcrV, the antigen-binding protein specifically recognizing the second epitope on *Pseudomonas* PcrV and the antigen-binding protein specifically recognizing *Pseudomonas* Psl is about 1:1:1 or about 1:1:2.

Anti-PcrV Antigen-Binding Domains and Antigen-Binding Proteins

In some embodiments, the antigen-binding domain or antigen-binding protein specifically recognizing *Pseudomonas* PcrV include, but are not limited to, humanized antibodies, chimeric antibodies, mouse antibodies, human antibodies, and antibodies comprising the heavy chain and/or light chain CDRs discussed herein. In one aspect, the antigen-binding domains or proteins are isolated antibodies that bind to PcrV. Contemplated antigen-binding domains or proteins specifically recognizing *Pseudomonas* PcrV can include the entire or a fragment of full-length anti-PcrV antibodies (e.g., full-length IgG1, IgG2 or IgG4), anti-PcrV scFvs, multi-specific (such as bispecific) anti-PcrV antibodies, anti-PcrV immunoconjugates, and the like. In some embodiments, the anti-PcrV antibody is a Fab, a Fab', a F(ab)'2, a Fab'-SH, a single-chain Fv (scFv), an Fv fragment, a dAb, a Fd, or a diabody. In some embodiments, reference to an antigen-binding domain or protein that specifically binds to PcrV means that the antigen-binding domain or protein binds to PcrV with an affinity that is at least about 10 times (including for example at least about any of 10, $10^2$, $10^3$, $10^4$, $10^5$, $10^6$, or $10^7$ times) its binding affinity for non-target. In some embodiments, the non-target is an antigen that is not PcrV.

Binding affinity can be determined by methods known in the art, such as ELISA, fluorescence activated cell sorting (FACS) analysis, or radioimmunoprecipitation assay (RIA). Kd can be determined by methods known in the art, such as surface plasmon resonance (SPR) assay or biolayer interferometry (BLI).

In certain aspects, the antigen-binding domain or protein specifically recognizing *Pseudomonas* PcrV (a) promotes, mediates, or enhances opsonophagocytic killing (OPK) of *P. aeruginosa*, and/or (b) disrupts the activity of the type III toxin secretion system.

Although antigen-binding domains or proteins containing human sequences (e.g., human heavy and light chain variable domain sequences comprising human CDR sequences) are extensively discussed herein, non-human antigen-binding domains or proteins are also contemplated. In some embodiments, non-human antigen-binding domains or proteins comprise human CDR sequences from an antigen-binding domain or protein as described herein and non-human framework sequences. Non-human framework sequences include, in some embodiments, any sequence that can be used for generating synthetic heavy and/or light chain variable domains using one or more human CDR sequences as described herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. In some embodiments, a non-human antigen-binding domains or proteins includes an antigen-binding domain or protein generated by grafting one or more human CDR sequences as described herein onto a non-human framework sequence (e.g., a mouse or chicken framework sequence).

The complete amino acid sequence of an exemplary PcrV protein comprises or consists of the amino acid sequence of SEQ ID NO: 86. In some embodiments, the antigen-binding domain or protein specifically recognizing *Pseudomonas* PcrV described herein specifically recognizes an epitope within *Pseudomonas* PcrV. In some embodiments, the antigen-binding domain or protein is specific for *Pseudomonas* PcrV and does not exhibit species cross-reactivity or other types of non-*Pseudomonas* protein cross-reactivity.

In some embodiments, the antigen-binding domain or protein specifically recognizing *Pseudomonas* PcrV described herein specifically binds to a linear epitope within *Pseudomonas* PcrV. In some embodiments, the antigen-binding domain or protein specifically recognizing *Pseudomonas* PcrV described herein specifically binds to a nonlinear epitope within *Pseudomonas* PcrV. In some embodiments, the antigen-binding domain or protein described herein specifically binds to an epitope on *Pseudomonas* PcrV, where the epitope comprises at least any one of 1, 2, 3, 4, 5 or 6 amino acid residues selected from the group of Gln160, Asp165, Asp170, Asp173, Thr175, and Ser202 of *Pseudomonas* PcrV, according to SEQ ID NO: 86. In some embodiments, the antigen-binding domain or protein specifically recognizing *Pseudomonas* PcrV or protein described herein specifically binds to an epitope on *Pseudomonas* PcrV, where the epitope comprises at least 2 amino acid residues selected from the group of Gln160, Asp165, Asp170, Asp173, Thr175, and Ser202 of *Pseudomonas* PcrV, according to SEQ ID NO: 86. In some embodiments, the antigen-binding domain or protein specifically recognizing *Pseudomonas* PcrV described herein specifically binds to an epitope on *Pseudomonas* PcrV, where the epitope comprises at least 3 amino acid residues selected from the group of Gln160, Asp165, Asp170, Asp173, Thr175, and Ser202 of *Pseudomonas* PcrV, according to SEQ ID NO: 86. In some embodiments, the antigen-binding domain or protein specifically recognizing *Pseudomonas* PcrV described herein specifically binds to an epitope on *Pseudomonas* PcrV, where the epitope comprises at least 4 amino acid residues selected from the group of Gln160, Asp165, Asp170, Asp173, Thr175, and Ser202 of *Pseudomonas* PcrV, according to SEQ ID NO: 86. In some embodiments, the antigen-binding domain or protein specifically recognizing *Pseudomonas* PcrV described herein specifically binds to an epitope on *Pseudomonas* PcrV, where the epitope comprises at least 5 amino acid residues selected from the group of Gln160, Asp165, Asp170, Asp173, Thr175, and Ser202 of *Pseudomonas* PcrV, according to SEQ ID NO: 86. In some embodiments, the antigen-binding domain or protein specifically recognizing *Pseudomonas* PcrV described herein specifically binds to an epitope on *Pseudomonas* PcrV, where the epitope comprises Gln160, Asp165, Asp170, Asp173, Thr175, and Ser202 of *Pseudomonas* PcrV, according to SEQ ID NO: 86.

In some embodiments, the bispecific molecule comprises an antibody heavy chain constant region and an antibody light chain constant region. In some embodiments, the bispecific molecule comprises an IgG1 heavy chain constant region. In some embodiments, the bispecific molecule comprises an IgG2 heavy chain constant region. In some embodiments, the bispecific molecule comprises an IgG3 heavy chain constant region. In some embodiments, the bispecific molecule comprises an IgG4 heavy chain constant region. In some embodiments, the IgG is a human IgG. In some embodiments, the heavy chain constant region comprises or consists of the amino acid sequence of SEQ ID NO: 89. In some embodiments, the heavy chain constant region comprises or consists of the amino acid sequence of SEQ ID NO: 90. In some embodiments, the bispecific molecule comprises a lambda light chain constant region. In some embodiments, the anti-PcrV antibody comprises a kappa light chain constant region. In some embodiments, the light chain constant region comprises or consists of the amino acid sequence of SEQ ID NO: 88. In some embodiments, the bispecific molecule comprises an antibody heavy chain variable domain and an antibody light chain variable domain.

Anti-Psl Antigen-Binding Domains and Antigen-Binding Proteins

In some embodiments, the antigen-binding domain or protein specifically recognizing *Pseudomonas* Psl include, but are not limited to, humanized antibodies, chimeric antibodies, mouse antibodies, human antibodies, and antibodies comprising the heavy chain and/or light chain CDRs discussed herein. In one aspect, the antigen-binding domains or proteins are isolated antibodies that bind to Psl. Contemplated antigen-binding domains or proteins specifically recognizing *Pseudomonas* Psl can include the entire or a fragment of full-length anti-Psl antibodies (e.g., full-length IgG1, IgG2 or IgG4), anti-Psl scFvs, multi-specific (such as bispecific) anti-Psl antibodies, anti-Psl immunoconjugates, and the like. In some embodiments, the anti-Psl antibody is a Fab, a Fab', a F(ab)'2, a Fab'-SH, a single-chain Fv (scFv), an Fv fragment, a dAb, a Fd, or a diabody. In some embodiments, reference to an antigen-binding domain or protein that specifically binds to Psl means that the antigen-binding domain or protein binds to Psl with an affinity that is at least about 10 times (including for example at least about any of 10, $10^2$, $10^3$, $10^4$, 105, $10^6$, or $10^7$ times) its binding affinity for non-target. In some embodiments, the non-target is an antigen that is not Psl.

Binding affinity can be determined by methods known in the art, such as ELISA, fluorescence activated cell sorting (FACS) analysis, or radioimmunoprecipitation assay (RIA). Kd can be determined by methods known in the art, such as surface plasmon resonance (SPR) assay or biolayer interferometry (BLI).

In certain aspects, the antigen-binding domain or protein specifically recognizing *Pseudomonas* Psl (a) promotes, mediates, or enhances opsonophagocytic killing (OPK) of *P. aeruginosa*, and/or (b) prevents the binding of *P. aeruginosa* to epithelial cells.

Although antigen-binding domains or proteins containing human sequences (e.g., human heavy and light chain variable domain sequences comprising human CDR sequences) are extensively discussed herein, non-human antigen-binding domains or proteins are also contemplated. In some embodiments, non-human antigen-binding domains or proteins comprise human CDR sequences from an antigen-binding domain or protein as described herein and non-human framework sequences. Non-human framework sequences include, in some embodiments, any sequence that can be used for generating synthetic heavy and/or light chain variable domains using one or more human CDR sequences as described herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. In some embodiments, a non-human antigen-binding domains or proteins includes an antigen-binding domain or protein generated by grafting one or more human CDR sequences as described herein onto a non-human framework sequence (e.g., a mouse or chicken framework sequence).

In some embodiments, the antigen-binding domain or protein specifically recognizing *Pseudomonas* Psl described herein specifically recognizes an epitope within *Pseudomonas* Psl. In some embodiments, the antigen-binding domain or protein is specific for *Pseudomonas* Psl and does not exhibit species cross-reactivity or other types of non-*Pseudomonas* protein cross-reactivity.

In some embodiments, the bispecific molecule comprises an antibody heavy chain constant region and an antibody light chain constant region. In some embodiments, the bispecific molecule comprises an IgG1 heavy chain constant region. In some embodiments, the bispecific molecule comprises an IgG2 heavy chain constant region. In some embodiments, the bispecific molecule comprises an IgG3 heavy chain constant region. In some embodiments, the bispecific molecule comprises an IgG4 heavy chain constant region. In some embodiments, the IgG is a human IgG. In some embodiments, the heavy chain constant region comprises or consists of the amino acid sequence of SEQ ID NO: 89. In some embodiments, the heavy chain constant region comprises or consists of the amino acid sequence of SEQ ID NO: 90. In some embodiments, the bispecific molecule comprises a lambda light chain constant region. In some embodiments, the anti-PcrV antibody comprises a kappa light chain constant region. In some embodiments, the light chain constant region comprises or consists of the amino acid sequence of SEQ ID NO: 88. In some embodiments, the bispecific molecule comprises an antibody heavy chain variable domain and an antibody light chain variable domain.

Binding Affinity

Binding affinity can be indicated by Kd, Koff, Kon, or Ka. The term "Koff", as used herein, is intended to refer to the off-rate constant for dissociation of an antigen-binding domain from the antigen-binding domain/antigen complex, as determined from a kinetic selection set up. The term "Kon", as used herein, is intended to refer to the on-rate constant for association of an antibody to the antigen to form the antigen-binding domain/antigen complex. The term dissociation constant "Kd", as used herein, refers to the dissociation constant of a particular antibody-antigen interaction, and describes the concentration of antigen required to occupy one half of all of the antigen-binding domains present in a solution of antibody molecules at equilibrium, and is equal to Koff/Kon. The measurement of Kd presupposes that all binding agents are in solution. In the case where the antigen-binding domain is tethered to a cell wall, e.g., in a yeast expression system, the corresponding equilibrium rate constant is expressed as EC50, which gives a good approximation of Kd. The affinity constant, Ka, is the inverse of the dissociation constant, Kd. In some embodiments, the antigen-binding domain is comprised within an antigen-binding protein.

The dissociation constant (Kd) is used as an indicator showing affinity of antigen-binding domain moieties to antigens. For example, easy analysis is possible by the Scatchard method using antibodies marked with a variety of marker agents, as well as by using Biacore (made by Amersham Biosciences), analysis of biomolecular interactions by surface plasmon resonance, according to the user's manual and attached kit. The Kd value that can be derived using these methods is expressed in units of M. An antibody that specifically binds to a target may have a Kd of, for example, $\leq 10^{-7}$ M, $\leq 10^{-8}$ M, $\leq 10^{-9}$ M, $\leq 10^{-10}$ M, $\leq 10^{-11}$ M, $\leq 10^{-12}$ M, or $\leq 10^{-13}$ M.

Binding specificity of the antibody can be determined experimentally by methods known in the art. Such methods comprise, but are not limited to, Western blots, ELISA-, RIA-, ECL-, IRMA-, EIA-, BIAcore-tests and peptide scans.

In some embodiments, the antigen-binding domain specifically recognizing PcrV specifically binds to a target PcrV with a Kd of about $10^{-7}$ M to about $10^{-13}$ M (such as about $10^{-7}$ M to about $10^{-13}$ M, about $10^{-8}$ M to about $10^{-13}$ M, about $10^{-9}$ M to about $10^{-13}$ M, or about $10^{-10}$ M to about $10^{-12}$ M). Thus in some embodiments, the Kd of the binding between the antigen-binding domain specifically recognizing PcrV and PcrV, is about $10^{-7}$ M to about $10^{-13}$ M, $1\times10^{-7}$ M to about $5\times10^{-13}$ M, about $10^{-7}$ M to about $10^{-12}$ M, about $10^{-7}$ M to about $10^{-11}$ M, about $10^{-7}$ M to about $10^{-10}$ M, about $10^{-7}$ M to about $10^{-9}$ M, about $10^{-8}$ M to about $10^{-13}$ M, about $1\times10^{-8}$ M to about $5\times10^{-13}$ M, about $10^{-8}$ M to about $10^{-12}$ M, about $10^{-8}$ M to about $10^{-11}$ M, about $10^{-8}$ M to about $10^{-10}$ M, about $10^{-8}$ M to about $10^{-9}$ M, about $5\times10^{-9}$ M to about $1\times10^{-13}$ M, about $5\times10^{-9}$ M to about $1\times10^{-12}$ M, about $5\times10^{-9}$ M to about $1\times10^{-11}$ M, about $5\times10^{-9}$ M to about $1\times10^{-10}$ M, about $10^{-9}$ M to about $10^{-13}$ M, about $10^{-9}$ M to about $10^{-12}$ M, about $10^{-9}$ M to about $10^{-11}$ M, about $10^{-9}$ M to about $10^{-10}$ M, about $5\times10^{-10}$ M to about $1\times10^{-13}$ M, about $5\times10^{-10}$ M to about $1\times10^{-12}$ M, about $5\times10^{-10}$ M to about $1\times10^{-11}$ M, about $10^{-10}$ M to about $10^{-13}$ M, about $1\times10^{-10}$ M to about $5\times10^{-13}$ M, about $1\times10^{-10}$M to about $1\times10^{-12}$ M, about $1\times10^{-10}$M to about $5\times10^{-12}$ M, about $1\times10^{-10}$ M to about $1\times10^{-11}$ M, about $10^{-11}$ M to about $10^{-13}$ M, about $1\times10^{-11}$ M to about $5\times10^{-13}$ M, about $10^{-11}$ M to about $10^{-12}$ M, or about $10^{-12}$ M to about $10^{-13}$ M. In some embodiments, the Kd of the binding between the antigen-binding domain specifically recognizing PcrV and a PcrV is about $10^{-7}$ M to about $10^{-13}$ M.

In some embodiments, the Kd of the binding between the antigen-binding domain specifically recognizing PcrV and a non-target is higher than the Kd of the binding between the antigen-binding domain specifically recognizing PcrV and the target, and is herein referred to in some embodiments as the binding affinity of the antigen-binding domain specifically recognizing PcrV to the target (e.g., PcrV) is higher than that to a non-target. In some embodiments, the non-target is an antigen that is not PcrV. In some embodiments, the Kd of the binding between antigen-binding domain specifically recognizing PcrV and a non-PcrV target can be at least about 10 times, such as about 10-100 times, about 100-1000 times, about $10^3$-$10^4$ times, about $10^4$-$10^5$ times, about $10^5$-$10^6$ times, about $10^6$-$10^7$ times, about $10^7$-108 times, about 108-109 times, about $10^9$-$10^{10}$ times, about $10^{10}$-$10^{11}$ times, or about $10^{11}$-$10^{12}$ times of the Kd of the binding between the antigen-binding domain specifically recognizing PcrV and a target PcrV.

In some embodiments, the antigen-binding domain specifically recognizing Psl specifically binds to a target Psl with a Kd of about $10^{-7}$ M to about $10^{-13}$ M (such as about $10^{-7}$ M to about $10^{-13}$ M, about $10^{-8}$ M to about $10^{-13}$ M, about $10^{-9}$ M to about $10^{-13}$ M, or about $10^{-10}$ M to about $10^{-12}$ M). Thus in some embodiments, the Kd of the binding between the antigen-binding domain specifically recognizing Psl and Psl, is about $10^{-7}$ M to about $10^{-13}$ M, about $1\times10^{-7}$ M to about $5\times10^{-13}$ M, about $10^{-7}$ M to about $10^{-12}$ M, about $10^{-7}$ M to about $10^{-11}$ M, about $10^{-7}$ M to about $10^{-10}$ M, about $10^{-7}$ M to about $10^{-9}$ M, about $10^{-8}$ M to about $10^{-13}$ M, about $1\times10^{-8}$ M to about $5\times10^{-13}$ M, about $10^{-8}$ M to about $10^{-12}$ M, about $10^{-8}$ M to about $10^{-1}$ M, about $10^{-8}$ M to about $10^{-10}$ M, about $10^{-8}$ M to about $10^{-9}$ M, about $5\times10^{-9}$ M to about $1\times10^{-13}$ M, about $5\times10^{-9}$ M to about $1\times10^{-12}$ M, about $5\times10^{-9}$ M to about $1\times10^{-11}$ M, about $5\times10^{-9}$ M to about $1\times10^{-10}$ M, about $10^{-9}$ M to about $10^{-13}$ M, about $10^{-9}$ M to about $10^{-12}$ M, about $10^{-9}$ M to about $10^{-11}$ M, about $10^{-9}$ M to about $10^{-10}$ M, about $5\times10^{-10}$ M to about $1\times10^{-13}$ M, about $5\times10^{-10}$ M to about $1\times10^{-12}$ M, about $5\times10^{-10}$ M to about $1\times10^{-11}$ M, about $10^{-10}$ M to about $10^{-13}$ M, about $1\times10^{-1}$ M to about $5\times10^{-13}$ M, about $1\times10^{-10}$M to about $1\times10^{-12}$ M, about $1\times10^{-10}$M to about $5\times10^{-12}$ M, about $1\times10^{-10}$M to about $1\times10^{-1}$ M, about $10^{-11}$ M to about $10^{-13}$ M, about $1\times10^{-1}$ M to about $5\times10^{-13}$ M, about $10^{-11}$ M to about $10^{-12}$ M, or about $10^{-12}$ M to about $10^{-13}$ M. In some embodiments, the Kd of the binding between the antigen-binding domain specifically recognizing Psl and a Psl is about $10^{-7}$ M to about $10^{-13}$ M.

In some embodiments, the Kd of the binding between the antigen-binding domain specifically recognizing Psl and a non-target is higher than the Kd of the binding between the antigen-binding domain specifically recognizing Psl and the target, and is herein referred to in some embodiments as the binding affinity of the antigen-binding domain specifically recognizing Psl to the target (e.g., Psl) is higher than that to a non-target. In some embodiments, the non-target is an antigen that is not Psl. In some embodiments, the Kd of the binding between antigen-binding domain specifically recognizing Psl and a non-Psl target can be at least about 10 times, such as about $10^{-100}$ times, about 100-1000 times, about $10^3$-$10^4$ times, about $10^4$-$10^5$ times, about $10^5$-$10^6$ times, about $10^6$-$10^7$ times, about $10^7$-108 times, about 108-109 times, about $10^9$-$10^{10}$ times, about $10^{10}$-$10^{11}$ times, or about $10^{11}$-$10^{12}$ times of the Kd of the binding between the antigen-binding domain specifically recognizing Psl and a target Psl.

Nucleic Acids

Nucleic acid molecules encoding the PcrV-binding domains or proteins, the Psl-binding domains or proteins, and the bispecific molecules are also contemplated. In some embodiments, there is provided a nucleic acid (or a set of nucleic acids) encoding a full-length anti-PcrV antibody or anti-Psl antibody, including any of the full-length anti-PcrV or anti-Psl antibodies described herein. In some embodiments, the nucleic acid (or a set of nucleic acids) encoding the antigen-binding domain, antigen-binding protein or bispecific molecule described herein may further comprises a nucleic acid sequence encoding a peptide tag (such as protein purification tag, e.g., His-tag, HA tag).

Also contemplated here are isolated host cells comprising an anti-PcrV antibody, anti-Psl antibody, or bispecific antibody that specifically recognizing *Pseudomonas* PcrV and *Pseudomonas* Psl, an isolated nucleic acid encoding the polypeptide components of the anti-PcrV antibody, anti-Psl antibody, or bispecific antibody that specifically recognizing *Pseudomonas* PcrV and *Pseudomonas* Psl, or a vector comprising a nucleic acid encoding the polypeptide components of the anti-PcrV antibody, anti-Psl antibody, or bispecific antibody that specifically recognizing *Pseudomonas* PcrV and *Pseudomonas* Psl described herein.

The present application also includes variants to these nucleic acid sequences. For example, the variants include nucleotide sequences that hybridize to the nucleic acid sequences encoding the antigen-binding domains, antigen-binding proteins or bispecific molecules of the present application under at least moderately stringent hybridization conditions.

The present application also provides vectors in which a nucleic acid of the present application is inserted.

In brief summary, the expression of an antigen-binding domain, antigen-binding protein or bispecific molecule by a natural or synthetic nucleic acid encoding the antigen-binding domain, antigen-binding protein or bispecific molecule can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequence.

The nucleic acids of the present application may also be used for nucleic acid immunization and gene therapy, using standard gene delivery protocols. Methods for gene delivery are known in the art. See, e.g., U.S. Pat. Nos. 5,399,346; 5,580,859; 5,589,466, incorporated by reference herein in their entireties. In some embodiments, the application provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Green and Sambrook (2013, *Molecular Cloning: A Laboratory Manual*, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the application should not be limited to the use of constitutive promoters. Inducible promoters are also contemplated as part of the application. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the expression of the antigen-binding domain, antigen-binding protein or bispecific molecule is inducible. In some embodiments, a nucleic acid sequence encoding the antigen-binding domain, antigen-binding protein or bispecific molecule is operably linked to an inducible promoter, including any inducible promoter described herein.

Inducible Promoters

The use of an inducible promoter provides a molecular switch capable of turning on expression of the polynucleotide sequence which it is operatively linked when such expression is desired, or turning off the expression when expression is not desired. Exemplary inducible promoter systems for use in eukaryotic cells include, but are not limited to, hormone-regulated elements (e.g., see Mader, S. and White, J. H. (1993) Proc. Natl. Acad. Sci. USA 90:5603-5607), synthetic ligand-regulated elements (see, e.g., Spencer, D. M. et al 1993) Science 262: 1019-1024) and ionizing radiation-regulated elements (e.g., see Manome, Y. et al. (1993) Biochemistry 32: 10607-10613; Datta, R. et al. (1992) Proc. Natl. Acad. Sci. USA 89: 1014-10153). Further exemplary inducible promoter systems for use in in vitro or in vivo mammalian systems are reviewed in Gingrich et al. (1998) Annual Rev. Neurosci 21:377-405. In some embodiments, the inducible promoter system for use to express the antigen-binding domain, antigen-binding protein or bispecific molecule is the Tet system. In some embodiments, the inducible promoter system for use to express the antigen-binding domain, antigen-binding protein or bispecific molecule is the lac repressor system from *E. coli*.

An exemplary inducible promoter system for use in the present application is the Tet system. Such systems are based on the Tet system described by Gossen et al. (1993). In an exemplary embodiment, a polynucleotide of interest is under the control of a promoter that comprises one or more Tet operator (TetO) sites. In the inactive state, Tet repressor (TetR) will bind to the TetO sites and repress transcription from the promoter. In the active state, e.g., in the presence of an inducing agent such as tetracycline (Tc), anhydrotetracycline, doxycycline (Dox), or an active analog thereof, the inducing agent causes release of TetR from TetO, thereby allowing transcription to take place. Doxycycline is a member of the tetracycline family of antibiotics having the chemical name of 1-dimethylamino-2,4a,5,7,12-pentahydroxy-11-methyl-4,6-dioxo-1,4a,11,11a,12,12a-hexahydro-tetracene-3-carboxamide.

In one embodiment, a TetR is codon-optimized for expression in mammalian cells, e.g., murine or human cells. Most amino acids are encoded by more than one codon due to the degeneracy of the genetic code, allowing for substantial variations in the nucleotide sequence of a given nucleic acid without any alteration in the amino acid sequence encoded by the nucleic acid. However, many organisms display differences in codon usage, also known as "codon bias" (i.e., bias for use of a particular codon(s) for a given amino acid). Codon bias often correlates with the presence of a predominant species of tRNA for a particular codon, which in turn increases efficiency of mRNA translation. Accordingly, a coding sequence derived from a particular organism (e.g., a prokaryote) may be tailored for improved expression in a different organism (e.g., a eukaryote) through codon optimization.

Other specific variations of the Tet system include the following "Tet-Off" and "Tet-On" systems. In the Tet-Off system, transcription is inactive in the presence of Tc or Dox. In that system, a tetracycline-controlled transactivator protein (tTA), which is composed of TetR fused to the strong transactivating domain of VP16 from Herpes simplex virus, regulates expression of a target nucleic acid that is under transcriptional control of a tetracycline-responsive promoter element (TRE). The TRE is made up of TetO sequence concatamers fused to a promoter (commonly the minimal promoter sequence derived from the human cytomegalovirus (hCMV) immediate-early promoter). In the absence of Tc or Dox, tTA binds to the TRE and activates transcription of the target gene. In the presence of Tc or Dox, tTA cannot bind to the TRE, and expression from the target gene remains inactive.

Conversely, in the Tet-On system, transcription is active in the presence of Tc or Dox. The Tet-On system is based on a reverse tetracycline-controlled transactivator, rtTA. Like tTA, rtTA is a fusion protein comprised of the TetR repressor and the VP16 transactivation domain. However, a four amino acid change in the TetR DNA binding moiety alters rtTA's binding characteristics such that it can only recognize the tetO sequences in the TRE of the target transgene in the presence of Dox. Thus, in the Tet-On system, transcription of the TRE-regulated target gene is stimulated by rtTA only in the presence of Dox.

Another inducible promoter system is the lac repressor system from *E. coli* (See Brown et al., Cell 49:603-612 (1987)). The lac repressor system functions by regulating transcription of a polynucleotide of interest operably linked to a promoter comprising the lac operator (lacO). The lac repressor (lacR) binds to LacO, thus preventing transcription of the polynucleotide of interest. Expression of the polynucleotide of interest is induced by a suitable inducing agent, e.g., isopropyl-β-D-thiogalactopyranoside (IPTG).

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tel et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, there is provided nucleic acid encoding an antigen-binding domain, antigen-binding protein or bispecific molecule according to any of the antigen-binding domain, antigen-binding protein or bispecific molecule described herein. In some embodiments, the nucleic acid comprises one or more nucleic acid sequences encoding the heavy and light chains of the antigen-binding domain, antigen-binding protein or bispecific molecule. In some embodiments, each of the one or more nucleic acid sequences is contained in separate vectors. In some embodiments, at least some of the nucleic acid sequences are contained in the same vector. In some embodiments, all of the nucleic acid sequences are contained in the same vector. Vectors may be selected, for example, from the group consisting of mammalian expression vectors and viral vectors (such as those derived from retroviruses, adenoviruses, adeno-associated viruses, herpes viruses, and lentiviruses).

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Green and Sambrook (2013, Molecular Cloning: A Laboratory Manual, Cold Spring Harbor Laboratory, New York). In some embodiments, the introduction of a polynucleotide into a host cell is carried out by calcium phosphate transfection.

Biological methods for introducing a polynucleotide of interest into a host cell include the use of DNA and RNA vectors. Viral vectors, and especially retroviral vectors, have become the most widely used method of inserting genes into mammalian, e.g., human cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce exogenous nucleic acids into a host cell or otherwise expose a cell to the inhibitor of the present application, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the application.

Preparation of Antigen-Binding Proteins and Bispecific Molecules

In some embodiments, the antigen-binding protein (e.g. an antigen-binding protein that specifically recognizes PcrV or Psl) is a monoclonal antibody. In some embodiments, the antigen-binding protein or the bispecific molecule or derived from a monoclonal antibody. In some embodiments, the antigen-binding protein or the bispecific molecule comprises $V_H$ and $V_L$ domains, or variants thereof, from the monoclonal antibody. In some embodiments, the antigen-binding protein or the bispecific molecule further comprises $C_H1$ and $C_L$ domains, or variants thereof, from the monoclonal antibody. Monoclonal antibodies can be prepared, e.g., using known methods in the art, including hybridoma methods, yeast display, phage display methods, or using recombinant DNA methods. Additionally, exemplary yeast display and phage display methods are described herein and in the Examples below.

In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro. The immunizing agent can include a polypeptide or a fusion protein of the protein of interest. Generally, peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which prevents the growth of HGPRT-deficient cells.

In some embodiments, the immortalized cell lines fuse efficiently, support stable high-level expression of antibody by the selected antibody-producing cells, and are sensitive to a medium such as HAT medium. In some embodiments, the immortalized cell lines are murine myeloma lines, which can be obtained, for instance, from the Salk Institute Cell Distribution Center, San Diego, California and the American Type Culture Collection, Manassas, Virginia. Human myeloma and mouse-human heteromyeloma cell lines also have been described for the production of human monoclonal antibodies.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones can be sub cloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the sub clones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In some embodiments, according to any of the antigen-binding proteins or bispecific molecules described herein, the antigen-binding protein or bispecific molecule comprises sequences from a clone selected from an antibody library (such as a phage library presenting scFv or Fab fragments). The clone may be identified by screening combinatorial libraries for antibody fragments with the desired activity or activities. For example, a variety of methods are known in the art for generating phage display libraries and screening such libraries for antibodies possessing the desired binding characteristics. Such methods are reviewed, e.g., in Hoogenboom et al., *Methods in Molecular Biology* 178:1-37 (O'Brien et al., ed., Human Press, Totowa, N.J., 2001) and further described, e.g., in McCafferty et al., *Nature* 348:552-554; Clackson et al., *Nature* 352: 624-628 (1991); Marks et al., *J. Mol. Biol.* 222: 581-597 (1992); Marks and Bradbury, *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); *Fellouse, Proc. Natl. Acad. Sci. USA* 101(34): 12467-12472 (2004); and Lee et al., *J. Immunol. Methods* 284(1-2): 119-132(2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phages typically display antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

The antigen-binding proteins or bispecific molecules can be prepared using phage display to screen libraries for antigen-binding moieties specific to the target antigen (such as PcrV or Psl). The library can be a human scFv phage display library having a diversity of at least $1 \times 10^9$ (such as at least about any of $1 \times 10^9$, $2.5 \times 10^9$, $5 \times 10^9$, $7.5 \times 10^9$, $1 \times 10^{10}$, $2.5 \times 10^{10}$, $5 \times 10^{10}$, $7.5 \times 10^{10}$, or $1 \times 1^{110}$) unique human antibody fragments. In some embodiments, the library is a naïve human library constructed from DNA extracted from human PMBCs and spleens from healthy donors, encompassing all human heavy and light chain subfamilies. In some embodiments, the library is a naïve human library constructed from DNA extracted from PBMCs isolated from patients with various diseases, such as patients with autoimmune diseases, cancer patients, and patients with infectious diseases. In some embodiments, the library is a semi-synthetic human library, wherein heavy chain CDR3 is completely randomized, with all amino acids (with the exception of cysteine) equally likely to be present at any given position (see, e.g., Hoet, R. M. et al., *Nat. Biotechnol.* 23(3):344-348, 2005). In some embodiments, the heavy chain CDR3 of the semi-synthetic human library has a length from about 5 to about 24 (such as about any of 5, 6, 7, 8, 9, 10, 11, 12, 13, 14, 15, 16, 17, 18, 19, 20, 21, 22, 23, or 24) amino acids. In some embodiments, the library is a fully-synthetic phage display library. In some embodiments, the library is a non-human phage display library.

Phage clones that bind to the target antigen (such as PcrV or Psl) with high affinity can be selected by iterative binding of phage to the target antigen, which is bound to a solid support (such as, for example, beads for solution panning or mammalian cells for cell panning), followed by removal of non-bound phage and by elution of specifically bound phage. The bound phage clones are then eluted and used to infect an appropriate host cell, such as *E. coli* XL1-Blue, for expression and purification. The panning can be performed for multiple (such as about any of 2, 3, 4, 5, 6 or more) rounds with solution panning, cell panning, or a combination of both, to enrich for phage clones binding specifically to the target antigen. Enriched phage clones can be tested for specific binding to the target antigen by any methods known in the art, including for example ELISA and FACS.

Monoclonal antibodies and bispecific molecules can also be made by recombinant DNA methods, such as those described in U.S. Pat. No. 4,816,567. DNA encoding the monoclonal antibodies of the application can be readily isolated and sequenced using conventional procedures (e.g., by using oligonucleotide probes that are capable of binding specifically to genes encoding the heavy and light chains of murine antibodies). Hybridoma cells as described above or antigen-specific phage clones of the application can serve as a source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains and/or framework regions in place of the homologous non-human sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the application, or can be substituted for the variable domains of one antigen-combining site of an antibody of the application to create a chimeric bivalent antibody. In some embodiments, additional variable domains targeting a different epitope or antigen can be included to generate a chimeric bispecific antibody.

The antigen-binding proteins can be monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using any method known in the art.

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. In some embodiments, the first heavy-chain constant region (CH1) containing the site necessary for light-chain binding is present in at least one of the fusions. DNAs encoding the immunoglobulin heavy-chain fusions and, if desired, the immunoglobulin light chain, are inserted into separate expression vectors, and are co-transfected into a suitable host organism. In some embodiments, antibody variable domains targeting different epitopes or different antigens can be fused to immunoglobulin constant-domain sequences to generate a chimeric bispecific molecule.

Human and Humanized Antibodies

The antigen-binding proteins or bispecific molecules can comprise humanized antibody moieties or human antibody moieties. Humanized forms of non-human (e.g., murine) antibody moieties are chimeric immunoglobulins, immunoglobulin chains, or fragments thereof (such as Fv, Fab, Fab', F(ab')$_2$, scFv, or other antigen-binding subsequences of antibodies) that typically contain minimal sequence derived from non-human immunoglobulin. Humanized antibody moieties include human immunoglobulins, immunoglobulin chains, or fragments thereof (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibody moieties can also comprise residues that are found neither in the recipient antibody nor in the imported CDR or framework sequences. In general, the humanized antibody can comprise substantially at least one, and typically two, variable domains, in which all or substantially all of the CDR regions correspond to those of a non-human immunoglobulin, and all or substantially all of the FR regions are those of a human immunoglobulin consensus sequence.

Generally, a humanized antibody or humanized antibody moiety has one or more amino acid residues introduced into it from a source that is non-human. These non-human amino acid residues are often referred to as "import" residues, which are typically taken from an "import" variable domain. According to some embodiments, humanization can be essentially performed following the method of Winter and co-workers (Jones et al., *Nature,* 321: 522-525 (1986); Riechmann et al., *Nature,* 332: 323-327 (1988); Verhoeyen et al., *Science,* 239: 1534-1536 (1988)), by substituting rodent CDRs or CDR sequences for the corresponding sequences of a human antibody. Accordingly, such "humanized" antibody moieties are antibody moieties (U.S. Pat. No. 4,816,567), wherein substantially less than an intact human variable domain has been substituted by the corresponding sequence from a non-human species. In practice, humanized antibody moieties are typically human antibody moieties in which some CDR residues and possibly some FR residues are substituted by residues from analogous sites in rodent antibodies.

As an alternative to humanization, human antibody moieties can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *PNAS USA,* 90:2551 (1993); Jakobovits et al., *Nature,* 362:255-258 (1993); Bruggemann et al., *Year in Immunol.,* 7:33 (1993); U.S. Pat. Nos. 5,545, 806, 5,569,825, 5,591,669; 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; and 5,661,016, and Marks et al., *Bio/Technology,* 10: 779-783 (1992); Lonberg et al., *Nature,* 368: 856-859 (1994); Morrison, *Nature,* 368: 812-813 (1994); Fishwild et al., *Nature Biotechnology,* 14: 845-851 (1996); Neuberger, *Nature Biotechnology,* 14: 826 (1996); Lonberg and Huszar, *Intern. Rev. Immunol.,* 13: 65-93 (1995).

Human antibodies or human antibody moieties may also be generated by in vitro activated B cells (see U.S. Pat. Nos. 5,567,610 and 5,229,275) or by using various techniques known in the art, including phage display libraries. Hoogenboom and Winter, *J. Mol. Biol.,* 227:381 (1991); Marks et al., *J. Mol. Biol.,* 222:581 (1991). The techniques of Cole et al. and Boerner et al. are also available for the preparation of human monoclonal antibodies. Cole et al., *Monoclonal Antibodies and Cancer Therapy, Alan R. Liss,* p. 77 (1985) and Boerner et al., *J. Immunol.,* 147(1): 86-95 (1991).

Anti-PcrV, Anti-Psl Antibody or Bispecififc Antibody Specifically Recognizing *Pseudomonas* PcrV and *Pseudomonas* Psl Variants In some embodiments, amino acid sequences of the antigen-binding domains or antigen-binding proteins (e.g., antibody moieties specifically recognizing PcrV or Psl, or bispecific antibody specifically recognizing *Pseudomonas* PcrV and Psl) variants provided herein are contemplated. For example, it may be desirable to improve the binding affinity and/or other biological properties of the antigen-binding domain or antigen-binding protein. Amino acid sequences of an antigen-binding entity variants may be prepared by introducing appropriate modifications into the nucleotide sequence encoding the antigen-binding entity, or by peptide synthesis. Such modifications include, for example, deletions from, and/or insertions into and/or substitutions of residues within the amino acid sequences of the antigen-binding entity. Any combination of deletion, insertion, and substitution can be made to arrive at the final construct, provided that the final construct possesses the desired characteristics, e.g., antigen-binding.

In some embodiments, variants of the antigen-binding domains or antigen-binding proteins having one or more amino acid substitutions are provided. Sites of interest for substitutional mutagenesis include the HVRs and FRs. Amino acid substitutions may be introduced into an antibody of interest and the products screened for a desired activity, e.g., improved bioactivity, retained/improved antigen binding, decreased immunogenicity, reduced pathogen binding to epithelial cells or improved opsonophagocytic killing (OPK) of pathogens, such as *P. aeruginosa.* In some embodiments, the amino acid substitutions described herein are limited to "exemplary substitutions" shown in Table 7 of this application. In some embodiments, the amino acid substitutions are limited to "preferred substitutions" shown in Table 7 of this application.

Conservative substitutions are shown in Table 7 below

TABLE 7

| CONSERVATIVE SUBSTITITIONS | | |
| --- | --- | --- |
| Original Residue | Exemplary Substitutions | Preferred Substitutions |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |

TABLE 7-continued

CONSERVATIVE SUBSTITITIONS

| Original Residue | Exemplary Substitutions | Preferred Substitutions |
|---|---|---|
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:

a. hydrophobic: Norleucine, Met, Ala, Val, Leu, Ile;

b. neutral hydrophilic: Cys, Ser, Thr, Asn, Gln;

c. acidic: Asp, Glu;

d. basic: His, Lys, Arg;

e. residues that influence chain orientation: Gly, Pro;

f. aromatic: Trp, Tyr, Phe.

Non-conservative substitutions will entail exchanging a member of one of these classes for another class.

An exemplary substitutional variant is an affinity matured antibody, which may be conveniently generated, e.g., using phage display-based affinity maturation techniques. Briefly, one or more CDR residues are mutated and the variant antibody moieties displayed on phage and screened for a particular biological activity (e.g., bioactivity based on RBC lysis inhibition assay or binding affinity). Alterations (e.g., substitutions) may be made in HVRs, e.g., to improve bioactivity based on RBC lysis inhibition assay or antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or specificity determining residues (SDRs), with the resulting variant $V_H$ and $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).)

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant $V_H$ and $V_L$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., Ala or Glu) to determine whether the interaction of the antibody with antigen is affected. Further substitutions may be introduced at the amino acid locations to demonstrate functional sensitivity to the initial substitutions. Alternatively, or additionally, a crystal structure of an antigen-antibody complex can be determined to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antigen-binding moiety with an N-terminal methionyl residue. Other insertional variants of the antigen-binding moiety include the fusion to the N- or C-terminus of the antigen-binding moiety to an enzyme (e.g. for ADEPT) or a polypeptide which increases the serum half-life of the antigen-binding moiety.

Fc Region Variants

In some embodiments, one or more amino acid modifications may be introduced into the Fc region of an antigen-binding moiety (e.g., a full-length anti-PcrV, anti-Psl antibody, bispecific antibody specifically recognizing *Pseudomonas* PcrV and Psl, anti-PcrV, anti-Psl, or bispecific molecule specifically recognizing *Pseudomonas* PcrV and Psl Fc fusion protein) provided herein, thereby generating an Fc region variant. In some embodiments, the Fc region variant has enhanced ADCC effector function, often related to binding to Fc receptors (FcRs). In some embodiments, the Fc region variant has decreased ADCC effector function. There are many examples of changes or mutations to Fc sequences that can alter effector function. For example, WO 00/42072 and Shields et al. *J Biol. Chem.* 9(2): 6591-6604 (2001) describe antibody variants with improved or diminished binding to FcRs. The contents of those publications are specifically incorporated herein by reference.

Antibody-Dependent Cell-Mediated Cytotoxicity (ADCC) is a mechanism of action of therapeutic antibodies against tumor cells. ADCC is a cell-mediated immune defense whereby an effector cell of the immune system actively lyses a target cell (e.g., an infected cell), whose membrane-surface antigens have been bound by specific antigen-binding moieties (e.g., an anti-PcrV antibody, anti-Psl antibody, or bispecific antibody specifically recognizing *Pseudomonas* PcrV and Psl). The typical ADCC involves activation of NK cells by antibodies. An NK cell expresses CD16 which is an Fc receptor. This receptor recognizes, and binds to, the Fc portion of an antibody bound to the surface of a target cell. The most common Fc receptor on the surface of an NK cell is called CD16 or FcγRIII. Binding of the Fc receptor to the Fc region of an antibody results in NK cell activation, release of cytolytic granules and consequent target cell apoptosis.

In some embodiments, the application contemplates an anti-PcrV antibody variant, anti-Psl antibody variant or bispecific antibody variant specifically recognizing *Pseudomonas* PcrV and Psl (such as a full-length anti-PcrV antibody, anti-Psl antibody or bispecific antibody variant specifically recognizing *Pseudomonas* PcrV and Psl) comprising an Fc region that possesses some but not all effector functions, which makes it a desirable candidate for applications in which the half-life of the anti-PcrV antibody, anti-Psl antibody, or bispecific antibody specifically recognizing *Pseudomonas* PcrV and Psl in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, alterations are made in the Fc region that result in altered (i.e., either improved or diminished) opsonization, e.g. such as described in Moore et al., MAbs. 2(2): 181-189 (2010).

In some embodiments, there is provided an anti-PcrV antibody, anti-Psl antibody, or bispecific antibody specifically recognizing *Pseudomonas* PcrV and Psl (such as a full-length anti-PcrV antibody, anti-Psl antibody, or bispecific antibody specifically recognizing *Pseudomonas* PcrV and Psl) variant comprising a variant Fc region comprising one or more amino acid substitutions which increase half-life and/or improve binding to the neonatal Fc receptor (FcRn). Antibodies with increased half-lives and improved binding to FcRn are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

Anti-PcrV antibodies, anti-Psl antibodies or bispecific antibodies specifically recognizing *Pseudomonas* PcrV and Psl (such as full-length anti-PcrV antibodies, anti-Psl antibodies, or bispecific antibody specifically recognizing *Pseudomonas* PcrV and Psl) comprising any of the Fc variants described herein, or combinations thereof, are contemplated.

Glycosylation Variants

In some embodiments, an anti-PcrV antibody, anti-Psl antibody, or bispecific antibody specifically recognizing *Pseudomonas* PcrV and Psl (such as a full-length anti-PcrV antibody, anti-Psl antibody, or bispecific antibody specifically recognizing *Pseudomonas* PcrV and Psl) provided herein is altered to increase or decrease the extent to which the anti-PcrV antibody, anti-Psl antibody or bispecific antibody specifically recognizing *Pseudomonas* PcrV and Psl is glycosylated. Addition or deletion of glycosylation sites to an anti-PcrV antibody, anti-Psl antibody or bispecific antibody specifically recognizing *Pseudomonas* PcrV and Psl may be conveniently accomplished by altering the amino acid sequence of the anti-PcrV antibody, anti-Psl antibody, or bispecific antibody specifically recognizing *Pseudomonas* PcrV and Psl or polypeptide portion thereof such that one or more glycosylation sites is created or removed.

Where the anti-PcrV antibody, anti-Psl antibody, or bispecific antibody specifically recognizing *Pseudomonas* PcrV and Psl comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-PcrV antibody, anti-Psl antibody, or bispecific antibody specifically recognizing *Pseudomonas* PcrV and Psl of the application may be made in order to create anti-PcrV antibody, anti-Psl antibody, or bispecific antibody specifically recognizing *Pseudomonas* PcrV and Psl variants with certain improved properties.

The N-glycans attached to the CH2 domain of Fc is heterogeneous. Antibodies or Fc fusion proteins generated in CHO cells are fucosylated by fucosyltransferase activity. See Shoji-Hosaka et al., J. Biochem. 2006, 140:777-83. Normally, a small percentage of naturally occurring afucosylated IgGs may be detected in human serum. N-glycosylation of the Fc is important for binding to FcγR; and afucosylation of the N-glycan increases Fc's binding capacity to FcγRIIIa. Increased FcγRIIIa binding can enhance ADCC, which can be advantageous in certain antibody therapeutic applications in which cytotoxicity is desirable.

In some embodiments, an enhanced effector function can be detrimental when Fc-mediated cytotoxicity is undesirable. In some embodiments, the Fc fragment or CH2 domain is not glycosylated. In some embodiments, the N-glycosylation site in the CH2 domain is mutated to prevent from glycosylation.

In some embodiments, anti-PcrV antibody, anti-Psl antibody, or bispecific antibody specifically recognizing *Pseudomonas* PcrV and Psl (such as a full-length anti-PcrV antibody, anti-Psl antibody, or bispecific antibody specifically recognizing *Pseudomonas* PcrV and Psl) variants are provided comprising an Fc region wherein a carbohydrate structure attached to the Fc region has reduced fucose or lacks fucose, which may improve ADCC function. Specifically, anti-PcrV antibodies, anti-Psl antibodies or bispecific antibodies specifically recognizing *Pseudomonas* PcrV and Psl are contemplated herein that have reduced fucose relative to the amount of fucose on the same anti-PcrV antibody, anti-Psl antibody, or bispecific antibody specifically recognizing *Pseudomonas* PcrV and Psl produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In some embodiments, the anti-PcrV antibody, anti-Psl antibody, or bispecific antibody specifically recognizing *Pseudomonas* PcrV and Psl is one wherein less than about 50%, 40%, 30%, 20%, 10%, or 5% of the N-linked glycans thereon comprise fucose. For example, the amount of fucose in such an anti-PcrV antibody, anti-Psl antibody, or bispecific antibody specifically recognizing *Pseudomonas* PcrV and Psl may be from 1% to 80%, from 1% to 65%, from 5% to 65% or from 20% to 40%. In some embodiments, the anti-PcrV antibody, anti-Psl antibody, or bispecific antibody specifically recognizing *Pseudomonas* PcrV and Psl is one wherein none of the N-linked glycans thereon comprise fucose, i.e., wherein the anti-PcrV antibody, anti-Psl antibody, or bispecific antibody specifically recognizing *Pseudomonas* PcrV and Psl is completely without fucose, or has no fucose or is afucosylated. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as α-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Anti-PcrV antibody, anti-Psl antibody, or bispecific antibody specifically recognizing *Pseudomonas* PcrV and Psl (such as a full-length anti-PcrV antibody, anti-Psl antibody, or bispecific antibody specifically recognizing *Pseudomonas* PcrV and Psl) variants are further provided with bisected oligosaccharides, e.g., in which a biantennary oligosaccharide attached to the Fc region of the anti-PcrV antibody, anti-Psl antibody, or bispecific antibody specifically recognizing *Pseudomonas* PcrV and Psl is bisected by GlcNAc. Such anti-PcrV antibody, anti-Psl antibody, or bispecific antibody specifically recognizing *Pseudomonas* PcrV and Psl (such as a full-length anti-PcrV antibody, anti-Psl antibody, or bispecific antibody specifically recognizing *Pseudomonas* PcrV and Psl) variants may have reduced fucosylation and/or improved ADCC function. Examples of such antibody variants are described, e.g., in WO 2003/011878 (Jean-Mairet et al.); U.S. Pat. No. 6,602,684 (Umana et al.); US 2005/0123546 (Umana et al.), and Ferrara et al., *Biotechnology and Bioengineering*, 93(5): 851-861 (2006). Anti-PcrV antibody, anti-Psl antibody, or bispecific antibody specifically recognizing *Pseudomonas* PcrV and Psl (such as full-length anti-PcrV antibody, anti-Psl antibody, or bispecific antibody specifically recognizing *Pseudomonas* PcrV and Psl) variants with at least one galactose residue in the oligosaccharide attached to the Fc region are also provided. Such anti-PcrV antibody, anti-Psl antibody, or bispecific antibody specifically recognizing *Pseudomonas* PcrV and Psl variants may have improved CDC function. Such antibody variants are described, e.g., in WO 1997/30087 (Patel et al.); WO 1998/58964 (Raju, S.); and WO 1999/22764 (Raju, S.).

In some embodiments, the anti-PcrV antibody, anti-Psl antibody, or bispecific antibody specifically recognizing *Pseudomonas* PcrV and Psl (such as a full-length anti-PcrV antibody, anti-Psl antibody, or bispecific antibody specifically recognizing *Pseudomonas* PcrV and Psl) variants comprising an Fc region are capable of binding to an FcγRIII. In some embodiments, the anti-PcrV antibody, anti-Psl antibody, or bispecific antibody specifically recognizing *Pseudomonas* PcrV and Psl (such as a full-length anti-PcrV antibody, anti-Psl antibody, or bispecific antibody specifically recognizing *Pseudomonas* PcrV and Psl) variants comprising an Fc region have ADCC activity in the presence of human effector cells (e.g., T cell) or have increased ADCC activity in the presence of human effector cells compared to the otherwise same anti-PcrV antibody, anti-Psl antibody, or bispecific antibody specifically recognizing *Pseudomonas* PcrV and Psl (such as a full-length anti-PcrV antibody, anti-Psl antibody, or bispecific antibody specifically recognizing *Pseudomonas* PcrV and Psl) comprising a human wild-type Fc region.

Cysteine Engineered Variants

In some embodiments, it may be desirable to create cysteine engineered anti-PcrV antibody, anti-Psl antibody, or bispecific antibody specifically recognizing *Pseudomonas* PcrV and Psl (such as a full-length anti-PcrV antibody, anti-Psl antibody, or bispecific antibody specifically recognizing *Pseudomonas* PcrV and Psl) in which one or more amino acid residues are substituted with cysteine residues.

In some embodiments, the substituted residues occur at accessible sites of the anti-PcrV antibody, anti-Psl antibody, or bispecific antibody specifically recognizing *Pseudomonas* PcrV and Psl. By substituting those residues with cysteine, reactive thiol groups are thereby positioned at accessible sites of the anti-PcrV antibody, anti-Psl antibody, or bispecific antibody specifically recognizing *Pseudomonas* PcrV and Psl and may be used to conjugate the anti-PcrV antibody, anti-Psl antibody, or bispecific antibody specifically recognizing *Pseudomonas* PcrV and Psl to other moieties, such as drug moieties or linker-drug moieties, to create an anti-PcrV, anti-Psl or bispecific antibody specifically recognizing *Pseudomonas* PcrV and Psl immunoconjugate, as described further herein. Cysteine engineered anti-PcrV antibodies, anti-Psl antibodies, or bispecific antibodies specifically recognizing *Pseudomonas* PcrV and Psl (e.g., full-length anti-PcrV antibodies, anti-Psl antibodies, or bispecific antibodies specifically recognizing *Pseudomonas* PcrV and Psl) may be generated as described, e.g., in U.S. Pat. No. 7,521,541.

Derivatives

In some embodiments, a bispecific antibody specifically recognizing *Pseudomonas* PcrV and Psl (such as a full-length bispecific antibody specifically recognizing *Pseudomonas* PcrV and Psl) provided herein may be further modified to contain additional non-proteinaceous moieties that are known in the art and readily available. The moieties suitable for derivatization of the bispecific antibodies specifically recognizing *Pseudomonas* PcrV and Psl include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the bispecific antibodies specifically recognizing *Pseudomonas* PcrV and Psl may vary, and if more than one polymer are attached, they can be the same or different molecules. In general, the number and/or type of polymers used for derivatization can be determined based on considerations including, but not limited to, the particular properties or functions of the bispecific antibody specifically recognizing *Pseudomonas* PcrV and Psl to be improved, whether the bispecific antibody specifically recognizing *Pseudomonas* PcrV and Psl derivative will be used in a therapy under defined conditions, etc.

Pharmaceutical Compositions

Also provided herein are compositions (such as pharmaceutical compositions, also referred to herein as formulations) comprising any of the anti-PcrV antibodies, anti-Psl antibodies, or bispecific antibodies specifically recognizing *Pseudomonas* PcrV and Psl (such as a full-length anti-PcrV antibody, anti-Psl antibody, or bispecific antibody specifically recognizing *Pseudomonas* PcrV and Psl), nucleic acids encoding the antibodies, vectors comprising the nucleic acids encoding the antibodies, or host cells comprising the nucleic acids or vectors described herein. In some embodiments, there is provided a pharmaceutical composition comprising any one of the anti-PcrV antibodies, anti-Psl antibodies, or bispecific antibodies specifically recognizing *Pseudomonas* PcrV and Psl described herein and a pharmaceutically acceptable carrier.

Suitable formulations of the anti-PcrV antibodies, anti-Psl antibodies, or bispecific antibodies specifically recognizing *Pseudomonas* PcrV and Psl are obtained by mixing an anti-PcrV antibody, anti-Psl antibody, or bispecific antibody specifically recognizing *Pseudomonas* PcrV and Psl having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary formulations are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be treated herein. Lipofectins or liposomes can be used to deliver the anti-PcrV antibodies, anti-Psl antibodies, or bispecific antibodies specifically recognizing *Pseudomonas* PcrV and Psl of this application into cells.

The formulation herein may also contain one or more active compounds in addition to the anti-PcrV antibody, anti-Psl antibody, or bispecific antibody specifically recognizing *Pseudomonas* PcrV and Psl (such as a full-length anti-PcrV antibody, anti-Psl antibody, or bispecific antibody specifically recognizing *Pseudomonas* PcrV and Psl) as necessary for the particular indication being treated, preferably those with complementary activities that do not adversely affect each other. For example, it may be desirable to further provide an anti-neoplastic agent, a growth inhibitory agent, a cytotoxic agent, or a chemotherapeutic agent in addition to the anti-PcrV antibody, anti-Psl antibody, or bispecific antibody specifically recognizing *Pseudomonas* PcrV and Psl. Such molecules are suitably present in combination in amounts that are effective for the purpose intended. The effective amount of such other agents depends on the amount of anti-PcrV antibody, anti-Psl antibody, or bispecific antibody specifically recognizing *Pseudomonas* PcrV and Psl present in the formulation, the type of disease or disorder or treatment, and other factors discussed above. These are generally used in the same dosages and with administration routes as described herein or about from 1 to 99% of the heretofore employed dosages.

The anti-PcrV antibodies, anti-Psl antibodies, or bispecific antibodies specifically recognizing *Pseudomonas* PcrV and Psl (e.g., full-length anti-PcrV antibodies, anti-Psl antibodies, or bispecific antibodies specifically recognizing *Pseudomonas* PcrV and Psl) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Sustained-release preparations may be prepared.

Sustained-release preparations of the anti-PcrV antibodies, anti-Psl antibodies, or bispecific antibodies specifically recognizing *Pseudomonas* PcrV and Psl (e.g., full-length anti-PcrV antibodies, anti-Psl antibodies, or bispecific antibody specifically recognizing *Pseudomonas* PcrV and Psl) can be prepared. Suitable examples of sustained-release preparations include semipermeable matrices of solid hydrophobic polymers containing the antibody (or fragment thereof), which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D (–)-3-hydroxybutyric acid. While polymers such as ethylene-vinyl acetate and lactic acid-glycolic acid enable release of molecules for over 100 days, certain hydro gels release proteins for shorter time periods. When encapsulated antibody remain in the body for a long time, they can denature or aggregate as a result of exposure to moisture at 37° C., resulting in a loss of biological activity and possible changes in immunogenicity. Rational strategies can be devised for stabilization of anti-PcrV antibodies, anti-Psl antibodies, or bispecific antibody specifically recognizing *Pseudomonas* PcrV and Psl depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In some embodiments, the anti-PcrV antibody, anti-Psl antibody, or bispecific antibody specifically recognizing *Pseudomonas* PcrV and Psl (such as a full-length anti-PcrV antibody, anti-Psl antibody, or bispecific antibody specifically recognizing *Pseudomonas* PcrV and Psl) is formulated in a buffer comprising a citrate, NaCl, acetate, succinate, glycine, polysorbate 80 (Tween 80), or any combination of the foregoing. In some embodiments, the anti-PcrV antibody, anti-Psl antibody, or bispecific antibody specifically recognizing *Pseudomonas* PcrV and Psl is formulated in a buffer comprising about 100 mM to about 150 mM glycine. In some embodiments, the anti-PcrV antibody, anti-Psl antibody, or bispecific antibody specifically recognizing *Pseudomonas* PcrV and Psl is formulated in a buffer comprising about 50 mM to about 100 mM NaCl. In some embodiments, the anti-PcrV antibody, anti-Psl antibody, or bispecific antibody specifically recognizing *Pseudomonas* PcrV and Psl is formulated in a buffer comprising about 10 mM to about 50 mM acetate. In some embodiments, the anti-PcrV antibody, anti-Psl antibody or bispecific antibody specifically recognizing *Pseudomonas* PcrV and Psl is formulated in a buffer comprising about 10 mM to about 50 mM succinate. In some embodiments, the anti-PcrV antibody, anti-Psl antibody, or bispecific antibody specifically recognizing *Pseudomonas* PcrV and Psl is formulated in a buffer comprising about 0.005% to about 0.02% polysorbate 80. In some embodiments, the anti-PcrV antibody, anti-Psl antibody, or bispecific antibody specifically recognizing *Pseudomonas* PcrV and Psl is formulated in a buffer having a pH between about 5.1 and 5.6. In some embodiments, the anti-PcrV antibody, anti-Psl antibody, or bispecific antibody specifically recognizing *Pseudomonas* PcrV and Psl is formulated in a buffer comprising 10 mM citrate, 100 mM NaCl, 100 mM glycine, and 0.01% polysorbate 80, wherein the formulation is at pH 5.5.

The formulations to be used for in vivo administration must be sterile. This is readily accomplished by, e.g., filtration through sterile filtration membranes.

Methods of Treatment or Prevention of *Pseudomonas* Infection Using Combinations of Antigen-Binding Moieties Specifically Recognizing PcrV and/or Psl Methods of Treatment or Prevention Using a Bispecific Molecule Specifically Recognizing PcrV and/or Psl In certain aspects, there is provided a method of treating a *Pseudomonas* infection in an individual comprising administering to the individual an effective amount of a composition comprising any of the bispecific molecules specifically recognizing *Pseudomonas* PcrV and *Pseudomonas* Psl described herein, and/or any of the pharmaceutical compositions comprising antigen-binding proteins specifically recognizing *Pseudomonas* PcrV and/or antigen-binding proteins specifically recognizing *Pseudomonas* Psl described herein. In some embodiments, the method of treating a *Pseudomonas* infection further provides therapeutic or prophylactic effect on diseases and/or conditions associated with *Pseudomonas* infection. In some aspects, there is provided a method of preventing a *Pseudomonas* infection in an individual comprising administering to the individual an effective amount of a composition comprising any of the bispecific molecules or pharmaceutical compositions described herein. In some embodiments, there is provided use of any one of the bispecific molecules or pharmaceutical compositions described above in the manufacture of a medicament for treating a disease or condition.

Diseases and/or conditions associated with *Pseudomonas* infection include, but are not limited to fever, chills, fatigues, muscle and joint pain, swelling of joints, headache, diarrhea, skin rashes, pus in wounds, bacteremia, acute pneumonia, intraperitoneal infection. Further exemplary diseases include, but are not limited to, respiratory tract infections, bacteremia, septic shock, suppurative arthritis, enteritis, skin and soft tissue infections (such as burn wound infections), urinary tract infections, intestinal infections, ulcerative keratitis, chronic suppurative otitis media, mastoiditis, sinusitis, and endocarditis. In some embodiments, the method of treating or preventing a *Pseudomonas* infection reduces rate of mortality resulting from the *Pseudomonas* infection.

In some embodiments, there is provided a method of treating or preventing a *Pseudomonas* infection in an individual comprising administering to the individual an effective amount of a composition comprising a bispecific molecule specifically recognizing *Pseudomonas* PcrV and *Pseudomonas* Psl.

In some embodiments, there is provided a method of treating or preventing a *Pseudomonas* infection in an individual comprising administering to the individual an effective amount of a composition comprising a bispecific molecule specifically recognizing *Pseudomonas* PcrV and *Pseudomonas* Psl, wherein the first antigen-binding domain specifically recognizing *Pseudomonas* PcrV comprises: a $V_H$ comprising an HC-CDR1 comprising the amino acid sequence of any one of SEQ ID NOs: 1-3, an HC-CDR2 comprising the amino acid sequence of SEQ ID NO: 4 or 5, and an HC-CDR3 comprising the amino acid sequence of any one of SEQ ID NOs: 6-9; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12 or 13. In some embodiments, the first antigen-binding domain specifically recognizing *Pseudomonas* PcrV comprises a $V_H$ comprising the amino acid sequence of any one of SEQ ID NOs: 91-94 and 161-164 and a $V_L$ comprising the amino acid sequence of SEQ ID NO: 112, 113, 182 or 183.

In some embodiments, there is provided a method of treating or preventing a *Pseudomonas* infection in an individual comprising administering to the individual an effective amount of a composition comprising a bispecific molecule specifically recognizing *Pseudomonas* PcrV and *Pseudomonas* Psl, wherein the first antigen-binding domain specifically recognizing *Pseudomonas* PcrV comprises: a $V_H$ comprising an HC-CDR1 comprising the amino acid sequence of SEQ ID NO: 22, an HC-CDR2 comprising the amino acid sequence of any one of SEQ ID NOs: 23-25, and an HC-CDR3 comprising the amino acid sequence of any one of SEQ ID NOs: 26-29; and a $V_L$ comprising: an LC-CDR1 comprising the amino acid sequence of any one of SEQ ID NOs: 30-32, an LC-CDR2 comprising the amino acid sequence of SEQ ID NO: 33 or 34, and an LC-CDR3 comprising the amino acid sequence of any one of SEQ ID NOs: 35-37. In some embodiments, the first antigen-binding domain specifically recognizing *Pseudomonas* PcrV comprises a $V_H$ comprising the amino acid sequence of any one of SEQ ID NOs: 95-102 and 165-172 and a $V_L$ comprising the amino acid sequence of any one of SEQ ID NOs: 114-116 and 184-186.

In some embodiments, there is provided a method of treating or preventing a *Pseudomonas* infection in an individual comprising administering to the individual an effective amount of a composition comprising a bispecific molecule specifically recognizing *Pseudomonas* PcrV and *Pseudomonas* Psl, wherein the second antigen-binding domain specifically recognizing *Pseudomonas* Psl comprises: (a) a $V_H$ comprising an HC-CDR1 comprising the amino acid sequence of SEQ ID NO: 48, an HC-CDR2 comprising the amino acid sequence of SEQ ID NOs: 52 or 53, and an HC-CDR3 comprising the amino acid sequence of any one of SEQ ID NOs: 57-60; and a $V_L$ comprising: an LC-CDR1 comprising the amino acid sequence of SEQ ID NO: 65 or 66, an LC-CDR2 comprising the amino acid sequence of SEQ ID NO: 70, and an LC-CDR3 comprising the amino acid sequence of SEQ ID NO: 74; or (b) a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 62 or 63; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of any one of SEQ ID NOs: 76-79. In some embodiments, the first antigen-binding domain specifically recognizing *Pseudomo-*

*nas* PcrV comprises a $V_H$ comprising the amino acid sequence of any one of SEQ ID NOs: 103-106 and 173-176 and a $V_L$ comprising the amino acid sequence of SEQ ID NOs: 117, 118, 187 or 188. In some embodiments, the first antigen-binding domain specifically recognizing *Pseudomonas* PcrV comprises a $V_H$ comprising the amino acid sequence of SEQ ID NOs: 109, 110, 179, or 180 and a $V_L$ comprising the amino acid sequence of any one of SEQ ID NOs: 120-123 and 190-193.

In some embodiments, the first antigen-binding domain specifically recognizing *Pseudomonas* PcrV comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12. In some embodiments, the first antigen-binding domain specifically recognizing *Pseudomonas* PcrV comprises a $V_H$ comprising the amino acid sequence of SEQ ID NO: 91 or 161 and a $V_L$ Comprising the amino acid sequence of SEQ ID NO: 112 or 182. In some embodiments, the first antigen-binding domain specifically recognizing *Pseudomonas* PcrV comprises a $V_H$ comprising an HC-CDR1, an HC-CDR2 and an HC-CDR3 of the $V_H$ Comprising the amino acid sequence of SEQ ID NO: 91 or 161; and a $V_L$ comprising an LC-CDR1, an LC-CDR2, and an LC-CDR3 of the $V_L$ comprising the amino acid sequence of SEQ ID NO: 112 or 182.

In some embodiments, the first antigen-binding domain specifically recognizing *Pseudomonas* PcrV comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13. In some embodiments, the first antigen-binding domain specifically recognizing *Pseudomonas* PcrV comprises a $V_H$ comprising the amino acid sequence of SEQ ID NO: 92 or 162 and a $V_L$ Comprising the amino acid sequence of SEQ ID NO: 113 or 183. In some embodiments, the first antigen-binding domain specifically recognizing *Pseudomonas* PcrV comprises a $V_H$ comprising an HC-CDR1, an HC-CDR2 and an HC-CDR3 of the $V_H$ Comprising the amino acid sequence of SEQ ID NO: 92 or 162; and a $V_L$ comprising an LC-CDR1, an LC-CDR2, and an LC-CDR3 of the $V_L$ comprising the amino acid sequence of SEQ ID NO: 113 or 183.

In some embodiments, the first antigen-binding domain specifically recognizing *Pseudomonas* PcrV comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 8; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12. In some embodiments, the first antigen-binding domain specifically recognizing *Pseudomonas* PcrV comprises a $V_H$ comprising the amino acid sequence of SEQ ID NO: 93 or 163 and a $V_L$ Comprising the amino acid sequence of SEQ ID NO: 112 or 182. In some embodiments, the first antigen-binding domain specifically recognizing *Pseudomonas* PcrV comprises a $V_H$ comprising an HC-CDR1, an HC-CDR2 and an HC-CDR3 of the $V_H$ Comprising the amino acid sequence of SEQ ID NO: 93 or 163; and a $V_L$ comprising an LC-CDR1, an LC-CDR2, and an LC-CDR3 of the $V_L$ comprising the amino acid sequence of SEQ ID NO: 112 or 182.

In some embodiments, the first antigen-binding domain specifically recognizing *Pseudomonas* PcrV comprises: a $V_H$ comprising an HC-CDR1 comprising the amino acid sequence SEQ ID NO: 3, an HC-CDR2 comprising the amino acid sequence of SEQ ID NO: 5, and an HC-CDR3 comprising the amino acid sequence of SEQ ID NO: 9; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13. In some embodiments, the first antigen-binding domain specifically recognizing *Pseudomonas* PcrV comprises a $V_H$ comprising the amino acid sequence of SEQ ID NO: 94 or 164 and a $V_L$ Comprising the amino acid sequence of SEQ ID NO: 113 or 183. In some embodiments, the first antigen-binding domain specifically recognizing *Pseudomonas* PcrV comprises a $V_H$ comprising an HC-CDR1, an HC-CDR2 and an HC-CDR3 of the $V_H$ Comprising the amino acid sequence of SEQ ID NO: 94 or 164; and a $V_L$ comprising an LC-CDR1, an LC-CDR2, and an LC-CDR3 of the $V_L$ comprising the amino acid sequence of SEQ ID NO: 113 or 183.

In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 23, and an HC-CDR3 comprising the amino acid sequence of SEQ ID NO: 26; and a $V_L$ comprising: an LC-CDR1 comprising the amino acid sequence of SEQ ID NO: 30, an LC-CDR2 comprising the amino acid sequence of SEQ ID NO: 33, and an LC-CDR3 comprising the amino acid sequence of SEQ ID NO: 35. In some embodiments, the first antigen-binding domain specifically recognizing *Pseudomonas* PcrV comprises a $V_H$ comprising the amino acid sequence of SEQ ID NO: 95 or 165 and a $V_L$ Comprising the amino acid sequence of SEQ ID NO: 114 or 184. In some embodiments, the first antigen-binding domain specifically recognizing *Pseudomonas* PcrV comprises a $V_H$ comprising an HC-CDR1, an HC-CDR2 and an HC-CDR3 of the $V_H$ Comprising the amino acid sequence of SEQ ID NO: 95 or 165; and a $V_L$ comprising an LC-CDR1, an LC-CDR2, and an LC-CDR3 of the $V_L$ comprising the amino acid sequence of SEQ ID NO: 114 or 184.

In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 27; and a $V_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36. In some embodiments, the first antigen-binding domain specifically recognizing *Pseudomonas* PcrV comprises a $V_H$ comprising the amino acid sequence of SEQ ID NO: 96 or 166 and a $V_L$ Comprising the amino acid sequence of SEQ ID NO: 115 or 185. In some embodiments, the first antigen-binding domain specifically recognizing *Pseudomonas* PcrV comprises a $V_H$ comprising an HC-CDR1, an HC-CDR2 and an HC-CDR3 of the $V_H$ Comprising the amino acid sequence of SEQ ID NO: 96 or 166; and a $V_L$ comprising an LC-CDR1, an LC-CDR2, and an LC-CDR3 of the $V_L$ comprising the amino acid sequence of SEQ ID NO: 115 or 185.

In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 25, and an HC-CDR3 comprising the amino acid sequence of SEQ ID NO: 27; and a $V_L$ comprising: an LC-CDR1 comprising the amino acid sequence of SEQ ID NO: 32, an LC-CDR2 comprising the amino acid sequence of SEQ ID NO: 34, and an LC-CDR3 comprising the amino acid sequence of SEQ ID NO: 37. In some embodiments, the first antigen-binding domain specifically recognizing *Pseudomonas* PcrV comprises a $V_H$ comprising the amino acid sequence of SEQ ID NO: 97 or 167 and a $V_L$ Comprising the amino acid sequence of SEQ ID NO: 116 or 186. In some embodiments, the first antigen-binding domain specifically recognizing *Pseudomonas* PcrV comprises a $V_H$ comprising an HC-CDR1, an HC-CDR2 and an HC-CDR3 of the $V_H$ Comprising the amino acid sequence of SEQ ID NO: 97 or 167; and a $V_L$ comprising an LC-CDR1, an LC-CDR2, and an LC-CDR3 of the $V_L$ comprising the amino acid sequence of SEQ ID NO: 116 or 186.

In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 25, and an HC-CDR3 comprising the amino acid sequence of SEQ ID NO: 28; and a $V_L$ comprising: an LC-CDR1 comprising the amino acid sequence of SEQ ID NO: 32, an LC-CDR2 comprising the amino acid sequence of SEQ ID NO: 34, and an LC-CDR3 comprising the amino acid sequence of SEQ ID NO: 37. In some embodiments, the first antigen-binding domain specifically recognizing *Pseudomonas* PcrV comprises a $V_H$ comprising the amino acid sequence of SEQ ID NO: 98 or 168 and a $V_L$ Comprising the amino acid sequence of SEQ ID NO: 116 or 186. In some embodiments, the first antigen-binding domain specifically recognizing *Pseudomonas* PcrV comprises a $V_H$ comprising an HC-CDR1, an HC-CDR2 and an HC-CDR3 of the $V_H$ Comprising the amino acid sequence of SEQ ID NO: 98 or 168; and a $V_L$ comprising an LC-CDR1, an LC-CDR2, and an LC-CDR3 of the $V_L$ comprising the amino acid sequence of SEQ ID NO: 116 or 186. In some embodiments, the first antigen-binding domain specifically recognizing *Pseudomonas* PcrV comprises a $V_H$ comprising the amino acid sequence of SEQ ID NO: 99 or 169 and a $V_L$ comprising the amino acid sequence of SEQ ID NO: 115 or 185. In some embodiments, the first antigen-binding domain specifically recognizing *Pseudomonas* PcrV comprises a $V_H$ comprising an HC-CDR1, an HC-CDR2 and an HC-CDR3 of the $V_H$ comprising the amino acid sequence of SEQ ID NO: 99 or 169; and a $V_L$ Comprising an LC-CDR1, an LC-CDR2, and an LC-CDR3 of the $V_L$ comprising the amino acid sequence of SEQ ID NO: 115 or 185.

In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 28; and a $V_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36.

In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 25, and an HC-CDR3 comprising the amino acid sequence of SEQ ID NO: 26; and a $V_L$ comprising: an LC-CDR1 comprising the amino acid sequence of SEQ ID NO: 32, an LC-CDR2 comprising the amino acid sequence of SEQ ID NO: 34, and an LC-CDR3 comprising the amino acid sequence of SEQ ID NO: 37. In some embodiments, the first antigen-binding domain specifically recognizing *Pseudomonas* PcrV comprises a $V_H$ comprising the amino acid sequence of SEQ ID NO: 100 or 170 and a $V_L$ comprising the amino acid sequence of SEQ ID NO: 116 or 186. In some embodiments, the first antigen-binding domain specifically recognizing *Pseudomonas* PcrV comprises a $V_H$ comprising an HC-CDR1, an HC-CDR2 and an HC-CDR3 of the $V_H$ Comprising the amino acid sequence of SEQ ID NO: 100 or 170; and a $V_L$ comprising an LC-CDR1, an LC-CDR2, and an LC-CDR3 of the $V_L$ comprising the amino acid sequence of SEQ ID NO: 116 or 186.

In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 26; and a $V_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36. In some embodiments, the first antigen-binding domain specifically recognizing *Pseudomonas* PcrV comprises a $V_H$ comprising the amino acid sequence of SEQ ID NO: 101 or 171 and a $V_L$ comprising the amino acid sequence of SEQ ID NO: 115 or 185. In some embodiments, the first antigen-binding domain specifically recognizing *Pseudomonas* PcrV comprises a $V_H$ comprising an HC-CDR1, an HC-CDR2 and an HC-CDR3 of the $V_H$ Comprising the amino acid sequence of SEQ ID NO: 101 or 171; and a $V_L$ comprising an LC-CDR1, an LC-CDR2, and an LC-CDR3 of the $V_L$ comprising the amino acid sequence of SEQ ID NO: 115 or 185.

In some embodiments, the first antigen-binding domain specifically recognizing *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 23, and an HC-CDR3 comprising the amino acid sequence of SEQ ID NO: 29; and a $V_L$ comprising: an LC-CDR1 comprising the amino acid sequence of SEQ ID NO: 30, an LC-CDR2 comprising the amino acid sequence of SEQ ID NO: 33, and an LC-CDR3 comprising the amino acid sequence of SEQ ID NO: 35. In some embodiments, the first antigen-binding domain specifically recognizing *Pseudomonas* PcrV comprises a $V_H$ comprising the amino acid sequence of SEQ ID NO: 102 or 172 and a $V_L$ comprising the amino acid sequence of SEQ ID NO: 114 or 184. In some embodiments, the first antigen-binding domain specifically recognizing *Pseudomonas* PcrV comprises a $V_H$ comprising an HC-CDR1, an HC-CDR2 and an HC-CDR3 of the $V_H$ Comprising the amino acid sequence of SEQ ID NO: 102 or 172; and a $V_L$ comprising an LC-CDR1, an LC-CDR2, and an LC-CDR3 of the $V_L$ comprising the amino acid sequence of SEQ ID NO: 114 or 184.

In some embodiments, the second antigen-binding domain specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NOs: 52 or 53, and an HC-CDR3 comprising the amino acid sequence of any one of SEQ ID NOs: 57-60; and a $V_L$ comprising: an LC-CDR1 comprising the amino acid sequence of SEQ ID NO: 65 or 66, an LC-CDR2 comprising the amino acid sequence of SEQ ID NO: 70, and an LC-CDR3 comprising the amino acid sequence of SEQ ID NO: 74.

In some embodiments, the second antigen-binding domain specifically recognizing *Pseudomonas* Psl comprises: a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 62 or 63; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of any one of SEQ ID NOs: 76-79.

In some embodiments, the second antigen-binding domain specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the second antigen-binding domain specifically recognizing *Pseudomonas* Psl comprises a $V_H$ comprising the amino acid sequence of SEQ ID NO: 103 or 173 and a $V_L$ comprising the amino acid sequence of SEQ ID NO: 117 or 187. In some embodiments, the second antigen-binding domain specifically recognizing *Pseudomonas* Psl comprises a $V_H$ comprising an HC-CDR1, an HC-CDR2 and an HC-CDR3 of the $V_H$ Comprising the amino acid sequence of SEQ ID NO: 103 or 173; and a $V_L$ comprising an LC-CDR1, an LC-CDR2, and an LC-CDR3 of the $V_L$ comprising the amino acid sequence of SEQ ID NO: 117 or 187.

In some embodiments, the second antigen-binding domain specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 53, and an HC-CDR3 comprising the amino acid sequence of SEQ ID NO: 58; and a $V_L$ comprising: an LC-CDR1 comprising the amino acid sequence of SEQ ID NO: 66, an LC-CDR2 comprising the amino acid sequence of SEQ ID NO: 70, and an LC-CDR3 comprising the amino acid sequence of SEQ ID NO: 74. In some embodiments, the second antigen-binding domain specifically recognizing *Pseudomonas* Psl comprises a $V_H$ comprising the amino acid sequence of SEQ ID NO: 104 or 174 and a $V_L$ comprising the amino acid sequence of SEQ ID NO: 118 or 188. In some embodiments, the second antigen-binding domain specifically recognizing *Pseudomonas* Psl comprises a $V_H$ comprising an HC-CDR1, an HC-CDR2 and an HC-CDR3 of the $V_H$ Comprising the amino acid sequence of SEQ ID NO: 104 or 174 and a $V_L$ comprising an LC-CDR1, an LC-CDR2, and an LC-CDR3 of the $V_L$ comprising the amino acid sequence of SEQ ID NO: 118 or 188.

In some embodiments, the second antigen-binding domain specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 59; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the second antigen-binding domain specifically recognizing *Pseudomonas* Psl comprises a $V_H$ comprising the amino acid sequence of SEQ ID NO: 105 or 175 and a $V_L$ comprising the amino acid sequence of SEQ ID NO: 117 or 187. In some embodiments, the second antigen-binding domain specifically recognizing *Pseudomonas* Psl comprises a $V_H$ comprising an HC-CDR1, an HC-CDR2 and an HC-CDR3 of the $V_H$ Comprising the amino acid sequence of SEQ ID NO: 105 or 175; and a $V_L$ comprising an LC-CDR1, an LC-CDR2, and an LC-CDR3 of the $V_L$ comprising the amino acid sequence of SEQ ID NO: 117 or 187.

In some embodiments, the second antigen-binding domain specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 53; and an HC-CDR3 comprising the amino acid sequence of SEQ ID NO: 60; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the second antigen-binding domain specifically recognizing *Pseudomonas* Psl comprises a $V_H$ comprising the amino acid sequence of SEQ ID NO: 106 or 176 and a $V_L$ comprising the amino acid sequence of SEQ ID NO: 117 or 187. In some embodiments, the second antigen-binding domain specifically recognizing *Pseudomonas* Psl comprises a $V_H$ comprising an HC-CDR1, an HC-CDR2 and an HC-CDR3 of the $V_H$ Comprising the amino acid sequence of SEQ ID NO: 106 or 176; and a $V_L$ comprising an LC-CDR1, an LC-CDR2, and an LC-CDR3 of the $V_L$ comprising the amino acid sequence of SEQ ID NO: 117 or 187.

In some embodiments, the second antigen-binding domain specifically recognizing *Pseudomonas* Psl comprises: a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75. In some embodiments, the second antigen-binding domain specifically recognizing *Pseudomonas* Psl comprises a $V_H$ comprising the amino acid sequence of SEQ ID NO: 107, 108, 177 or 178 and a $V_L$ comprising the amino acid sequence of SEQ ID NO: 119 or 189. In some embodiments, the second antigen-binding domain specifically recognizing *Pseudomonas* Psl comprises a $V_H$ comprising an HC-CDR1, an HC-CDR2 and an HC-CDR3 of the $V_H$ Comprising the amino acid sequence of SEQ ID NO: 107 108, 177 or 178 and a $V_L$ comprising an LC-CDR1, an LC-CDR2, and an LC-CDR3 of the $V_L$ comprising the amino acid sequence of SEQ ID NO: 119 or 189.

In some embodiments, the second antigen-binding domain specifically recognizing *Pseudomonas* Psl comprises: a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 62; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 76. In some embodiments, the second antigen-binding domain specifically recognizing *Pseudomonas* Psl comprises a $V_H$ comprising the amino acid sequence of SEQ ID NO: 109 or 179 and a $V_L$ comprising the amino acid sequence of SEQ ID NO: 120 or 190. In some embodiments, the second antigen-binding domain specifically recognizing *Pseudomonas* Psl comprises a $V_H$ comprising an HC-CDR1, an HC-CDR2 and an HC-CDR3 of the $V_H$ Comprising the amino acid sequence of SEQ ID NO: 109 or 179; and a $V_L$ comprising an LC-CDR1, an LC-CDR2, and an LC-CDR3 of the $V_L$ comprising the amino acid sequence of SEQ ID NO: 120 or 190.

In some embodiments, the second antigen-binding domain specifically recognizing *Pseudomonas* Psl comprises: a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 63; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 77. In some embodiments, the second antigen-binding domain specifically recognizing *Pseudomonas* Psl comprises a $V_H$ comprising the amino acid sequence of SEQ ID NO: 110 and a $V_L$ comprising the amino acid sequence of SEQ ID NO: 121. In some embodiments, the second antigen-binding domain specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 110; and a $V_L$ comprising an LC-CDR1, an LC-CDR2, and an LC-CDR3 of the $V_L$ comprising the amino acid sequence of SEQ ID NO: 121.

In some embodiments, the second antigen-binding domain specifically recognizing *Pseudomonas* Psl comprises: a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 63; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 78. In some embodiments, the second antigen-binding domain specifically recognizing *Pseudomonas* Psl comprises a $V_H$ comprising the amino acid sequence of SEQ ID NO: 110 or 180 and a $V_L$ comprising the amino acid sequence of SEQ ID NO: 122 or 192. In some embodiments, the second antigen-binding domain specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 110 or 180; and a $V_L$ comprising an LC-CDR1, an LC-CDR2, and an LC-CDR3 of the $V_L$ comprising the amino acid sequence of SEQ ID NO: 122 or 192.

In some embodiments, the second antigen-binding domain specifically recognizing *Pseudomonas* Psl comprises: a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 63; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 79. In some embodiments, the second antigen-binding domain specifically recognizing *Pseudomonas* Psl comprises a $V_H$ comprising the amino acid sequence of SEQ ID NO: 110 or 180 and a $V_L$ comprising the amino acid sequence of SEQ ID NO: 123 or 193. In some embodiments, the second antigen-binding domain specifically recognizing *Pseudomonas* Psl comprises a $V_H$ comprising an HC-CDR1, an HC-CDR2 and an HC-CDR3 of the $V_H$ Comprising the amino acid sequence of SEQ ID NO: 110 or 180; and a $V_L$ comprising an LC-CDR1, an LC-CDR2, and an LC-CDR3 of the $V_L$ comprising the amino acid sequence of SEQ ID NO: 123 or 193.

In some embodiments, the second antigen-binding domain specifically recognizing *Pseudomonas* Psl comprises: a $V_H$ comprising an HC-CDR1 comprising the amino acid sequence of SEQ ID NO: 51, an HC-CDR2 comprising the amino acid sequence of SEQ ID NOs 56, and an HC-CDR3 comprising the amino acid sequence of SEQ ID NO: 64; and a $V_L$ comprising: an LC-CDR1 comprising the amino acid sequence of SEQ ID NO: 69, an LC-CDR2 comprising the amino acid sequence of SEQ ID NO: 73, and an LC-CDR3 comprising the amino acid sequence of SEQ ID NO: 80. In some embodiments, the second antigen-binding domain specifically recognizing *Pseudomonas* Psl comprises a $V_H$ comprising the amino acid sequence of SEQ ID NO: 111 or 181 and a $V_L$ comprising the amino acid sequence of SEQ ID NO: 124 or 194. In some embodiments, the second antigen-binding domain specifically recognizing *Pseudomonas* Psl comprises a $V_H$ comprising an HC-CDR1, an HC-CDR2 and an HC-CDR3 of the $V_H$ Comprising the amino acid sequence of SEQ ID NO: 111 or 181; and a $V_L$ comprising an LC-CDR1, an LC-CDR2, and an LC-CDR3 of the $V_L$ comprising the amino acid sequence of SEQ ID NO: 124 or 194.

In some embodiments, there is provided a method of treating or preventing a *Pseudomonas* infection in an individual comprising administering to the individual an effective amount of a composition comprising a bispecific molecule specifically recognizing *Pseudomonas* PcrV and *Pseudomonas* Psl, wherein the bispecific molecule comprises a first antigen-binding domain specifically recognizing *Pseudomonas* PcrV, and a second antigen-binding domain specifically recognizing *Pseudomonas* Psl, wherein the first antigen-binding domain comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; and wherein the second antigen-binding domain comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74.

In some embodiments, there is provided a method of treating or preventing a *Pseudomonas* infection in an individual comprising administering to the individual an effective amount of a composition comprising a bispecific molecule specifically recognizing *Pseudomonas* PcrV and *Pseudomonas* Psl, wherein the bispecific molecule comprises a first antigen-binding domain specifically recognizing *Pseudomonas* PcrV, and a second antigen-binding domain specifically recognizing *Pseudomonas* Psl, wherein the first antigen-binding domain comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; and wherein the second antigen-binding domain comprises: a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75.

In some embodiments, there is provided a method of treating or preventing a *Pseudomonas* infection in an individual comprising administering to the individual an effective amount of a composition comprising a bispecific molecule specifically recognizing *Pseudomonas* PcrV and *Pseudomonas* Psl, wherein the bispecific molecule comprises a first antigen-binding domain specifically recognizing *Pseudomonas* PcrV, and a second antigen-binding domain specifically recognizing *Pseudomonas* Psl, wherein the first antigen-binding domain comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13; and wherein the second antigen-binding domain comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74.

In some embodiments, there is provided a method of treating or preventing a *Pseudomonas* infection in an individual comprising administering to the individual an effective amount of a composition comprising a bispecific molecule specifically recognizing *Pseudomonas* PcrV and *Pseudomonas* Psl, wherein the bispecific molecule comprising a first antigen-binding domain specifically recognizing *Pseudomonas* PcrV, and a second antigen-binding domain specifically recognizing *Pseudomonas* Psl, wherein the first antigen-binding domain comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13; and wherein the second antigen-binding domain comprises: a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75.

In some embodiments, the method of treating or preventing a *Pseudomonas* infection in an individual comprising administering an effective amount of a bispecific molecule specifically recognizing *Pseudomonas* PcrV and *Pseudomonas* Psl is more efficacious than administering a same valency amount of an antigen-binding protein specifically recognizing *Pseudomonas* PcrV or a same valency amount of an antigen-binding protein specifically recognizing *Pseudomonas* PSL. In some embodiments, the method comprising administering an effective amount of a bispecific molecule specifically recognizing *Pseudomonas* PcrV and *Pseudomonas* Psl enhances opsonophagocytic killing (OPK) of *P. aeruginosa* by about any one of 10%, 20%, 30%, 40%, 50%, 60%, 70%, 80%, 90%, 100%, 2-fold, 5-fold, 10-fold, 20-fold, 50-fold, or 100-fold more compared to administering a same valency amount of an antigen-binding protein specifically recognizing *Pseudomonas* PcrV or a same valency amount of an antigen-binding protein specifically recognizing *Pseudomonas* Psl. In some embodiments, the method comprising administering an effective amount of a bispecific molecule specifically recognizing *Pseudomonas* PcrV and *Pseudomonas* Psl disrupts the activity of the type III toxin secretion system by about any one of 10%, 20%, 30%, 40%, 50%, 60%, 70%, 80%, 90%, 100%, 2-fold, 5-fold, 10-fold, 20-fold, 50-fold, or 100-fold more compared to administering a same valency amount of an antigen-binding protein specifically recognizing *Pseudomonas* PcrV or a same valency amount of an antigen-binding protein specifically recognizing *Pseudomonas* Psl. In some embodiments, the method comprising administering an effective amount of a bispecific molecule specifically recognizing *Pseudomonas* PcrV and *Pseudomonas* Psl inhibits binding of *P. aeruginosa* to epithelial cells by about any one of 10%, 20%, 30%, 40%, 50%, 60%, 70%, 80%, 90%, 100%, 2-fold, 5-fold, 10-fold, 20-fold, 50-fold, or 100-fold more compared to administering a same valency amount of an antigen-binding protein specifically recognizing *Pseudomonas* PcrV or a same valency amount of an antigen-binding protein specifically recognizing *Pseudomonas* Psl. In some embodiments, the method comprising administering an effective amount of a pharmaceutical composition comprising administering an effective amount of a bispecific molecule specifically recognizing *Pseudomonas* PcrV and *Pseudomonas* Psl inhibits red blood cell lysis by *P. aeruginosa* by about any one of 10%, 20%, 30%, 40%, 50%, 60%, 70%, 80%, 90%, 100%, 2-fold, 5-fold, 10-fold, 20-fold, 50-fold, or 100-fold more compared to administering a same valency amount of an antigen-binding protein specifically recognizing *Pseudomonas* PcrV or a same valency amount of an antigen-binding protein specifically recognizing *Pseudomonas* Psl. In some embodiments, the method comprising administering an effective amount of a bispecific molecule specifically recognizing *Pseudomonas* PcrV and *Pseudomonas* Psl improves patient survival by about any one of 10%, 20%, 30%, 40%, 50%, 60%, 70%, 80%, 90%, 100%, 2-fold, 5-fold, 10-fold, 20-fold, 50-fold, or 100-fold more compared to administering a same valency amount of an antigen-binding protein specifically recognizing *Pseudomonas* PcrV or a same valency amount of an antigen-binding protein specifically recognizing *Pseudomonas* Psl. Methods of treatment or prevention using a pharmaceutical composition comprising antigen-binding proteins recognizing PcrV and/or Psl In some embodiments, there is provided a method of treating or preventing a *Pseudomonas* infection in an individual comprising administering to the individual an effective amount of a pharmaceutical composition comprising (i) an antigen-binding protein specifically recognizing a first epitope on *Pseudomonas* PcrV and (ii) an antigen-binding protein specifically recognizing a second epitope on *Pseudomonas* PcrV and/or an antigen-binding protein specifically recognizing *Pseudomonas* Psl.

In some embodiments, there is provided a method of treating or preventing a *Pseudomonas* infection in an individual comprising administering to the individual an effective amount of a pharmaceutical composition comprising (i) an antigen-binding protein specifically recognizing a first epitope on *Pseudomonas* PcrV and (ii) an antigen-binding protein specifically recognizing a second epitope on *Pseudomonas* PcrV and/or an antigen-binding protein specifically recognizing *Pseudomonas* PSL, wherein: the antigen-binding protein specifically recognizing the first epitope on *Pseudomonas* PcrV comprises: (a) a heavy chain variable domain $(V_H)$ comprising a heavy chain complementarity determining region (HC-CDR) 1 comprising $DX_1X_2MS$ (SEQ ID NO: 20), wherein $X_1$ is N or Y, and $X_2$ is Y, H or P; an HC-CDR2 comprising $X_1ISESGGSTNYADSVKG$ (SEQ ID NO: 15), wherein $X_1$ is V or G; and an HC-CDR3 comprising $GRFSTX_1SX_2HFX_3RAVYGMDV$ (SEQ ID NO: 21), wherein $X_1$ is L, S, N or D, $X_2$ is S or A, $X_3$ is F or Y; and a light chain variable domain $(V_L)$ comprising a light chain complementarity determining region (LC-CDR) 1 comprising RASQGISSYLA (SEQ ID NO: 10); an LC-CDR2 comprising AASTLQS (SEQ ID NO: 11), and an LC-CDR3 comprising $QQLSSYPLX_1$(SEQ ID NO: 19), wherein $X_1$ is S or T; or (b) a $V_H$ comprising an HC-CDR1 comprising $X_1X_2X_3MS$ (SEQ ID NO: 17), wherein $X_1$ is D or S, $X_2$ is Y or N, and $X_3$ is P, H, Y or S; an HC-CDR2 comprising $X_1ISESGGSTX_2X_3ADSVKG$ (SEQ ID NO: 18), wherein $X_1$ is G or V; $X_2$ is N or Y; and $X_3$ is D or Y; and an HC-CDR3 comprising $GRFX_1X_2X_3X_4X_5X_6FX_7RAVYGMDV$ (SEQ ID NO: 38), wherein $X_1$ is S or C, $X_2$ is T, G, D, Y, Q or A, $X_3$ is S, D, N, E, L, A, or Y, $X_4$ is S, T, Y, or A, $X_5$ is S, H, Q, A, R, K, G, E, Y or D, $X_6$ is H or C, and $X_7$ is F or Y; and a $V_L$ comprising an LC-CDR1 comprising $RASQGIX_1SYLA$ (SEQ ID NO: 209), wherein $X_1$ is S or R; an LC-CDR2 comprising AASTLQS (SEQ ID NO: 11); and an LC-CDR3 comprising $QQLX_1SYPLX_2$ (SEQ ID NO: 210), wherein $X_1$ is S, N or K, and $X_2$ is S or T.

In some embodiments, there is provided a method of treating and/or preventing a *Pseudomonas* infection in an individual comprising administering to the individual an effective amount of a pharmaceutical composition comprising (i) an antigen-binding protein specifically recognizing *Pseudomonas* Psl and (ii) an antigen-binding protein specifically recognizing a first epitope on *Pseudomonas* PcrV and/or an antigen-binding protein specifically recognizing a second epitope on *Pseudomonas* PcrV.

In some embodiments, there is provided a method of treating and/or preventing a *Pseudomonas* infection in an individual comprising administering to the individual an effective amount of a pharmaceutical composition comprising (i) an antigen-binding protein specifically recognizing *Pseudomonas* Psl and (ii) an antigen-binding protein specifically recognizing a first epitope on *Pseudomonas* PcrV and/or an antigen-binding protein specifically recognizing a second epitope on *Pseudomonas* PcrV, wherein: the antigen-binding protein specifically recognizing *Pseudomonas* Psl comprises: (a) a $V_H$ comprising a HC-CDR1 comprising SSGDYWG (SEQ ID NO: 48); an HC-CDR2 comprising SIHNX$_1$GSTYYNPSLKG (SEQ ID NO: 81), wherein X$_1$ is S or Q; and an HC-CDR3 comprising QFGSETYYX$_1$GIX$_2$P (SEQ ID NO: 82), wherein X$_1$ is T, N or P, and X$_2$ is D or Q; and a $V_L$ comprising an LC-CDR1 comprising RSSQSLLHSX$_1$GYNYLD (SEQ ID NO: 83), wherein X$_1$ is N or R; an LC-CDR2 comprising LGSNRAS (SEQ ID NO: 70), and an LC-CDR3 comprising MQALQTPYT (SEQ ID NO: 74); or (b) a $V_H$ Comprising a HC-CDR1 comprising IHSVH (SEQ ID NO: 50); an HC-CDR2 comprising TIISSGTTTTYAQSFQD (SEQ ID NO: 55); and an HC-CDR3 comprising DGX$_1$S (SEQ ID NO: 84), wherein X$_1$ is D or T; and a $V_L$ comprising an LC-CDR1 comprising RASQGISSWLA (SEQ ID NO: 68); an LC-CDR2 comprising HASTLES (SEQ ID NO: 72), and an LC-CDR3 comprising LQAX$_1$SLPHT (SEQ ID NO: 85), wherein X$_1$ is N, F, S or K; or (c) a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75; or (d) a $V_H$ comprising an HC-CDR1 comprising the amino acid sequence of SEQ ID NO: 51, an HC-CDR2 comprising the amino acid sequence of SEQ ID NO: 56, and an HC-CDR3 comprising the amino acid sequence of SEQ ID NO: 64; and a $V_L$ comprising: an LC-CDR1 comprising the amino acid sequence of SEQ ID NO: 69, an LC-CDR2 comprising the amino acid sequence of SEQ ID NO: 73, and an LC-CDR3 comprising the amino acid sequence of SEQ ID NO: 80.

In some embodiments, the antigen-binding protein specifically recognizing the first epitope on *Pseudomonas* PcrV comprises: (a) a heavy chain variable domain ($V_H$) comprising a heavy chain complementarity determining region (HC-CDR) 1 comprising DX$_1$X$_2$MS (SEQ ID NO: 20), wherein X$_1$ is N or Y, and X$_2$ is Y, H or P; an HC-CDR2 comprising X$_1$ISESGGSTNYADSVKG (SEQ ID NO: 15), wherein X$_1$ is V or G; and an HC-CDR3 comprising GRFSTX$_1$SX$_2$HFX$_3$RAVYGMDV (SEQ ID NO: 21), wherein X$_1$ is L, S, N or D, X$_2$ is S or A, X$_3$ is F or Y; and a light chain variable domain ($V_L$) comprising a light chain complementarity determining region (LC-CDR) 1 comprising RASQGISSYLA (SEQ ID NO: 10); an LC-CDR2 comprising AASTLQS (SEQ ID NO: 11), and an LC-CDR3 comprising QQLSSYPLX$_1$ (SEQ ID NO: 19), wherein X$_1$ is S or T; or (b) a $V_H$ comprising an HC-CDR1 comprising X$_1$X$_2$X$_3$MS (SEQ ID NO: 17), wherein X$_1$ is D or S, X$_2$ is Y or N, and X$_3$ is P, H, Y or S; an HC-CDR2 comprising X$_1$ISESGGSTX$_2$X$_3$ADSVKG (SEQ ID NO: 18), wherein X$_1$ is G or V; X$_2$ is N or Y; and X$_3$ is D or Y; and an HC-CDR3 comprising GRFX$_1$X$_2$X$_3$X$_4$X$_5$X$_6$FX$_7$RAVYGMDV (SEQ ID NO: 38), wherein X$_1$ is S or C, X$_2$ is T, G, D, Y, Q or A, X$_3$ is S, D, N, E, L, A, or Y, X$_4$ is S, T, Y, or A, X$_5$ is S, H, Q, A, R, K, G, E, Y or D, X$_6$ is H or C, and X$_7$ is F or Y; and a $V_L$ comprising an LC-CDR1 comprising RASQGIX$_1$SYLA (SEQ ID NO: 209), wherein X$_1$ is S or R; an LC-CDR2 comprising AASTLQS (SEQ ID NO: 11); and an LC-CDR3 comprising QQLX$_1$SYPLX$_2$ (SEQ ID NO: 210), wherein X$_1$ is S, N or K, and X$_2$ is S or T.

In some embodiments, the antigen-binding protein specifically recognizing the first epitope on *Pseudomonas* PcrV comprises: a $V_H$ comprising a HC-CDR1 comprising DNX$_1$MS (SEQ ID NO: 14), wherein X$_1$ is Y or H; an HC-CDR2 comprising X$_1$ISESGGSTNYADSVKG (SEQ ID NO: 15), wherein X$_1$ is V or G; and an HC-CDR3 comprising GRFSTX$_1$SSHFX$_2$RAVYGMDV (SEQ ID NO: 16), wherein X$_1$ is L or S, X$_2$ is F or Y; and a $V_L$ comprising an LC-CDR1 comprising RASQGISSYLA (SEQ ID NO: 10); an LC-CDR2 comprising AASTLQS (SEQ ID NO: 11), and an LC-CDR3 comprising QQLSSYPLX$_1$ (SEQ ID NO: 19), wherein X$_1$ is S or T.

In some embodiments, the antigen-binding protein specifically recognizing the first epitope on *Pseudomonas* PcrV comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12. In some embodiments, the antigen-binding protein specifically recognizing the first epitope on *Pseudomonas* PcrV comprises a $V_H$ comprising the amino acid sequence of SEQ ID NO: 91 and a $V_L$ comprising the amino acid sequence of SEQ ID NO: 112. In some embodiments, the antigen-binding protein specifically recognizing the first epitope on *Pseudomonas* PcrV comprises a $V_H$ comprising an HC-CDR1, an HC-CDR2 and an HC-CDR3 of the $V_H$ comprising the amino acid sequence of SEQ ID NO: 91; and a $V_L$ comprising an LC-CDR1, an LC-CDR2, and an LC-CDR3 of the $V_L$ comprising the amino acid sequence of SEQ ID NO: 112.

In some embodiments, the antigen-binding protein specifically recognizing the first epitope on *Pseudomonas* PcrV comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13. In some embodiments, antigen-binding protein specifically recognizing the first epitope on *Pseudomonas* PcrV comprises a $V_H$ comprising the amino acid sequence of SEQ ID NO: 92 and a $V_L$ comprising the amino acid sequence of SEQ ID NO: 113. In some embodiments, the antigen-binding protein specifically recognizing the first epitope on *Pseudomonas* PcrV comprises a $V_H$ comprising an HC-CDR1, an HC-CDR2 and an HC-CDR3 of the $V_H$ comprising the amino acid sequence of SEQ ID NO: 92; and a $V_L$ comprising an LC-CDR1, an LC-CDR2, and an LC-CDR3 of the $V_L$ comprising the amino acid sequence of SEQ ID NO: 113.

In some embodiments, the antigen-binding protein specifically recognizing the first epitope on *Pseudomonas* PcrV comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 8; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12. In some embodiments, antigen-binding protein specifically recognizing the first epitope on *Pseudomonas* PcrV comprises a $V_H$ comprising the amino acid sequence of SEQ ID NO: 93 and a $V_L$ comprising the amino acid sequence of SEQ ID NO: 112. In some embodiments, the antigen-binding protein specifically recognizing the first epitope on *Pseudomonas* PcrV comprises a $V_H$ comprising an HC-CDR1, an HC-CDR2 and an HC-CDR3 of the $V_H$ comprising the amino acid sequence of SEQ ID NO: 93; and a $V_L$ comprising an LC-CDR1, an LC-CDR2, and an LC-CDR3 of the $V_L$ comprising the amino acid sequence of SEQ ID NO: 112.

In some embodiments the antigen-binding protein specifically recognizing the first epitope on *Pseudomonas* PcrV comprises: a $V_H$ comprising an HC-CDR1 comprising the amino acid sequence SEQ ID NO: 3, an HC-CDR2 comprising the amino acid sequence of SEQ ID NO: 5, and an HC-CDR3 comprising the amino acid sequence of SEQ ID NO: 9; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13. In some embodiments, the antigen-binding protein specifically recognizing the first epitope on *Pseudomonas* PcrV comprises a $V_H$ comprising the amino acid sequence of SEQ ID NO: 94 and a $V_L$ comprising the amino acid sequence of SEQ ID NO: 113. In some embodiments, the antigen-binding protein specifically recognizing the first epitope on *Pseudomonas* PcrV comprises a $V_H$ comprising an HC-CDR1, an HC-CDR2 and an HC-CDR3 of the $V_H$ comprising the amino acid sequence of SEQ ID NO: 94; and a $V_L$ comprising an LC-CDR1, an LC-CDR2, and an LC-CDR3 of the $V_L$ comprising the amino acid sequence of SEQ ID NO: 113.

In some embodiments, the antigen-binding protein specifically recognizing the second epitope on *Pseudomonas* PcrV comprises: (a) a $V_H$ comprising a HC-CDR1 comprising SYWMH (SEQ ID NO: 22); an HC-CDR2 comprising RINEX$_1$EX$_2$SISYADSVKG (SEQ ID NO: 44), wherein X$_1$ is D or N, and X$_2$ is T, G or R; and an HC-CDR3 comprising DGPYDX$_1$X$_2$DI (SEQ ID NO: 45), wherein X$_1$ is S, A, or T, and X$_2$ is F or L; and a $V_L$ comprising an LC-CDR1 comprising RASQX$_1$VX$_2$X$_3$NLA (SEQ ID NO: 46), wherein X$_1$ is S, G or N, X$_2$ is S, R or K and X$_3$ is S or N; an LC-CDR2 comprising X$_1$ASSRAT (SEQ ID NO: 42), wherein X$_1$ is D or H, and an LC-CDR3 comprising QQYGX$_1$X$_2$PX$_3$T (SEQ ID NO: 47), wherein X$_1$ is S, L or N, X$_2$ is S, Q or E and X$_3$ is L or I; or (b) a $V_H$ comprising an HC-CDR1 comprising SYWMH (SEQ ID NO: 22); an HC-CDR2 comprising RINEX$_1$EX$_2$SISYADSVKG (SEQ ID NO: 211), wherein X$_1$ is D, N, I, L or V, X$_2$ is S, T, R, G or N; and an HC-CDR3 comprising DGPYDX$_1$X$_2$DI (SEQ ID NO: 45), wherein X$_1$ is S, A or T, X$_2$ is F or L; and a $V_L$ comprising an LC-CDR1 comprising RASQX$_1$VX$_2$X$_3$NLA (SEQ ID NO: 212), wherein X$_1$ is N, G, D or S, X$_2$ is K, R, S, N or T, X$_3$ is N, G, S or D; an LC-CDR2 comprising X$_1$ASSRAT (SEQ ID NO: 213), wherein X$_1$ is D, N, H or A; and an LC-CDR3 comprising QQYGX$_1$X$_2$PX$_3$T (SEQ ID NO: 214), wherein X$_1$ is S, T, E, H, N, A, D, M or L, X$_2$ is S, Q, E, T, D, G, H, L, N, V or Y, and X$_3$ is I, L or V. In some embodiments, the antigen-binding protein specifically recognizing the second epitope on *Pseudomonas* PcrV comprises: a $V_H$ comprising a HC-CDR1 comprising SYWMH (SEQ ID NO: 22); an HC-CDR2 comprising RINEX$_1$EX$_2$SISYADSVKG (SEQ ID NO: 39), wherein X$_1$ is D or N, X$_2$ is T or G; and an HC-CDR3 comprising DGPYDX$_1$LDI (SEQ ID NO: 40), wherein X$_1$ is S or A; and a $V_L$ comprising an LC-CDR1 comprising RASQX$_1$VX$_2$X$_3$NLA (SEQ ID NO: 41), wherein X$_1$ is S or G, X$_2$ is S or R and X$_3$ is S or N; an LC-CDR2 comprising X$_1$ASSRAT (SEQ ID NO: 42), wherein X$_1$ is D or H, and an LC-CDR3 comprising QQYGX$_1$X$_2$PX$_3$T (SEQ ID NO: 43), wherein X$_1$ is S or L, X$_2$ is S or Q and X$_3$ is L or I.

In some embodiments, the antigen-binding protein specifically recognizing the second epitope on *Pseudomonas* PcrV comprises: a $V_H$ comprising an HC-CDR1 comprising the amino acid sequence of SEQ ID NO: 22, an HC-CDR2 comprising the amino acid sequence of any one of SEQ ID NOs: 23-25, and an HC-CDR3 comprising the amino acid sequence of any one of SEQ ID NOs: 26-29; and a $V_L$ comprising: an LC-CDR1 comprising the amino acid sequence of any one of SEQ ID NOs: 30-32, an LC-CDR2 comprising the amino acid sequence of SEQ ID NO: 33 or 34, and an LC-CDR3 comprising the amino acid sequence of any one of SEQ ID NOs: 35-37.

In some embodiments, the antigen-binding protein specifically recognizing the second epitope on *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 23, and an HC-CDR3 comprising the amino acid sequence of SEQ ID NO: 26; and a $V_L$ comprising: an LC-CDR1 comprising the amino acid sequence of SEQ ID NO: 30, an LC-CDR2 comprising the amino acid sequence of SEQ ID NO: 33, and an LC-CDR3 comprising the amino acid sequence of SEQ ID NO: 35. In some embodiments, the antigen-binding protein specifically recognizing the second epitope on *Pseudomonas* PcrV comprises a $V_H$ comprising the amino acid sequence of SEQ ID NO: 95 and a $V_L$ comprising the amino acid sequence of SEQ ID NO: 114. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 95; and a $V_L$ comprising an LC-CDR1, an LC-CDR2, and an LC-CDR3 of the $V_L$ comprising the amino acid sequence of SEQ ID NO: 114.

In some embodiments, the antigen-binding protein specifically recognizing the second epitope on *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 27; and a $V_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36. In some embodiments, the antigen-binding protein specifically recognizing the second epitope on *Pseudomonas* PcrV comprises a $V_H$ comprising the amino acid sequence of SEQ ID NO: 96 and a $V_L$ comprising the amino acid sequence of SEQ ID NO: 115. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 96; and a $V_L$ comprising an LC-CDR1, an LC-CDR2, and an LC-CDR3 of the $V_L$ comprising the amino acid sequence of SEQ ID NO: 115.

In some embodiments, the antigen-binding protein specifically recognizing the second epitope on *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 25, and an HC-CDR3 comprising the amino acid sequence of SEQ ID NO: 27; and a $V_L$ comprising: an LC-CDR1 comprising the amino acid sequence of SEQ ID NO: 32, an LC-CDR2 comprising the amino acid sequence of SEQ ID NO: 34, and an LC-CDR3 comprising the amino acid sequence of SEQ ID NO: 37. In some embodiments, the antigen-binding protein specifically recognizing the second epitope on *Pseudomonas* PcrV comprises a $V_H$ comprising the amino acid sequence of SEQ ID NO: 97 and a $V_L$ comprising the amino acid sequence of SEQ ID NO: 116. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 97; and a $V_L$ comprising an LC-CDR1, an LC-CDR2, and an LC-CDR3 of the $V_L$ comprising the amino acid sequence of SEQ ID NO: 116.

In some embodiments, the antigen-binding protein specifically recognizing the second epitope on *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 25, and an HC-CDR3 comprising the amino acid sequence of SEQ ID NO: 28; and a $V_L$ comprising: an LC-CDR1 comprising the amino acid sequence of SEQ ID NO: 32, an LC-CDR2 comprising the amino acid sequence of SEQ ID NO: 34, and an LC-CDR3 comprising the amino acid sequence of SEQ ID NO: 37. In some embodiments, the antigen-binding protein specifically recognizing the second epitope on *Pseudomonas* PcrV comprises a $V_H$ comprising the amino acid sequence of SEQ ID NO: 98 and a $V_L$ comprising the amino acid sequence of SEQ ID NO: 116. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 98; and a $V_L$ comprising an LC-CDR1, an LC-CDR2, and an LC-CDR3 of the $V_L$ comprising the amino acid sequence of SEQ ID NO: 116.

In some embodiments, the antigen-binding protein specifically recognizing the second epitope on *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 28; and a $V_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36. In some embodiments, the antigen-binding protein specifically recognizing the second epitope on *Pseudomonas* PcrV comprises a $V_H$ comprising the amino acid sequence of SEQ ID NO: 99 and a $V_L$ comprising the amino acid sequence of SEQ ID NO: 115. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 99; and a $V_L$ comprising an LC-CDR1, an LC-CDR2, and an LC-CDR3 of the $V_L$ comprising the amino acid sequence of SEQ ID NO: 115.

In some embodiments, the antigen-binding protein specifically recognizing the second epitope on *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 25, and an HC-CDR3 comprising the amino acid sequence of SEQ ID NO: 26; and a $V_L$ comprising: an LC-CDR1 comprising the amino acid sequence of SEQ ID NO: 32, an LC-CDR2 comprising the amino acid sequence of SEQ ID NO: 34, and an LC-CDR3 comprising the amino acid sequence of SEQ ID NO: 37. In some embodiments, the antigen-binding protein specifically recognizing the second epitope on *Pseudomonas* PcrV comprises a $V_H$ comprising the amino acid sequence of SEQ ID NO: 100 and a $V_L$ comprising the amino acid sequence of SEQ ID NO: 116. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 100; and a $V_L$ comprising an LC-CDR1, an LC-CDR2, and an LC-CDR3 of the $V_L$ comprising the amino acid sequence of SEQ ID NO: 116.

In some embodiments, the antigen-binding protein specifically recognizing the second epitope on *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 26; and a $V_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36. In some embodiments, the antigen-binding protein specifically recognizing the second epitope on *Pseudomonas* PcrV comprises a $V_H$ comprising the amino acid sequence of SEQ ID NO: 101 and a $V_L$ comprising the amino acid sequence of SEQ ID NO: 115. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 101; and a $V_L$ comprising an LC-CDR1, an LC-CDR2, and an LC-CDR3 of the $V_L$ comprising the amino acid sequence of SEQ ID NO: 115.

In some embodiments, the antigen-binding protein specifically recognizing the second epitope on *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 23, and an HC-CDR3 comprising the amino acid sequence of SEQ ID NO: 29; and a $V_L$ comprising: an LC-CDR1 comprising the amino acid sequence of SEQ ID NO: 30, an LC-CDR2 comprising the amino acid sequence of SEQ ID NO: 33, and an LC-CDR3 comprising the amino acid sequence of SEQ ID NO: 35. In some embodiments, the antigen-binding protein specifically recognizing the second epitope on *Pseudomonas* PcrV comprises a $V_H$ comprising the amino acid sequence of SEQ ID NO: 102 and a $V_L$ comprising the amino acid sequence of SEQ ID NO: 114. In some embodiments, the antigen-binding protein specifically recognizing the second epitope on *Pseudomonas* PcrV comprises a $V_H$ comprising an HC-CDR1, an HC-CDR2 and an HC-CDR3 of the $V_H$ comprising the amino acid sequence of SEQ ID NO: 102; and a $V_L$ comprising an LC-CDR1, an LC-CDR2, and an LC-CDR3 of the $V_L$ comprising the amino acid sequence of SEQ ID NO: 114.

In some embodiments, the antigen-binding protein specifically recognizing *Pseudomonas* Psl comprises: a $V_H$ comprising a HC-CDR1 comprising SSGDYWG (SEQ ID NO: 48); an HC-CDR2 comprising SIHNX$_1$GSTYYNPSLKG (SEQ ID NO: 81), wherein X$_1$ is S or Q; and an HC-CDR3 comprising QFGSETYYX$_1$GIX$_2$P (SEQ ID NO: 82), wherein X$_1$ is T, N or P, and X$_2$ is D or Q; and a $V_L$ comprising an LC-CDR1 comprising RSSQSLLHSX$_1$GYNYLD (SEQ ID NO: 83), wherein X$_1$ is N or R; an LC-CDR2 comprising LGSNRAS (SEQ ID NO: 70), and an LC-CDR3 comprising MQALQTPYT (SEQ ID NO: 74). In some embodiments, the second antigen-binding domain specifically recognizing *Pseudomonas* Psl comprises: (a) a $V_H$ comprising a HC-CDR1 comprising SSGDYWG (SEQ ID NO: 48); an HC-CDR2 comprising SIHNX$_1$GSTYYNPSLKG (SEQ ID NO: 125), wherein X$_1$ is S, K or Q; and an HC-CDR3 comprising QFGSETYYX$_1$GIX$_2$P (SEQ ID NO: 126), wherein X$_1$ is N, S, V, T or P, and X$_2$ is D, Y, C, H, S, R, A, E, G, K, W, V, or Q; and a $V_L$ comprising an LC-CDR1 comprising RSSQSLLHSX$_1$GYNYLD (SEQ ID NO: 127), wherein X$_1$ is N, A, V, F, R, G, H, Q, W or P; an LC-CDR2 comprising LGSNRAS (SEQ ID NO: 70), and an LC-CDR3 comprising MQALQTP X$_1$T (SEQ ID NO: 128), wherein X$_1$ is R or Y.

In some embodiments, the antigen-binding protein specifically recognizing *Pseudomonas* Psl comprises: a $V_H$ comprising a HC-CDR1 comprising IHSVH (SEQ ID NO: 50); an HC-CDR2 comprising TIISSGTTTTYAQSFQD (SEQ ID NO: 55); and an HC-CDR3 comprising DGX$_1$S (SEQ ID NO: 84), wherein X$_1$ is D or T; and a $V_L$ comprising an LC-CDR1 comprising RASQGISSWLA (SEQ ID NO: 68); an LC-CDR2 comprising HASTLES (SEQ ID NO: 72), and an LC-CDR3 comprising LQAX$_1$SLPHT (SEQ ID NO: 85), wherein X$_1$ is N, F, S or K. In some embodiments, the second antigen-binding domain specifically recognizing *Pseudomonas* Psl comprises: (a) a $V_H$ comprising a HC-CDR1 comprising IHSVH (SEQ ID NO: 50); an HC-CDR2 comprising TIISSGTTTTYAQSFQD (SEQ ID NO: 55); and an HC-CDR3 comprising X$_1$X$_2$X$_3$X$_4$ (SEQ ID NO: 129), wherein X$_1$ is D, Y, or N, wherein X$_2$ is G or A, wherein X$_3$ is D or T and wherein X$_4$ is S, A or T; and a $V_L$ comprising an LC-CDR1 comprising RASQGISSWLA (SEQ ID NO: 68); an LC-CDR2 comprising HASTLES (SEQ ID NO: 72) and an LC-CDR3 comprising LQAX$_1$SLPHT (SEQ ID NO: 130), wherein X$_1$ is N, D, Y, F, P, G, K, H, A, C, E, Q, R, S, T, V, W or L.

In some embodiments, the antigen-binding protein specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NOs: 52 or 53, and an HC-CDR3 comprising the amino acid sequence of any one of SEQ ID NOs: 57-60; and a $V_L$ comprising: an LC-CDR1 comprising the amino acid sequence of SEQ ID NO: 65 or 66, an LC-CDR2 comprising the amino acid sequence of SEQ ID NO: 70, and an LC-CDR3 comprising the amino acid sequence of SEQ ID NO: 74.

In some embodiments, the antigen-binding protein specifically recognizing *Pseudomonas* Psl comprises: a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 62 or 63; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of any one of SEQ ID NOs: 76-79.

In some embodiments, the antigen-binding protein specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the antigen-binding protein specifically recognizing *Pseudomonas* Psl comprises a $V_H$ comprising the amino acid sequence of SEQ ID NO: 103 and a $V_L$ comprising the amino acid sequence of SEQ ID NO: 117. In some embodiments, the antigen-binding protein specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 103; and a $V_L$ comprising an LC-CDR1, an LC-CDR2, and an LC-CDR3 of the $V_L$ comprising the amino acid sequence of SEQ ID NO: 117.

In some embodiments, the antigen-binding protein specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 53, and an HC-CDR3 comprising the amino acid sequence of SEQ ID NO: 58; and a $V_L$ comprising: an LC-CDR1 comprising the amino acid sequence of SEQ ID NO: 66, an LC-CDR2 comprising the amino acid sequence of SEQ ID NO: 70, and an LC-CDR3 comprising the amino acid sequence of SEQ ID NO: 74. In some embodiments, the antigen-binding protein specifically recognizing *Pseudomonas* Psl comprises a $V_H$ comprising the amino acid sequence of SEQ ID NO: 104 and a $V_L$ comprising the amino acid sequence of SEQ ID NO: 118. In some embodiments, the antigen-binding protein specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 104 and a $V_L$ comprising an LC-CDR1, an LC-CDR2, and an LC-CDR3 of the $V_L$ comprising the amino acid sequence of SEQ ID NO: 118.

In some embodiments, the antigen-binding protein specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 59; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the antigen-binding protein specifically recognizing *Pseudomonas* Psl comprises a $V_H$ comprising the amino acid sequence of SEQ ID NO: 105 and a $V_L$ comprising the amino acid sequence of SEQ ID NO: 117. In some embodiments, the antigen-binding protein specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 105;

and a V_L comprising an LC-CDR1, an LC-CDR2, and an LC-CDR3 of the V_L comprising the amino acid sequence of SEQ ID NO: 117.

In some embodiments, the antigen-binding protein specifically recognizing *Pseudomonas* Psl comprises: a V_H comprising an HC-CDR1 comprising the amino acid sequence of SEQ ID NO: 48, an HC-CDR2 comprising the amino acid sequence of SEQ ID NO: 53; and an HC-CDR3 comprising the amino acid sequence of SEQ ID NO: 60; and a V_L comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the antigen-binding protein specifically recognizing *Pseudomonas* Psl comprises a V_H comprising the amino acid sequence of SEQ ID NO: 106 and a V_L comprising the amino acid sequence of SEQ ID NO: 117. In some embodiments, the antigen-binding protein specifically recognizing *Pseudomonas* Psl comprises a V_H comprising an HC-CDR1, an HC-CDR2 and an HC-CDR3 of the V_H comprising the amino acid sequence of SEQ ID NO: 106; and a V_L comprising an LC-CDR1, an LC-CDR2, and an LC-CDR3 of the V_L comprising the amino acid sequence of SEQ ID NO: 117.

In some embodiments, the antigen-binding protein specifically recognizing *Pseudomonas* Psl comprises: a V_H comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a V_L comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75. In some embodiments, the antigen-binding protein specifically recognizing *Pseudomonas* Psl comprises a V_H comprising the amino acid sequence of SEQ ID NO: 107 or 108 and a V_L comprising the amino acid sequence of SEQ ID NO: 119. In some embodiments, the antigen-binding protein specifically recognizing *Pseudomonas* Psl comprises a V_H comprising an HC-CDR1, an HC-CDR2 and an HC-CDR3 of the V_H comprising the amino acid sequence of SEQ ID NO: 107 or 108; and a V_L comprising an LC-CDR1, an LC-CDR2, and an LC-CDR3 of the V_L comprising the amino acid sequence of SEQ ID NO: 119.

In some embodiments, the antigen-binding protein specifically recognizing *Pseudomonas* Psl comprises: a V_H comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 62; and a V_L comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 76. In some embodiments, the antigen-binding protein specifically recognizing *Pseudomonas* Psl comprises a V_H comprising the amino acid sequence of SEQ ID NO: 109 and a V_L comprising the amino acid sequence of SEQ ID NO: 120. In some embodiments, the antigen-binding protein specifically recognizing *Pseudomonas* Psl comprises a V_H comprising an HC-CDR1, an HC-CDR2 and an HC-CDR3 of the V_H comprising the amino acid sequence of SEQ ID NO: 109; and a V_L comprising an LC-CDR1, an LC-CDR2, and an LC-CDR3 of the V_L comprising the amino acid sequence of SEQ ID NO: 120.

In some embodiments, the antigen-binding protein specifically recognizing *Pseudomonas* Psl comprises: a V_H comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 63; and a V_L comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 77. In some embodiments, the antigen-binding protein specifically recognizing *Pseudomonas* Psl comprises a V_H comprising the amino acid sequence of SEQ ID NO: 110 and a V_L comprising the amino acid sequence of SEQ ID NO: 121. In some embodiments, the antigen-binding protein specifically recognizing *Pseudomonas* Psl comprises a V_H comprising an HC-CDR1, an HC-CDR2 and an HC-CDR3 of the V_H comprising the amino acid sequence of SEQ ID NO: 110; and a V_L comprising an LC-CDR1, an LC-CDR2, and an LC-CDR3 of the V_L comprising the amino acid sequence of SEQ ID NO: 121.

In some embodiments, the antigen-binding protein specifically recognizing *Pseudomonas* Psl comprises: a V_H comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 63; and a V_L comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 78. In some embodiments, the antigen-binding protein specifically recognizing *Pseudomonas* Psl comprises a V_H comprising the amino acid sequence of SEQ ID NO: 110 and a V_L comprising the amino acid sequence of SEQ ID NO: 122. In some embodiments, the antigen-binding protein specifically recognizing *Pseudomonas* Psl comprises a V_H comprising an HC-CDR1, an HC-CDR2 and an HC-CDR3 of the V_H comprising the amino acid sequence of SEQ ID NO: 110; and a V_L comprising an LC-CDR1, an LC-CDR2, and an LC-CDR3 of the V_L comprising the amino acid sequence of SEQ ID NO: 122.

In some embodiments, the antigen-binding protein specifically recognizing *Pseudomonas* Psl comprises: a V_H comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 63; and a V_L comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 79. In some embodiments, the antigen-binding protein specifically recognizing *Pseudomonas* Psl comprises a V_H comprising the amino acid sequence of SEQ ID NO: 110 and a V_L comprising the amino acid sequence of SEQ ID NO: 123. In some embodiments, the antigen-binding protein specifically recognizing *Pseudomonas* Psl comprises a V_H comprising an HC-CDR1, an HC-CDR2 and an HC-CDR3 of the V_H comprising the amino acid sequence of SEQ ID NO: 110; and a V_L comprising an LC-CDR1, an LC-CDR2, and an LC-CDR3 of the V_L comprising the amino acid sequence of SEQ ID NO: 123.

In some embodiments, the antigen-binding protein specifically recognizing *Pseudomonas* Psl comprises: a V_H comprising an HC-CDR1 comprising the amino acid sequence of SEQ ID NO: 51, an HC-CDR2 comprising the amino acid sequence of SEQ ID NOs 56, and an HC-CDR3 comprising the amino acid sequence of SEQ ID NO: 64; and a $V_L$ comprising: an LC-CDR1 comprising the amino acid sequence of SEQ ID NO: 69, an LC-CDR2 comprising the amino acid sequence of SEQ ID NO: 73, and an LC-CDR3 comprising the amino acid sequence of SEQ ID NO: 80. In some embodiments, the antigen-binding protein specifically recognizing *Pseudomonas* Psl comprises a $V_H$ comprising the amino acid sequence of SEQ ID NO: 111 and a $V_L$ comprising the amino acid sequence of SEQ ID NO: 124. In some embodiments, the antigen-binding protein specifically recognizing *Pseudomonas* Psl comprises a $V_H$ comprising an HC-CDR1, an HC-CDR2 and an HC-CDR3 of the $V_H$ comprising the amino acid sequence of SEQ ID NO: 111; and a $V_L$ comprising an LC-CDR1, an LC-CDR2, and an LC-CDR3 of the $V_L$ comprising the amino acid sequence of SEQ ID NO: 124.

In some embodiments, wherein the method comprises administering a pharmaceutical composition comprising (i) an antigen-binding protein specifically recognizing *Pseudomonas* Psl and (ii) an antigen-binding protein specifically recognizing a first epitope on *Pseudomonas* PcrV and/or an antigen-binding protein specifically recognizing a second epitope on *Pseudomonas* PcrV, the ratio by molar mass of the antigen-binding protein specifically recognizing *Pseudomonas* Psl to the antigen-binding protein specifically recognizing the first epitope on *Pseudomonas* PcrV is about any one of: 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or 1:20. In some embodiments, the ratio by molar mass of the antigen-binding protein specifically recognizing *Pseudomonas* Psl to the antigen-binding protein specifically recognizing the first epitope on *Pseudomonas* PcrV is about any one of: 5:1, 4:1, 3:1, 2:1, 1:1, 1:2, 1:3, 1:4 or 1:5. In some embodiments, the ratio by molar mass of the antigen-binding protein specifically recognizing *Pseudomonas* Psl to the antigen-binding protein specifically recognizing the first epitope on *Pseudomonas* PcrV is about 2:1 or about 1:1.

In some embodiments, wherein the method comprises administering a pharmaceutical composition comprising (i) an antigen-binding protein specifically recognizing *Pseudomonas* Psl and (ii) an antigen-binding protein specifically recognizing a first epitope on *Pseudomonas* PcrV and/or an antigen-binding protein specifically recognizing a second epitope on *Pseudomonas* PcrV, the ratio by molar mass of the antigen-binding protein specifically recognizing *Pseudomonas* Psl to the antigen-binding protein specifically recognizing the second epitope on *Pseudomonas* PcrV is about any one of: 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or 1:20. In some embodiments, the ratio by molar mass of the antigen-binding protein specifically recognizing *Pseudomonas* Psl to the antigen-binding protein specifically recognizing the second epitope on *Pseudomonas* PcrV is about any one of: 5:1, 4:1, 3:1, 2:1, 1:1, 1:2, 1:3, 1:4 or 1:5. In some embodiments, the ratio by molar mass of the antigen-binding protein specifically recognizing *Pseudomonas* Psl to the antigen-binding protein specifically recognizing the second epitope on *Pseudomonas* PcrV is about 2:1 or about 1:1.

In some embodiments, wherein the method comprises administering a pharmaceutical composition comprising (i) an antigen-binding protein specifically recognizing a first epitope on *Pseudomonas* PcrV and (ii) an antigen-binding protein specifically recognizing a second epitope on *Pseudomonas* PcrV and/or an antigen-binding protein specifically recognizing *Pseudomonas* Psl, the ratio by molar mass of the antigen-binding protein specifically recognizing the first epitope on *Pseudomonas* PcrV to the antigen-binding protein specifically recognizing the second epitope on *Pseudomonas* PcrV is about any one of: 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or 1:20. In some embodiments, the ratio by molar mass of the antigen-binding protein specifically recognizing the first epitope on *Pseudomonas* PcrV to the antigen-binding protein specifically recognizing the second epitope on *Pseudomonas* PcrV is about any one of: 5:1, 4:1, 3:1, 2:1, 1:1, 1:2, 1:3, 1:4 or 1:5. In some embodiments, the ratio by molar mass of the antigen-binding protein specifically recognizing the first epitope on *Pseudomonas* PcrV to the antigen-binding protein specifically recognizing the second epitope on *Pseudomonas* PcrV is about 1:1 or 2:1.

In some embodiments, wherein the method comprises administering a pharmaceutical composition comprising (i) an antigen-binding protein specifically recognizing a first epitope on *Pseudomonas* PcrV and (ii) an antigen-binding protein specifically recognizing a second epitope on *Pseudomonas* PcrV and/or an antigen-binding protein specifically recognizing *Pseudomonas* Psl, the ratio by molar mass of the antigen-binding protein specifically recognizing the first epitope on *Pseudomonas* PcrV to the antigen-binding protein specifically recognizing the second epitope on *Pseudomonas* PcrV is about any one of: 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or 1:20. In some embodiments, the ratio by molar mass of the antigen-binding protein specifically recognizing the first epitope on *Pseudomonas* PcrV to the antigen-binding protein specifically recognizing the antigen-binding protein specifically recognizing *Pseudomonas* Psl is about any one of: 5:1, 4:1, 3:1, 2:1, 1:1, 1:2, 1:3, 1:4 or 1:5. In some embodiments, the ratio by molar mass of the antigen-binding protein specifically recognizing the first epitope on *Pseudomonas* PcrV to the antigen-binding protein specifically recognizing *Pseudomonas* Psl is about 1:1 or about 1:2.

In some embodiments, there is provided a pharmaceutical composition comprising an antigen-binding protein specifically recognizing a first epitope on *Pseudomonas* PcrV and an antigen-binding protein specifically recognizing *Pseudomonas* Psl, wherein the antigen-binding protein specifically recognizing the first epitope on *Pseudomonas* PcrV comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ Comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; and wherein the antigen-binding protein specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the ratio by molar mass of the antigen-binding protein specifically recognizing the first epitope on *Pseudomonas* PcrV to the antigen-binding protein specifically recognizing *Pseudomonas* Psl is about 1:1 or about 1:2.

In some embodiments, there is provided a method of treating a *Pseudomonas* infection in an individual, comprising administering an effective amount of a pharmaceutical composition comprising an antigen-binding protein specifically recognizing a first epitope on *Pseudomonas* PcrV and an antigen-binding protein specifically recognizing *Pseudomonas* PSL, wherein the antigen-binding protein specifically recognizing the first epitope on *Pseudomonas* PcrV comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; and wherein the antigen-binding protein specifically recognizing *Pseudomonas* Psl comprises: a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75. In some embodiments, the ratio by molar mass of the antigen-binding protein specifically recognizing the first epitope on *Pseudomonas* PcrV to the antigen-binding protein specifically recognizing *Pseudomonas* Psl is about 1:1 or about 1:2.

In some embodiments, there is provided a method of treating a *Pseudomonas* infection in an individual, comprising administering an effective amount of a pharmaceutical composition comprising an antigen-binding protein specifically recognizing a first epitope on *Pseudomonas* PcrV and an antigen-binding protein specifically recognizing *Pseudomonas* PSL, wherein the antigen-binding protein specifically recognizing the first epitope on *Pseudomonas* PcrV comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13; and wherein the antigen-binding protein specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the ratio by molar mass of the antigen-binding protein specifically recognizing the first epitope on *Pseudomonas* PcrV to the antigen-binding protein specifically recognizing *Pseudomonas* Psl is about 1:1 or about 1:2.

In some embodiments, there is provided a method of treating a *Pseudomonas* infection in an individual, comprising administering an effective amount of a pharmaceutical composition comprising an antigen-binding protein specifically recognizing a first epitope on *Pseudomonas* PcrV and an antigen-binding protein specifically recognizing *Pseudomonas* PSL, wherein the antigen-binding protein specifically recognizing the first epitope on *Pseudomonas* PcrV comprises: a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13; and wherein the antigen-binding protein specifically recognizing *Pseudomonas* Psl comprises: a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75. In some embodiments, the ratio by molar mass of the antigen-binding protein specifically recognizing the first epitope on *Pseudomonas* PcrV to the antigen-binding protein specifically recognizing *Pseudomonas* Psl is about 1:1 or about 1:2.

In some embodiments, there is provided a method of treating a *Pseudomonas* infection in an individual, comprising administering an effective amount of a pharmaceutical composition comprising an antigen-binding protein specifically recognizing a first epitope on *Pseudomonas* PcrV, an antigen-binding protein specifically recognizing a second epitope on *Pseudomonas* PcrV and an antigen-binding protein specifically recognizing *Pseudomonas* PSL, wherein the antigen-binding protein specifically recognizing the first epitope on *Pseudomonas* PcrV comprises: a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; wherein the antigen-binding protein specifically recognizing the second epitope on *Pseudomonas* PcrV comprises: a $V_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 27; and a $V_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36; and wherein the antigen-binding protein specifically recognizing *Pseudomonas* Psl comprises: a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74. In some embodiments, the ratio by molar mass of the antigen-binding protein specifically recognizing the first epitope on *Pseudomonas* PcrV, the antigen-binding protein specifically recognizing the second epitope on *Pseudomonas* PcrV and the antigen-binding protein specifically recognizing *Pseudomonas* Psl is about 1:1:1 or about 1:1:2.

In some embodiments, the method of treating or preventing a *Pseudomonas* infection in an individual, comprising administering an effective amount of a pharmaceutical composition comprising an antigen-binding protein specifically recognizing *Pseudomonas* PcrV and an antigen-binding protein specifically recognizing *Pseudomonas* Psl is more efficacious than administering a same molar mass amount of an antigen-binding protein specifically recognizing *Pseudomonas* PcrV or a same molar mass amount of an antigen-binding protein specifically recognizing *Pseudomonas* Psl. In some embodiments, the method comprising administering an effective amount of a pharmaceutical composition comprising an antigen-binding protein specifically recognizing *Pseudomonas* PcrV and an antigen-binding protein specifically recognizing *Pseudomonas* Psl enhances opsonophagocytic killing (OPK) of *P. aeruginosa* by about any one of 10%, 20%, 30%, 40%, 50%, 60%, 70%, 80%, 90%, 100%, 2-fold, 5-fold, 10-fold, 20-fold, 50-fold, or 100-fold more compared to administering a same molar mass amount of an antigen-binding protein specifically recognizing *Pseudomonas* PcrV or a same molar mass amount of an antigen-binding protein specifically recognizing *Pseudomonas* Psl. In some embodiments, the method comprising administering an effective amount of a pharmaceutical composition comprising an antigen-binding protein specifically recognizing *Pseudomonas* PcrV and an antigen-binding protein specifically recognizing *Pseudomonas* Psl disrupts the activity of the type III toxin secretion system by about any one of 10%, 20%, 30%, 40%, 50%, 60%, 70%, 80%, 90%, 100%, 2-fold, 5-fold, 10-fold, 20-fold, 50-fold, or 100-fold more compared to administering a same molar mass amount of an antigen-binding protein specifically recognizing *Pseudomonas* PcrV or a same molar mass amount of an antigen-binding protein specifically recognizing *Pseudomonas* PSL. In some embodiments, the method comprising administering an effective amount of a pharmaceutical composition comprising an antigen-binding protein specifically recognizing *Pseudomonas* PcrV and an antigen-binding protein specifically recognizing *Pseudomonas* Psl inhibits binding of *P. aeruginosa* to epithelial cells by about any one of 10%, 20%, 30%, 40%, 50%, 60%, 70%, 80%, 90%, 100%, 2-fold, 5-fold, 10-fold, 20-fold, 50-fold, or 100-fold more compared to administering a same molar mass amount of an antigen-binding protein specifically recognizing *Pseudomonas* PcrV or a same molar mass amount of an antigen-binding protein specifically recognizing *Pseudomonas* Psl. In some embodiments, the method comprising administering an effective amount of a pharmaceutical composition comprising an antigen-binding protein specifically recognizing *Pseudomonas* PcrV and an antigen-binding protein specifically recognizing *Pseudomonas* Psl inhibits red blood cell lysis by *P. aeruginosa* by about any one of 10%, 20%, 30%, 40%, 50%, 60%, 70%, 80%, 90%, 100%, 2-fold, 5-fold, 10-fold, 20-fold, 50-fold, or 100-fold more compared to administering a same molar mass amount of an antigen-binding protein specifically recognizing *Pseudomonas* PcrV or a same molar mass amount of an antigen-binding protein specifically recognizing *Pseudomonas* Psl. In some embodiments, the method comprising administering an antigen-binding protein specifically recognizing *Pseudomonas* PcrV and an antigen-binding protein specifically recognizing *Pseudomonas* Psl improves patient survival by about any one of 10%, 20%, 30%, 40%, 50%, 60%, 70%, 80%, 90%, 100%, 2-fold, 5-fold, 10-fold, 20-fold, 50-fold, or 100-fold more compared to administering a same molar mass amount of an antigen-binding protein specifically recognizing *Pseudomonas* PcrV or a same molar mass amount of an antigen-binding protein specifically recognizing *Pseudomonas* Psl.

Articles of Manufacture and Kits

In some embodiments of the application, there is provided an article of manufacture containing materials useful for treating or preventing a *Pseudomonas* infection in an individual, or for delivering a bispecific molecule (such as a bispecific antibody recognizing PcrV and Psl) or a pharmaceutical composition comprising antigen-binding proteins specifically recognizing one or more epitopes on PcrV and antigen-binding proteins specifically recognizing one or more epitopes on Psl, to a cell attached by a pathogen expressing PcrV and Psl. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein, and may have a sterile access port (for example the container may be an intravenous solution bag or a vial having a stopper pierceable by a hypodermic injection needle). In some embodiments, at least one active agent in the composition is a bispecific molecule or an antigen-binding protein of the application. The label or package insert indicates that the composition is used for treating the particular condition. The label or package insert will further comprise instructions for administering the bispecific molecule or the pharmaceutical composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating bacterial infections. In some embodiments, the package insert indicates that the composition is used for treating *Pseudomonas* infections.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., useful for treating or preventing a *Pseudomonas* infection in an individual, or for delivering an anti-PcrV antibody, anti-Psl antibody, or bispecific antibody specifically recognizing *Pseudomonas* PcrV and Psl (such as a full-length anti-PcrV antibody, anti-Psl antibody, or bispecific antibody specifically recognizing *Pseudomonas* PcrV and Psl) to a cell attached by a pathogen expressing PcrV or Psl, optionally in combination with the articles of manufacture. Kits of the application include one or more containers comprising anti-PcrV antibody, anti-Psl antibody, or bispecific antibody specifically recognizing *Pseudomonas* PcrV and Psl composition (or unit dosage form and/or article of manufacture), and in some embodiments, further comprise another agent (such as the agents described herein) and/or instructions for use in accordance with any of the methods described herein. The kit may further comprise a description of selection of individuals suitable for treatment. Instructions supplied in the kits of the application are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising an anti-PcrV antibody, anti-Psl antibody, or bispecific antibody specifically recognizing *Pseudomonas* PcrV and Psl (such as a full-length anti-PcrV antibody, anti-Psl antibody, or bispecific antibody specifically recognizing *Pseudomonas* PcrV and Psl). In some embodiments, the kit comprises a) a composition comprising any one of the anti-PcrV antibodies, anti-Psl antibodies, or bispecific antibodies specifically recognizing *Pseudomonas* PcrV and Psl described herein, and b) an effective amount of at least one other agent, wherein the other agent enhances the effect (e.g., treatment effect, detecting effect) of the anti-PcrV antibody, anti-Psl antibody, or bispecific antibody specifically recognizing *Pseudomonas* PcrV and Psl. In some embodiments, the kit comprises a) a composition comprising any one of the anti-PcrV antibodies, anti-Psl antibodies, or bispecific antibody specifically recognizing *Pseudomonas* PcrV and Psl described herein, and b) instructions for administering the anti-PcrV antibody, anti-Psl antibody, or bispecific antibody specifically recognizing *Pseudomonas* PcrV and Psl composition to an individual for treating a *Pseudomonas* infection in an individual. In some embodiments, the kit comprises a) a composition comprising any one of the anti-PcrV antibodies, anti-Psl antibodies, or bispecific antibodies specifically recognizing *Pseudomonas* PcrV and Psl described herein, b) an effective amount of at least one other agent, wherein the other agent enhances the effect (e.g., treatment effect, detecting effect) of the anti-PcrV antibody, anti-Psl antibody, or bispecific antibody specifically recognizing *Pseudomonas* PcrV and Psl, and c) instructions for administering the anti-PcrV antibody, anti-Psl antibody, or bispecific antibody specifically recognizing *Pseudomonas* PcrV and Psl composition and the other agent(s) to an individual for useful for treating a *Pseudomonas* infection in an individual. The anti-PcrV antibody, anti-Psl antibody, or bispecific antibody specifically recognizing *Pseudomonas* PcrV and Psl and the other agent(s) can be present in separate containers or in a single container. For example, the kit may comprise one distinct composition or two or more compositions wherein one composition comprises an anti-PcrV antibody, anti-Psl antibody, or bispecific antibody specifically recognizing *Pseudomonas* PcrV and Psl and another composition comprises another agent.

In some embodiments, the kit comprises a nucleic acid (or set of nucleic acids) encoding an anti-PcrV antibody, anti-Psl antibody, or bispecific antibody specifically recognizing *Pseudomonas* PcrV and Psl (such as a full-length anti-PcrV antibody, anti-Psl antibody, or bispecific antibody specifically recognizing *Pseudomonas* PcrV and PSL). In some embodiments, the kit comprises a) a nucleic acid (or set of nucleic acids) encoding an anti-PcrV antibody, anti-Psl antibody, or bispecific antibody specifically recognizing *Pseudomonas* PcrV and Psl, and b) a host cell for expressing the nucleic acid (or set of nucleic acids). In some embodiments, the kit comprises a) a nucleic acid (or set of nucleic acids) encoding an anti-PcrV antibody, anti-Psl antibody, or bispecific antibody specifically recognizing *Pseudomonas* PcrV and Psl and b) instructions for i) expressing the anti-PcrV antibody, anti-Psl antibody, or bispecific antibody specifically recognizing *Pseudomonas* PcrV and Psl in a host cell, ii) preparing a composition comprising the anti-PcrV antibody, anti-Psl antibody, or bispecific antibody specifically recognizing *Pseudomonas* PcrV and Psl, and iii) administering the composition comprising the anti-PcrV antibody, anti-Psl antibody, or bispecific antibody specifically recognizing *Pseudomonas* PcrV and Psl to an individual for treating or preventing a *Pseudomonas* infection in an individual. In some embodiments, the kit comprises a) a nucleic acid (or set of nucleic acids) encoding an anti-PcrV antibody, anti-Psl antibody, or bispecific antibody specifically recognizing *Pseudomonas* PcrV and Psl, b) a host cell for expressing the nucleic acid (or set of nucleic acids), and c) instructions for i) expressing the anti-PcrV antibody, anti-Psl antibody, or bispecific antibody specifically recognizing *Pseudomonas* PcrV and Psl in the host cell, ii) preparing a composition comprising the anti-PcrV antibody, anti-Psl antibody, or bispecific antibody specifically recognizing *Pseudomonas* PcrV and Psl and iii) administering the composition comprising the anti-PcrV antibody, anti-Psl antibody, or bispecific antibody specifically recognizing *Pseudomonas* PcrV and Psl to an individual for treating or preventing a *Pseudomonas* infection in an individual.

The kits of the application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the anti-PcrV antibody, anti-Psl antibody, or bispecific antibody specifically recognizing *Pseudomonas* PcrV and Psl compositions generally include information as to dosage, dosing schedule, and route of administration for the intended treatment. The containers may be unit doses, bulk packages (e.g., multidose packages) or sub-unit doses. For example, kits may be provided that contain sufficient dosages of an anti-PcrV antibody, anti-Psl antibody, or bispecific antibody specifically recognizing *Pseudomonas* PcrV and Psl (such as a full-length anti-PcrV antibody, anti-Psl antibody, or bispecific antibody specifically recognizing *Pseudomonas* PcrV and Psl) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the anti-PcrV antibody, anti-Psl antibody, or bispecific antibody specifically recognizing *Pseudomonas* PcrV and Psl and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of this application. The application will now be described in greater detail by reference to the following non-limiting examples. The following examples further illustrate the application but, of course, should not be construed as in any way limiting its scope.

EXAMPLES

*P. aeruginosa* strains 06-57/66 (CNCTC 57/66), and PAO1(05) (CNCTC PAO1) were used in the following experiments.

Example 1: Treatment of *P. aeruginosa* Infection Using Combination of Anti-PcrV Antibodies that Bind to Non-Overlapping Epitopes The ability of combination of anti-PcrV antibodies which bind to non-overlapping epitopes in neutralizing *P. aerugi-*

141                                                            142

*nosa* infection prophylactically was demonstrated with survival improvement in a mouse intraperitoneal infection model. PA49 lead antibody (and the optimized antibodies 6G12, 9C7) bind to non-overlapping epitopes compared to 13-42 lead antibody (and the optimized antibodies 7B1, 7C1) (data not shown). Survival improvement in mouse intraperitoneal infection model with combinations of anti-PcrV antibodies that bind to non-overlapping epitopes.

The ability of the combination of anti-PcrV antibodies 7C1 and 6G12, which bind to non-overlapping epitopes, to improve survival in mouse intraperitoneal infection model was evaluated in comparison to treatment with 7C1 or 6G12 alone. An HIV neutralizing antibody 10E8 (Huang J, et al., Broad and potent neutralization of HIV-1 by a gp41-specific human antibody. *Nature.* 2012 Nov. 15; 491(7424):406-12) was used as a negative control, herein named HIV-10E8.

In a prophylactic model, 7-8 weeks old BALB/c mice (Vital River Laboratory) were intraperitoneally injected with 7C1, 6G12, or a combination thereof 24 hrs before infection. Specifically, in a high antibody dose setting, the mice were administered with either anti-PcrV antibody clone 7C1 (at 5 mg/kg), anti-PcrV antibody clone 6G12 (at 5 mg/kg), or a combination of 7C1 and 6G12 (at 2.5 mg/kg each and 5 mg/kg total). In a low antibody dose setting, the mice were administered with either 7C1 (at 2.5 mg/kg), 6G12 (at 2.5 mg/kg), or a combination of 7C1 and 6G12 (at 1.25 mg/kg each and 2.5 mg/kg total). To induce intraperitoneal infection, the BALB/c mice were intraperitoneally inoculated with *P. aeruginosa* (06-57/66 strain) suspended in a 300 µl inoculum at double the lethal dose ($2 \times LD90=5 \times 10^5$ CFU). Mouse survival was recorded for up to 7 days post-infection.

Figure 1B:
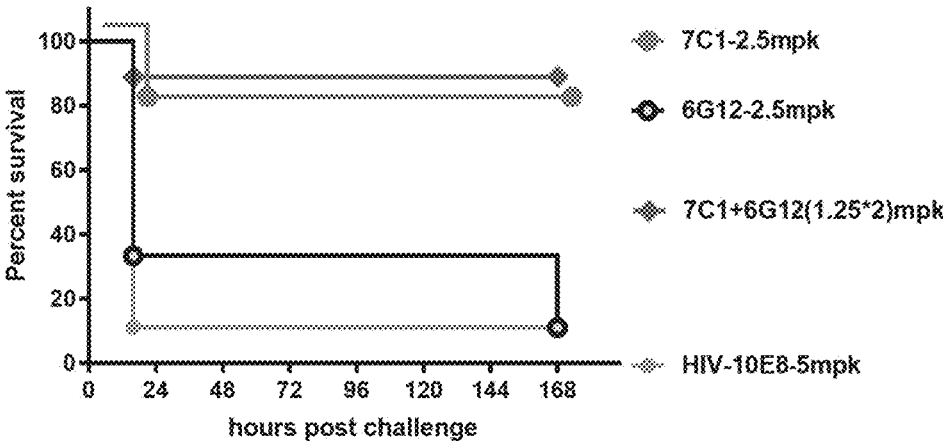

As shown in FIG. 1A, at the high antibody dose setting (5 mg/kg total), the combination of 7C1 and 6G12 (at 2.5 mg/kg each) exhibited higher survival improvement compared to 7C1 alone (at 5 mg/kg), and statistically higher survival improvement compared to 6G12 alone (at 5 mg/kg) ($p<0.005$). As shown in FIG. 1B, at the lower antibody dose setting (2.5 mg/kg total), the combination of 7C1 and 6G12 (at 1.25 mg/kg each) exhibited higher survival improvement compared to 7C1 alone (at 2.5 mg/kg), and statistically higher survival improvement compared to 6G12 alone (at 2.5 mg/kg) ($p<0.005$). These results here show that the combination of anti-PcrV antibodies provides better effect than a particular anti-PcrV antibody alone and demonstrate the clinical potential of using combinations of anti-PcrV antibodies binding to non-overlapping epitopes disclosed herein in neutralizing *P. aeruginosa*.

Example 2: Treatment of *P. aeruginosa* Infection Using Combination of Anti-PcrV Antibodies and Anti-Psl Antibodies The ability of combination of anti-PcrV and anti-Psl antibodies in neutralizing *P. aeruginosa* infection prophylactically was demonstrated with survival improvement in a mouse intraperitoneal infection model.
Survival Improvement in Mouse Intraperitoneal Infection Model with Anti-PcrV Antibodies, Anti-Psl Antibodies, or Combination Thereof The ability of the combination of anti-PcrV antibody 7C1 and anti-Psl antibody P59 to improve survival in mouse intraperitoneal infection model was evaluated in comparison to treatment with 7C1 or P59 alone. The results were also compared to reference anti-PcrV antibody V2L2-MD, or anti-Psl antibody Cam003, and the combination thereof. The ability of the combination of anti-PcrV antibody 7B1 and anti-Psl antibody P59 to improve survival in mouse intraperitoneal infection model was compared to the combination of reference anti-PcrV antibody V2L2-MD and anti-Psl antibody Ps10096. HIV-10E8 was used as negative control.

Figure 2A:
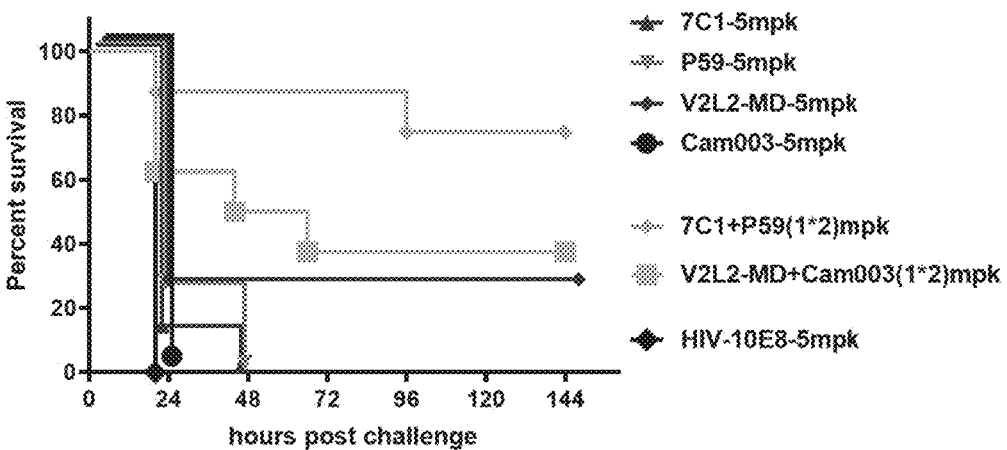
FIG. 2A shows the ability of the combination of anti-PcrV antibody (7C1) and anti-Psl antibody (P59) to improve survival in a mouse intraperitoneal infection model at 4 times the lethal dose (4×LD90) of *P. aeruginosa* inoculation compared to the anti-PcrV or anti-Psl alone.
Figure 2B:
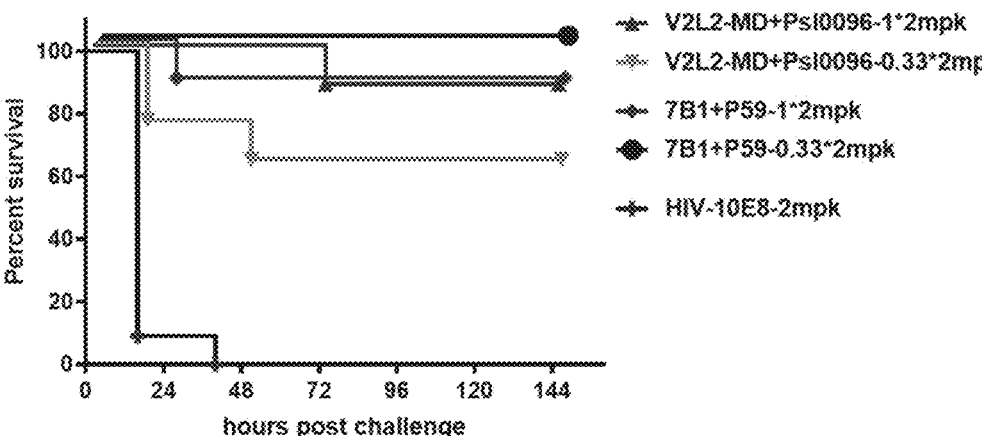
FIG. 2B shows the ability of the combination of anti-PcrV antibody (7B1) and anti-Psl antibody (P59) to improve survival in a mouse intraperitoneal infection model at 4 times the lethal dose (4×LD90) of *P. aeruginosa* inoculation compared to reference anti-PcrV antibody V2L2-MD and reference anti-Psl antibody Cam-003.

In a prophylactic model, 7-8 weeks old BALB/c mice (Vital River Laboratory) were intraperitoneally injected with anti-PSL, anti-PcrV, or a combination thereof 24 h before infection. Specifically, for one test group, the mice were administered with either anti-PcrV antibody 7C1 (at 5 mg/kg), anti-Psl antibody P59 (at 5 mg/kg), or a combination of 7C1 and P59 (at 1 mg/kg each and 2 mg/kg total). For the corresponding reference group, the mice were administered with either anti-PcrV antibody V2L2-MD (at 5 mg/kg), anti-Psl antibody Cam003 (at 5 mg/kg), or a combination of V2L2-MD and Cam003 (at 1 mg/kg each and 2 mg/kg total) (FIG. 2A). For a separate test group, in a high antibody dose setting, the mice were administered with a combination of 7B1 and P59 (at 1 mg/kg each and 2 mg/kg total); for the corresponding reference group, the mice were administered with a combination of V2L2-MD and Ps10096 (at 1 mg/kg each and 2 mg/kg total). In a low antibody dose setting, the mice were administered with a combination of 7B1 and P59 (at 0.33 mg/kg each and 0.66 mg/kg total); for the corresponding reference groups, the mice were administered with or a combination of V2L2-MD and Ps10096 (at 0.33 mg/kg each and 0.66 mg/kg total) (FIG. 2B). To induce intraperitoneal infection, the BALB/c mice were intraperitoneally inoculated with *P. aeruginosa* (06-57/66 strain) suspended in a 300 µl inoculum at quadruple the lethal dose ($4 \times LD90=9 \times 10^5$ CFU). Mouse survival was recorded for up to 7 days post-infection.

As shown in FIG. 2A, a lower total dose of the combination of 7C1 and P59 (at 2 mg/kg total) exhibited statistically higher survival improvement compared to 7C1 alone (at 5 mg/kg), or P59 alone (at 5 mg/kg) ($p<0.001$). In addition, the combination of 7C1 and P59 (at 2 mg/kg total) also exhibited higher survival improvement compared to reference anti-PcrV antibody V2L2-MD (at 5 mg/kg), reference anti-Psl antibody Cam-003 (at 5 mg/kg), or the combination of V2L2-MD and Cam-003 (at 2 mg/kg total). As shown in FIG. 2B, at both the high or low antibody dose setting, the combination of 7B1 and P59 exhibited comparable or higher survival improvement compared to combination of reference anti-PcrV antibody V2L2-MD and anti-PSL antibody Ps10096, and exhibited higher survival improvement that is statistically significant compared to negative control HIV-10E8 ($p<0.005$). These results here show that the combination disclosed herein can achieve better survival protection even at a lower dose as compared to the reference antibody combination and demonstrate the clinical potential of using the combination of anti-PcrV antibodies and anti-Psl antibodies disclosed herein in neutralizing *P. aeruginosa*.

Example 3: Treatment of *P. aeruginosa* Infection Using Combination of Anti-PcrV Antibodies and Anti-Psl Antibodies in a Mouse Bacteremia Model The ability of the combination of anti-PcrV antibodies and anti-Psl in neutralizing *P. aeruginosa* infection prophylactically was demonstrated with survival improvement in a mouse bacteremia model. The mouse bacteremia model caused by intravenous infection was generated as described previously (See Ajitha Thanabalasuriar et. al, Bispecific antibody targets multiple *Pseudomonas aeruginosa* evasion mechanisms in the lung vasculature, J Clin Invest. 2017; 127(6):2249-2261).

Survival Improvement in Mouse Bacteremia Model with Combinations of Anti-PcrV Antibodies and Anti-Psl Antibodies The ability of the 2 combinations of anti-PcrV antibody 7B1 and anti-Psl antibody P59 or 3F12 to improve survival in the mouse bacteremia model was evaluated in comparison to the combination of reference anti-PcrV and anti-Psl antibodies. HIV-10E8 was used as negative control.

In a prophylactic model, 7-8 weeks old BALB/c mice (Vital River Laboratory) were intraperitoneally injected with a combination of anti-PcrV antibody 7B1 and anti-Psl antibody P59, a combination of anti-PcrV antibody 7B1 and anti-Psl antibody 3F12, or a combination of reference anti-PcrV antibody V2L2-MD and anti-Psl antibody Ps10096 24 h before infection. BALB/c mice were intravenously inoculated with *P. aeruginosa* (06-57/66 strain), which represents the highly virulent cytotoxic *P. aeruginosa* serotype associated with clinical disease at double the lethal dose ($2\times LD90=5\times10^5$ CFU). Mice survival were recorded for up to 7 days post-infection.

Figure 3:
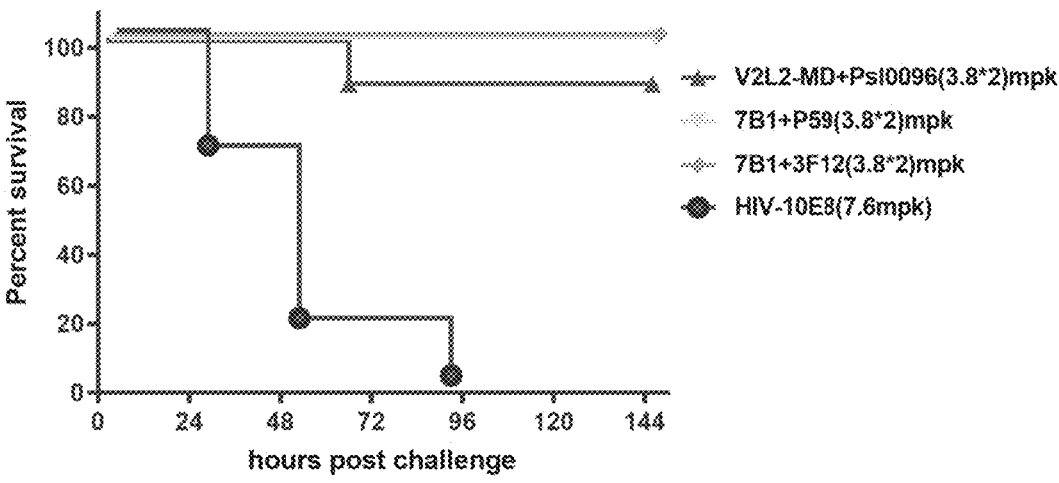
FIG. 3 shows the ability of the combination of anti-PcrV antibody (7B1) and anti-Psl antibody (P59, 3F12) to improve survival in a mouse bacteremia model at double the lethal dose (2×LD90) of *P. aeruginosa* inoculation compared to combination of reference anti-PcrV antibody V2L2-MD and reference anti-Psl antibody Ps10096.

As shown in FIG. 3, all mice administered with either test combination of anti-PcrV and anti-Psl antibodies (7B1+P59, 7B1+3F12) survived, which exhibited better survival improvement when compared to the combination of reference antibodies V2L2-MD and Ps10096, and exhibited higher survival improvement that is statistically significant compared to negative control HIV-10E8 (p<0.005). These results here demonstrate the clinical potential of using combination of anti-PcrV antibodies and anti-Psl antibodies disclosed herein in neutralizing *P. aeruginosa*.

Example 4: Treatment of *P. aeruginosa* Infection Using Combination of Anti-PcrV Antibodies and Anti-Psl Antibodies at Different Antibody Ratios The efficacy of combination of anti-PcrV antibodies and anti-Psl at different ratios in neutralizing *P. aeruginosa* infection prophylactically was examined with survival improvement in a mouse intraperitoneal infection model. Survival Improvement in Mouse Intraperitoneal Infection Model with Combinations of Anti-PcrV Antibodies and Anti-Psl Antibodies The ability of the combination of anti-PcrV antibody 7B1 and anti-Psl antibody P59 or 6G7 to improve survival in mouse intraperitoneal infection model at different ratios was further examined at various ratios of 7B1: P59 or 7B1: 6G7. HIV-10E8 was used as a negative control.

In a prophylactic model, 7-8 weeks old BALB/c mice (Vital River Laboratory) were intraperitoneally injected with a combination of anti-Psl and anti-PcrV at different test ratios 24 h before infection. In the first test group, the mice were administered with a combination of 7B1 and P59 (0.67 mg/kg total), wherein the ratio of 7B1 to P59 was 4:1, 3:1, 2:1, 1:1, 1:2, 1:3, or 1:4. Control mice were administered with either 7B1 alone (0.67 mg/kg total) or P59 alone (0.67 mg/kg total). To induce intraperitoneal infection, the BALB/c mice were intraperitoneally inoculated with *P. aeruginosa* (06-57/66 strain) suspended in a 300 μl inoculum at four times the lethal dose ($4\times LD90=9\times10^5$ CFU). In the second test group, the mice were administered with a combination of 7B1 and 6G7 (2 mg/kg total) wherein the ratio of 7B1 to 6G7 was 5:1, 3:1, 1:1, 1:3, or 1:5. A higher dose *P. aeruginosa* infection was used to elucidate the efficacy at different antibody ratios. To induce intraperitoneal infection, the BALB/c mice were intraperitoneally inoculated with *P. aeruginosa* (06-57/66 strain) suspended in a 300 μl inoculum at six times the lethal dose ($6\times LD90=1.2\times10^6$ CFU). Mouse survival was recorded for up to 7 days post-infection.

Figure 4A:
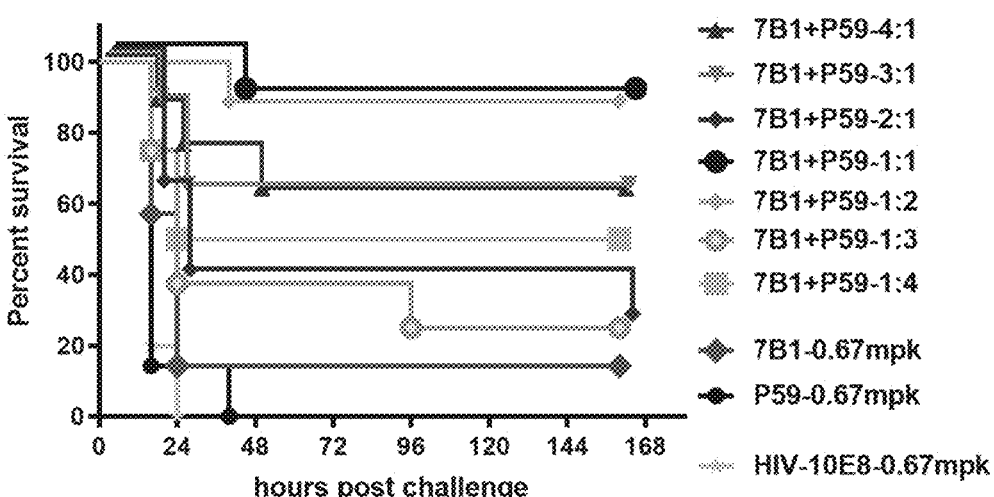
FIGS. 4A and 4B show the ability of the combination of anti-PcrV antibody (7B1) and anti-Psl antibody (P59 or 6G7), at different ratios, to improve survival in a mouse intraperitoneal infection model at 4 or 6 times the lethal dose (4 or 6×LD90) of *P. aeruginosa* inoculation.
Figure 4B:
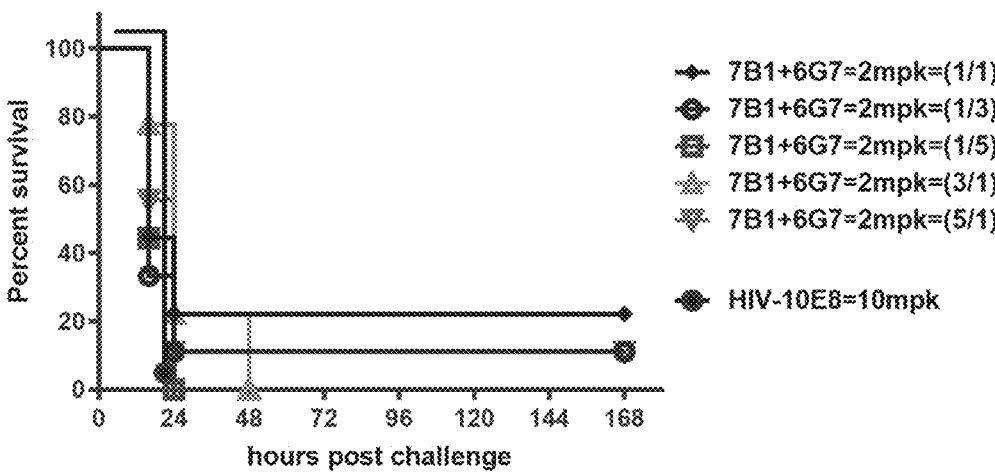

As shown in FIG. 4A, at four times the lethal dose ($4\times LD90=9\times10^5$ CFU), the combination of 7B1 and P59 at 1:1 or 1:2 anti-PcrV to anti-Psl ratio exhibited the highest survival improvement out of the 5 test ratios; and exhibited, with statistical significance, higher survival improvement compared to equivalent amount of either 7B1 alone or P59 alone (p<0.005). As shown in FIG. 4B, at six times the lethal dose ($6\times LD90=1.2\times10^6$ CFU), most of the mice expired within 48 hours. The combination of 7B1 and 6G7 at 1:1 ratio exhibited the highest survival improvement out of the 5 test ratios, and exhibited higher survival improvement compared to negative control HIV-10E8, which is statistically significant (p<0.005). These results here demonstrate the combination of anti-PcrV antibodies and anti-Psl antibodies disclosed herein neutralized *P. aeruginosa* more efficaciously than either antibody alone, and showed higher efficacies at an (anti-PcrV to anti-Psl) ratio of 1:1 or 1:2.

Example 5: Treatment of *P. aeruginosa* Infection Using Combination of Anti-PcrV Antibodies Binding Non-Overlapping Epitopes and Anti-Psl Antibodies The ability of combination of two anti-PcrV antibodies that bind non-overlapping epitopes and an anti-Psl antibody in neutralizing *P. aeruginosa* infection prophylactically was demonstrated with survival improvement in a mouse intraperitoneal infection model. Survival improvement in mouse intraperitoneal infection model with combinations of anti-PcrV antibodies that bind to non-overlapping epitopes and anti-Psl antibodies The ability of the combination of anti-PcrV antibodies 7C1 and 6G12, or the combination of anti-PcrV antibodies 7B1 and 9C7, which bind to non-overlapping epitopes and anti-Psl antibody P59 to improve survival in mouse intraperitoneal infection model was evaluated in comparison to treatment with the combination of 7C1 and P59 or the combination of 7B1 and P59, respectively. HIV-10E8 was used as negative control.

In a prophylactic model, 7-8 weeks old BALB/c mice (Vital River Laboratory) were intraperitoneally injected with an equalized or half the total amount of antibody combination 7C1+P59+6G12 compared to antibody combination 7C1+P59 24 h before infection. In the first test group, the mice were administered with either the combination of 7C1 and P59 (at 1 mg/kg each and 2 mg/kg total) or the combination of 7C1, P59 and 6G12 (at 0.67 mg/kg each and 2 mg/kg total; or at 0.33 mg/kg each and 1 mg/kg total). To induce intraperitoneal infection, the BALB/c mice were intraperitoneally inoculated with *P. aeruginosa* (06-57/66 strain) suspended in a 300 μl inoculum at four the lethal dose ($4\times LD90=9\times10^5$ CFU). Mouse survival was recorded for up to 7 days post-infection. In the second test group, the mice were administered with either the combination of 7B1 and P59 (at 1 mg/kg each and 2 mg/kg total; at 0.2 mg/kg each and 0.4 mg/kg total; or at 0.04 mg/kg each and 0.08 mg/kg total) or the combination of 7B1, P59 and 9C7 (at 0.67 mg/kg each and 2 mg/kg total; at 0.133 mg/kg each and 0.4 mg/kg total; or at 0.027 mg/kg each and 0.08 mg/kg total). To induce intraperitoneal infection, the BALB/c mice were intraperitoneally inoculated with *P. aeruginosa* (06-57/66 strain) suspended in a 300 μl inoculum at five times the lethal dose ($5\times LD90=1\times10^6$ CFU). Mouse survival was recorded for up to 7 days post-infection.

Figure 5A:
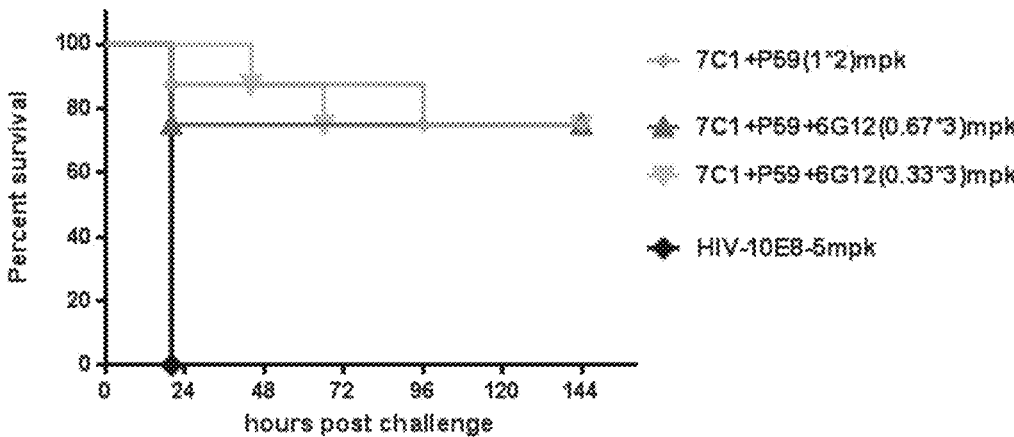
FIGS. 5A and 5B show the ability of the combination of anti-PcrV antibodies (7C1, 7B1, 6G12, or 9C7) and anti-Psl antibody (P59), at the indicated antibody doses, to improve survival in a mouse intraperitoneal infection model at 4 or 5 times the lethal dose (4 or 5×LD90) of *P. aeruginosa* inoculation.
Figure 5B:
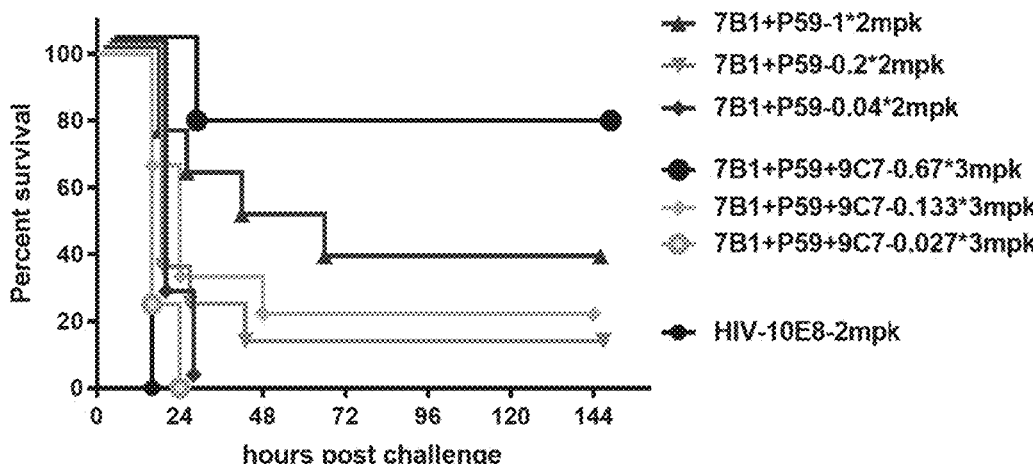

As shown in FIG. 5A, even at half the total antibody amount, the combination of 7C1+P59+6G12 exhibited comparable survival improvement compared to the combination of 7C1+P59. As shown in FIG. 5B, at both the 2 mg/kg and 0.4 mg/kg total antibody dose setting, the combination of 7B1+P59+9C7 exhibited higher survival improvement compared to the combination of 7B1+P59. These results here demonstrate the clinical potential of using combination of two anti-PcrV antibodies that bind non-overlapping epitopes and an anti-Psl antibody described herein in neutralizing *P. aeruginosa*.

Example 6: Generation and Characterization of Bispecific Antibodies Recognizing PcrV and Psl The structure of an exemplary anti-PcrV/Psl bispecific antibody is demonstrated in FIG. 6. In this exemplary anti-PcrV/anti-Psl bispecific antibody, the chimeric heavy chain comprises the heavy chain of an anti-PcrV antibody, wherein a Psl scFv is inserted at the hinge region between CH1 and CH2 domains, giving rise to a chimeric heavy chain with the sequence of $V_H$-CH1-upper hinge/linker-scFv ($V_H$-linker-$V_L$)-linker/lower hinge-CH2-CH3. In addition, two cysteines were introduced into the scFv sequence by substitution ($V_H$-Cys44 and $V_L$—Cys100, positions were relative to the scFv $V_H$ or $V_L$ sequence) to facilitate the formation of disulfide bond to stabilize the scFv structure.

The light chain of the exemplary anti-PcrV/anti-Psl bispecific antibody comprises the light chain of the anti-PcrV antibody.

The various parts of the chimeric heavy chain were joined together using overlap PCR extension techniques.

Example 7: Characterization of In Vitro Activity of Bispecific Antibodies Recognizing PcrV and Psl The ability of the anti-PcrV/Psl bispecific antibody in inhibiting PcrV function was determined by the ability to inhibit lysis of red blood cells (RBCs) and cytotoxicity to human bronchoepithelial cell line A549 cells, whereas the ability of the bispecific antibody in inhibiting Psl function was determined by the ability to promote opsonophagocytic killing (OPK) of *Pseudomonas aeruginosa* and the ability to inhibit the attachment of *Pseudomonas aeruginosa* to epithelial cells.

Analysis of Activity Against PcrV as Determined by RBC Lysis Inhibition

Bispecific antibodies STS7B159255 (comprising the Fab of anti-PcrV antibody 7B1 and the scFv of anti-Psl antibody P5925), STS7B159215 (comprising the Fab of anti-PcrV antibody 7B1 and the scFV of anti-Psl antibody P5921), STS7B112015 (comprising the Fab of anti-PcrV antibody 7B1 and the scFv of anti-Psl antibody 3F1201), STS7B15923S (comprising the Fab of anti-PcrV antibody 7B1 and the scFv of anti-Psl antibody P5923), and STS7B159S (comprising the Fab of anti-PcrV antibody 7B1 and the scFv of anti-Psl antibody P59) were assessed for biological activity in inhibiting PcrV by RBC lysis assay. Briefly, red blood cells (RBCs) were prepared from fresh whole human or rabbit blood by centrifugation, supplemented with EDTA and rinsed with multiple phosphate-buffered saline (PBS) washes. Washed RBCs (2.5% [vol/vol] final) were resuspended in Dulbecco's modified Eagle's medium (DMEM) plus 10% fetal bovine serum (FBS) (Gibco) and combined with either the test bispecific antibodies, the reference bispecific antibody MedI3902, or the reference antibody V2L2-MD in wells of a round-bottom 96-well plate. Strain 57/66(O6) *P. aeruginosa* was grown to mid-log phase in 2×YT medium (Oxford), harvested by centrifugation, and resuspended in DMEM-fetal bovine serum (FBS) at an optical density at 600 nm (OD600) of 0.15. 10 microliters of bacterial suspension was added to the RBC-antibody mixture, mixed by agitation, and incubated for 3 hours at 37° C. and 5% CO2. The plates were briefly centrifuged (1000 rpm, 1 min) to pellet the intact RBCs, the supernatants transferred to a flat-bottom 96-well plate, and the OD405 was measured to detect any lysis, from which the relative amount of RBC lysis inhibition was calculated and plotted. The OD405 value of the well with the reference antibody V2L2-MD with saturated protection dose was designated as 100% inhibition, and that without adding any bispecific antibody was designated as 0% inhibition. $IC_{50}$ values for the antibodies were also determined.

Figures 7A, 7B:
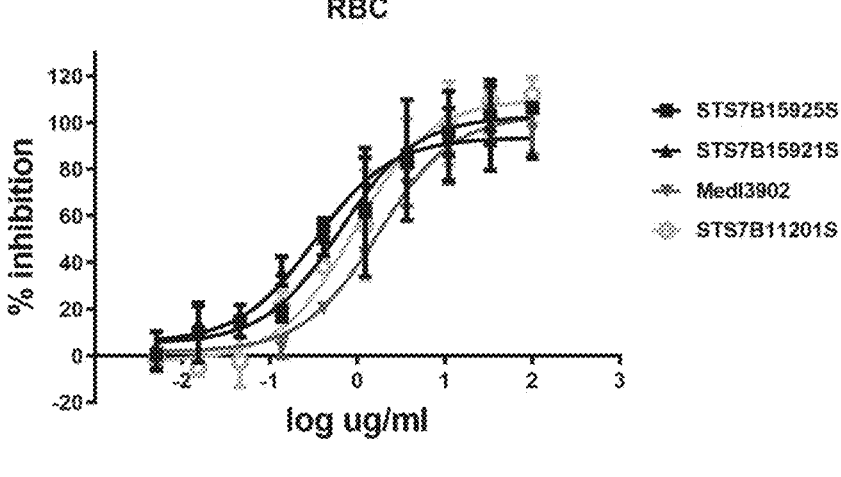
FIGS. 7A and 7B show the ability of anti-PcrV/anti-Psl bispecific antibodies in inhibiting RBC lysis by *P. aeruginosa* compared to reference bispecific antibody MedI3902.

As shown in FIGS. 7A and 7B, the inhibition on RBC lysis by bispecific antibodies STS7B15925S, STS7B15921S, STS7B112015, STS7B15923S, or STS7B159S was comparable to that of MedI3902, indicating that the optimized bispecific antibodies have comparable ability to inhibit PcrV as a reference bispecific antibody.

Analysis of Activity Against PcrV as Determined by A549 CTX Assay

To assay for ability to inhibit cytotoxicity (CTX) and cell lysis caused by *P. aeruginosa*, bispecific antibodies STS7B159255, STS7B159215, STS7B112015, STS7B15923S, STS7B159S, the reference bispecific antibody MedI3902, or the reference antibody V2L2-MD was added to human bronchoepithelial cell line A549 seeded in white 96-well plates (Nunc Nunclon Delta) in DMEM plus 10% fetal bovine serum. Log-phase strain PA103(011) *P. aeruginosa* was added at a multiplicity of infection (MOI) of 10 and incubated for 2 h at 37° C. and 5% CO2, followed by 20 minutes of equilibration at room temperature. Lactate dehydrogenase (LDH) released from lysed cells was quantified using the CytoTox-ONE kit (Promega), to assay membrane integrity, according to the manufacture's protocol. The fluorescence of the well with the reference antibody V2L2-MD with saturated protection dose was designated as 100% inhibition, and that without adding any bispecific antibody was designated as 0% inhibition, from which the relative amount of CTX inhibition was calculated and plotted. $IC_{50}$ values for the antibodies were also determined.

Figure 7C:
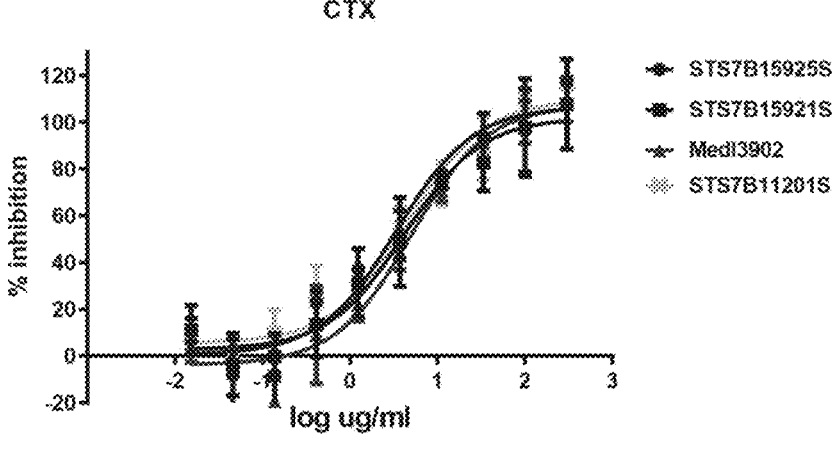
FIGS. 7C and 7D show the ability of anti-PcrV/anti-Psl bispecific antibodies in inhibiting A549 cell lysis by *P. aeruginosa* compared to reference bispecific antibody MedI3902.
Figure 7D:
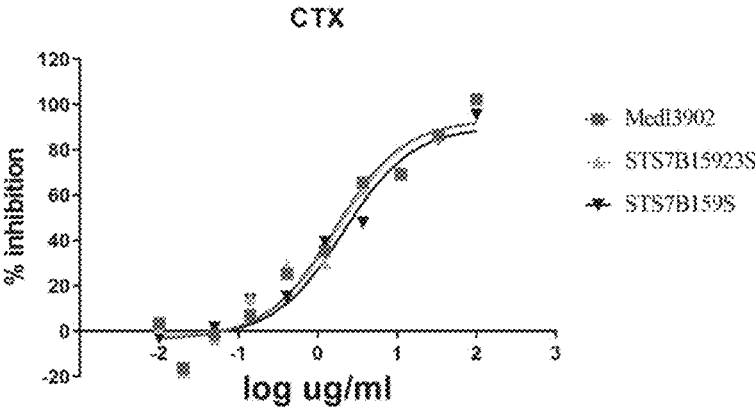

As shown in FIGS. 7C and 7D, the inhibition on A549 cell lysis by bispecific antibodies STS7B15925S, STS7B15921S, STS7B11201S, STS7B15923S, or STS7B159S was comparable to that of MedI3902, indicating that the bispecific antibodies have comparable ability to inhibit PcrV as a reference bispecific antibody.

Analysis of Activity Against Psl as Determined by Inhibition of Attachment of *P. aeruginosa* to A549 Cells The luminescent *P. aeruginosa* PAO1(05)-LUX was constructed by a PTN 7 transposon system as described in (Choi K H, et al. mini-Tn7 insertion in bacteria with single attTn7 sites: example *Pseudomonas aeruginosa*[J]. Nature Protocols, 2006, 1(1):153-161). The activity of the bispecific antibody in blocking *P. aeruginosa* attachment to A549 cells was determined by detecting the signal value of the luminescent *P. aeruginosa*. Bispecific antibodies STS7B159255, STS7B159215, STS7B112015, STS7B159235, STS7B1595, the reference bispecific antibody MedI3902, or the reference antibody Ps10096 was added to a confluent monolayer of A549 cells (an adenocarcinoma human alveolar basal epithelial cell line) seeded in white 96-well plates (Nunc Nunclon Delta) in DMEM plus 10% fetal bovine serum. Log-phase luminescent *P. aeruginosa* PAO1(05)-

LUX was then added to the cells at a multiplicity of infection (MOI) of 10 and incubated for 1 h at 37° C. and 5% CO2. Subsequently, the A549 cells were washed with PBS to remove the un-attached bacteria, followed by addition of 2YT culture medium. The amount of attached PAO1(05)-LUX was quantified following a brief incubation at 37° C., via luminescence readings. Specifically, the 96-well plate was tested in the self-luminous module, the luminescence of the well with the reference antibody Ps10096 with saturated protection dose was designated as 100% inhibition, and that without adding any bispecific antibody was designated as 0% inhibition, from which the relative amount of attachment inhibition was calculated and plotted. IC50 values for the antibodies were calculated using GraphPad Prism version6, 4 parameter method.

Figure 7E:
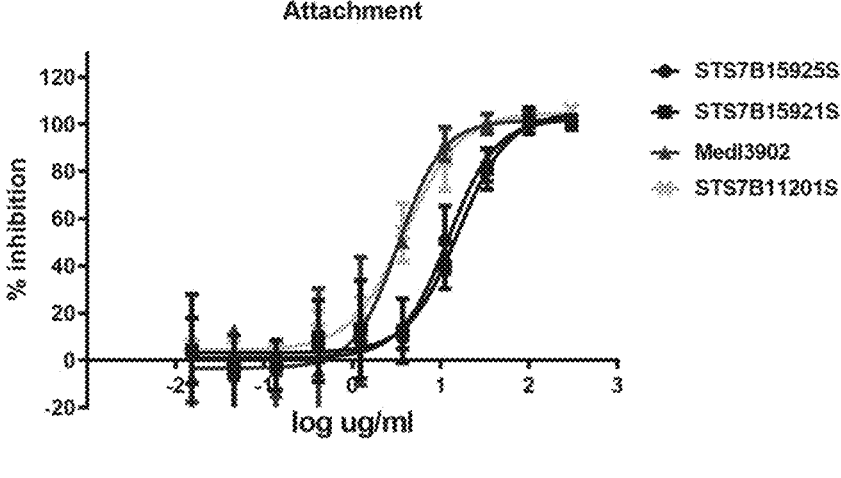
FIGS. 7E and 7F show the ability of anti-PcrV/anti-Psl bispecific antibodies in blocking attachment of *P. aeruginosa* compared to reference bispecific antibody MedI3902.
Figure 7F:
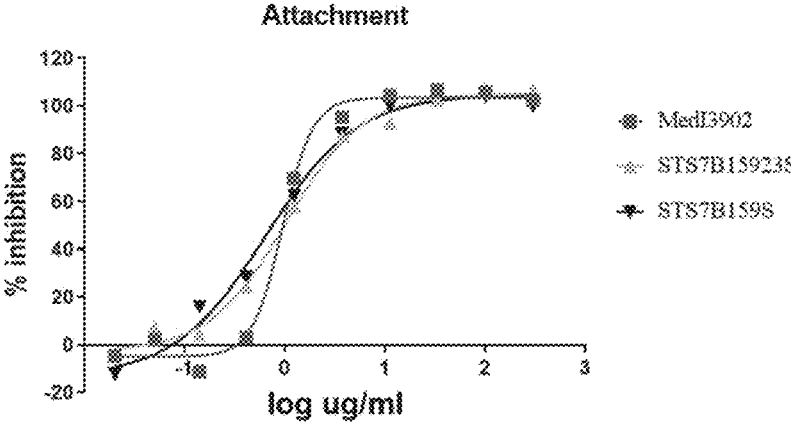

As shown in FIGS. 7E and 7F, the attachment inhibited by bispecific antibodies STS7B15925S, STS7B15921S, STS7B11201S, STS7B15923S, or STS7B1595 was comparable to that of MedI3902, indicating that the optimized bispecific antibodies have comparable ability to inhibit Psl as a reference bispecific antibody.

Analysis of Activity Against Psl as Determined by Opsonophagocytic Killing (OPK)

The luminescent *P. aeruginosa* PAO1(05)-LUX was constructed by a PTN 7 transposon system. The activity of bispecific antibodies STS7B15925S, STS7B15921S, STS7B11201S, STS7B15923S, or STS7B159S in mediating OPK was determined by detecting the signal value of the luminescent *P. aeruginosa*. OPK assays were performed as described in (DiGiandomenico, A., et al., *InfectImmun* 72, 7012-7021(2004)). Briefly, assays were performed in 96-well plates, with 25 µL/well of each diluted complement and differentiated HL-60 cells, infected with log-phase luminescent *P. aeruginosa* PAO1(05)-LUX, and treated 10 µL/well diluted bispecific antibodies. Specially, baby rabbit serum as a complement source (Creative Diagnostics) was diluted by culture medium to 10% concentration, the bispecific antibodies, the reference bispecific antibody MedI3902, or the reference antibody Ps10096 was subjected to a 3-fold ratio dilution into the culture medium, wherein log-phase luminescent *P. aeruginosa* PAO1(05)-LUX was added at a multiplicity of infection (MOI) of 0.1. The amount of PAO1(05)-LUX was quantified following a 4 hours incubation at 37° C. and 5% CO2 via luminescence values. The luminescence of the well with the reference antibody Ps10096 with saturated protection dose was designated as 100% killing, and that without adding any bispecific antibody was designated as 0% killing, from which the relative killing was calculated and plotted. $IC_{50}$ values for the antibodies were also calculated using GraphPad Prism version 6, 4-parameter method.

Figure 7G:
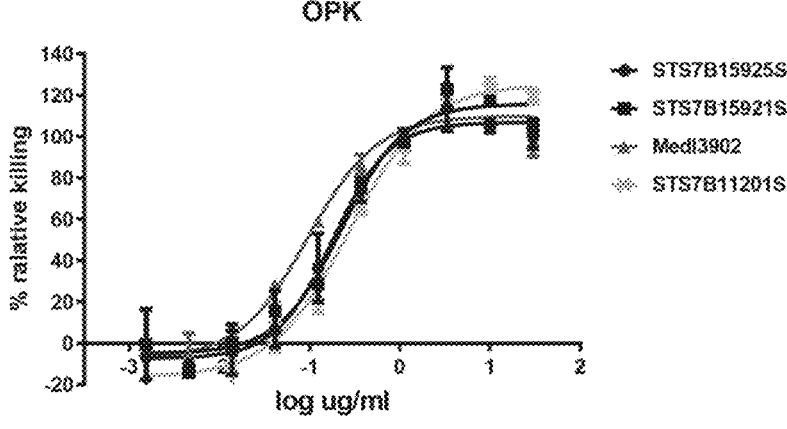
FIGS. 7G and 7H show the ability of anti-PcrV/anti-Psl bispecific antibodies in promoting OPK of *P. aeruginosa* compared to reference bispecific antibody MedI3902.
Figure 7H:
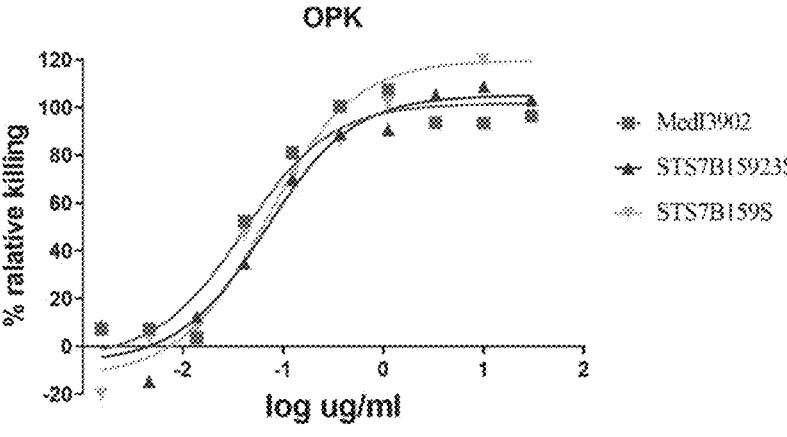

As shown in FIGS. 7G and 7H, the OPK mediated by optimized bispecific antibodies STS7B15925S, STS7B15921S, STS7B11201S, STS7B15923S, or STS7B159S was comparable to that of MedI3902, indicating that the optimized bispecific antibodies have comparable ability to inhibit Psl as a reference bispecific antibody.

Example 8: Characterization of PcrV and Psl Binding for Bispecific Antibodies

STS7B15925, STS7B1H9 and STS7B112 were further optimized by introducing variants in the $V_H$, $V_L$, and/or Fc, giving rise to STS7B15925M, STS7B15921M, STS7B1H9M, STS7B1H924M, STS7B112M, and STS7B11201M. For the ELISA experiment, synthetic PcrV or PAO1 was used to coat the wells of a 96-well plate. On the following day, after washing with PBST, blocking with 200 µL PBS-milk for an hour, and another wash with PBST, the respective antibodies were added and incubated for an hour at 37° C. The plate was washed with 0.1% TBST 6 times before 100 µL of Goat-anti-human Fc antibody-AP (1:3000 in PBS) was added to each well and incubated for an hour. After washing with 0.1% TBST for 6 times, 50 µL of pNPP (p-nitrophenyl phosphate) was added to each well and color was developed for $10^{-20}$ minutes at 37 C. Subsequently, the colorimetric signals were read by a microplate reader at 410 nm. The ELISA results (OD410) were analyzed and the EC50 values were calculated.

Figure 8A:
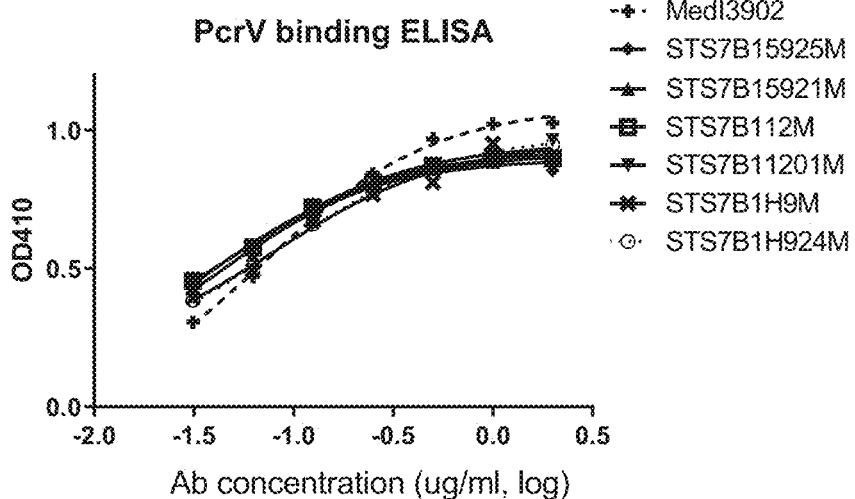
FIGS. 8A and 8B show the binding kinetics of various anti-PcrV/anti-Psl bispecific antibodies to PcrV and PAO1, respectively, compared to reference bispecific antibody MedI3902.
Figure 8B:
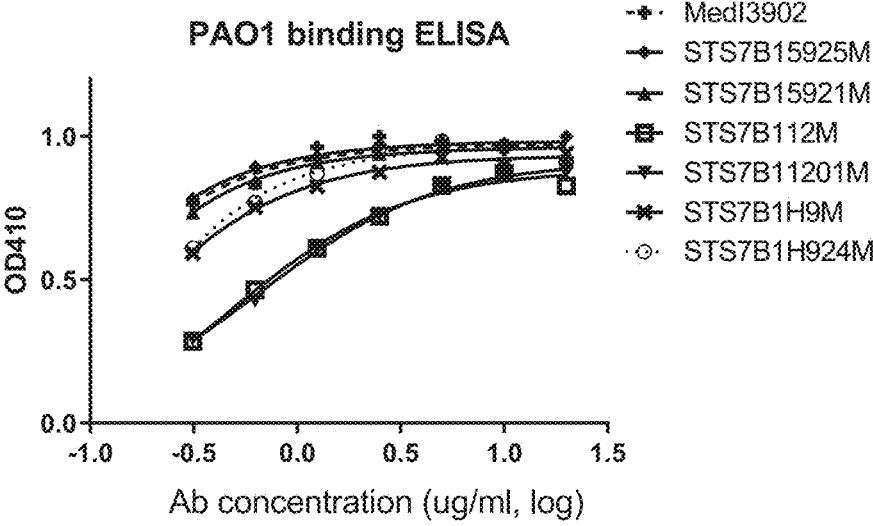

As shown in FIG. 8A, all of the tested bispecific antibodies (STS7B15925M, STS7B15921M, STS7B1H9M, STS7B1H924M, STS7B112M, and STS7B11201M) exhibited similar binding kinetics to PcrV. As shown in FIG. 8B, all the tested bispecific antibodies exhibited PAO1 binding.

Concurrent Binding of BsAb to Psl and PcrV (BLI)

Figure 8C:
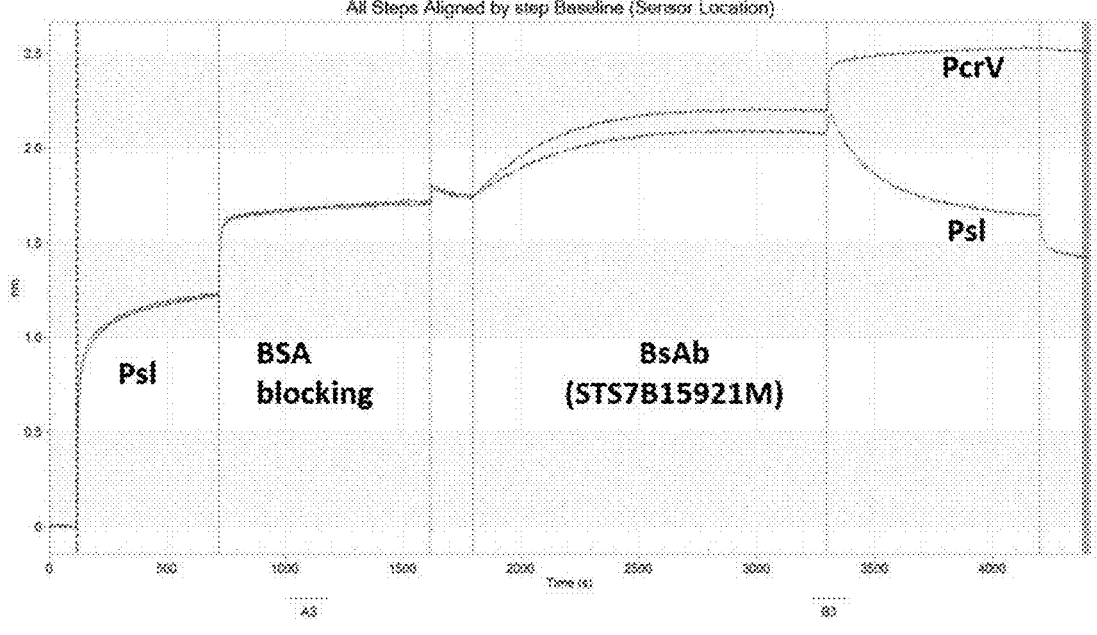
FIG. 8C shows a BIACORE analysis illustrating that anti-PcrV/anti-Psl antibody STS7B15921M can concurrently bind to Psl and PcrV.

The ability of the bispecific antibodies to concurrently bind Psl and PcrV was characterized using BioLayer Interferometry (BLI). Specifically, APS biosensors were first coated with Psl and blocked with PBS buffer containing 1% BSA for about 5 minutes. The bispecific antibody, was diluted with the PBS buffer to a concentration of 2 µg/mL, and loaded into the reaction wells. Either PcrV or Psl (as a control) was diluted with the PBS buffer to a concentration of 2 µg/mL and added to the reaction wells. Stable binding between the bispecific antibody and Psl or PcrV was monitored. The result of an exemplary antibody STS7B15921M was shown in FIG. 8C. The increase in binding upon the combination of Psl to STS7B15921M and the further increase in binding upon the subsequent addition of PcrV indicate that Psl-binding did not affect the ability of the bispecific antibody to bind PcrV. Therefore, the exemplary bispecific antibody (STS7B15921M) is able to concurrently bind Psl and PcrV. Other bispecific antibodies also exhibited ability to concurrently bind Psl and PcrV (data not shown).

Characterization of PcrV Binding for Optimized Bispecific Antibodies by Biacore

Binding affinity (Kd) of selected bispecific antibodies with respect to PcrV at 25° C. was determined using a real-time biosensor surface plasmon resonance assay (BIA-CORE™ T200). Briefly, the antibody was first captured on a CM5 chip to form an antibody surface. Serial dilutions of PcrV protein were injected over the antibody surface. Binding of antigen to antibody and dissociation of the bound complex were monitored in real time. Equilibrium dissociation constants (Kd) and dissociation rate constants were ascertained by performing kinetic analysis using BIA evaluation software.

As shown in Table 8, the Kon, Koff, and Kd of the bispecific antibody STS7B112015, STS7B1595 with regards to PcrV are comparable to that of 7B1, indicating the bispecific antibody format does not exhibit altered binding to PcrV as compared to that of monospecific antibody 7B1.

TABLE 8

| | | | | | | |
|---|---|---|---|---|---|---|
| Association and dissociation kinetics of anti-PcrV/Psl bispecific antibody compared with monospecific anti-PcrV antibody | | | | | | |
| Antibody | Kon (1/Ms) | Koff (1/s) | Kd (M) | Rmax (RU) | Chi$^2$ (RU$^2$) | U-value |
| STS7B11201S | 1.703E+5 | 4.516E−5 | 2.652E−10 | 59.24 | 0.128 | 2 |
| STS7B159S | 1.742E+5 | 3.127E−5 | 1.795E−10 | 49.50 | 0.349 | 7 |
| 7B1 | 1.439E+5 | 4.819E−5 | 3.349E−10 | 59.34 | 0.442 | 4 |

Characterization of Psl Binding for Optimized Bispecific Antibodies by ELISA

For the ELISA experiment, PAO1 was used to coat the wells of a 96-well plate, and incubated overnight at 4° C. On the following day, after washing with PBST, blocking with 200 μL PBS-milk for an hour, and another wash with PBST, the respective antibodies (bispecific antibodies STS7B112015, STS7B1595; anti-Psl antibodies P59, 3F1201; reference bispecific antibody MedI3902; reference anti-Psl antibody Ps10096) were added and incubated for an hour at 37° C. The plate was washed with 0.1% TBST 6 times before 100 μL of Goat-anti-human Fc antibody-AP (1:3000 in PBS) was added to each well and incubated for an hour. After washing with 0.1% TBST for 6 times, 50 μL of pNPP (p-nitrophenyl phosphate) was added to each well and color was developed for 10$^{-20}$ minutes at 37° C. before terminating the reaction with 3M NaOH. Subsequently, the colorimetric signals were read by a microplate reader at 410 nm. The ELISA results (OD410) were analyzed and the EC50 values were calculated.

Figure 8D:
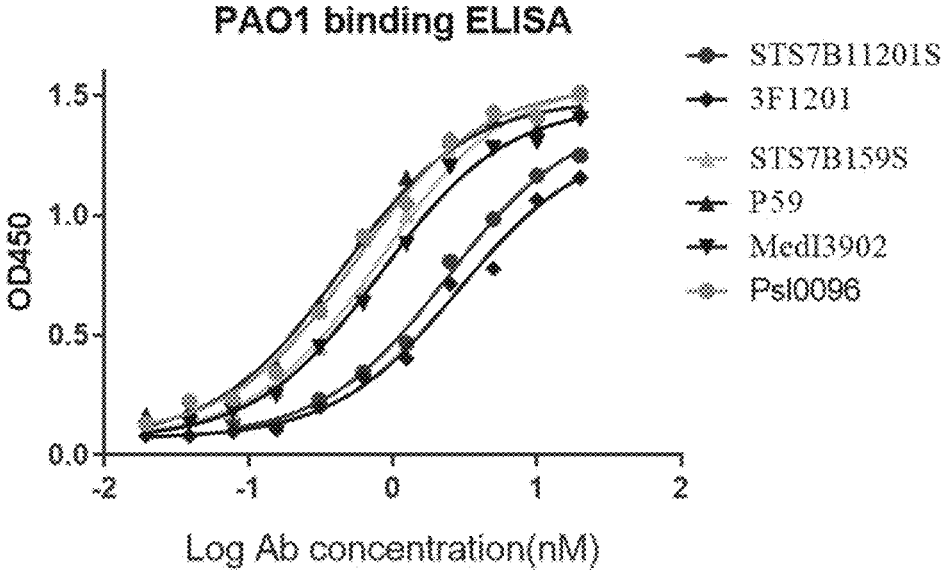
FIG. 8D shows the binding kinetics of anti-PcrV/anti-Psl bispecific antibodies (STS7B11201S, STS7B159S, reference MedI3902) compared to monospecific anti-Psl antibodies (3F1201, P59, Reference Ps10096).

As shown in FIG. 8D, the PAO1-binding kinetics of the bispecific antibodies STS7B11201S, STS7B159S are similar to that of monospecific anti-Psl antibodies and comparable to reference bispecific antibody MedI3902.

Characterization of Non-Specificity of the Bispecific Antibodies

The non-specific binding of the optimized bispecific antibodies was characterized by measuring cross-reactivity to BV particles and to PcrV/Psl-negative 293 cells.

Figure 8E:
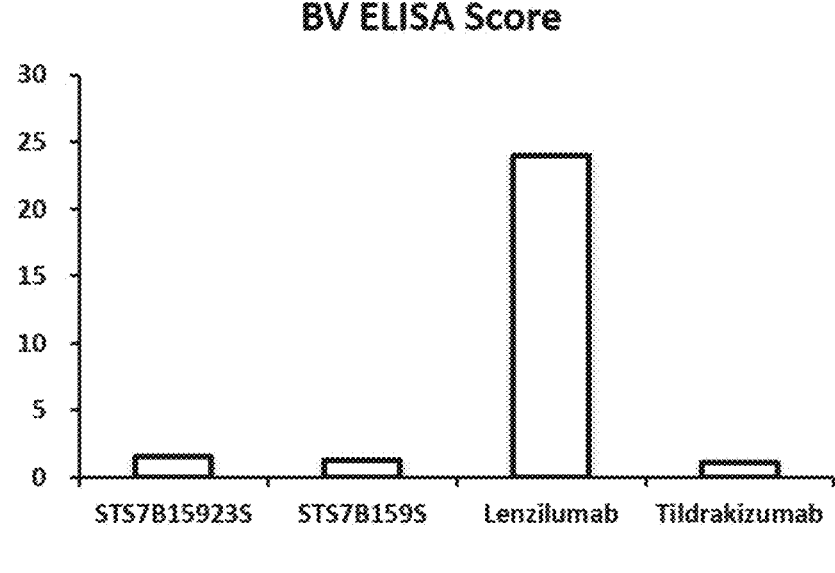
FIG. 8E shows the non-specificity of anti-PcrV/anti-Psl bispecific antibodies (STS7B15923S, STS7B159S) to BV particle.

Cross-reactivity to BVparticles: Using ELISA, bispecific antibodies STS7B15923S and STS7B159S were tested for cross-reactivity to BV particles according to the method described previously (See Hötzel I, et al, 2012, mAbs 4:6, 753-760). Lenzilumab was used as positive control, and Tildrakizumab was used as negative control. BV ELISA Score was the ratio of the OD value of the assay with the antibody tested to the OD value of the assay without adding the antibody. As shown in FIG. 8E, the positive control displayed a high level of binding to BV particles. In contrast, bispecific antibodies STS7B159235 and STS7B1595 displayed low levels of binding, similar to the negative control.

Figure 8F:
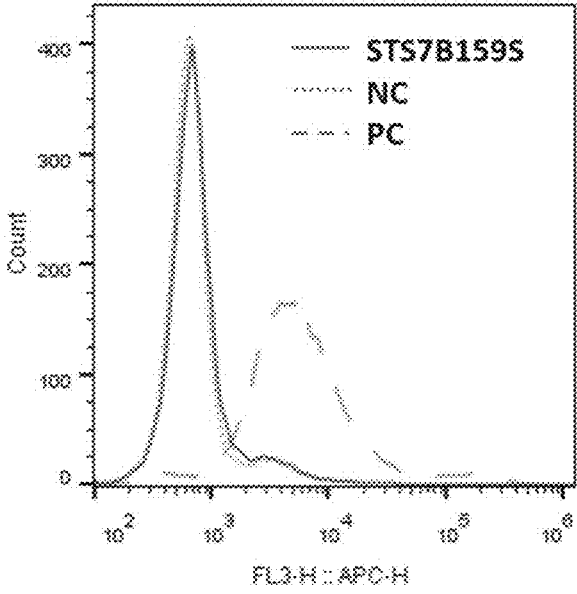
FIG. 8F shows the non-specificity of anti-PcrV/anti-Psl bispecific antibodies (STS7B15923S, STS7B159S) to PcrV- and Psl-negative 293 cells.
Figure 8G:
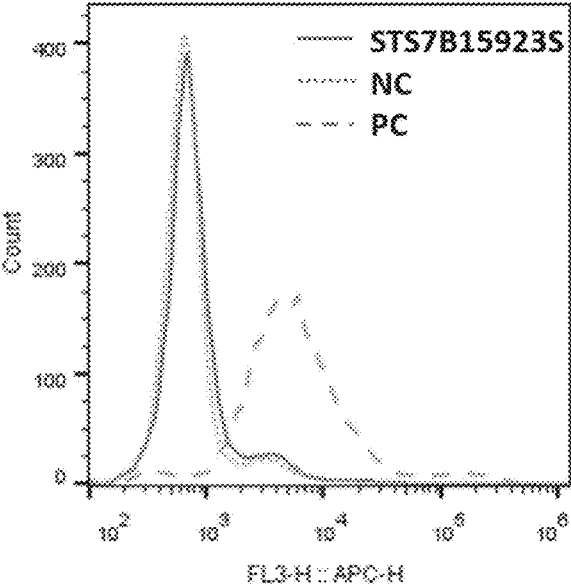

Cross-reactivity to 293 cells: Using FACS, bispecific antibodies STS7B159S and STS7B159235 were tested for cross-reactivity to PcrV- and PSL-negative 293 cells. Anti-NPHS2 was used as positive control (PC), null antibody was used as negative control (NC). As shown in FIG. 8F-8G, the positive control Anti-NPHS2 displayed a high level of binding to 293 cells, the bispecific antibodies STS7B1595 and STS7B159235 displayed similarly low levels of 293 cell binding as negative control (null antibody).

Taken together, these results indicated that bispecific antibodies STS7B159S and STS7B159235 displayed low non-specific binding.

Example 9: Characterization of In Vivo Activity of Bispecific Antibodies Recognizing PcrV and Psl The ability of the optimized bispecific antibodies to improve survival in a mouse intraperitoneal infection model was evaluated in comparison to treatment with reference bispecific antibody MedI3902.

Survival Improvement in Mouse Intraperitoneal Infection Model

The ability of the optimized bispecific antibody STS7B159255, STS7B159215, STS7B112015, STS7B159235, or STS7B1595 was evaluated in comparison to MedI3902. HIV-10E8 was used as negative control.

In a prophylactic model, 7-8 weeks old BALB/c mice (Vital River Laboratory) were intraperitoneally injected with bispecific antibody STS7B159255, STS7B159215, STS7B112015, STS7B159235, or STS7B1595 24 h before infection and evaluated in comparison to MedI3902. Specifically, in a medium antibody dose setting, the mice were administered with STS7B15925S, STS7B15921S, STS7B11201S or MedI3902 (at either 6 mg/kg, 2 mg/kg or 0.667 mg/kg antibody dose). To induce intraperitoneal infection, the BALB/c mice were intraperitoneally inoculated with *P. aeruginosa* (06-57/66 strain) suspended in a 300 μl inoculum at four times the lethal dose (4×LD90=9×10$^5$ CFU). Mouse survival was recorded for up to 7 days post-infection. Results were shown in FIG. 9A.

In high antibody dose test groups, the mice were administered with STS7B159S, STS7B15923S, STS7B11201S or MedI3902 (at either 60 mg/kg, 20 mg/kg, 6 mg/kg, or 2 mg/kg antibody dose). To induce intraperitoneal infection, the BALB/c mice were intraperitoneally inoculated with *P. aeruginosa* (06-57/66 strain) suspended in a 300 μl inoculum at four times the lethal dose (4×LD90=9×10$^5$ CFU). Mouse survival was recorded for up to 7 days post-infection. Results were shown in FIG. 9B.

Figure 9A:
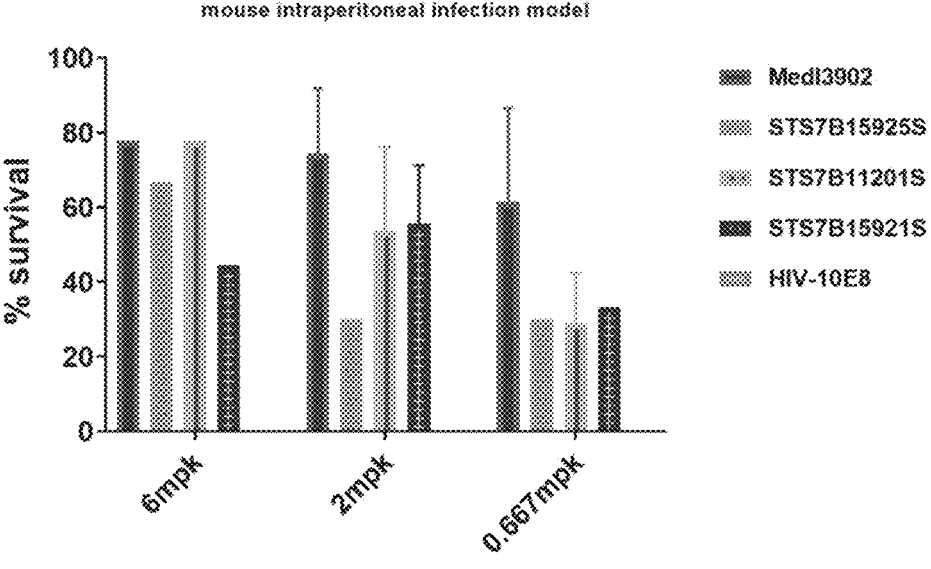
FIGS. 9A and 9B show the ability of various anti-PcrV/anti-Psl bispecific antibodies, at the indicated antibody doses, to improve survival in a mouse intraperitoneal infection of *P. aeruginosa* compared to reference bispecific antibody MedI3902.
Figure 9B:
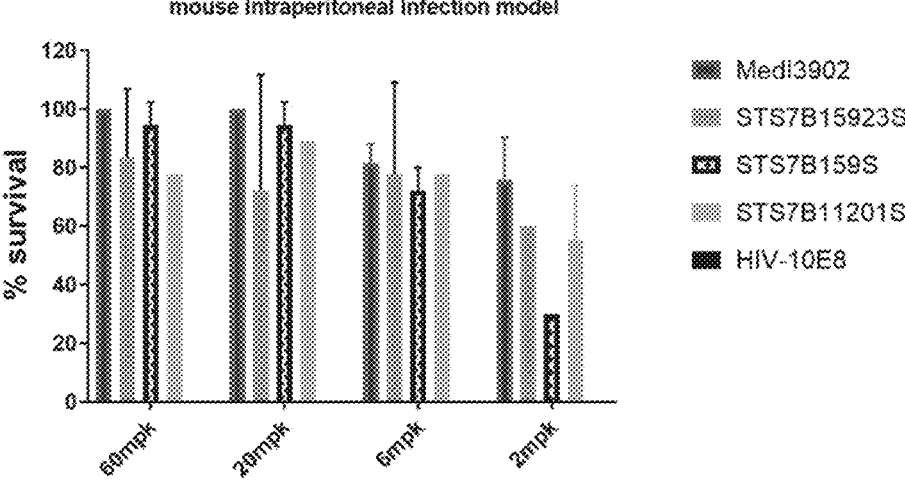

As shown in FIG. 9A and FIG. 9B, at different antibody doses, STS7B159255, STSB15921S, STS7B112015, STS7B159235, and STS7B159S exhibited similar survival improvement compared to the reference bispecific antibody MedI3902 without statistical significance, and exhibited higher survival improvement compared to HIV-10E8 with statistical significance (p<0.005). These results here demonstrate the clinical potential of using bispecific antibodies recognizing PcrV and Psl disclosed herein in neutralizing *P. aeruginosa.*

Survival Improvement in Mouse Intraperitoneal Infection Model

The ability of the bispecific antibodies STS7B15925 (comprising the Fab of anti-PcrV antibody 7B1 and the scFV of anti-Psl antibody P5925), STS7B1H9 (comprising the Fab of anti-PcrV antibody 7B1 and the scFV of anti-Psl antibody 7H9), STS7B112 (comprising the Fab of anti-PcrV antibody 7B1 and the scFV of anti-Psl antibody 3F12) to improve survival in mouse intraperitoneal infection model was evaluated in comparison to reference bispecific antibody MedI3902. HIV-10E8 was used as negative control.

In a prophylactic model, 7-8 weeks old BALB/c mice (Vital River Laboratory) were intraperitoneally injected with either STS7B15925, STS7B1H9, STS7B112 or MedI3902 24 h before infection. Specifically, the mice were administered with STS7B15925, STS7B1H9, STS7B112 or MedI3902 (at 0.44 mg/kg or 0.147 mg/kg). To induce intraperitoneal infection, the BALB/c mice were intraperitoneally inoculated with *P. aeruginosa* (06-57/66 strain) suspended in a 300 μl inoculum at six times the lethal dose ($6 \times LD90 = 1.2 \times 10^6$ CFU). Mouse survival was recorded for up to 7 days post-infection.

Figure 9C:
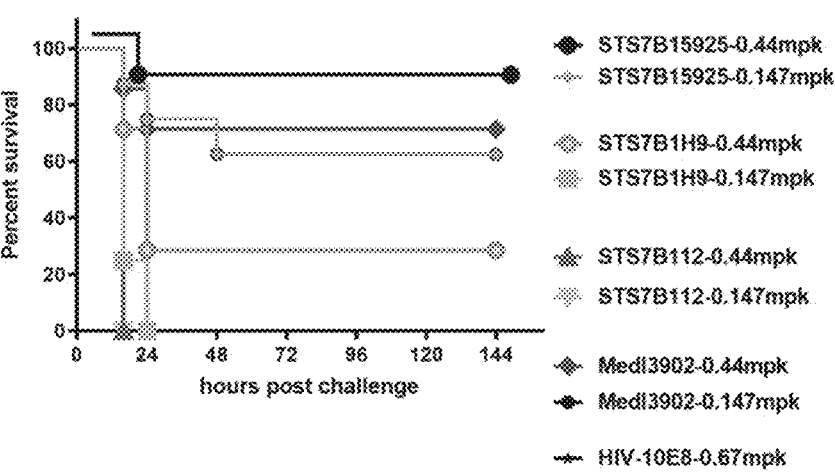
FIGS. 9C and 9D show the ability of various anti-PcrV/anti-Psl bispecific antibodies, at the indicated antibody doses, to improve survival in a mouse intraperitoneal infection of *P. aeruginosa* compared to reference bispecific antibody MedI3902.

As shown in FIG. 9C, at both 0.44 mg/kg and 0.147 mg/kg antibody dose settings, the bispecific antibody STS7B15925 exhibited higher survival improvement compared to STS7B1H9 or STS7B112, and exhibited comparable survival improvement compared to reference bispecific antibody MedI3902.

STS7B15925 and STS7B112 were further optimized by introducing variants in the $V_H$, $V_L$ and/or Fc variants, giving rise to STS7B15921M, STS7B15925M, STS7B11201M. The experiment was repeated, with mice being intraperitoneally injected with either STS7B15921M, STS7B15925M, STS7B11201M or MedI3902 (at 0.665 mg/kg) 24 h before infection with a *P. aeruginosa* (06-57/66 strain) inoculum at five times the lethal dose ($5 \times LD90 = 1 \times 10^6$ CFU).

Figure 9D:
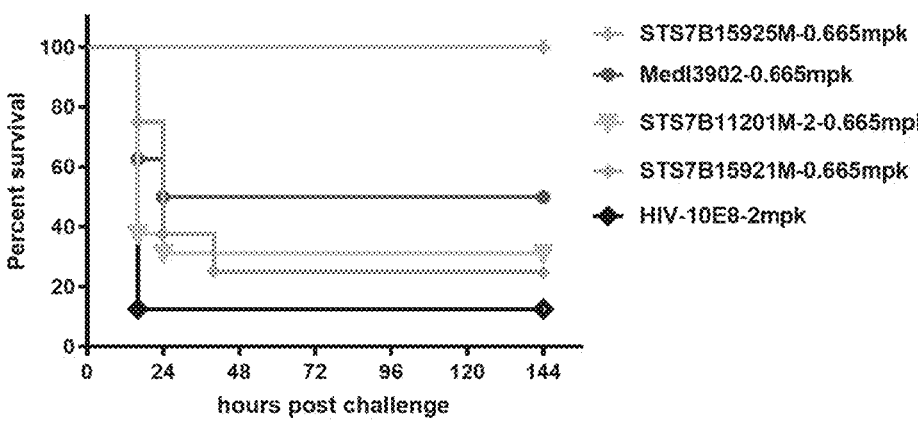

As shown in FIG. 9D, at 0.665 mg/kg antibody dose setting, the optimized bispecific antibody STS7B15921M and STS7B11201M exhibited comparable survival improvement compared to reference bispecific antibody MedI3902, and optimized bispecific antibody STS7B15925M exhibited higher survival improvement compared to reference bispecific antibody MedI3902, with statistical significance ($p < 0.05$).

Example 10: Comparison of In Vitro Activity of Bispecific Antibodies Recognizing PcrV and Psl with the Antibody Recognizing PcrV or Antibody Recognizing Psl The ability of the anti-PcrV/Psl bispecific antibody in inhibiting PcrV function is determined by the ability to inhibit lysis of RBCs and A549 cells, whereas the ability of the bispecific antibody in inhibiting Psl function is determined by the ability to promote opsonophagocytic killing (OPK) and the ability to inhibit attachment, and compared to that of anti-PcrV, or to that of anti-Psl antibodies.

Analysis of Activity Against PcrV as Determined by A549 CTX Assay

Figure 10A:
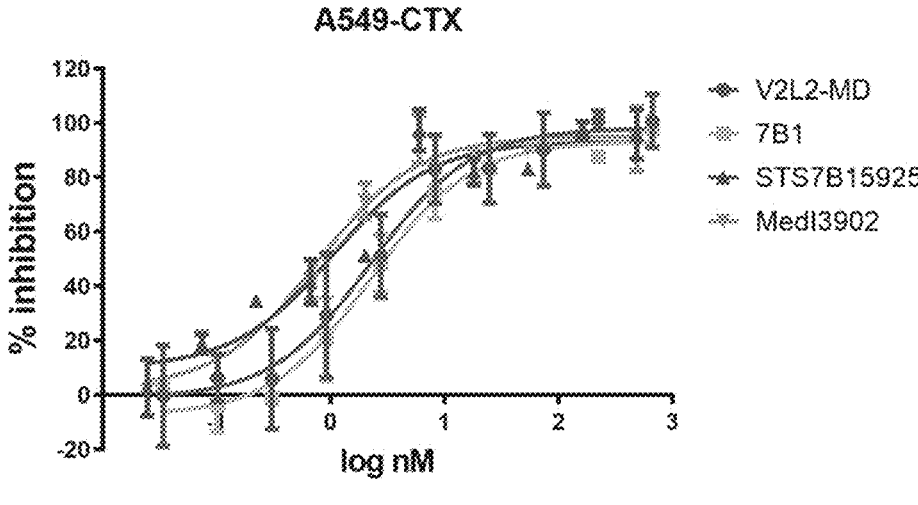
FIG. 10A shows the ability of anti-PcrV/anti-Psl bispecific antibody STS7B15925 in inhibiting A549 cell lysis by *P. aeruginosa* compared to monospecific anti-PcrV antibodies (7B1, Reference V2L2-MD) and reference bispecific antibody MedI3902.

A549 CTX assay was performed according to protocol described in Example 7. As shown in FIG. 10A, the inhibition on A549 cell lysis by STS7B15925 is comparable to that of MedI3902, and comparable to that of 7B1 or V2L2-MD, indicating that the bispecific antibody STS7B15925 has comparable ability to inhibit PcrV as monospecific anti-PcrV antibodies.

Analysis of Activity Against PcrV as Determined by RBC Lysis Inhibition

Figure 10B:
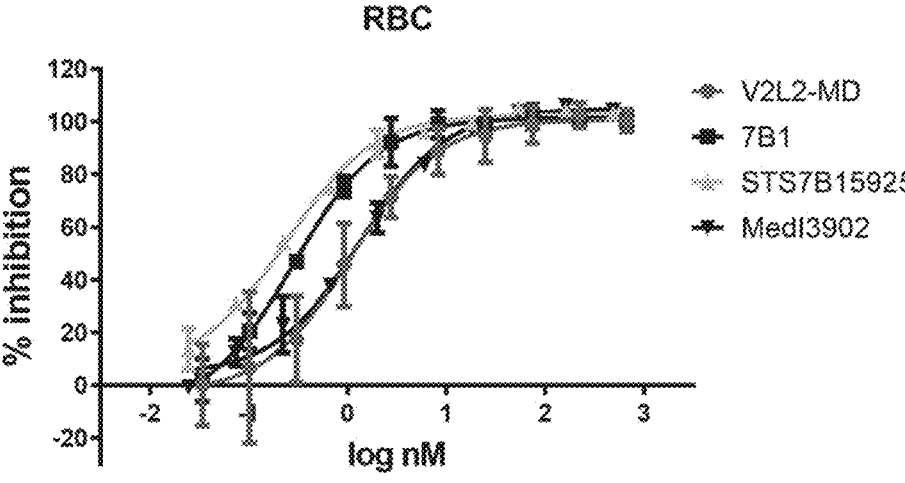
FIG. 10B shows the ability of anti-PcrV/anti-Psl bispecific antibody STS7B15925 in inhibiting RBC lysis by *P. aeruginosa* compared to monospecific anti-PcrV antibodies (7B1, Reference V2L2-MD) and reference bispecific antibody MedI3902.

RBC lysis inhibition assay was performed according to protocol described in Example 7. As shown in FIG. 10B, the inhibition on RBC lysis by STS7B15925 is comparable to that of MedI3902, and comparable to that of 7B1 or V2L2-MD, indicating that the bispecific antibody STS7B15925 has comparable ability to inhibit PcrV as monospecific anti-PcrV antibodies.

Analysis of Activity Against Psl as Determined by Opsonophagocytic Killing (OPK)

Figure 10C:
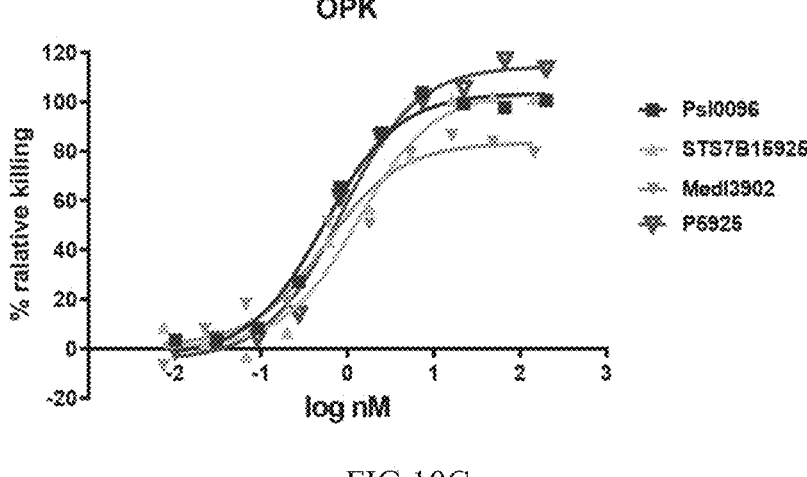
FIG. 10C shows the ability of anti-PcrV/anti-Psl bispecific antibody STS7B15925 in promoting OPK of *P. aeruginosa* compared to monospecific anti-Psl antibodies (P5925, Reference Ps10096) and reference bispecific antibody MedI3902.

OPK assay was performed according to protocol described in Example 7. As shown in FIG. 10C, the OPK mediated by STS7B15925 is comparable to that of MedI3902, and comparable to that of P5925 or Psl0096, indicating that the bispecific antibody STS7B15925 has comparable ability to inhibit Psl as monospecific anti-Psl antibodies.

Figure 10D:
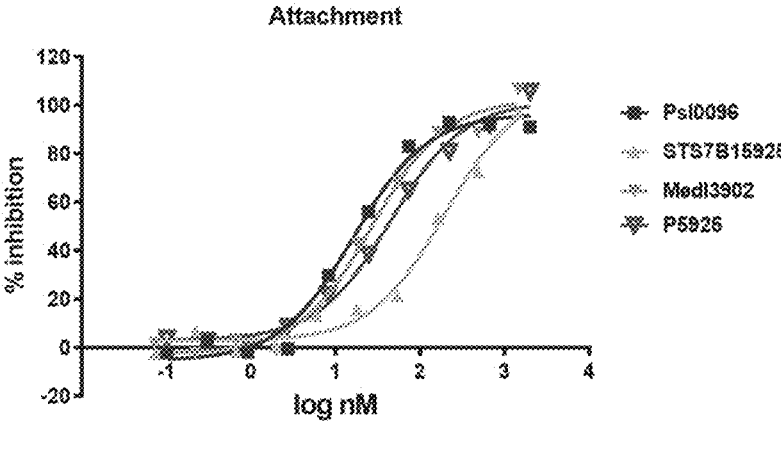
FIG. 10D shows the ability of anti-PcrV/anti-Psl bispecific antibody STS7B15925 in blocking attachment of *P. aeruginosa* compared to monospecific anti-Psl antibodies (P5925, Reference Ps10096) and reference bispecific antibody MedI3902.

Analysis of Activity Against Psl as Determined by Inhibition of Attachment of *P. aeruginosa* to A549 Cells Attachment assay was performed according to protocol described in Example 7. As shown in FIG. 10D, the inhibition on *P. aeruginosa* attachment mediated by STS7B15925 is comparable to that of MedI3902, and comparable to that of P5925 or Psl0096, indicating that the bispecific antibody STS7B15925 has comparable ability to inhibit Psl as monospecific anti-Psl antibodies.

Example 11: Comparison of In Vivo Activity of Bispecific Antibodies Recognizing PcrV and Psi with the Combination of Antibody Recognizing PcrV and Antibody Recognizing Psi The ability of bispecific antibody recognizing PcrV and Psl in neutralizing *P. aeruginosa* infection prophylactically was demonstrated with survival improvement in a mouse intraperitoneal infection model, and compared to that of combination of anti-PcrV and anti-Psl antibodies.

Survival Improvement in Mouse Intraperitoneal Infection Model with Combination of Anti-PcrV Antibodies, Anti-Psl Antibodies, or Combination Thereof The ability of the bispecific antibody STS7B15925 (comprising the Fab of anti-PcrV antibody 7B1 and the scFV of anti-Psl antibody P5925) to improve survival in mouse intraperitoneal infection model was evaluated in comparison to combination of corresponding anti-PcrV antibody 7B1 and anti-Psl antibody P5925 at different dosing concentrations. HIV-10E8 was used as negative control.

In a prophylactic model, 7-8 weeks old BALB/c mice (Vital River Laboratory) were intraperitoneally injected with either STS7B15925 or a combination of anti-Psl and anti-PcrV (equalized to give the same total amount of binding sites) 24 h before infection. Specifically, in a high antibody dose setting, the mice were administered with STS7B15925 (at 1.33 mg/kg); or a combination of 7B1 and P5925 (at 1 mg/kg each and 2 mg/kg total). In a medium antibody dose setting, the mice were administered with STS7B15925 (at 0.266 mg/kg); or a combination 7B1 and P5925 (at 0.2 mg/kg each and 0.4 mg/kg total). In a low antibody dose setting, the mice were administered with STS7B15925 (at 0.0532 mg/kg); or a combination 7B1 and P5925 (at 0.04 mg/kg each and 0.08 mg/kg total). To induce intraperitoneal infection, the BALB/c mice were intraperitoneally inoculated with *P. aeruginosa* (06-57/66 strain) suspended in a 300 μl inoculum at five times the lethal dose ($5 \times LD90 = 1 \times 10^6$ CFU). Mouse survival was recorded for up to 7 days post-infection.

Figure 11:
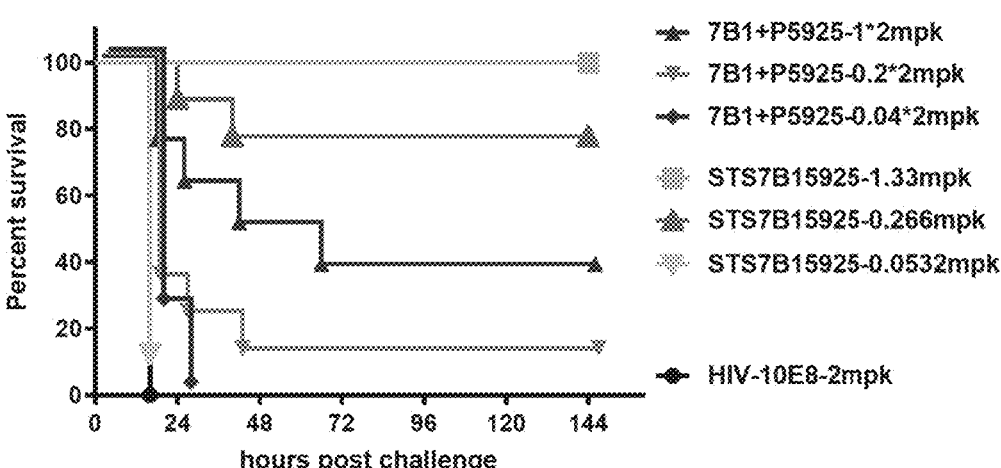
FIG. 11 shows the ability of combination of anti-PcrV antibody 7B1 and anti-Psl antibody P5925 or the corresponding anti-PcrV/anti-Psl bispecific antibody STS7B15925, at indicated antibody doses, to improve survival in a mouse intraperitoneal infection model at 5 times the lethal dose (5×LD90) of *P. aeruginosa* inoculation.

As shown in FIG. 11, at the medium and high antibody dose settings, STS7B15925 exhibited higher survival improvement compared to combination of 7B1 and P5925 with statistical significance ($p < 0.01$). These results here demonstrate the clinical potential of using bispecific antibodies recognizing PcrV and Psl disclosed herein in neutralizing *P. aeruginosa*.

US 12,570,728 B2

Figure 12A:
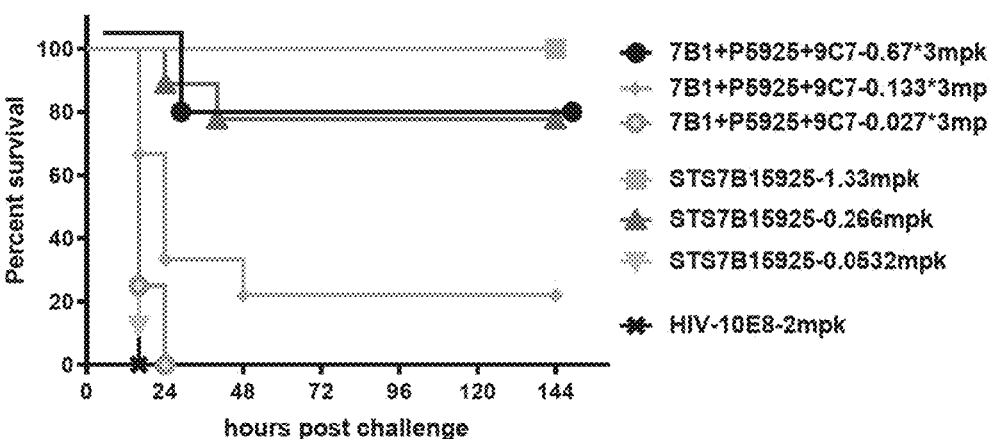
FIG. 12A shows the ability of combination of anti-PcrV antibody 7B1, anti-PcrV antibody 9C7 and anti-Psl antibody P5925 or the corresponding anti-PcrV/anti-Psl bispecific antibody STS7B15925, at indicated antibody doses, to improve survival in a mouse intraperitoneal infection model at 5 times the lethal dose (5×LD90) of *P. aeruginosa* inoculation.
Figure 12B:
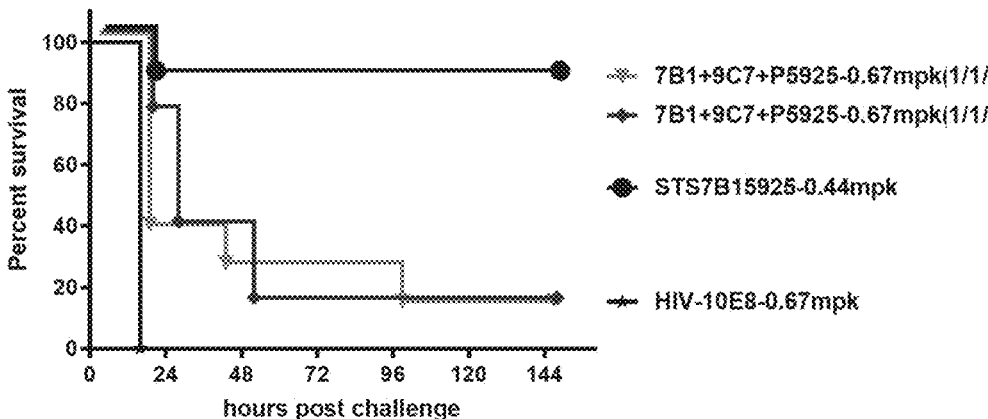
FIG. 12B shows the ability of combination of anti-PcrV antibody 7B1, anti-PcrV antibody 9C7, and anti-Psl antibody P5925 or the anti-PcrV/anti-Psl bispecific antibody STS7B15925, at indicated antibody doses, to improve survival in a mouse intraperitoneal infection model at 6 times the lethal dose (6×LD90) of *P. aeruginosa* inoculation.

Example 12: Comparison of In Vivo Activity of
Bispecific Antibodies Recognizing PcrV and Psl
with the Combination of Antibodies Recognizing
Different Epitope of PcrV and Antibody
Recognizing Psl The ability of bispecific antibody recognizing PcrV and
Psl in neutralizing *P. aeruginosa* infection prophylactically
was demonstrated with survival improvement in a mouse
intraperitoneal infection model, when compared to that of
combination of anti-PcrV and anti-Psl antibodies.
Survival Improvement in Mouse Intraperitoneal Infection
Model with Bispecific Antibodies, Combination of Anti-
PcrV Antibodies and Anti-Psl Antibodies
    The ability of the bispecific antibody STS7B15925 (com-
prising the Fab of anti-PcrV antibody 7B1 and the scFV of
anti-Psl antibody P5925) to improve survival in mouse
intraperitoneal infection model was evaluated in comparison
to combination of two anti-PcrV antibody 7B1 and 9C7
(which bind to non-overlapping epitopes) and an anti-Psl
antibody P5925 at different dosing concentrations. HIV-
10E8 was used as negative control.
    In a prophylactic model, 7-8 weeks old BALB/c mice
(Vital River Laboratory) were intraperitoneally injected with
either STS7B15925 or a combination of anti-Psl and anti-
PcrV (equalized to give the same total amount of binding
sites) 24 h before infection. Specifically, in a high antibody
dose setting, the mice were administered with STS7B15925
(at 1.33 mg/kg); or a combination of 7B1, 9C7 and P5925 (at
0.67 mg/kg each and 2 mg/kg total). In a medium antibody
dose setting, the mice were administered with STS7B15925
(at 0.266 mg/kg); or a combination 7B1, 9C7 and P5925 (at
0.133 mg/kg each and 0.4 mg/kg total). In a low antibody
dose setting, the mice were administered with STS7B15925
(at 0.0532 mg/kg); or a combination 7B1, 9C7 and P5925 (at
0.027 mg/kg each and 0.08 mg/kg total). To induce intrap-
eritoneal infection, the BALB/c mice were intraperitoneally
inoculated with *P. aeruginosa* (06-57/66 strain) suspended
in a 300 μl inoculum at five times the lethal dose
($5\times LD90=1\times 10^6$ CFU). Mouse survival was recorded for up
to 7 days post-infection.
    As shown in FIG. 12A, at the high antibody dose settings,
the bispecific antibody STS7B15925 exhibited higher sur-
vival improvement compared to combination of 7B1, 9C7
and P5925, and at the medium antibody dose setting,
STS7B15925 exhibited higher survival improvement com-
pared to combination of 7B1, 9C7 and P5925, with statis-
tical significance ($p<0.05$).
    To further compare the efficacy of bispecific antibody to
that of combination of anti-PcrV and anti-Psl antibodies the
experiment was repeated, where the mice were administered
with equal molar amounts of STS7B15925 (at 0.44 mg/kg);
or a combination of 7B1, 9C7 and P5925 (at 0.67 mg/kg total with 1:1:1 or 1:1:2 ratio) 24 h before infection with a
higher dose of *P. aeruginosa* (06-57/66 strain) inoculum at
six times the lethal dose ($6\times LD90=1.2\times 10^6$ CFU). Mouse
survival was recorded for up to 7 days post-infection.
    As shown in FIG. 12B, at a higher dose of *P. aeruginosa*
infection ($6\times LD90=1.2\times 10^6$ CFU), STS7B15925 exhibited
higher survival improvement compared to combination of
7B1, 9C7 and P5925 at either ratio, with statistical signifi-
cance ($p<0.05$).

Figure 13:
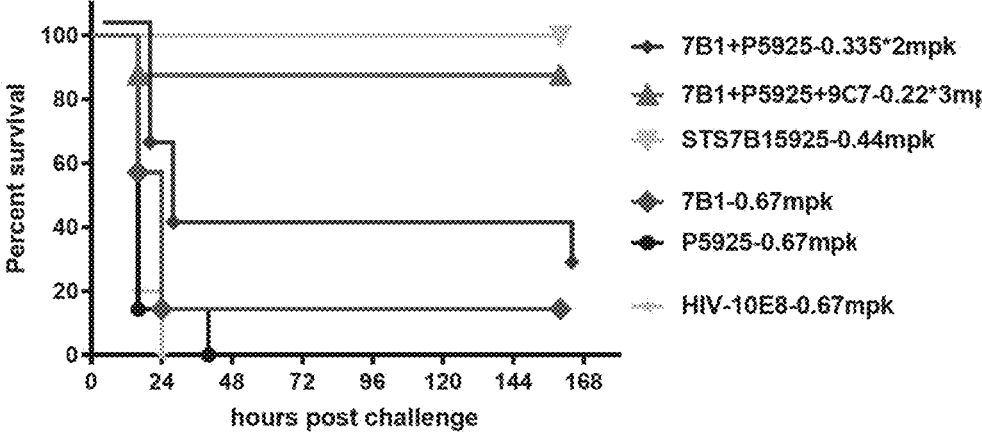
FIG. 13 shows the ability of combination of anti-PcrV antibody 7B1, anti-PcrV antibody 9C7, and anti-Psl antibody P5925 or the anti-PcrV/anti-Psl bispecific antibody STS7B15925, at indicated antibody doses, to improve survival in a mouse intraperitoneal infection model at 5 times the lethal dose (5×LD90) of *P. aeruginosa* inoculation, as compared to anti-PcrV antibody 7B1 or anti-Psl antibody P5925 alone.

Example 13: Treatment of *P. aeruginosa* Infection
Using Bispecific Antibodies Recognizing PcrV and
Psl, Combinations of Anti-PcrV and Anti-Psl
Antibodies The ability of bispecific antibody recognizing PcrV and
Psl in neutralizing *P. aeruginosa* infection prophylactically
was demonstrated with survival improvement in a mouse
intraperitoneal infection model, and compared to that of
anti-PcrV antibodies, anti-Psl antibodies, or combinations
thereof.
Survival Improvement in Mouse Intraperitoneal Infection
Model with Bispecific Antibody, Anti-PcrV Antibodies,
Anti-Psl Antibodies, or Combination Thereof
    The ability of the bispecific antibody STS7B15925 (com-
prising the Fab of anti-PcrV antibody 7B1 and the scFV of
anti-Psl antibody P5925) to improve survival in mouse
intraperitoneal infection model was evaluated in comparison
to combination of two anti-PcrV antibody 7B1 and 9C7
(which bind to non-overlapping epitopes) and an anti-Psl
antibody P5925, combination of anti-PcrV antibody 7B1
and anti-Psl antibody P5925, and also compared to 7B1
alone or P5925 alone. HIV-10E8 was used as negative
control.
    In a prophylactic model, 7-8 weeks old BALB/c mice
(Vital River Laboratory) were intraperitoneally injected with
either STS7B15925, anti-PSL, anti-PcrV or a combination
thereof (equalized to give the same total amount of binding
sites) 24 h before infection. Specifically, the mice were
administered with STS7B15925 (at 0.44 mg/kg); combina-
tion of 7B1, 9C7 and P5925 (at 0.22 mg/kg each and 0.66
mg/kg total), a combination of 7B1 and P5925 (at 0.335
mg/kg each and 0.67 mg/kg total), 7B1 alone (0.67 mg/kg)
or P5925 alone (0.67 mg/kg) To induce intraperitoneal
infection, the BALB/c mice were intraperitoneally inocu-
lated with *P. aeruginosa* (06-57/66 strain) suspended in a
300 μl inoculum at five times the lethal dose ($5\times LD90=1\times$
$10^6$ CFU). Mouse survival was recorded for up to 7 days
post-infection.
    As shown in FIG. 13, the bispecific antibody
STS7B15925 exhibited higher survival improvement com-
pared to combination of 7B1, 9C7 and P5925, and
STS7B15925 exhibited higher survival improvement com-
pared to 7B1 alone, P5925 alone or combination of 7B1 and
P5925, with statistical significance ($p<0.05$).

The invention claimed is:

1. A bispecific molecule comprising a first antigen-binding domain specifically recognizing *Pseudomonas* PcrV, and a second antigen-binding domain specifically recognizing *Pseudomonas* Psl, wherein the first antigen-binding domain comprises:

(a) a heavy chain variable domain (VH) comprising a heavy chain complementarity determining region (HC-CDR) 1 comprising DX$_1$X$_2$MS (SEQ ID NO: 20), wherein X$_1$ is N or Y, and X$_2$ is Y, H or P; an HC-CDR2 comprising X$_1$ISESGGSTNYADSVKG (SEQ ID NO: 15), wherein X$_1$ is V or G; and an HC-CDR3 comprising GRFSTX$_1$SX$_2$HFX$_3$RAVYGMDV (SEQ ID NO: 21), wherein X$_1$ is L, S, N or D, X$_2$ is S or A, X$_3$ is F or Y; and a light chain variable domain (V$_L$) comprising a light chain complementarity determining region (LC-CDR) 1 comprising RASQGISSYLA (SEQ ID NO: 10); an LC-CDR2 comprising AASTLQS (SEQ ID NO: 11), and an LC-CDR3 comprising QQLSSYPLX$_1$ (SEQ ID NO: 19), wherein X$_1$ is S or T; or (b) a V$_H$ comprising a HC-CDR1 comprising SYWMH (SEQ ID NO: 22); an HC-CDR2 comprising RINEX$_1$EX$_2$SISYADSVKG (SEQ ID NO: 44), wherein X$_1$ is D or N, and X$_2$ is T, G or R; and an HC-CDR3 comprising DGPYDX$_1$X$_2$DI (SEQ ID NO: 45), wherein X$_1$ is S, A, or T, and X$_2$ is F or L; and a V$_L$ comprising an LC-CDR1 comprising RASQX$_1$VX$_2$X$_3$NLA (SEQ ID NO: 46), wherein X$_1$ is S, G or N, X$_2$ is S, R or K and X$_3$ is S or N; an LC-CDR2 comprising X$_1$ASSRAT (SEQ ID NO: 42), wherein X$_1$ is D or H, and an LC-CDR3 comprising QQYGX$_1$X$_2$PX$_3$T (SEQ ID NO: 47), wherein X$_1$ is S, L or N, X$_2$ is S, Q or E and X$_3$ is L or I;

or wherein the first antigen-binding domain comprises:

(i) a V$_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12; or (ii) a $V_H$ comprising an HC-CDR1 comprising the amino acid sequence SEQ ID NO: 2, an HC-CDR2 comprising the amino acid sequence of SEQ ID NO: 5, and an HC-CDR3 comprising the amino acid sequence of SEQ ID NO: 7; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 13; or (iii) a $V_H$ comprising an HC-CDR1 comprising the amino acid sequence SEQ ID NO: 22, an HC-CDR2 comprising the amino acid sequence of SEQ ID NO: 23, and an HC-CDR3 comprising the amino acid sequence of SEQ ID NO: 26; and a $V_L$ comprising: an LC-CDR1 comprising the amino acid sequence of SEQ ID NO: 30, an LC-CDR2 comprising the amino acid sequence of SEQ ID NO: 33, and an LC-CDR3 comprising the amino acid sequence of SEQ ID NO: 35; or (iv) a $V_H$ comprising an HC-CDR1 comprising the amino acid sequence SEQ ID NO: 22, an HC-CDR2 comprising the amino acid sequence of SEQ ID NO: 24, and an HC-CDR3 comprising the amino acid sequence of SEQ ID NO: 27; and a $V_L$ comprising: an LC-CDR1 comprising the amino acid sequence of SEQ ID NO: 31, an LC-CDR2 comprising the amino acid sequence of SEQ ID NO: 34, and an LC-CDR3 comprising the amino acid sequence of SEQ ID NO: 36; and wherein the second antigen-binding domain comprises:

(a) a $V_H$ comprising a HC-CDR1 comprising SSGDYWG (SEQ ID NO: 48); an HC-CDR2 comprising SIHNX$_1$GSTYYNPSLKG (SEQ ID NO: 81), wherein X$_1$ is S or Q; and an HC-CDR3 comprising QFGSETYYX$_1$GIX$_2$P (SEQ ID NO: 82), wherein X$_1$ is T, N or P, and X$_2$ is D or Q; and a $V_L$ comprising an LC-CDR1 comprising RSSQSLLHSX$_1$GYNYLD (SEQ ID NO: 83), wherein X$_1$ is N or R; an LC-CDR2 comprising LGSNRAS (SEQ ID NO: 70), and an LC-CDR3 comprising MQALQTPYT (SEQ ID NO: 74); or (b) a $V_H$ comprising an HC-CDR1 comprising IHSVH (SEQ ID NO: 50); an HC-CDR2 comprising TIIS-SGTTTTYAQSFQD (SEQ ID NO: 55); and an HC-CDR3 comprising DGX$_1$S (SEQ ID NO: 84), wherein X$_1$ is D or T; and a $V_L$ comprising an LC-CDR1 comprising RASQGISSWLA (SEQ ID NO: 68); an LC-CDR2 comprising HASTLES (SEQ ID NO: 72), and an LC-CDR3 comprising LQAX$_1$SLPHT (SEQ ID NO: 85), wherein X$_1$ is N, F, S or K; or (c) a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75; or (d) a $V_H$ comprising an HC-CDR1 comprising the amino acid sequence of SEQ ID NO: 51, an HC-CDR2 comprising the amino acid sequence of SEQ ID NOs 56, and an HC-CDR3 comprising the amino acid sequence of SEQ ID NO: 64; and a $V_L$ comprising: an LC-CDR1 comprising the amino acid sequence of SEQ ID NO: 69, an LC-CDR2 comprising the amino acid sequence of SEQ ID NO: 73, and an LC-CDR3 comprising the amino acid sequence of SEQ ID NO: 80;

or wherein the second antigen-binding domain comprises:

(i) a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74; or (ii) a $V_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 62; and a $V_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 76.

2. The bispecific molecule of claim 1, wherein (i) the first antigen-binding domain comprises:

a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12;

and the second antigen-binding domain comprises:

a $V_H$ comprising an HC-CDR1 comprising the amino acid sequence of SEQ ID NO: 48, an HC-CDR2 comprising the amino acid sequence of SEQ ID NO: 52, and an HC-CDR3 comprising the amino acid sequence of SEQ ID NO: 57; and a $V_L$ comprising: an LC-CDR1 comprising the amino acid sequence of SEQ ID NO: 65, an LC-CDR2 comprising the amino acid sequence of SEQ ID NO: 70, and an LC-CDR3 comprising the amino acid sequence of SEQ ID NO: 74;

or (ii) the first antigen-binding domain comprises:

a $V_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a $V_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12;

and wherein the second antigen-binding domain comprises:

a $V_H$ comprising an HC-CDR1 comprising the amino acid sequence of SEQ ID NO: 49, an HC-CDR2 comprising the amino acid sequence of SEQ ID NO: 54, and an HC-CDR3 comprising the amino acid sequence of SEQ ID NO: 61; and a $V_L$ comprising: an LC-CDR1 comprising the amino acid sequence of SEQ ID NO: 67, an LC-CDR2 comprising the amino acid sequence of SEQ ID NO: 71, and an LC-CDR3 comprising the amino acid sequence of SEQ ID NO: 75; or (iii) the first antigen-binding domain comprises:

a V$_H$ comprising an HC-CDR1 comprising the amino acid sequence SEQ ID NO: 1, an HC-CDR2 comprising the amino acid sequence of SEQ ID NO: 4, and an HC-CDR3 comprising the amino acid sequence of SEQ ID NO: 6; and a V$_L$ comprising: an LC-CDR1 comprising the amino acid sequence of SEQ ID NO: 10, an LC-CDR2 comprising the amino acid sequence of SEQ ID NO: 11, and an LC-CDR3 comprising the amino acid sequence of SEQ ID NO: 12;

and wherein the second antigen-binding domain comprises:

a V$_H$ comprising an HC-CDR1 comprising the amino acid sequence of SEQ ID NO: 50, an HC-CDR2 comprising the amino acid sequence of SEQ ID NO: 55, and an HC-CDR3 comprising the amino acid sequence of SEQ ID NO: 62; and a V$_L$ comprising: an LC-CDR1 comprising the amino acid sequence of SEQ ID NO: 68, an LC-CDR2 comprising the amino acid sequence of SEQ ID NO: 72, and an LC-CDR3 comprising the amino acid sequence of SEQ ID NO: 76.

3. The bispecific molecule of claim 1 comprising a first antigen-binding domain specifically recognizing *Pseudomonas* PcrV, and a second antigen-binding domain specifically recognizing *Pseudomonas* Psl, wherein the first antigen-binding domain comprises:

a) a V$_H$ comprising the amino acid sequence of any one of SEQ ID NOs: 91-94 and 161-164, or a variant thereof having at least about 90% sequence identity to the amino acid sequence of any one of SEQ ID NOs: 91-94 and 161-164; and a V$_L$ comprising the amino acid sequence of any one of SEQ ID NOs: 112-113 and 182-183, or a variant thereof having at least about 90% sequence identity to the amino acid sequence of any one of SEQ ID NOs: 112-113 and 182-183; or a V$_H$ comprising an HC-CDR1, an HC-CDR2, and an HC-CDR3 of a V$_H$ comprising the amino acid sequence of any one of SEQ ID NOs: 91-94 and 161-164; and a V$_L$ comprising an LC-CDR1, an LC-CDR2, and an LC-CDR3 of a V$_L$ comprising the amino acid sequence of any one of SEQ ID NOs: 112-113 and 182-183; or b) a V$_H$ comprising the amino acid sequence of any one of SEQ ID NOs: 95-102 and 165-172, or a variant thereof having at least about 90% sequence identity to the amino acid sequence of any one of SEQ ID NOs: 95-102 and 165-172; and a V$_L$ comprising the amino acid sequence of any one of SEQ ID NOs: 114-116 and 184-186, or a variant thereof having at least about 90% sequence identity to the amino acid sequence of any one of SEQ ID NOs: 114-116 and 184-186; or a V$_H$ comprising an HC-CDR1, an HC-CDR2, and an HC-CDR3 of a V$_H$ comprising the amino acid sequence of any one of SEQ ID NOs: 95-102 and 165-172; and a V$_L$ comprising an LC-CDR1, an LC-CDR2, and an LC-CDR3 of a V$_L$ comprising the amino acid sequence of any one of SEQ ID NOs: 114-116 and 184-186; or wherein the first antigen-binding domain comprises:

(i) a V$_H$ comprising the amino acid sequence of SEQ ID NO: 91 or 161, or a variant thereof having at least about 90% sequence identity to the amino acid sequence of SEQ ID NO: 91 or 161; and a V$_L$ comprising the amino acid sequence of SEQ ID NO: 112 or 182, or a variant thereof having at least about 90% sequence identity to the amino acid sequence of SEQ ID NO: 112 or 182; or a V$_H$ comprising an HC-CDR1, an HC-CDR2 and an HC-CDR3 of the V$_H$ comprising the amino acid sequence of SEQ ID NO: 91 or 161; and a V$_L$ comprising an LC-CDR1, an LC-CDR2, and an LC-CDR3 of the V$_L$ comprising the amino acid sequence of SEQ ID NO: 112 or 182; or (ii) a V$_H$ comprising the amino acid sequence of SEQ ID NO: 92 or 162, or a variant thereof having at least about 90% sequence identity to the amino acid sequence of SEQ ID NO: 92 or 162; and a V$_L$ comprising the amino acid sequence of SEQ ID NO: 113 or 183, or a variant thereof having at least about 90% sequence identity to the amino acid sequence of SEQ ID NO: 113 or 183; or a V$_H$ comprising an HC-CDR1, an HC-CDR2 and an HC-CDR3 of the V$_H$ comprising the amino acid sequence of SEQ ID NO: 92 or 162; and a V$_L$ comprising an LC-CDR1, an LC-CDR2, and an LC-CDR3 of the V$_L$ comprising the amino acid sequence of SEQ ID NO: 113 or 183; or (iii) a V$_H$ comprising the amino acid sequence of SEQ ID NO: 95 or 165, or a variant thereof having at least about 90% sequence identity to the amino acid sequence of SEQ ID NO: 95 or 165; and a V$_L$ comprising the amino acid sequence of SEQ ID NO: 114 or 184, or a variant thereof having at least about 90% sequence identity to the amino acid sequence of SEQ ID NO: 114 or 184; or a V$_H$ comprising an HC-CDR1, an HC-CDR2 and an HC-CDR3 of the V$_H$ comprising the amino acid sequence of SEQ ID NO: 95 or 165; and a V$_L$ comprising an LC-CDR1, an LC-CDR2, and an LC-CDR3 of the V$_L$ comprising the amino acid sequence of SEQ ID NO: 114 or 184; or (iv) a V$_H$ comprising the amino acid sequence of SEQ ID NO: 96 or 166, or a variant thereof having at least about 90% sequence identity to the amino acid sequence of SEQ ID NO: 96 or 166; and a V$_L$ comprising the amino acid sequence of SEQ ID NO: 115 or 185, or a variant thereof having at least about 90% sequence identity to the amino acid sequence of SEQ ID NO: 115 or 185; or a V$_H$ comprising an HC-CDR1, an HC-CDR2 and an HC-CDR3 of the V$_H$ comprising the amino acid sequence of SEQ ID NO: 96 or 166; and a V$_L$ comprising an LC-CDR1, an LC-CDR2, and an LC-CDR3 of the V$_L$ comprising the amino acid sequence of SEQ ID NO: 115 or 185;

and wherein the second antigen-binding domain comprises:

(i) a V$_H$ comprising the amino acid sequence of any one of SEQ ID NOs: 103-106 and 173-176, or a variant thereof having at least about 90% sequence identity to the amino acid sequence of any one of SEQ ID NOs: 103-106 and 173-176; and a V$_L$ comprising the amino acid sequence of any one of SEQ ID NOs: 117-118 and 187-188, or a variant thereof having at least about 90% sequence identity to the amino acid sequence of any one of SEQ ID NOs: 117-118 and 187-188; or a V$_H$ comprising an HC-CDR1, an HC-CDR2, and an HC-CDR3 of a V$_H$ comprising the amino acid sequence of any one of SEQ ID NOs: 103-106 and 173-176; and a V$_L$ comprising an LC-CDR1, an LC-CDR2, and an LC-CDR3 of a V$_L$ comprising the amino acid sequence of any one of SEQ ID NOs: 117-118 and 187-188; or (ii) a V$_H$ comprising the amino acid sequence of any one of SEQ ID NOs: 109-110 and 179-180, or a variant thereof having at least about 90% sequence identity to the amino acid sequence of any one of SEQ ID NOs: 109-110 and 179-180; and a V$_L$ comprising the amino acid sequence of any one of SEQ ID NOs: 120-123 and 190-193, or a variant thereof having at least about 90% sequence identity to the amino acid sequence of any one of SEQ ID NOs: 120-123 and 190-193; or a $V_H$ comprising an HC-CDR1, an HC-CDR2, and an HC-CDR3 of a $V_H$ comprising the amino acid sequence of any one of SEQ ID NOs: 109-110 and 179-180; and a $V_L$ comprising an LC-CDR1, an LC-CDR2, and an LC-CDR3 of a $V_L$ comprising the amino acid sequence of any one of SEQ ID NOs: 120-123 and 190-193; or (iii) a $V_H$ comprising the amino acid sequence of any one of SEQ ID NOs: 107-108 and 177-178, or a variant thereof having at least about 90% sequence identity to the amino acid sequence of any one of SEQ ID NOs: 107-108 and 177-178; and a $V_L$ comprising the amino acid sequence of any one of SEQ ID NOs: 119 and 189, or a variant thereof having at least about 90% sequence identity to the amino acid sequence of any one of SEQ ID NOs: 119 and 189; or a $V_H$ comprising an HC-CDR1, an HC-CDR2, and an HC-CDR3 of a $V_H$ comprising the amino acid sequence of any one of SEQ ID NOs: 107-108 and 177-178; and a $V_L$ comprising an LC-CDR1, an LC-CDR2, and an LC-CDR3 of a $V_L$ comprising the amino acid sequence of any one of SEQ ID NOs: 119 and 189; or (iv) a $V_H$ comprising the amino acid sequence of any one of SEQ ID NOs: 111 and 181, or a variant thereof having at least about 90% sequence identity to the amino acid sequence of any one of SEQ ID NOs: 111 and 181; and a $V_L$ comprising the amino acid sequence of any one of SEQ ID NOs: 124 and 194, or a variant thereof having at least about 90% sequence identity to the amino acid sequence of SEQ ID NOs: 124 and 194; or a $V_H$ comprising an HC-CDR1, an HC-CDR2, and an HC-CDR3 of a $V_H$ comprising the amino acid sequence of any one of SEQ ID NOs: 111 and 181; and a $V_L$ comprising an LC-CDR1, an LC-CDR2, and an LC-CDR3 of a $V_L$ comprising the amino acid sequence of any one of SEQ ID NOs: 124 and 194;

or wherein the second antigen-binding domain comprises:

(i) a $V_H$ comprising the amino acid sequence of SEQ ID NO: 103 or 173, or a variant thereof having at least about 90% sequence identity to the amino acid sequence of SEQ ID NO: 103 or 173; and a $V_L$ comprising the amino acid sequence of SEQ ID NO: 117 or 187, or a variant thereof having at least about 90% sequence identity to the amino acid sequence of SEQ ID NO: 117 or 187; or a $V_H$ comprising an HC-CDR1, an HC-CDR2 and an HC-CDR3 of the $V_H$ comprising the amino acid sequence of SEQ ID NO: 103 or 173; and a $V_L$ comprising an LC-CDR1, an LC-CDR2, and an LC-CDR3 of the $V_L$ comprising the amino acid sequence of SEQ ID NO: 117 or 187; or (ii) a $V_H$ comprising the amino acid sequence of SEQ ID NO: 109 or 179, or a variant thereof having at least about 90% sequence identity to the amino acid sequence of SEQ ID NO: 109 or 179; and a $V_L$ comprising the amino acid sequence of SEQ ID NO: 120 or 190, or a variant thereof having at least about 90% sequence identity to the amino acid sequence of SEQ ID NO: 120 or 190; or a $V_H$ comprising an HC-CDR1, an HC-CDR2 and an HC-CDR3 of the $V_H$ comprising the amino acid sequence of SEQ ID NO: 109 or 179; and a $V_L$ comprising an LC-CDR1, an LC-CDR2, and an LC-CDR3 of the $V_L$ comprising the amino acid sequence of SEQ ID NO: 120 or 190.

4. The bispecific molecule of claim 1, wherein (i) the first antigen-binding domain comprises: a $V_H$ comprising the amino acid sequence of SEQ ID NO: 91 or 161, or a variant thereof having at least about 90% sequence identity to the amino acid sequence of SEQ ID NO: 91 or 161; and a $V_L$ comprising the amino acid sequence of SEQ ID NO: 112 or 182, or a variant thereof having at least about 90% sequence identity to the amino acid sequence of SEQ ID NO: 112 or 182; and wherein the second antigen-binding domain comprises: a $V_H$ comprising the amino acid sequence of SEQ ID NO: 103 or 173, or a variant thereof having at least about 90% sequence identity to the amino acid sequence of SEQ ID NO: 103 or 173; and a $V_L$ comprising the amino acid sequence of SEQ ID NO: 117 or 187, or a variant thereof having at least about 90% sequence identity to the amino acid sequence of SEQ ID NO: 117 or 187; or (ii) wherein the first antigen-binding domain comprises: a $V_H$ comprising the amino acid sequence of SEQ ID NO: 91 or 161, or a variant thereof having at least about 90% sequence identity to the amino acid sequence of SEQ ID NO: 91 or 161; and a $V_L$ comprising the amino acid sequence of SEQ ID NO: 112 or 182, or a variant thereof having at least about 90% sequence identity to the amino acid sequence of SEQ ID NO: 112 or 182; and wherein the second antigen-binding domain comprises: a $V_H$ comprising the amino acid sequence of SEQ ID NO: 109 or 179, or a variant thereof having at least about 90% sequence identity to the amino acid sequence of SEQ ID NO: 109 or 179; and a $V_L$ comprising the amino acid sequence of SEQ ID NO: 120 or 190, or a variant thereof having at least about 90% sequence identity to the amino acid sequence of SEQ ID NO: 120 or 190; or (iii) wherein the first antigen-binding domain comprises: a $V_H$ comprising the amino acid sequence of SEQ ID NO: 91 or 161, or a variant thereof having at least about 90% sequence identity to the amino acid sequence of SEQ ID NO: 91 or 161; and a $V_L$ comprising the amino acid sequence of SEQ ID NO: 112 or 182, or a variant thereof having at least about 90% sequence identity to the amino acid sequence of SEQ ID NO: 112 or 182; and wherein the second antigen-binding domain comprises: a Vu comprising the amino acid sequence of SEQ ID NO: 107 or 177, or a variant thereof having at least about 90% sequence identity to the amino acid sequence of SEQ ID NO: 107 or 177; and a $V_L$ comprising the amino acid sequence of SEQ ID NO: 119 or 189, or a variant thereof having at least about 90% sequence identity to the amino acid sequence of SEQ ID NO: 119 or 189.

5. The bispecific molecule of claim 1, wherein:

a) the first antigen binding domain is a Fab arm specifically recognizing PcrV, the second antigen binding domain is a single-chain variable fragment (scFv) specifically recognizing Psl, wherein the molecule further comprises an Fc region comprising CH2 and CH3 domains; and wherein the scFv is interconnected to the Fab arm via a first polypeptide linker (L1) and to the Fc region via a second polypeptide linker (L2); and wherein the bispecific molecule is bivalent for binding to each of PcrV and Psl; or b) the first antigen binding domain is a single-chain variable fragment (scFv) specifically recognizing PcrV, the second antigen binding domain is a Fab arm specifically recognizing Psl, wherein the molecule further comprises an Fc region comprising CH2 and CH3 domains; and wherein the scFv is interconnected to the Fab arm via a first polypeptide linker (L1) and to the Fc region via a second polypeptide linker (L2); and wherein the bispecific molecule is bivalent for binding to each of PcrV and Psl.

6. The bispecific molecule of claim 1, wherein the bispecific molecule comprises:

the amino acid sequence of SEQ ID NO: 135, 136 or 159, or a variant thereof having at least about 90% sequence identity to the amino acid sequence of SEQ ID NO: 135, 136 or 159; and/or the amino acid sequence of any one of SEQ ID NOs: 195-208, or a variant thereof having at least about 90% sequence identity to the amino acid sequence of any one of SEQ ID NOs: 195-208;

or wherein the bispecific molecule comprises:

a) the amino acid sequence of SEQ ID NO: 135, or a variant thereof having at least about 90% sequence identity to the amino acid sequence of SEQ ID NO: 135; and the amino acid sequence of any one of SEQ ID NOs: 195-207, or a variant thereof having at least about 90% sequence identity to the amino acid sequence of any one of SEQ ID NOs: 195-207;

b) the amino acid sequence of SEQ ID NO: 136, or a variant thereof having at least about 90% sequence identity to the amino acid sequence of SEQ ID NO: 136; and the amino acid sequence of any one of SEQ ID NOs: 195-207, or a variant thereof having at least about 90% sequence identity to the amino acid sequence of any one of SEQ ID NOs: 195-207; or c) the amino acid sequence of SEQ ID NO: 159, or a variant thereof having at least about 90% sequence identity to the amino acid sequence of SEQ ID NO: 159; and the amino acid sequence of SEQ ID NOs: 208, or a variant thereof having at least about 90% sequence identity to the amino acid sequence of SEQ ID NOs: 208.

7. The bispecific molecule of claim 5, wherein (i) the Fc region is selected from the group consisting of an Fc region from an IgG1, IgG2, IgG3, IgG4, IgA, IgM, IgE, and IgD; and/or (ii) the Fc region comprises a variant Fc region; and/or (iii) the Fc region is aglycosylated, or the Fc region is deglycosylated; and/or (iv) the Fc region has reduced fucosylation or is afucosylated; and/or (v) the variant Fc region comprises a substitution at one or more of positions 239, 282, 289, 297, 312, 324, 330, 335, 337, 339, 356, 359, 361, 383, 384, 398, 400, 440, 422, and 442, as numbered by the EU index; or the variant Fc region comprises a substitution at position 297; or the variant Fc region comprises a substitution at position 297 and wherein the substitution at position 297 is 297Q.

8. The bispecific molecule of claim 1, wherein the bispecific molecule comprises a chimeric heavy chain comprising the amino acid sequence of any one of SEQ ID NOs: 137-152 and 160, or a variant thereof having at least about 90% sequence identity to the amino acid sequence of any one of SEQ ID NOs: 137-152 and 160; and/or a light chain comprising the amino acid sequence of SEQ ID NO: 135, 136 or 159, or a variant thereof having at least about 90% sequence identity to the amino acid sequence of SEQ ID NO: 135, 136 or 159;

or wherein the bispecific molecule comprises:

a) a chimeric heavy chain comprising the amino acid sequence of any one of SEQ ID NOS: 137-152, or a variant thereof having at least about 90% sequence identity to the amino acid sequence of any one of SEQ ID NOs: 137-152; and a light chain comprising the amino acid sequence of SEQ ID NO: 135, or a variant thereof having at least about 90% sequence identity to the amino acid sequence of SEQ ID NO: 135;

b) a chimeric heavy chain comprising the amino acid sequence of any one of SEQ ID NOS: 137-152, or a variant thereof having at least about 90% sequence identity to the amino acid sequence of any one of SEQ ID NOs: 137-152; and a light chain comprising the amino acid sequence of SEQ ID NO: 136, or a variant thereof having at least about 90% sequence identity to the amino acid sequence of SEQ ID NO: 136; or c) a chimeric heavy chain comprising the amino acid sequence of SEQ ID NO: 160, or a variant thereof having at least about 90% sequence identity to the amino acid sequence of SEQ ID NO: 160; and a light chain comprising the amino acid sequence of SEQ ID NO: 159, or a variant thereof having at least about 90% sequence identity to the amino acid sequence of SEQ ID NO: 159.

9. A pharmaceutical composition comprising: the bispecific molecule of claim 1 and a pharmaceutically acceptable vehicle.

10. The pharmaceutical composition of claim 9 wherein the antigen-binding protein specifically recognizing *Pseudomonas* Psl comprises:

(i) a $V_H$ comprising the amino acid sequence of any one of SEQ ID NOs: 103-106 and 173-176, or a variant thereof having at least about 90% sequence identity to the amino acid sequence of any one of SEQ ID NOs: 103-106 and 173-176; and a $V_L$ comprising the amino acid sequence of any one of SEQ ID NOs: 117-118 and 187-188, or a variant thereof having at least about 90% sequence identity to the amino acid sequence of any one of SEQ ID NOs: 117-118 and 187-188; or a $V_H$ comprising an HC-CDR1, an HC-CDR2, and an HC-CDR3 of a $V_H$ comprising the amino acid sequence of any one of SEQ ID NOs: 103-106 and 173-176; and a $V_L$ comprising an LC-CDR1, an LC-CDR2, and an LC-CDR3 of a $V_L$ comprising the amino acid sequence of any one of SEQ ID NOs: 117-118 and 187-188; or (ii) a $V_H$ comprising the amino acid sequence of any one of SEQ ID NOs: 109-110 and 179-180, or a variant thereof having at least about 90% sequence identity to the amino acid sequence of any one of SEQ ID NOs: 109-110 and 179-180; and a $V_L$ comprising the amino acid sequence of any one of SEQ ID NOs: 120-123 and 190-193, or a variant thereof having at least about 90% sequence identity to the amino acid sequence of any one of SEQ ID NOs: 120-123 and 190-193; or a $V_H$ comprising an HC-CDR1, an HC-CDR2, and an HC-CDR3 of a $V_H$ comprising the amino acid sequence of any one of SEQ ID NOs: 109-110 and 179-180; and a $V_L$ comprising an LC-CDR1, an LC-CDR2, and an LC-CDR3 of a $V_L$ comprising the amino acid sequence of any one of SEQ ID NOs: 120-123 and 190-193; or (iii) a $V_H$ comprising the amino acid sequence of any one of SEQ ID NOs: 107-108 and 177-178, or a variant thereof having at least about 90% sequence identity to the amino acid sequence of any one of SEQ ID NOs: 107-108 and 177-178; and a $V_L$ comprising the amino acid sequence of any one of SEQ ID NOs: 119 and 189, or a variant thereof having at least about 90% sequence identity to the amino acid sequence of any one of SEQ ID NOs: 119 and 189; or a $V_H$ comprising an HC- CDR1, an HC-CDR2, and an HC-CDR3 of a $V_H$ comprising the amino acid sequence of any one of SEQ ID NOs: 107-108 and 177-178; and a $V_L$ comprising an LC-CDR1, an LC-CDR2, and an LC-CDR3 of a $V_L$ comprising the amino acid sequence of any one of SEQ ID NOs: 119 and 189; or (iv) a $V_H$ comprising the amino acid sequence of any one of SEQ ID NOs: 111 and 181, or a variant thereof having at least about 90% sequence identity to the amino acid sequence of any one of SEQ ID NOs: 111 and 181; and a $V_L$ comprising the amino acid sequence of any one of SEQ ID NOs: 124 and 194, or a variant thereof having at least about 90% sequence identity to the amino acid sequence of any one of SEQ ID NOs: 124 and 194; or a $V_H$ comprising an HC-CDR1, an HC-CDR2, and an HC-CDR3 of a $V_H$ comprising the amino acid sequence of any one of SEQ ID NOs: 111 and 181; and a $V_L$ comprising an LC-CDR1, an LC-CDR2, and an LC-CDR3 of a $V_L$ comprising the amino acid sequence of any one of SEQ ID NOs: 124 and 194;

or wherein the antigen-binding protein specifically recognizing *Pseudomonas* Psl comprises:

(i) a $V_H$ comprising the amino acid sequence of SEQ ID NO: 103 or 173, or a variant thereof having at least about 90% sequence identity to the amino acid sequence of SEQ ID NO: 103 or 173; and a $V_L$ comprising the amino acid sequence of SEQ ID NO: 117 or 187, or a variant thereof having at least about 90% sequence identity to the amino acid sequence of SEQ ID NO: 117 or 187; or a $V_H$ comprising an HC-CDR1, an HC-CDR2 and an HC-CDR3 of the $V_H$ comprising the amino acid sequence of SEQ ID NO: 103 or 173; and a $V_L$ comprising an LC-CDR1, an LC-CDR2, and an LC-CDR3 of the $V_L$ comprising the amino acid sequence of SEQ ID NO: 117 or 187; or (ii) a $V_H$ comprising the amino acid sequence of SEQ ID NO: 109 or 179, or a variant thereof having at least about 90% sequence identity to the amino acid sequence of SEQ ID NO: 109 or 179; and a $V_L$ comprising the amino acid sequence of SEQ ID NO: 120 or 190, or a variant thereof having at least about 90% sequence identity to the amino acid sequence of SEQ ID NO: 120 or 190; or a $V_H$ comprising an HC-CDR1, an HC-CDR2 and an HC-CDR3 of the $V_H$ comprising the amino acid sequence of SEQ ID NO: 109 or 179; and a $V_L$ comprising an LC-CDR1, an LC-CDR2, and an LC-CDR3 of the $V_L$ comprising the amino acid sequence of SEQ ID NO: 120 or 190.

11. A method of treating a *Pseudomonas aeruginosa* infection or condition in an individual in need thereof, comprising administering to the individual an effective amount of an effective amount of the bispecific molecule of claim 1.

12. The method of claim 11, wherein the antigen-binding protein specifically recognizing *Pseudomonas* Psl comprises:

(i) a $V_H$ comprising the amino acid sequence of any one of SEQ ID NOs: 103-106 and 173-176, or a variant thereof having at least about 90% sequence identity to the amino acid sequence of any one of SEQ ID NOs: 103-106 and 173-176; and a $V_L$ comprising the amino acid sequence of any one of SEQ ID NOs: 117-118 and 187-188, or a variant thereof having at least about 90% sequence identity to the amino acid sequence of any one of SEQ ID NOs: 117-118 and 187-188; or a $V_H$ comprising an HC-CDR1, an HC-CDR2, and an HC-CDR3 of a $V_H$ comprising the amino acid sequence of any one of SEQ ID NOs: 103-106 and 173-176; and a $V_L$ comprising an LC-CDR1, an LC-CDR2, and an LC-CDR3 of a $V_L$ comprising the amino acid sequence of any one of SEQ ID NOs: 117-118 and 187-188; or (ii) a $V_H$ comprising the amino acid sequence of any one of SEQ ID NOs: 109-110 and 179-180, or a variant thereof having at least about 90% sequence identity to the amino acid sequence of any one of SEQ ID NOs: 109-110 and 179-180; and a $V_L$ comprising the amino acid sequence of any one of SEQ ID NOs: 120-123 and 190-193, or a variant thereof having at least about 90% sequence identity to the amino acid sequence of any one of SEQ ID NOs: 120-123 and 190-193; or a $V_H$ comprising an HC-CDR1, an HC-CDR2, and an HC-CDR3 of a $V_H$ comprising the amino acid sequence of any one of SEQ ID NOs: 109-110 and 179-180; and a $V_L$ comprising an LC-CDR1, an LC-CDR2, and an LC-CDR3 of a $V_L$ comprising the amino acid sequence of any one of SEQ ID NOs: 120-123 and 190-193; or (iii) a $V_H$ comprising the amino acid sequence of any one of SEQ ID NOs: 107-108 and 177-178, or a variant thereof having at least about 90% sequence identity to the amino acid sequence of any one of SEQ ID NOs: 107-108 and 177-178; and a $V_L$ comprising the amino acid sequence of any one of SEQ ID NOs: 119 and 189, or a variant thereof having at least about 90% sequence identity to the amino acid sequence of any one of SEQ ID NOs: 119 and 189; or a $V_H$ comprising an HC-CDR1, an HC-CDR2, and an HC-CDR3 of a $V_H$ comprising the amino acid sequence of any one of SEQ ID NOs: 107-108 and 177-178; and a $V_L$ comprising an LC-CDR1, an LC-CDR2, and an LC-CDR3 of a $V_L$ comprising the amino acid sequence of any one of SEQ ID NOs: 119 and 189; or (iv) a $V_H$ comprising the amino acid sequence of any one of SEQ ID NOs: 111 and 181, or a variant thereof having at least about 90% sequence identity to the amino acid sequence of any one of SEQ ID NOs: 111 and 181; and a $V_L$ comprising the amino acid sequence of any one of SEQ ID NOs: 124 and 194, or a variant thereof having at least about 90% sequence identity to the amino acid sequence of any one of SEQ ID NOs: 124 and 194; or a $V_H$ comprising an HC-CDR1, an HC-CDR2, and an HC-CDR3 of a $V_H$ comprising the amino acid sequence of any one of SEQ ID NOs: 111 and 181; and a $V_L$ comprising an LC-CDR1, an LC-CDR2, and an LC-CDR3 of a $V_L$ comprising the amino acid sequence of any one of SEQ ID NOs: 124 and 194;

or wherein the antigen-binding protein specifically recognizing *Pseudomonas* Psl comprises:

(i) a $V_H$ comprising the amino acid sequence of SEQ ID NO: 103 or 173, or a variant thereof having at least about 90% sequence identity to the amino acid sequence of SEQ ID NO: 103 or 173; and a $V_L$ comprising the amino acid sequence of SEQ ID NO: 117 or 187, or a variant thereof having at least about 90% sequence identity to the amino acid sequence of SEQ ID NO: 117 or 187; or a $V_H$ comprising an HC-CDR1, an HC-CDR2 and an HC-CDR3 of the $V_H$ comprising the amino acid sequence of SEQ ID NO: 103 or 173; and a $V_L$ comprising an LC-CDR1, an LC-CDR2, and an LC-CDR3 of the $V_L$ comprising the amino acid sequence of SEQ ID NO: 117 or 187; or (ii) a $V_H$ comprising the amino acid sequence of SEQ ID NO: 109 or 179, or a variant thereof having at least about 90% sequence identity to the amino acid sequence of SEQ ID NO: 109 or 179; and a $V_L$ comprising the amino acid sequence of SEQ ID NO: 120 or 190, or a variant thereof having at least about 90% sequence identity to the amino acid sequence of SEQ ID NO: 120 or 190; or a $V_H$ comprising an HC-CDR1, an HC-CDR2 and an HC-CDR3 of the $V_H$ comprising the amino acid sequence of SEQ ID NO: 109 or 179; and a $V_L$ comprising an LC-CDR1, an LC-CDR2, and an LC-CDR3 of the $V_L$ comprising the amino acid sequence of SEQ ID NO: 120 or 190.

13. The method of claim 11, the infection or condition comprises one or more symptoms selection from the group consisting of fever, chills, fatigues, muscle and joint pain, swelling of joints, headache, diarrhea, skin rashes, pus in wounds, bacteremia, acute pneumonia, intraperitoneal infection, respiratory tract infections, septic shock, suppurative arthritis, enteritis, skin and soft tissue infections, urinary tract infections, intestinal infections, ulcerative keratitis, chronic suppurative otitis media, mastoiditis, sinusitis, or endocarditis, and combinations thereof.

\* \* \* \* \*